US009950068B2

(12) United States Patent
De Fougerolles et al.

(10) Patent No.: US 9,950,068 B2
(45) **Date of Patent: *Apr. 24, 2018**

(54) DELIVERY AND FORMULATION OF ENGINEERED NUCLEIC ACIDS

(71) Applicant: ModernaTX, Inc., Cambridge, MA (US)

(72) Inventors: Antonin De Fougerolles, Waterloo (BE); Sayda M. Elbashir, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/379,284

(22) Filed: Dec. 14, 2016

(65) Prior Publication Data

US 2017/0258915 A1 Sep. 14, 2017

Related U.S. Application Data

(60) Division of application No. 14/337,513, filed on Jul. 22, 2014, now Pat. No. 9,533,047, which is a continuation of application No. 13/897,382, filed on May 18, 2013, now abandoned, which is a continuation of application No. 13/437,034, filed on Apr. 2, 2012, now Pat. No. 8,710,200.

(60) Provisional application No. 61/470,451, filed on Mar. 31, 2011.

(51) Int. Cl.

| | |
|---|---|
| ***A61K 31/7088*** | (2006.01) |
| ***A61K 31/7115*** | (2006.01) |
| ***C07K 14/535*** | (2006.01) |
| ***C12N 15/87*** | (2006.01) |
| ***C12N 9/64*** | (2006.01) |
| ***A61K 47/18*** | (2017.01) |
| ***A61K 38/48*** | (2006.01) |
| ***A61K 47/22*** | (2006.01) |
| ***A61K 47/28*** | (2006.01) |
| ***A61K 38/19*** | (2006.01) |
| *A61K 48/00* | (2006.01) |

(52) U.S. Cl.

CPC .......... *A61K 47/18* (2013.01); *A61K 31/7088* (2013.01); *A61K 31/7115* (2013.01); *A61K 38/193* (2013.01); *A61K 38/4846* (2013.01); *A61K 47/22* (2013.01); *A61K 47/28* (2013.01); *C07K 14/535* (2013.01); *C12N 9/644* (2013.01); *C12N 15/87* (2013.01); *A61K 48/00* (2013.01)

(58) Field of Classification Search

None

See application file for complete search history.

(56) References Cited

U.S. PATENT DOCUMENTS

| | | | |
|---|---|---|---|
| 2,008,526 | A | 7/1935 | Wappler et al. |
| 3,552,394 | A | 1/1971 | Horn |
| 3,737,524 | A | 6/1973 | Ebel et al. |
| 3,766,907 | A | 10/1973 | Muenzer |
| 3,906,092 | A | 9/1975 | Hilleman et al. |
| 4,373,071 | A | 2/1983 | Itakura |
| 4,399,216 | A | 8/1983 | Axel et al. |
| 4,401,796 | A | 8/1983 | Itakura |
| 4,411,657 | A | 10/1983 | Galindo |
| 4,415,732 | A | 11/1983 | Caruthers et al. |
| 4,458,066 | A | 7/1984 | Caruthers et al. |
| 4,474,569 | A | 10/1984 | Newkirk |
| 4,500,707 | A | 2/1985 | Caruthers et al. |
| 4,579,849 | A | 4/1986 | MacCoss et al. |
| 4,588,585 | A | 5/1986 | Mark et al. |
| 4,668,777 | A | 5/1987 | Caruthers et al. |
| 4,737,462 | A | 4/1988 | Mark et al. |
| 4,816,567 | A | 3/1989 | Cabilly et al. |
| 4,879,111 | A | 11/1989 | Chong |
| 4,957,735 | A | 9/1990 | Huang |
| 4,959,314 | A | 9/1990 | Mark et al. |
| 4,973,679 | A | 11/1990 | Caruthers et al. |
| 5,012,818 | A | 5/1991 | Joishy |
| 5,017,691 | A | 5/1991 | Lee et al. |
| 5,021,335 | A | 6/1991 | Tecott et al. |
| 5,036,006 | A | 7/1991 | Sanford et al. |
| 5,047,524 | A | 9/1991 | Andrus et al. |
| 5,116,943 | A | 5/1992 | Koths et al. |
| 5,130,238 | A | 7/1992 | Malek et al. |
| 5,132,418 | A | 7/1992 | Caruthers et al. |
| 5,153,319 | A | 10/1992 | Caruthers et al. |
| 5,168,038 | A | 12/1992 | Tecott et al. |
| 5,169,766 | A | 12/1992 | Schuster et al. |
| 5,194,370 | A | 3/1993 | Berninger et al. |
| 5,199,441 | A | 4/1993 | Hogle |

(Continued)

FOREIGN PATENT DOCUMENTS

| | | | |
|---|---|---|---|
| CA | 2376634 | A1 | 12/2000 |
| CA | 2473135 | A1 | 6/2003 |

(Continued)

OTHER PUBLICATIONS

US 2002/0198163 A1, 12/2002, Felgner et al. (withdrawn)
Akinc, et al. (2010) "Targeted Delivery of RNAi Therapeutics With Endogenous and Exogenous Ligand-Based Mechanisms", Journal of Gene and Cell Therapy, 18(7): 1357-64.*
Interview Materials Attachment, Table 140.Flux, from U.S. Appl. No. 14/337,513, dated Aug. 15, 2017. Provided by John Covert and Debra Milasincic, 13 pages long.*
Aasen, T., et al., "Efficient and Rapid Generation of Induced Pluripotent Stem Cells from Human Keratinocytes," Nature Biotechnology 26(11):1276-1284, Nature America Publishing, United States (2008).

(Continued)

*Primary Examiner* — Robert M Kelly
(74) *Attorney, Agent, or Firm* — Clark & Elbing LLP

(57) ABSTRACT

Provided are formulations, compositions and methods for delivering biological moieties such as modified nucleic acids into cells to modulate protein expression. Such compositions and methods include the delivery of biological moieties, and are useful for production of proteins.

20 Claims, 20 Drawing Sheets

(56) References Cited

U.S. PATENT DOCUMENTS 5,240,855 A 8/1993 Tomes
5,262,530 A 11/1993 Andrus et al.
5,273,525 A 12/1993 Hofmann
5,298,422 A 3/1994 Schwartz et al.
5,332,671 A 7/1994 Ferrara et al.
5,399,491 A 3/1995 Kacian et al.
5,409,818 A 4/1995 Davey et al.
5,426,180 A 6/1995 Kool
5,437,990 A 8/1995 Burg et al.
5,457,041 A 10/1995 Ginaven et al.
5,466,586 A 11/1995 Davey et al.
5,484,401 A 1/1996 Rodriguez et al.
5,489,677 A 2/1996 Sanghvi et al.
5,514,545 A 5/1996 Eberwine
5,527,288 A 6/1996 Gross et al.
5,545,522 A 8/1996 Van Gelder et al.
5,554,517 A 9/1996 Davey et al.
5,580,859 A 12/1996 Felgner et al.
5,588,960 A 12/1996 Edwards et al.
5,589,466 A 12/1996 Felgner et al.
5,663,153 A 9/1997 Hutcherson et al.
5,665,545 A 9/1997 Malek et al.
5,672,491 A 9/1997 Khosla et al.
5,674,267 A 10/1997 Mir et al.
5,677,124 A 10/1997 Dubois et al.
5,679,512 A 10/1997 Laney et al.
5,693,622 A 12/1997 Wolff et al.
5,693,761 A 12/1997 Queen et al.
5,697,901 A 12/1997 Eriksson
5,700,642 A 12/1997 Monforte et al.
5,702,384 A 12/1997 Umeyama et al.
5,703,055 A 12/1997 Felgner et al.
5,712,127 A 1/1998 Malek et al.
5,716,785 A 2/1998 Van Gelder et al.
5,736,137 A 4/1998 Anderson et al.
5,756,264 A 5/1998 Schwartz et al.
5,759,179 A 6/1998 Balbierz
5,766,903 A 6/1998 Sarnow et al.
5,773,244 A 6/1998 Ares, Jr. et al.
5,776,456 A 7/1998 Anderson et al.
5,789,554 A 8/1998 Leung et al.
5,807,707 A 9/1998 Andrews et al.
5,824,307 A 10/1998 Johnson
5,824,497 A 10/1998 Andrews et al.
5,840,299 A 11/1998 Bendig et al.
5,843,439 A 12/1998 Anderson et al.
5,848,996 A 12/1998 Eldor
5,849,546 A 12/1998 Sousa et al.
5,851,829 A 12/1998 Marasco et al.
5,861,501 A 1/1999 Benseler et al.
5,869,230 A 2/1999 Sukhatme
5,889,136 A 3/1999 Scaringe et al.
5,891,636 A 4/1999 Van Gelder et al.
5,914,269 A 6/1999 Bennett et al.
5,955,310 A 9/1999 Widner et al.
5,958,688 A 9/1999 Eberwine et al.
5,962,271 A 10/1999 Chenchik et al.
5,962,272 A 10/1999 Chenchik et al.
5,965,720 A 10/1999 Gryaznov et al.
5,965,726 A 10/1999 Pavlakis et al.
5,980,887 A 11/1999 Isner et al.
5,989,911 A 11/1999 Fournier et al.
5,994,511 A 11/1999 Lowman et al.
6,004,573 A 12/1999 Rathi et al.
6,019,747 A 2/2000 McPhee
6,022,715 A 2/2000 Merenkova et al.
6,057,494 A 5/2000 Koops et al.
6,063,603 A 5/2000 Davey et al.
6,074,642 A 6/2000 Wang et al.
6,090,382 A 7/2000 Salfeld et al.
6,090,591 A 7/2000 Burg et al.
6,096,503 A 8/2000 Sutcliffe et al.
6,100,024 A 8/2000 Hudson et al.
6,124,091 A 9/2000 Petryshyn
6,132,419 A 10/2000 Hofmann
6,147,055 A 11/2000 Hobart et al.
6,177,274 B1 1/2001 Park et al.
6,187,287 B1 2/2001 Leung et al.
6,190,315 B1 2/2001 Kost et al.
6,210,931 B1 4/2001 Feldstein et al.
6,214,804 B1 4/2001 Felgner et al.
6,217,912 B1 4/2001 Park et al.
6,228,640 B1 5/2001 Cezayirli et al.
6,234,990 B1 5/2001 Rowe et al.
6,235,883 B1 5/2001 Jakobovits et al.
6,239,116 B1 5/2001 Krieg et al.
6,251,665 B1 6/2001 Cezayirli et al.
6,255,076 B1 7/2001 Widner et al.
6,258,558 B1 7/2001 Szostak et al.
6,261,584 B1 7/2001 Peery et al.
6,265,387 B1 7/2001 Wolff et al.
6,265,389 B1 7/2001 Burke
6,267,987 B1 7/2001 Park et al.
6,291,170 B1 9/2001 Van Gelder et al.
6,300,484 B1 10/2001 Duhl
6,303,378 B1 10/2001 Bridenbaugh et al.
6,303,573 B1 10/2001 Ruoslahti et al.
6,322,967 B1 11/2001 Parkin
6,326,174 B1 12/2001 Joyce et al.
6,334,856 B1 1/2002 Allen et al.
6,355,245 B1 3/2002 Evans et al.
6,368,801 B1 4/2002 Faruqi
6,376,248 B1 4/2002 Hawley-Nelson et al.
6,395,253 B2 5/2002 Levy et al.
6,399,061 B1 6/2002 Anderson et al.
6,406,705 B1 6/2002 Davis et al.
6,410,276 B1 6/2002 Burg et al.
6,413,942 B1 7/2002 Felgner et al.
6,433,155 B1 8/2002 Umansky et al.
6,440,096 B1 8/2002 Lastovich et al.
6,455,043 B1 9/2002 Grillo-Lopez
6,491,657 B2 12/2002 Rowe et al.
6,500,419 B1 12/2002 Hone et al.
6,500,919 B1 12/2002 Adema et al.
6,514,498 B1 2/2003 Antonsson et al.
6,514,948 B1 2/2003 Raz et al.
6,517,869 B1 2/2003 Park et al.
6,520,949 B2 2/2003 St. Germain et al.
6,525,183 B2 2/2003 Vinayak et al.
6,527,216 B2 3/2003 Eagelman et al.
6,528,262 B1 3/2003 Gilad et al.
6,534,312 B1 3/2003 Shiver et al.
6,552,006 B2 4/2003 Raz et al.
6,555,525 B2 4/2003 Burke
6,565,572 B2 5/2003 Chappius
6,572,857 B1 6/2003 Casimiro et al.
6,586,524 B2 7/2003 Sagara
6,589,940 B1 7/2003 Raz et al.
6,610,044 B2 8/2003 Mathiesen
6,610,661 B1 8/2003 Carson et al.
6,613,026 B1 9/2003 Palasis et al.
6,617,106 B1 9/2003 Benner
6,623,457 B1 9/2003 Rosenberg
6,652,886 B2 11/2003 Ahn et al.
6,653,468 B1 11/2003 Guzaev et al.
6,664,066 B2 12/2003 Parks
6,670,178 B1 12/2003 Selden et al.
6,676,938 B1 1/2004 Teti et al.
6,696,038 B1 2/2004 Mahato et al.
6,743,211 B1 6/2004 Prausnitz et al.
6,743,823 B1 6/2004 Summar et al.
6,777,187 B2 8/2004 Makarov et al.
6,808,888 B2 10/2004 Zhang et al.
6,818,421 B2 11/2004 Kossmann et al.
6,835,393 B2 12/2004 Hoffman et al.
6,835,827 B2 12/2004 Vinayak et al.
6,890,319 B1 5/2005 Crocker
6,896,885 B2 5/2005 Hanna
6,900,302 B2 5/2005 Teti et al.
6,902,734 B2 6/2005 Giles-Komar et al.
6,924,365 B1 8/2005 Miller et al.
6,949,245 B1 9/2005 Sliwkowski
6,960,193 B2 11/2005 Rosenberg
6,962,694 B1 11/2005 Soegaard et al.

(56) References Cited

U.S. PATENT DOCUMENTS

| | | | |
|---|---|---|---|
| 7,001,890 | B1 | 2/2006 | Wagner et al. |
| 7,052,891 | B2 | 5/2006 | Leung et al. |
| 7,074,596 | B2 | 7/2006 | Darzynkiewicz et al. |
| 7,125,554 | B2 | 10/2006 | Forsberg et al. |
| 7,135,010 | B2 | 11/2006 | Buckman et al. |
| 7,169,750 | B2 | 1/2007 | Bridger et al. |
| 7,195,761 | B2 | 3/2007 | Holtzman et al. |
| 7,198,899 | B2 | 4/2007 | Schleyer et al. |
| 7,202,226 | B2 | 4/2007 | Murray et al. |
| 7,208,478 | B2 | 4/2007 | Carson et al. |
| 7,226,439 | B2 | 6/2007 | Prausnitz et al. |
| 7,226,595 | B2 | 6/2007 | Antonsson et al. |
| 7,268,120 | B1 | 9/2007 | Horton et al. |
| 7,276,489 | B2 | 10/2007 | Agrawal et al. |
| 7,316,925 | B2 | 1/2008 | Draghia-Akli et al. |
| 7,320,961 | B2 | 1/2008 | Kempf et al. |
| 7,329,741 | B2 | 2/2008 | Duhl |
| 7,335,471 | B2 | 2/2008 | Guillerez et al. |
| 7,348,004 | B2 | 3/2008 | Peters et al. |
| 7,354,742 | B2 | 4/2008 | Kamme et al. |
| 7,371,404 | B2 | 5/2008 | Panzner et al. |
| 7,374,778 | B2 | 5/2008 | Hoffman et al. |
| 7,374,930 | B2 | 5/2008 | Oh et al. |
| 7,378,262 | B2 | 5/2008 | Sobek et al. |
| 7,384,739 | B2 | 6/2008 | Kitabayashi et al. |
| 7,404,956 | B2 | 7/2008 | Peters et al. |
| 7,422,739 | B2 | 9/2008 | Anderson et al. |
| 7,476,506 | B2 | 1/2009 | Schleyer et al. |
| 7,476,709 | B2 | 1/2009 | Moody et al. |
| 7,479,543 | B2 | 1/2009 | Tsuchiya et al. |
| 7,498,414 | B2 | 3/2009 | Zhu |
| 7,501,486 | B2 | 3/2009 | Zhang et al. |
| 7,521,054 | B2 | 4/2009 | Pastan et al. |
| 7,547,678 | B2 | 6/2009 | Kempf et al. |
| 7,550,264 | B2 | 6/2009 | Getts et al. |
| 7,575,572 | B2 | 8/2009 | Sweeney |
| 7,579,318 | B2 | 8/2009 | Divita et al. |
| 7,615,225 | B2 | 11/2009 | Forsberg et al. |
| 7,629,311 | B2 | 12/2009 | Tobinick et al. |
| 7,641,901 | B2 | 1/2010 | Goldenberg et al. |
| 7,667,033 | B2 | 2/2010 | Alvarado |
| 7,682,612 | B1 | 3/2010 | White et al. |
| 7,699,852 | B2 | 4/2010 | Frankel et al. |
| 7,708,994 | B2 | 5/2010 | Benyunes |
| 7,709,452 | B2 | 5/2010 | Pitard |
| 7,718,425 | B2 | 5/2010 | Reinke et al. |
| 7,737,108 | B1 | 6/2010 | Hoffman et al. |
| 7,745,391 | B2 | 6/2010 | Mintz et al. |
| 7,763,253 | B2 | 7/2010 | Hedlund et al. |
| 7,776,523 | B2 | 8/2010 | Garcia et al. |
| 7,794,719 | B2 | 9/2010 | Bardroff et al. |
| 7,799,900 | B2 | 9/2010 | Adams et al. |
| 7,820,161 | B1 | 10/2010 | Curd et al. |
| 7,820,624 | B2 | 10/2010 | Hart et al. |
| 7,829,092 | B2 | 11/2010 | Lobb et al. |
| 7,846,895 | B2 | 12/2010 | Shi et al. |
| 7,862,820 | B2 | 1/2011 | Peters et al. |
| 7,884,184 | B2 | 2/2011 | De Groot et al. |
| 7,906,490 | B2 | 3/2011 | Kool |
| 7,943,168 | B2 | 5/2011 | Schlesinger et al. |
| 7,943,581 | B2 | 5/2011 | Divita et al. |
| 7,964,571 | B2 | 6/2011 | Fewell et al. |
| 7,999,087 | B2 | 8/2011 | Dellinger et al. |
| 8,003,129 | B2 | 8/2011 | Hoffman et al. |
| 8,008,449 | B2 | 8/2011 | Korman et al. |
| 8,039,214 | B2 | 10/2011 | Dahl et al. |
| 8,048,999 | B2 | 11/2011 | Yamanaka et al. |
| 8,057,821 | B2 | 11/2011 | Slobodkin et al. |
| 8,058,069 | B2 | 11/2011 | Yaworski et al. |
| 8,101,385 | B2 | 1/2012 | Cload et al. |
| 8,105,596 | B2 | 1/2012 | Goldenberg |
| 8,108,385 | B2 | 1/2012 | Kraft et al. |
| 8,137,911 | B2 | 3/2012 | Dahl et al. |
| 8,153,768 | B2 | 4/2012 | Kunz et al. |
| 8,158,360 | B2 | 4/2012 | Heise et al. |
| 8,158,601 | B2 | 4/2012 | Chen et al. |
| 8,178,660 | B2 | 5/2012 | Weiner et al. |
| 8,183,345 | B2 | 5/2012 | Fay et al. |
| 8,183,352 | B2 | 5/2012 | Ayyavoo et al. |
| 8,202,983 | B2 | 6/2012 | Dellinger et al. |
| 8,217,016 | B2 | 7/2012 | Hoerr et al. |
| 8,226,950 | B2 | 7/2012 | Lobb et al. |
| 8,242,081 | B2 | 8/2012 | Divita et al. |
| 8,242,087 | B2 | 8/2012 | Adelfinskaya et al. |
| 8,242,258 | B2 | 8/2012 | Dellinger et al. |
| 8,246,958 | B2 | 8/2012 | Bendig et al. |
| 8,278,036 | B2 | 10/2012 | Kariko et al. |
| 8,304,183 | B2 | 11/2012 | Sooknanan |
| 8,304,532 | B2 | 11/2012 | Adamo et al. |
| 8,309,706 | B2 | 11/2012 | Dellinger et al. |
| 8,329,172 | B2 | 12/2012 | Grillo-Lopez |
| 8,329,182 | B2 | 12/2012 | Peters et al. |
| 8,329,887 | B2 | 12/2012 | Dahl et al. |
| 8,333,799 | B2 | 12/2012 | Bales, Jr. et al. |
| 8,344,153 | B2 | 1/2013 | Cottrell et al. |
| 8,349,321 | B2 | 1/2013 | Burke et al. |
| 8,367,328 | B2 | 2/2013 | Asada et al. |
| 8,367,631 | B2 | 2/2013 | Pitard |
| 8,383,340 | B2 | 2/2013 | Ketterer et al. |
| 8,394,763 | B2 | 3/2013 | Forte et al. |
| 8,399,007 | B2 | 3/2013 | Taft et al. |
| 8,404,222 | B2 | 3/2013 | Harris |
| 8,404,799 | B2 | 3/2013 | Podobinski et al. |
| 8,414,927 | B2 | 4/2013 | Richard |
| 8,415,325 | B2 | 4/2013 | Kiick et al. |
| 8,420,123 | B2 | 4/2013 | Troiano et al. |
| 8,420,605 | B2 | 4/2013 | Ulijn et al. |
| 8,431,160 | B2 | 4/2013 | O'Hagan et al. |
| 8,435,504 | B2 | 5/2013 | Kozlowski |
| 8,440,231 | B2 | 5/2013 | Smyth et al. |
| 8,440,614 | B2 | 5/2013 | Castor |
| 8,444,992 | B2 | 5/2013 | Borkowski |
| 8,449,884 | B2 | 5/2013 | Rivera et al. |
| 8,449,916 | B1 | 5/2013 | Bellaire et al. |
| 8,450,298 | B2 | 5/2013 | Mahon et al. |
| 8,454,946 | B2 | 6/2013 | Shen |
| 8,454,948 | B2 | 6/2013 | Pearlman et al. |
| 8,460,696 | B2 | 6/2013 | Slobodkin et al. |
| 8,460,709 | B2 | 6/2013 | Ausborn et al. |
| 8,461,132 | B2 | 6/2013 | Cohen et al. |
| 8,466,122 | B2 | 6/2013 | Heyes et al. |
| 8,470,560 | B2 | 6/2013 | Bergmann-Leitner et al. |
| 8,470,771 | B2 | 6/2013 | Gao et al. |
| 8,476,234 | B2 | 7/2013 | Fima et al. |
| 8,496,945 | B2 | 7/2013 | Schlesinger et al. |
| 8,506,928 | B2 | 8/2013 | Ferrara et al. |
| 8,506,966 | B2 | 8/2013 | Podda et al. |
| 8,512,964 | B2 | 8/2013 | Tontonoz et al. |
| 8,518,871 | B2 | 8/2013 | Hsu et al. |
| 8,529,538 | B2 | 9/2013 | Pang et al. |
| 8,529,939 | B2 | 9/2013 | Masters et al. |
| 8,530,429 | B2 | 9/2013 | Robbins et al. |
| 8,530,625 | B2 | 9/2013 | Kaplan et al. |
| 8,535,655 | B2 | 9/2013 | O'Shea et al. |
| 8,535,701 | B2 | 9/2013 | Peery et al. |
| 8,535,702 | B2 | 9/2013 | Richard et al. |
| 8,545,843 | B2 | 10/2013 | Curd et al. |
| 8,557,231 | B2 | 10/2013 | Langer et al. |
| 8,557,244 | B1 | 10/2013 | White et al. |
| 8,562,992 | B2 | 10/2013 | Adams et al. |
| 8,563,041 | B2 | 10/2013 | Grayson et al. |
| 8,568,784 | B2 | 10/2013 | Lillard et al. |
| 8,569,256 | B2 | 10/2013 | Heyes et al. |
| 8,580,297 | B2 | 11/2013 | Essler et al. |
| 8,603,499 | B2 | 12/2013 | Zale et al. |
| 8,603,500 | B2 | 12/2013 | Zale et al. |
| 8,603,501 | B2 | 12/2013 | Zale et al. |
| 8,603,534 | B2 | 12/2013 | Zale et al. |
| 8,603,535 | B2 | 12/2013 | Troiano et al. |
| 8,609,142 | B2 | 12/2013 | Troiano et al. |
| 8,609,822 | B2 | 12/2013 | Elson et al. |
| 8,613,951 | B2 | 12/2013 | Zale et al. |
| 8,613,954 | B2 | 12/2013 | Zale et al. |
| 8,617,608 | B2 | 12/2013 | Zale et al. |

(56) References Cited

U.S. PATENT DOCUMENTS 8,618,240 B2 12/2013 Podobinski et al.
8,623,367 B2 1/2014 Momm et al.
8,628,801 B2 1/2014 Garreta et al.
8,636,696 B2 1/2014 Ross et al.
8,636,994 B2 1/2014 Bossard et al.
8,637,028 B2 1/2014 Alexis et al.
8,637,083 B2 1/2014 Troiano et al.
8,642,076 B2 2/2014 Manoharan et al.
8,652,487 B2 2/2014 Maldonado
8,652,528 B2 2/2014 Troiano et al.
8,658,211 B2 2/2014 Rozema et al.
8,658,733 B2 2/2014 Jorgedal et al.
8,663,599 B1 3/2014 Sung et al.
8,663,692 B1 3/2014 Mueller et al.
8,663,700 B2 3/2014 Troiano et al.
8,664,194 B2 3/2014 De Fougerolles et al.
8,668,926 B1 3/2014 Mousa et al.
8,680,069 B2 3/2014 De Fougerolles et al.
8,685,368 B2 4/2014 Reineke
8,685,458 B2 4/2014 Miller et al.
8,691,223 B2 4/2014 Van Den Brink et al.
8,691,750 B2 4/2014 Constien et al.
8,691,785 B2 4/2014 Teng et al.
8,691,963 B2 4/2014 Brahmbhatt et al.
8,691,966 B2 4/2014 Kariko et al.
8,696,637 B2 4/2014 Ross
8,697,098 B2 4/2014 Perumal et al.
8,703,204 B2 4/2014 Bloom et al.
8,709,483 B2 4/2014 Farokhzad et al.
8,710,200 B2 * 4/2014 Schrum .............. A61K 31/7088
536/23.1
8,715,677 B2 5/2014 Bartlett et al.
8,715,689 B2 5/2014 Kinney et al.
8,715,694 B2 5/2014 Apt et al.
8,715,736 B2 5/2014 Sachdeva et al.
8,715,741 B2 5/2014 Maitra et al.
8,716,465 B2 5/2014 Rossi et al.
8,722,341 B2 5/2014 Fouchier et al.
8,728,491 B2 5/2014 Sesardic et al.
8,728,527 B2 5/2014 Singh
8,728,772 B2 5/2014 Suzuki et al.
8,734,832 B2 5/2014 O'Hagan et al.
8,734,846 B2 5/2014 Ali et al.
8,734,853 B2 5/2014 Sood et al.
8,735,566 B2 5/2014 Brahmbhatt et al.
8,735,570 B2 5/2014 Miller et al.
8,748,089 B2 6/2014 Kariko et al.
8,754,062 B2 6/2014 De Fougerolles et al.
8,802,438 B2 8/2014 Rossi et al.
8,808,982 B2 8/2014 Dahl et al.
8,822,663 B2 9/2014 Schrum et al.
8,835,108 B2 9/2014 Kariko et al.
8,846,348 B2 9/2014 Jendrisak et al.
8,853,179 B2 10/2014 Mauro et al.
8,853,377 B2 10/2014 Guild et al.
8,871,230 B2 10/2014 Rudolph et al.
8,883,506 B2 11/2014 Rossi et al.
8,999,380 B2 4/2015 Bancel et al.
9,334,328 B2 5/2016 Schrum et al.
9,533,047 B2 * 1/2017 de Fougerolles .. A61K 31/7088
2001/0001066 A1 5/2001 Cezayirli et al.
2001/0005506 A1 6/2001 Cezayirli et al.
2001/0014753 A1 8/2001 Soloveichik et al.
2002/0001842 A1 1/2002 Chapman
2002/0064517 A1 5/2002 Cederholm-Williams
2002/0111471 A1 8/2002 Lo et al.
2002/0123099 A1 9/2002 Weiner et al.
2002/0123723 A1 9/2002 Sorenson et al.
2002/0127592 A1 9/2002 Ichihara et al.
2002/0130430 A1 9/2002 Castor
2002/0132788 A1 9/2002 Lewis et al.
2002/0143204 A1 10/2002 Evain et al.
2003/0026841 A1 2/2003 Trubetskoy et al.
2003/0032615 A1 2/2003 Felgner et al.
2003/0050468 A1 3/2003 Shiver et al.
2003/0073619 A1 4/2003 Mahato et al.
2003/0077604 A1 4/2003 Sun et al.
2003/0082768 A1 5/2003 Baskerville et al.
2003/0083272 A1 5/2003 Wiederholt et al.
2003/0138419 A1 7/2003 Radic et al.
2003/0143743 A1 7/2003 Schuler et al.
2003/0153735 A1 8/2003 Breece et al.
2003/0158133 A1 8/2003 Movsesian
2003/0170273 A1 9/2003 O'Hagan et al.
2003/0171253 A1 9/2003 Ma et al.
2003/0186237 A1 10/2003 Ginsberg et al.
2003/0191303 A1 10/2003 Vinayak et al.
2003/0192068 A1 10/2003 Deboer et al.
2003/0225016 A1 12/2003 Fearon et al.
2004/0005667 A1 1/2004 Ratti et al.
2004/0018525 A1 1/2004 Wirtz et al.
2004/0106567 A1 6/2004 Hagstrom et al.
2004/0110191 A1 6/2004 Winkler et al.
2004/0122216 A1 6/2004 Nielsen et al.
2004/0142474 A1 7/2004 Mahato et al.
2004/0147027 A1 7/2004 Troy et al.
2004/0167090 A1 8/2004 Monahan et al.
2004/0171041 A1 9/2004 Dahl et al.
2004/0171980 A1 9/2004 Mitragotri et al.
2004/0197802 A1 10/2004 Dahl et al.
2004/0202658 A1 10/2004 Benyunes
2004/0209274 A2 10/2004 Daly
2004/0236268 A1 11/2004 Mitragotri et al.
2004/0259081 A1 12/2004 Watzele et al.
2005/0032730 A1 2/2005 Von Der Mulbe et al.
2005/0037494 A1 2/2005 Hecker et al.
2005/0054026 A1 3/2005 Atsushi et al.
2005/0059624 A1 3/2005 Hoerr et al.
2005/0064596 A1 3/2005 Riemen et al.
2005/0089913 A1 4/2005 Williams
2005/0112141 A1 5/2005 Terman
2005/0130201 A1 6/2005 Deras et al.
2005/0137155 A1 6/2005 McSwiggen et al.
2005/0147618 A1 7/2005 Rivera et al.
2005/0153333 A1 7/2005 Sooknanan
2005/0181016 A1 8/2005 Freyman et al.
2005/0232919 A1 10/2005 Grasso et al.
2005/0250723 A1 11/2005 Hoerr et al.
2006/0008910 A1 1/2006 MacLachlan et al.
2006/0018971 A1 1/2006 Scott et al.
2006/0032372 A1 2/2006 Dauber et al.
2006/0035226 A1 2/2006 Scheinert et al.
2006/0057111 A1 3/2006 Hedlund et al.
2006/0083780 A1 4/2006 Heyes et al.
2006/0160743 A1 7/2006 Zhang et al.
2006/0172003 A1 8/2006 Meers et al.
2006/0172966 A1 8/2006 Lipford et al.
2006/0188490 A1 8/2006 Hoerr et al.
2006/0204566 A1 9/2006 Smyth-Templeton et al.
2006/0241076 A1 10/2006 Uhlmann et al.
2006/0247195 A1 11/2006 Ray
2006/0265771 A1 11/2006 Lewis et al.
2006/0275747 A1 12/2006 Hardy et al.
2007/0037147 A1 2/2007 Garcia et al.
2007/0037148 A1 2/2007 Fong et al.
2007/0048741 A1 3/2007 Getts et al.
2007/0054278 A1 3/2007 Cargill
2007/0072175 A1 3/2007 Cooper et al.
2007/0087437 A1 4/2007 Hu
2007/0105124 A1 5/2007 Getts et al.
2007/0105799 A1 5/2007 Hermanson
2007/0117112 A1 5/2007 Diener et al.
2007/0122882 A1 5/2007 Nakagawa et al.
2007/0141030 A1 6/2007 Yu et al.
2007/0143878 A1 6/2007 Bhat et al.
2007/0178103 A1 8/2007 Fey et al.
2007/0213287 A1 9/2007 Fewell et al.
2007/0224635 A1 9/2007 Bouquin
2007/0252295 A1 11/2007 Panzner et al.
2007/0265220 A1 11/2007 Rossi et al.
2007/0280929 A1 12/2007 Hoerr et al.
2008/0008711 A1 1/2008 Schleyer et al.
2008/0020431 A1 1/2008 Getts et al.
2008/0025944 A1 1/2008 Hoerr et al.

(56) References Cited

U.S. PATENT DOCUMENTS

| | | | |
|---|---|---|---|
| 2008/0075698 | A1 | 3/2008 | Sawada et al. |
| 2008/0076174 | A1 | 3/2008 | Selden et al. |
| 2008/0119645 | A1 | 5/2008 | Griffey et al. |
| 2008/0166414 | A1 | 7/2008 | Hanes et al. |
| 2008/0166793 | A1 | 7/2008 | Beer et al. |
| 2008/0171711 | A1 | 7/2008 | Hoerr et al. |
| 2008/0220471 | A1 | 9/2008 | Davis et al. |
| 2008/0260706 | A1 | 10/2008 | Rabinovich et al. |
| 2008/0261905 | A1 | 10/2008 | Herdewijn et al. |
| 2008/0267873 | A1 | 10/2008 | Hoerr et al. |
| 2008/0274463 | A1 | 11/2008 | Chen et al. |
| 2008/0275468 | A1 | 11/2008 | Chuang et al. |
| 2008/0286813 | A1 | 11/2008 | George-Hyslop et al. |
| 2008/0293143 | A1 | 11/2008 | Lin et al. |
| 2009/0042825 | A1 | 2/2009 | Matar et al. |
| 2009/0042829 | A1 | 2/2009 | Matar et al. |
| 2009/0048167 | A1 | 2/2009 | Hillman |
| 2009/0053775 | A1 | 2/2009 | Dahl et al. |
| 2009/0093433 | A1 | 4/2009 | Woolf et al. |
| 2009/0144839 | A1 | 6/2009 | Inana et al. |
| 2009/0169550 | A1 | 7/2009 | Dummer |
| 2009/0170090 | A1 | 7/2009 | Ignatov et al. |
| 2009/0208418 | A1 | 8/2009 | Kohler et al. |
| 2009/0208500 | A1 | 8/2009 | Joly et al. |
| 2009/0226470 | A1 | 9/2009 | Mauro et al. |
| 2009/0227660 | A1 | 9/2009 | Oh et al. |
| 2009/0264511 | A1 | 10/2009 | De Fougerolles et al. |
| 2009/0281298 | A1 | 11/2009 | Manoharan et al. |
| 2009/0286852 | A1 | 11/2009 | Kariko et al. |
| 2009/0324584 | A1 | 12/2009 | Hoerr et al. |
| 2010/0003337 | A1 | 1/2010 | Hanes et al. |
| 2010/0004313 | A1 | 1/2010 | Slobodkin et al. |
| 2010/0004315 | A1 | 1/2010 | Slobodkin et al. |
| 2010/0009424 | A1 | 1/2010 | Forde et al. |
| 2010/0009865 | A1 | 1/2010 | Herdewijn et al. |
| 2010/0015232 | A1 | 1/2010 | Besenbacher et al. |
| 2010/0021429 | A1 | 1/2010 | Brentzel, Jr. et al. |
| 2010/0028943 | A1 | 2/2010 | Thomas et al. |
| 2010/0047261 | A1 | 2/2010 | Hoerr et al. |
| 2010/0086922 | A1 | 4/2010 | Bryant et al. |
| 2010/0120024 | A1 | 5/2010 | Cload et al. |
| 2010/0129877 | A1 | 5/2010 | Sahin et al. |
| 2010/0137407 | A1 | 6/2010 | Abe et al. |
| 2010/0178271 | A1 | 7/2010 | Bridger et al. |
| 2010/0189729 | A1 | 7/2010 | Hoerr et al. |
| 2010/0196318 | A1 | 8/2010 | Lieberburg |
| 2010/0203076 | A1 | 8/2010 | Fotin-Mleczek et al. |
| 2010/0215580 | A1 | 8/2010 | Hanes et al. |
| 2010/0233141 | A1 | 9/2010 | Polach et al. |
| 2010/0239608 | A1 | 9/2010 | Von Der Muelbe et al. |
| 2010/0258135 | A1 | 10/2010 | Persson |
| 2010/0260817 | A1 | 10/2010 | Slobodkin et al. |
| 2010/0261231 | A1 | 10/2010 | Kore et al. |
| 2010/0266587 | A1 | 10/2010 | McLachlan |
| 2010/0273220 | A1 | 10/2010 | Yanik et al. |
| 2010/0285135 | A1 | 11/2010 | Wendorf et al. |
| 2010/0291156 | A1 | 11/2010 | Barner et al. |
| 2010/0293625 | A1 | 11/2010 | Reed |
| 2010/0297750 | A1 | 11/2010 | Natsume et al. |
| 2010/0305196 | A1 | 12/2010 | Probst et al. |
| 2011/0002934 | A1 | 1/2011 | Luqman et al. |
| 2011/0020352 | A1 | 1/2011 | Garcia et al. |
| 2011/0045022 | A1 | 2/2011 | Tsai |
| 2011/0053829 | A1 | 3/2011 | Baumhof et al. |
| 2011/0065103 | A1 | 3/2011 | Sahin et al. |
| 2011/0077287 | A1 | 3/2011 | Von Der Muelbe et al. |
| 2011/0086904 | A1 | 4/2011 | Russell |
| 2011/0091473 | A1 | 4/2011 | Golab et al. |
| 2011/0091879 | A1 | 4/2011 | Hillebrand et al. |
| 2011/0097716 | A1 | 4/2011 | Natt et al. |
| 2011/0112040 | A1 | 5/2011 | Liu et al. |
| 2011/0143397 | A1 | 6/2011 | Kariko et al. |
| 2011/0143436 | A1 | 6/2011 | Dahl et al. |
| 2011/0165123 | A1 | 7/2011 | Hartmann et al. |
| 2011/0165159 | A1 | 7/2011 | Grillo-Lopez et al. |
| 2011/0172126 | A1 | 7/2011 | Brust |
| 2011/0182919 | A1 | 7/2011 | Peters et al. |
| 2011/0200582 | A1 | 8/2011 | Baryza et al. |
| 2011/0218231 | A1 | 9/2011 | Fewell et al. |
| 2011/0244026 | A1 | 10/2011 | Guild et al. |
| 2011/0245756 | A1 | 10/2011 | Arora et al. |
| 2011/0247090 | A1 | 10/2011 | Reed |
| 2011/0250225 | A1 | 10/2011 | Fotin-Mleczek et al. |
| 2011/0250237 | A1 | 10/2011 | O'Hagan et al. |
| 2011/0269950 | A1 | 11/2011 | Von Der Mulbe et al. |
| 2011/0274697 | A1 | 11/2011 | Thomas et al. |
| 2011/0275793 | A1 | 11/2011 | Debart et al. |
| 2011/0287006 | A1 | 11/2011 | Friess et al. |
| 2011/0294717 | A1 | 12/2011 | Ali et al. |
| 2011/0300205 | A1 | 12/2011 | Geall et al. |
| 2011/0311472 | A1 | 12/2011 | Hoerr et al. |
| 2012/0009145 | A1 | 1/2012 | Slobodkin et al. |
| 2012/0009221 | A1 | 1/2012 | Hoerr et al. |
| 2012/0009649 | A1 | 1/2012 | Dahl et al. |
| 2012/0015899 | A1 | 1/2012 | Lomonossoff et al. |
| 2012/0021043 | A1 | 1/2012 | Kramps et al. |
| 2012/0027813 | A1 | 2/2012 | Podda et al. |
| 2012/0046346 | A1 | 2/2012 | Rossi et al. |
| 2012/0053333 | A1 | 3/2012 | Mauro et al. |
| 2012/0060293 | A1 | 3/2012 | Stelter et al. |
| 2012/0065252 | A1 | 3/2012 | Schrum et al. |
| 2012/0076836 | A1 | 3/2012 | Hori et al. |
| 2012/0094906 | A1 | 4/2012 | Guyon et al. |
| 2012/0095077 | A1 | 4/2012 | Burrows et al. |
| 2012/0114686 | A1 | 5/2012 | Schneewind et al. |
| 2012/0121718 | A1 | 5/2012 | Lai et al. |
| 2012/0128699 | A1 | 5/2012 | Kandimalla et al. |
| 2012/0129759 | A1 | 5/2012 | Liu et al. |
| 2012/0156251 | A1 | 6/2012 | Brito et al. |
| 2012/0156679 | A1 | 6/2012 | Dahl et al. |
| 2012/0171290 | A1 | 7/2012 | Coursaget et al. |
| 2012/0177724 | A1 | 7/2012 | Irvine et al. |
| 2012/0178702 | A1 | 7/2012 | Huang et al. |
| 2012/0189700 | A1 | 7/2012 | Aguilar et al. |
| 2012/0195917 | A1 | 8/2012 | Sahin et al. |
| 2012/0195936 | A1 | 8/2012 | Rudolph et al. |
| 2012/0207840 | A1 | 8/2012 | De Los Pinos |
| 2012/0213818 | A1 | 8/2012 | Hoerr et al. |
| 2012/0219573 | A1 | 8/2012 | Baumhof et al. |
| 2012/0225070 | A1 | 9/2012 | Smith et al. |
| 2012/0232133 | A1 | 9/2012 | Balazs et al. |
| 2012/0237975 | A1 | 9/2012 | Schrum et al. |
| 2012/0251618 | A1 | 10/2012 | Schrum et al. |
| 2012/0252117 | A1 | 10/2012 | Selden et al. |
| 2012/0258046 | A1 | 10/2012 | Mutzke |
| 2012/0276048 | A1 | 11/2012 | Panzara et al. |
| 2012/0282247 | A1 | 11/2012 | Schneewind et al. |
| 2012/0282249 | A1 | 11/2012 | Fox et al. |
| 2012/0295832 | A1 | 11/2012 | Constien et al. |
| 2012/0301955 | A1 | 11/2012 | Thomas et al. |
| 2012/0321719 | A1 | 12/2012 | McDonnell et al. |
| 2012/0322864 | A1 | 12/2012 | Rossi et al. |
| 2012/0322865 | A1 | 12/2012 | Rossi et al. |
| 2013/0012426 | A1 | 1/2013 | De Los Pinos |
| 2013/0012450 | A1 | 1/2013 | De Los Pinos |
| 2013/0012566 | A1 | 1/2013 | De Los Pinos |
| 2013/0017223 | A1 | 1/2013 | Hope et al. |
| 2013/0017265 | A1 | 1/2013 | Farokhzad et al. |
| 2013/0022538 | A1 | 1/2013 | Rossi et al. |
| 2013/0029418 | A1 | 1/2013 | Angel et al. |
| 2013/0059360 | A1 | 3/2013 | Bossard et al. |
| 2013/0064894 | A1 | 3/2013 | Martin et al. |
| 2013/0065942 | A1 | 3/2013 | Matar et al. |
| 2013/0071450 | A1 | 3/2013 | Copp-Howland |
| 2013/0072670 | A1 | 3/2013 | Srivastava et al. |
| 2013/0072709 | A1 | 3/2013 | McManus et al. |
| 2013/0084289 | A1 | 4/2013 | Curd et al. |
| 2013/0090287 | A1 | 4/2013 | Alessi et al. |
| 2013/0090372 | A1 | 4/2013 | Budzik et al. |
| 2013/0102034 | A1 | 4/2013 | Schrum |
| 2013/0102545 | A1 | 4/2013 | Gao et al. |
| 2013/0108629 | A1 | 5/2013 | Dumont et al. |
| 2013/0111615 | A1 | 5/2013 | Kariko et al. |
| 2013/0115192 | A1 | 5/2013 | Ali et al. |

(56) References Cited

U.S. PATENT DOCUMENTS

| | | | |
|---|---|---|---|
| 2013/0115196 | A1 | 5/2013 | Hantash et al. |
| 2013/0115247 | A1 | 5/2013 | De Los Pinos |
| 2013/0115272 | A1 | 5/2013 | De Fougerolles et al. |
| 2013/0115273 | A1 | 5/2013 | Yang et al. |
| 2013/0115274 | A1 | 5/2013 | Knopov et al. |
| 2013/0115293 | A1 | 5/2013 | Sabnis et al. |
| 2013/0116307 | A1 | 5/2013 | Heyes et al. |
| 2013/0116408 | A1 | 5/2013 | De Los Pinos |
| 2013/0121954 | A1 | 5/2013 | Wakefield et al. |
| 2013/0121988 | A1 | 5/2013 | Hoerr et al. |
| 2013/0122104 | A1 | 5/2013 | Yaworski et al. |
| 2013/0123338 | A1 | 5/2013 | Heyes et al. |
| 2013/0123351 | A1 | 5/2013 | Dewitt |
| 2013/0123481 | A1 | 5/2013 | De Fougerolles et al. |
| 2013/0129627 | A1 | 5/2013 | Delehanty et al. |
| 2013/0129726 | A1 | 5/2013 | Lee |
| 2013/0129785 | A1 | 5/2013 | Manoharan et al. |
| 2013/0129794 | A1 | 5/2013 | Kleiner et al. |
| 2013/0129830 | A1 | 5/2013 | Chen et al. |
| 2013/0130348 | A1 | 5/2013 | Gu et al. |
| 2013/0133483 | A1 | 5/2013 | Yang et al. |
| 2013/0136746 | A1 | 5/2013 | Schneewind et al. |
| 2013/0137644 | A1 | 5/2013 | Alluis et al. |
| 2013/0138032 | A1 | 5/2013 | Kim et al. |
| 2013/0142818 | A1 | 6/2013 | Baumhof et al. |
| 2013/0142868 | A1 | 6/2013 | Hoekman et al. |
| 2013/0142876 | A1 | 6/2013 | Howard et al. |
| 2013/0149318 | A1 | 6/2013 | Reynolds et al. |
| 2013/0149375 | A1 | 6/2013 | Geall |
| 2013/0149783 | A1 | 6/2013 | Yockman et al. |
| 2013/0150295 | A1 | 6/2013 | Jaworowicz |
| 2013/0150625 | A1 | 6/2013 | Budzik et al. |
| 2013/0150822 | A1 | 6/2013 | Ross |
| 2013/0156721 | A1 | 6/2013 | Cheng et al. |
| 2013/0156776 | A1 | 6/2013 | Chang et al. |
| 2013/0156845 | A1 | 6/2013 | Manoharan et al. |
| 2013/0156849 | A1 | 6/2013 | De Fougerolles et al. |
| 2013/0164219 | A1 | 6/2013 | Brinkmann et al. |
| 2013/0164343 | A1 | 6/2013 | Hanes et al. |
| 2013/0164348 | A1 | 6/2013 | Palasis et al. |
| 2013/0164400 | A1 | 6/2013 | Knopov et al. |
| 2013/0165499 | A1 | 6/2013 | Vaishnaw et al. |
| 2013/0165504 | A1 | 6/2013 | Bancel et al. |
| 2013/0165772 | A1 | 6/2013 | Traverso et al. |
| 2013/0171138 | A1 | 7/2013 | Peters et al. |
| 2013/0171175 | A1 | 7/2013 | Pierce et al. |
| 2013/0171183 | A1 | 7/2013 | Schneewind et al. |
| 2013/0171241 | A1 | 7/2013 | Geall |
| 2013/0171646 | A1 | 7/2013 | Park et al. |
| 2013/0172406 | A1 | 7/2013 | Zale et al. |
| 2013/0172600 | A1 | 7/2013 | Chang et al. |
| 2013/0177499 | A1 | 7/2013 | Brahmbhatt et al. |
| 2013/0177523 | A1 | 7/2013 | Ghandehari et al. |
| 2013/0177587 | A1 | 7/2013 | Robinson et al. |
| 2013/0177611 | A1 | 7/2013 | Kaplan et al. |
| 2013/0177633 | A1 | 7/2013 | Schutt et al. |
| 2013/0177634 | A1 | 7/2013 | Schutt et al. |
| 2013/0177635 | A1 | 7/2013 | Schutt et al. |
| 2013/0177636 | A1 | 7/2013 | Schutt et al. |
| 2013/0177637 | A1 | 7/2013 | Schutt et al. |
| 2013/0177638 | A1 | 7/2013 | Schutt et al. |
| 2013/0177639 | A1 | 7/2013 | Geall et al. |
| 2013/0177640 | A1 | 7/2013 | Geall et al. |
| 2013/0178541 | A1 | 7/2013 | Stanton et al. |
| 2013/0183244 | A1 | 7/2013 | Hanes et al. |
| 2013/0183355 | A1 | 7/2013 | Jain et al. |
| 2013/0183372 | A1 | 7/2013 | Schutt et al. |
| 2013/0183373 | A1 | 7/2013 | Schutt et al. |
| 2013/0183375 | A1 | 7/2013 | Schutt et al. |
| 2013/0183718 | A1 | 7/2013 | Rohayem |
| 2013/0184207 | A1 | 7/2013 | Fares et al. |
| 2013/0184443 | A1 | 7/2013 | Bentley et al. |
| 2013/0184453 | A1 | 7/2013 | Davis |
| 2013/0189295 | A1 | 7/2013 | Arico et al. |
| 2013/0189351 | A1 | 7/2013 | Geall |
| 2013/0189741 | A1 | 7/2013 | Meis et al. |
| 2013/0195759 | A1 | 8/2013 | Mirkin et al. |
| 2013/0195765 | A1 | 8/2013 | Gho et al. |
| 2013/0195846 | A1 | 8/2013 | Friess et al. |
| 2013/0195898 | A1 | 8/2013 | O'Hagan et al. |
| 2013/0195967 | A1 | 8/2013 | Guild et al. |
| 2013/0195968 | A1 | 8/2013 | Geall et al. |
| 2013/0195969 | A1 | 8/2013 | Geall et al. |
| 2013/0197068 | A1 | 8/2013 | Kariko et al. |
| 2013/0202595 | A1 | 8/2013 | Pierce et al. |
| 2013/0202645 | A1 | 8/2013 | Barner et al. |
| 2013/0202684 | A1 | 8/2013 | Geall et al. |
| 2013/0203115 | A1 | 8/2013 | Schrum et al. |
| 2013/0209454 | A1 | 8/2013 | Diskin et al. |
| 2013/0209456 | A1 | 8/2013 | Kano et al. |
| 2013/0236419 | A1 | 9/2013 | Schneewind et al. |
| 2013/0236500 | A1 | 9/2013 | Zale et al. |
| 2013/0236533 | A1 | 9/2013 | Von Andrian et al. |
| 2013/0236550 | A1 | 9/2013 | Ausborn et al. |
| 2013/0236556 | A1 | 9/2013 | Lai et al. |
| 2013/0236968 | A1 | 9/2013 | Manoharan et al. |
| 2013/0236974 | A1 | 9/2013 | De Fougerolles |
| 2013/0237592 | A1 | 9/2013 | De Fougerolles et al. |
| 2013/0237593 | A1 | 9/2013 | De Fougerolles et al. |
| 2013/0237594 | A1 | 9/2013 | De Fougerolles et al. |
| 2013/0243747 | A1 | 9/2013 | Fima et al. |
| 2013/0243827 | A1 | 9/2013 | Troiano et al. |
| 2013/0243848 | A1 | 9/2013 | Lobovkina et al. |
| 2013/0243867 | A1 | 9/2013 | Mohapatra et al. |
| 2013/0244278 | A1 | 9/2013 | De Fougerolles et al. |
| 2013/0244279 | A1 | 9/2013 | De Fougerolles et al. |
| 2013/0244282 | A1 | 9/2013 | Schrum et al. |
| 2013/0244972 | A1 | 9/2013 | Ben-Shalom et al. |
| 2013/0245091 | A1 | 9/2013 | Rozema et al. |
| 2013/0245103 | A1 | 9/2013 | De Fougerolles et al. |
| 2013/0245106 | A1 | 9/2013 | De Fougerolles et al. |
| 2013/0245107 | A1 | 9/2013 | De Fougerolles et al. |
| 2013/0251679 | A1 | 9/2013 | Pearlman et al. |
| 2013/0251766 | A1 | 9/2013 | Zale et al. |
| 2013/0251816 | A1 | 9/2013 | Zale et al. |
| 2013/0251817 | A1 | 9/2013 | Zale et al. |
| 2013/0252281 | A1 | 9/2013 | De Fougerolles et al. |
| 2013/0259923 | A1 | 10/2013 | Bancel et al. |
| 2013/0259924 | A1 | 10/2013 | Bancel et al. |
| 2013/0266553 | A1 | 10/2013 | Ballance et al. |
| 2013/0266611 | A1 | 10/2013 | Rabinovich et al. |
| 2013/0266617 | A1 | 10/2013 | Mirosevich et al. |
| 2013/0266640 | A1 | 10/2013 | De Fougerolles et al. |
| 2013/0272994 | A1 | 10/2013 | Fu et al. |
| 2013/0273039 | A1 | 10/2013 | Grillo-Lopez |
| 2013/0273047 | A1 | 10/2013 | Rivera et al. |
| 2013/0273081 | A1 | 10/2013 | Monaci et al. |
| 2013/0273104 | A1 | 10/2013 | Podda et al. |
| 2013/0273109 | A1 | 10/2013 | Settembre et al. |
| 2013/0273117 | A1 | 10/2013 | Podobinski et al. |
| 2013/0274194 | A1 | 10/2013 | Dumont et al. |
| 2013/0274504 | A1 | 10/2013 | Colletti et al. |
| 2013/0274523 | A1 | 10/2013 | Bawiec, III et al. |
| 2013/0280334 | A1 | 10/2013 | Karp et al. |
| 2013/0280339 | A1 | 10/2013 | Zale et al. |
| 2013/0281658 | A1 | 10/2013 | Rozema et al. |
| 2013/0281671 | A1 | 10/2013 | Peters et al. |
| 2013/0287832 | A1 | 10/2013 | O'Hagan et al. |
| 2013/0289093 | A1 | 10/2013 | Bhat et al. |
| 2013/0295183 | A1 | 11/2013 | Troiano et al. |
| 2013/0295191 | A1 | 11/2013 | Troiano et al. |
| 2013/0302432 | A1 | 11/2013 | Zale et al. |
| 2013/0302433 | A1 | 11/2013 | Troiano et al. |
| 2013/0315831 | A1 | 11/2013 | Shi et al. |
| 2013/0317079 | A1 | 11/2013 | Wakefield et al. |
| 2013/0323179 | A1 | 12/2013 | Popov et al. |
| 2013/0323310 | A1 | 12/2013 | Smyth et al. |
| 2013/0330401 | A1 | 12/2013 | Payne et al. |
| 2013/0338210 | A1 | 12/2013 | Manoharan et al. |
| 2013/0344091 | A1 | 12/2013 | Berger et al. |
| 2013/0344158 | A1 | 12/2013 | Zale et al. |
| 2014/0004593 | A1 | 1/2014 | Boldog et al. |
| 2014/0005379 | A1 | 1/2014 | Gu |
| 2014/0010861 | A1 | 1/2014 | Bancel et al. |

(56) References Cited

U.S. PATENT DOCUMENTS

2014/0017327 A1 1/2014 Cheng et al.
2014/0017329 A1 1/2014 Mousa
2014/0030292 A1 1/2014 Franti et al.
2014/0030351 A1 1/2014 Zale et al.
2014/0037573 A1 2/2014 Eliasof et al.
2014/0037660 A1 2/2014 Fotin-Mleczek et al.
2014/0037714 A1 2/2014 Quay et al.
2014/0039032 A1 2/2014 Kuboyama et al.
2014/0044772 A1 2/2014 MacLachlan et al.
2014/0044791 A1 2/2014 Basilion et al.
2014/0045913 A1 2/2014 Kuboyama et al.
2014/0045950 A1 2/2014 Lacko et al.
2014/0050775 A1 2/2014 Slobodkin et al.
2014/0056867 A1 2/2014 Lebowitz et al.
2014/0056970 A1 2/2014 Panzner et al.
2014/0057109 A1 2/2014 Menchen et al.
2014/0065172 A1 3/2014 Echeverri et al.
2014/0065204 A1 3/2014 Hayes et al.
2014/0065228 A1 3/2014 Yaworski et al.
2014/0066363 A1 3/2014 Bhunia et al.
2014/0073687 A1 3/2014 Chien et al.
2014/0073715 A1 3/2014 Fonnum et al.
2014/0073738 A1 3/2014 Fonnum et al.
2014/0079774 A1 3/2014 Brinker et al.
2014/0079776 A1 3/2014 Lippard et al.
2014/0080766 A1 3/2014 Pirie et al.
2014/0081012 A1 3/2014 Desimone et al.
2014/0093575 A1 4/2014 Hammond et al.
2014/0093579 A1 4/2014 Zale et al.
2014/0100178 A1 4/2014 Ansari et al.
2014/0105930 A1 4/2014 Springer
2014/0105964 A1 4/2014 Bancel et al.
2014/0105965 A1 4/2014 Bancel et al.
2014/0105966 A1 4/2014 Bancel et al.
2014/0106260 A1 4/2014 Cargnello et al.
2014/0107189 A1 4/2014 Bancel et al.
2014/0107227 A1 4/2014 Masters et al.
2014/0107229 A1 4/2014 Kormann et al.
2014/0107349 A1 4/2014 Bentley et al.
2014/0107594 A1 4/2014 Guo et al.
2014/0113137 A1 4/2014 Podobinski et al.
2014/0113959 A1 4/2014 Bancel et al.
2014/0113960 A1 4/2014 Bancel et al.
2014/0121263 A1 5/2014 Fitzgerald et al.
2014/0121393 A1 5/2014 Manoharan et al.
2014/0121587 A1 5/2014 Sallberg et al.
2014/0127227 A1 5/2014 Chang
2014/0127301 A1 5/2014 Alexis et al.
2014/0128269 A1 5/2014 Hinz et al.
2014/0128329 A1 5/2014 Gore et al.
2014/0134129 A1 5/2014 Thalhamer et al.
2014/0134201 A1 5/2014 Tureci et al.
2014/0134230 A1 5/2014 Frank et al.
2014/0135380 A1 5/2014 Hadwiger et al.
2014/0135381 A1 5/2014 Hadwiger et al.
2014/0141025 A1 5/2014 Kudirka et al.
2014/0141037 A1 5/2014 Swanson et al.
2014/0141067 A1 5/2014 Bancel et al.
2014/0141068 A1 5/2014 Bancel et al.
2014/0141070 A1 5/2014 Geall et al.
2014/0141089 A1 5/2014 Liang
2014/0141483 A1 5/2014 Bossard et al.
2014/0142165 A1 5/2014 Grayson et al.
2014/0142254 A1 5/2014 Fonnum et al.
2014/0147432 A1 5/2014 Bancel et al.
2014/0147454 A1 5/2014 Chakraborty et al.
2014/0148502 A1 5/2014 Bancel et al.
2014/0148503 A1 5/2014 Giangrande et al.
2014/0155472 A1 6/2014 Bancel et al.
2014/0155473 A1 6/2014 Bancel et al.
2014/0155474 A1 6/2014 Bancel et al.
2014/0155475 A1 6/2014 Bancel et al.
2014/0161873 A1 6/2014 Bancel et al.
2014/0162934 A1 6/2014 Constien et al.
2014/0162962 A1 6/2014 Constien et al.
2014/0170175 A1 6/2014 Constien et al.
2014/0171485 A1 6/2014 Bancel et al.
2014/0178429 A1 6/2014 Tsai
2014/0178438 A1 6/2014 Sahin et al.
2014/0179771 A1 6/2014 Bancel et al.
2014/0186432 A1 7/2014 Bancel et al.
2014/0193482 A1 7/2014 Bancel et al.
2014/0193484 A1 7/2014 Bertholet Girardin et al.
2014/0194494 A1 7/2014 Bancel et al.
2014/0199371 A1 7/2014 Bancel et al.
2014/0200261 A1 7/2014 Hoge et al.
2014/0200262 A1 7/2014 Bancel et al.
2014/0200263 A1 7/2014 Bancel et al.
2014/0200264 A1 7/2014 Bancel et al.
2014/0206752 A1 7/2014 Afeyan et al.
2014/0206753 A1 7/2014 Guild et al.
2014/0206755 A1 7/2014 Bancel et al.
2014/0206852 A1 7/2014 Hoge et al.
2014/0212498 A1 7/2014 Brito et al.
2014/0212504 A1 7/2014 Weers et al.
2014/0220083 A1 8/2014 Brito et al.
2014/0221465 A1 8/2014 Bancel et al.
2014/0227237 A1 8/2014 June et al.
2014/0227300 A1 8/2014 Chin et al.
2014/0227346 A1 8/2014 Geall et al.
2014/0242152 A1 8/2014 Geall et al.
2014/0243399 A1 8/2014 Schrum et al.
2014/0248312 A1 9/2014 Rappuoli et al.
2014/0248314 A1 9/2014 Swanson et al.
2014/0249208 A1 9/2014 Bancel et al.
2014/0255467 A1 9/2014 Bancel et al.
2014/0255468 A1 9/2014 Bancel et al.
2014/0255472 A1 9/2014 Geall et al.
2014/0271829 A1 9/2014 Lilja et al.
2014/0275227 A1 9/2014 Hoge et al.
2014/0275229 A1 9/2014 Bancel et al.
2014/0288160 A1 9/2014 Guild et al.
2014/0294938 A1 10/2014 Guild et al.
2014/0294939 A1 10/2014 Guild et al.
2014/0294940 A1 10/2014 Guild et al.
2014/0308746 A1 10/2014 Rossi et al.
2014/0309277 A1 10/2014 Baryza et al.
2014/0315988 A1 10/2014 Dahl et al.
2014/0328825 A1 11/2014 Meis et al.
2014/0341995 A1 11/2014 Rudolph et al.
2014/0343129 A1 11/2014 De Fougerolles et al.
2014/0363876 A1 12/2014 Jendrisak et al.
2014/0370545 A1 12/2014 Mauro et al.
2014/0371302 A1 12/2014 Afeyan et al.
2014/0378538 A1 12/2014 Bancel
2015/0004217 A1 1/2015 Guild et al.
2015/0005372 A1 1/2015 Hoge et al.
2015/0017206 A1 1/2015 Rueckl et al.
2015/0017211 A1 1/2015 De Fougerolles et al.
2015/0030576 A1 1/2015 Bancel
2015/0038558 A1 2/2015 Kariko et al.
2015/0044277 A1 2/2015 Bancel et al.
2015/0050354 A1 2/2015 Bouchon et al.
2015/0051268 A1 2/2015 Bancel et al.
2015/0056253 A1 2/2015 Bancel et al.
2015/0064235 A1 3/2015 Bancel et al.
2015/0064236 A1 3/2015 Bancel et al.
2015/0064725 A1 3/2015 Schrum et al.
2015/0086614 A1 3/2015 Bancel et al.
2015/0111248 A1 4/2015 Bancel et al.
2015/0141499 A1 5/2015 Bancel et al.

FOREIGN PATENT DOCUMENTS

CA 2795695 A1 10/2011
EP 0194809 A1 9/1986
EP 0204401 A1 12/1986
EP 0366400 A2 5/1990
EP 0427073 A2 5/1991
EP 0427074 A2 5/1991
EP 0726319 A2 8/1996
EP 0735144 A1 10/1996
EP 0737750 A2 10/1996
EP 0771873 A2 5/1997

(56) References Cited

FOREIGN PATENT DOCUMENTS

| | | | |
|---|---|---|---|
| EP | 0839912 | A1 | 5/1998 |
| EP | 0969862 | A2 | 1/2000 |
| EP | 1026253 | A2 | 8/2000 |
| EP | 1083232 | A1 | 3/2001 |
| EP | 1224943 | A1 | 7/2002 |
| EP | 1361277 | A1 | 11/2003 |
| EP | 1393745 | A1 | 3/2004 |
| EP | 1083232 | B1 | 2/2005 |
| EP | 1301614 | B1 | 11/2006 |
| EP | 1873180 | A1 | 1/2008 |
| EP | 1905844 | A2 | 4/2008 |
| EP | 1964922 | A1 | 9/2008 |
| EP | 2072618 | A1 | 6/2009 |
| EP | 1056873 | B1 | 3/2010 |
| EP | 2191840 | A1 | 6/2010 |
| EP | 2092064 | B1 | 9/2010 |
| EP | 2246422 | A1 | 11/2010 |
| EP | 1619254 | B1 | 12/2010 |
| EP | 2292771 | A2 | 3/2011 |
| EP | 2377938 | A1 | 10/2011 |
| EP | 2468290 | A1 | 6/2012 |
| EP | 2476430 | A1 | 7/2012 |
| EP | 2484770 | A1 | 8/2012 |
| EP | 1907590 | B1 | 9/2012 |
| EP | 2535419 | A2 | 12/2012 |
| EP | 2188379 | B1 | 1/2013 |
| EP | 2548960 | A1 | 1/2013 |
| EP | 2620161 | A1 | 7/2013 |
| EP | 2073848 | B1 | 8/2013 |
| EP | 2623121 | A1 | 8/2013 |
| EP | 1404860 | B1 | 11/2013 |
| EP | 2695608 | A2 | 2/2014 |
| EP | 2160464 | B1 | 5/2014 |
| EP | 2607379 | B1 | 5/2014 |
| EP | 2732825 | A1 | 5/2014 |
| JP | 2002508299 | A | 3/2002 |
| JP | 2006500926 | A | 1/2006 |
| JP | 2009509551 | A | 3/2009 |
| MD | WO-2012177760 | A1 | 12/2012 |
| WO | WO-8906700 | A1 | 7/1989 |
| WO | WO-8907947 | A1 | 9/1989 |
| WO | WO-8909622 | A1 | 10/1989 |
| WO | WO-9011092 | A1 | 10/1990 |
| WO | WO-9116024 | A1 | 10/1991 |
| WO | WO-9201813 | A1 | 2/1992 |
| WO | WO-9216553 | A1 | 10/1992 |
| WO | WO-9309236 | A1 | 5/1993 |
| WO | WO-9314778 | A1 | 8/1993 |
| WO | WO-9512665 | A1 | 5/1995 |
| WO | WO-9524485 | A2 | 9/1995 |
| WO | WO-9526204 | A1 | 10/1995 |
| WO | WO-9529697 | A1 | 11/1995 |
| WO | WO-9533835 | A1 | 12/1995 |
| WO | WO-9535375 | A1 | 12/1995 |
| WO | WO-9617086 | A1 | 6/1996 |
| WO | WO-9711085 | A1 | 3/1997 |
| WO | WO-9712519 | A1 | 4/1997 |
| WO | WO-9730064 | A1 | 8/1997 |
| WO | WO-9741210 | A1 | 11/1997 |
| WO | WO-9746680 | A1 | 12/1997 |
| WO | WO-9748370 | A2 | 12/1997 |
| WO | WO-9800547 | A1 | 1/1998 |
| WO | WO-9812207 | A1 | 3/1998 |
| WO | WO-9819710 | A2 | 5/1998 |
| WO | WO-9834640 | A2 | 8/1998 |
| WO | WO-9847913 | A2 | 10/1998 |
| WO | WO-9855495 | A2 | 12/1998 |
| WO | WO-9906073 | A1 | 2/1999 |
| WO | WO-9914346 | A2 | 3/1999 |
| WO | WO-9920766 | A2 | 4/1999 |
| WO | WO-9920774 | A2 | 4/1999 |
| WO | WO-9933982 | A2 | 7/1999 |
| WO | WO-9942618 | A1 | 8/1999 |
| WO | WO-9943835 | A2 | 9/1999 |
| WO | WO-9952503 | A2 | 10/1999 |
| WO | WO-9954457 | A1 | 10/1999 |
| WO | WO-0026226 | A1 | 5/2000 |
| WO | WO-0027340 | A2 | 5/2000 |
| WO | WO-0029561 | A2 | 5/2000 |
| WO | WO-0039327 | A1 | 7/2000 |
| WO | WO-0050586 | A2 | 8/2000 |
| WO | WO-0075304 | A1 | 12/2000 |
| WO | WO-0075356 | A1 | 12/2000 |
| WO | WO-0100650 | A1 | 1/2001 |
| WO | WO-0104313 | A1 | 1/2001 |
| WO | WO-0114424 | A2 | 3/2001 |
| WO | WO-0121810 | A1 | 3/2001 |
| WO | WO-0155306 | A2 | 8/2001 |
| WO | WO-0178779 | A2 | 10/2001 |
| WO | WO-0192523 | A2 | 12/2001 |
| WO | WO-0193902 | A2 | 12/2001 |
| WO | WO-0208435 | A1 | 1/2002 |
| WO | WO-0224873 | A1 | 3/2002 |
| WO | WO-0246477 | A2 | 6/2002 |
| WO | WO-02064799 | A2 | 8/2002 |
| WO | WO-02065093 | A2 | 8/2002 |
| WO | WO-02102839 | A2 | 12/2002 |
| WO | WO-03002604 | A2 | 1/2003 |
| WO | WO-03018798 | A2 | 3/2003 |
| WO | WO-03028656 | A2 | 4/2003 |
| WO | WO-03029401 | A2 | 4/2003 |
| WO | WO-03046578 | A2 | 6/2003 |
| WO | WO-03050258 | A2 | 6/2003 |
| WO | WO-03051923 | A2 | 6/2003 |
| WO | WO-03059194 | A2 | 7/2003 |
| WO | WO-03059381 | A2 | 7/2003 |
| WO | WO-03066649 | A1 | 8/2003 |
| WO | WO-03086280 | A2 | 10/2003 |
| WO | WO-03087815 | A2 | 10/2003 |
| WO | WO-03101401 | A2 | 12/2003 |
| WO | WO-2004005544 | A2 | 1/2004 |
| WO | WO-2004010106 | A2 | 1/2004 |
| WO | WO-2004035607 | A2 | 4/2004 |
| WO | WO-2004037972 | A2 | 5/2004 |
| WO | WO-2004058159 | A2 | 7/2004 |
| WO | WO-2004065561 | A2 | 8/2004 |
| WO | WO-2004067728 | A2 | 8/2004 |
| WO | WO-2004082703 | A1 | 9/2004 |
| WO | WO-2004085474 | A2 | 10/2004 |
| WO | WO-2004087868 | A2 | 10/2004 |
| WO | WO-2004092329 | A2 | 10/2004 |
| WO | WO-2005005622 | A2 | 1/2005 |
| WO | WO-2005009346 | A2 | 2/2005 |
| WO | WO-2005017107 | A2 | 2/2005 |
| WO | WO-2005040416 | A1 | 5/2005 |
| WO | WO-2005044859 | A2 | 5/2005 |
| WO | WO-2005047536 | A2 | 5/2005 |
| WO | WO-2005062967 | A2 | 7/2005 |
| WO | WO-2005098433 | A2 | 10/2005 |
| WO | WO-2005103081 | A2 | 11/2005 |
| WO | WO-2005117557 | A2 | 12/2005 |
| WO | WO-2005118857 | A2 | 12/2005 |
| WO | WO-2006008154 | A1 | 1/2006 |
| WO | WO-2006013107 | A1 | 2/2006 |
| WO | WO-2006022712 | A1 | 3/2006 |
| WO | WO-2006044456 | A1 | 4/2006 |
| WO | WO-2006044503 | A2 | 4/2006 |
| WO | WO-2006044505 | A2 | 4/2006 |
| WO | WO-2006044682 | A1 | 4/2006 |
| WO | WO-2006046978 | A2 | 5/2006 |
| WO | WO-2006058088 | A2 | 6/2006 |
| WO | WO-2006063249 | A2 | 6/2006 |
| WO | WO-2006065479 | A2 | 6/2006 |
| WO | WO-2006065480 | A2 | 6/2006 |
| WO | WO-2006071903 | A2 | 7/2006 |
| WO | WO-2006095259 | A2 | 9/2006 |
| WO | WO-2006110581 | A2 | 10/2006 |
| WO | WO-2006110585 | A2 | 10/2006 |
| WO | WO-2006110599 | A2 | 10/2006 |
| WO | WO-2007005645 | A2 | 1/2007 |
| WO | WO-2007024323 | A2 | 3/2007 |
| WO | WO-2007024708 | A2 | 3/2007 |
| WO | WO-2007036366 | A2 | 4/2007 |
| WO | WO-2007041774 | A1 | 4/2007 |

(56) References Cited

FOREIGN PATENT DOCUMENTS

| | | | |
|---|---|---|---|
| WO | WO-2007059782 | A1 | 5/2007 |
| WO | WO-2007062495 | A1 | 6/2007 |
| WO | WO-2007064952 | A2 | 6/2007 |
| WO | WO-2007067968 | A2 | 6/2007 |
| WO | WO-2007069068 | A2 | 6/2007 |
| WO | WO-2007095976 | A2 | 8/2007 |
| WO | WO-2007100699 | A2 | 9/2007 |
| WO | WO-2007100789 | A2 | 9/2007 |
| WO | WO-2007104537 | A2 | 9/2007 |
| WO | WO-2008003319 | A1 | 1/2008 |
| WO | WO-2008011519 | A2 | 1/2008 |
| WO | WO-2008014979 | A2 | 2/2008 |
| WO | WO-2008019371 | A1 | 2/2008 |
| WO | WO-2008022046 | A2 | 2/2008 |
| WO | WO-2008042973 | A2 | 4/2008 |
| WO | WO-2008051245 | A2 | 5/2008 |
| WO | WO-2008052770 | A2 | 5/2008 |
| WO | WO-2008068631 | A2 | 6/2008 |
| WO | WO-2008078180 | A2 | 7/2008 |
| WO | WO-2008083949 | A2 | 7/2008 |
| WO | WO-2008091799 | A2 | 7/2008 |
| WO | WO-2008096370 | A2 | 8/2008 |
| WO | WO-2008107388 | A1 | 9/2008 |
| WO | WO-2008115504 | A2 | 9/2008 |
| WO | WO-2008134724 | A2 | 11/2008 |
| WO | WO-2008140615 | A2 | 11/2008 |
| WO | WO-2008143878 | A1 | 11/2008 |
| WO | WO-2008144365 | A2 | 11/2008 |
| WO | WO-2008151049 | A2 | 12/2008 |
| WO | WO-2008151058 | A2 | 12/2008 |
| WO | WO-2008153705 | A2 | 12/2008 |
| WO | WO-2008157688 | A2 | 12/2008 |
| WO | WO-2009006438 | A2 | 1/2009 |
| WO | WO-2009015071 | A1 | 1/2009 |
| WO | WO-2009024599 | A1 | 2/2009 |
| WO | WO-2009030254 | A1 | 3/2009 |
| WO | WO-2009030481 | A1 | 3/2009 |
| WO | WO-2009042971 | A2 | 4/2009 |
| WO | WO-2009046738 | A1 | 4/2009 |
| WO | WO-2009046739 | A1 | 4/2009 |
| WO | WO-2009046974 | A2 | 4/2009 |
| WO | WO-2009046975 | A1 | 4/2009 |
| WO | WO-2009068649 | A2 | 6/2009 |
| WO | WO-2009077134 | A2 | 6/2009 |
| WO | WO-2009095226 | A2 | 8/2009 |
| WO | WO-2009101407 | A2 | 8/2009 |
| WO | WO-2009113083 | A1 | 9/2009 |
| WO | WO-2009120927 | A2 | 10/2009 |
| WO | WO-2009127060 | A1 | 10/2009 |
| WO | WO-2009127230 | A1 | 10/2009 |
| WO | WO-2009147519 | A1 | 12/2009 |
| WO | WO-2009149253 | A2 | 12/2009 |
| WO | WO-2010009065 | A2 | 1/2010 |
| WO | WO-2010009277 | A2 | 1/2010 |
| WO | WO-2010027903 | A2 | 3/2010 |
| WO | WO-2010033906 | A2 | 3/2010 |
| WO | WO-2010037408 | A1 | 4/2010 |
| WO | WO-2010037539 | A1 | 4/2010 |
| WO | WO-2010042490 | A1 | 4/2010 |
| WO | WO-2010042877 | A1 | 4/2010 |
| WO | WO-2010054406 | A1 | 5/2010 |
| WO | WO-2010061996 | A1 | 6/2010 |
| WO | WO-2010068918 | A2 | 6/2010 |
| WO | WO-2010084371 | A1 | 7/2010 |
| WO | WO-2010088537 | A2 | 8/2010 |
| WO | WO-2010088927 | A1 | 8/2010 |
| WO | WO-2010098861 | A1 | 9/2010 |
| WO | WO-2010111290 | A1 | 9/2010 |
| WO | WO-2010120266 | A1 | 10/2010 |
| WO | WO-2010129709 | A1 | 11/2010 |
| WO | WO-2010141135 | A2 | 12/2010 |
| WO | WO-2010144740 | A1 | 12/2010 |
| WO | WO-2011005341 | A2 | 1/2011 |
| WO | WO-2011005799 | A2 | 1/2011 |
| WO | WO-2011025566 | A1 | 3/2011 |
| WO | WO-2011026641 | A1 | 3/2011 |
| WO | WO-2011032633 | A1 | 3/2011 |
| WO | WO-2011062965 | A2 | 5/2011 |
| WO | WO-2011068810 | A1 | 6/2011 |
| WO | WO-2011069164 | A2 | 6/2011 |
| WO | WO-2011069528 | A1 | 6/2011 |
| WO | WO-2011069529 | A1 | 6/2011 |
| WO | WO-2011069586 | A1 | 6/2011 |
| WO | WO-2011069587 | A1 | 6/2011 |
| WO | WO-2011071931 | A2 | 6/2011 |
| WO | WO-2011071936 | A2 | 6/2011 |
| WO | WO-2011076807 | A2 | 6/2011 |
| WO | WO-2011088309 | A1 | 7/2011 |
| WO | WO-2011120053 | A1 | 9/2011 |
| WO | WO-2011127032 | A1 | 10/2011 |
| WO | WO-2011127255 | A1 | 10/2011 |
| WO | WO-2011127933 | A1 | 10/2011 |
| WO | WO-2011128444 | A2 | 10/2011 |
| WO | WO-2011130624 | A2 | 10/2011 |
| WO | WO-2011133868 | A2 | 10/2011 |
| WO | WO-2011137206 | A1 | 11/2011 |
| WO | WO-2011144358 | A1 | 11/2011 |
| WO | WO-2011161653 | A1 | 12/2011 |
| WO | WO-2012003474 | A2 | 1/2012 |
| WO | WO-2012006359 | A1 | 1/2012 |
| WO | WO-2012006369 | A2 | 1/2012 |
| WO | WO-2012006372 | A1 | 1/2012 |
| WO | WO-2012006376 | A2 | 1/2012 |
| WO | WO-2012006377 | A2 | 1/2012 |
| WO | WO-2012006378 | A1 | 1/2012 |
| WO | WO-2012006380 | A2 | 1/2012 |
| WO | WO-2012010855 | A1 | 1/2012 |
| WO | WO-2012013326 | A1 | 2/2012 |
| WO | WO-2012019168 | A2 | 2/2012 |
| WO | WO-2012019630 | A1 | 2/2012 |
| WO | WO-2012019780 | A1 | 2/2012 |
| WO | WO-2012023044 | A1 | 2/2012 |
| WO | WO-2012024526 | A2 | 2/2012 |
| WO | WO-2012030683 | A2 | 3/2012 |
| WO | WO-2012030901 | A1 | 3/2012 |
| WO | WO-2012030904 | A2 | 3/2012 |
| WO | WO-2012031043 | A1 | 3/2012 |
| WO | WO-2012031046 | A2 | 3/2012 |
| WO | WO-2012034067 | A1 | 3/2012 |
| WO | WO-2012034077 | A2 | 3/2012 |
| WO | WO-2012045075 | A1 | 4/2012 |
| WO | WO-2012045082 | A2 | 4/2012 |
| WO | WO-2012050975 | A2 | 4/2012 |
| WO | WO-2012064429 | A2 | 5/2012 |
| WO | WO-2012065164 | A2 | 5/2012 |
| WO | WO-2012068295 | A1 | 5/2012 |
| WO | WO-2012068360 | A1 | 5/2012 |
| WO | WO-2012068470 | A2 | 5/2012 |
| WO | WO-2012072269 | A1 | 6/2012 |
| WO | WO-2012075040 | A2 | 6/2012 |
| WO | WO-2012088381 | A2 | 6/2012 |
| WO | WO-2012089225 | A1 | 7/2012 |
| WO | WO-2012089338 | A1 | 7/2012 |
| WO | WO-2012094304 | A1 | 7/2012 |
| WO | WO-2012094574 | A2 | 7/2012 |
| WO | WO-2012099755 | A1 | 7/2012 |
| WO | WO-2012099805 | A2 | 7/2012 |
| WO | WO-2012103985 | A2 | 8/2012 |
| WO | WO-2012110636 | A2 | 8/2012 |
| WO | WO-2012112582 | A2 | 8/2012 |
| WO | WO-2012113413 | A1 | 8/2012 |
| WO | WO-2012113513 | A1 | 8/2012 |
| WO | WO-2012116714 | A1 | 9/2012 |
| WO | WO-2012116715 | A1 | 9/2012 |
| WO | WO-2012116810 | A1 | 9/2012 |
| WO | WO-2012116811 | A1 | 9/2012 |
| WO | WO-2012117377 | A1 | 9/2012 |
| WO | WO-2012122318 | A2 | 9/2012 |
| WO | WO-2012125680 | A1 | 9/2012 |
| WO | WO-2012125812 | A1 | 9/2012 |
| WO | WO-2012125987 | A2 | 9/2012 |
| WO | WO-2012129483 | A1 | 9/2012 |
| WO | WO-2012131594 | A1 | 10/2012 |
| WO | WO-2012135025 | A2 | 10/2012 |

(56) References Cited

FOREIGN PATENT DOCUMENTS

WO WO-2012135805 A2 10/2012
WO WO-2012138453 A1 10/2012
WO WO-2012138530 A1 10/2012
WO WO-2012142240 A1 10/2012
WO WO-2012143407 A1 10/2012
WO WO-2012149045 A2 11/2012
WO WO-2012149246 A1 11/2012
WO WO-2012149252 A2 11/2012
WO WO-2012149255 A2 11/2012
WO WO-2012149259 A1 11/2012
WO WO-2012149265 A2 11/2012
WO WO-2012149282 A2 11/2012
WO WO-2012149301 A2 11/2012
WO WO-2012149376 A2 11/2012
WO WO-2012149393 A2 11/2012
WO WO-2012149536 A1 11/2012
WO WO-2012151234 A2 11/2012
WO WO-2012152910 A1 11/2012
WO WO-2012153297 A1 11/2012
WO WO-2012153338 A2 11/2012
WO WO-2012154202 A1 11/2012
WO WO-2012158613 A1 11/2012
WO WO-2012160177 A1 11/2012
WO WO-2012162174 A1 11/2012
WO WO-2012166241 A1 12/2012
WO WO-2012166923 A2 12/2012
WO WO-2012168259 A1 12/2012
WO WO-2012168491 A1 12/2012
WO WO-2012170607 A2 12/2012
WO WO-2012170889 A1 12/2012
WO WO-2012170930 A1 12/2012
WO WO-2012172495 A1 12/2012
WO WO-2012172521 A1 12/2012
WO WO-2013003475 A1 1/2013
WO WO-2013003887 A1 1/2013
WO WO-2013006437 A1 1/2013
WO WO-2013006824 A2 1/2013
WO WO-2013006825 A1 1/2013
WO WO-2013006834 A1 1/2013
WO WO-2013006837 A1 1/2013
WO WO-2013006838 A1 1/2013
WO WO-2013006842 A2 1/2013
WO WO-2013009717 A1 1/2013
WO WO-2013009736 A2 1/2013
WO WO-2013011325 A2 1/2013
WO WO-2013012476 A2 1/2013
WO WO-2013016460 A1 1/2013
WO WO-2013019669 A2 2/2013
WO WO 2013025834 A2 2/2013
WO WO-2013030778 A2 3/2013
WO WO-2013032829 A1 3/2013
WO WO-2013033438 A2 3/2013
WO WO-2013033563 A1 3/2013
WO WO-2013033620 A1 3/2013
WO WO-2013038375 A2 3/2013
WO WO 2013039857 A1 3/2013
WO WO-2013039861 A2 3/2013
WO WO-2013044219 A1 3/2013
WO WO-2013045505 A1 4/2013
WO WO-2013049234 A2 4/2013
WO WO-2013049247 A1 4/2013
WO WO-2013049328 A1 4/2013
WO WO-2013052167 A2 4/2013
WO WO-2013052523 A1 4/2013
WO WO-2013054307 A2 4/2013
WO WO-2013055331 A1 4/2013
WO WO-2013055905 A1 4/2013
WO WO-2013055971 A1 4/2013
WO WO-2013056132 A2 4/2013
WO WO-2013057687 A2 4/2013
WO WO-2013057715 A1 4/2013
WO WO-2013059496 A1 4/2013
WO WO-2013059509 A1 4/2013
WO WO-2013059922 A1 5/2013
WO WO-2013061208 A1 5/2013
WO WO-2013062140 A1 5/2013
WO WO-2013063468 A1 5/2013
WO WO-2013063530 A2 5/2013
WO WO-2013064911 A2 5/2013
WO WO-2013066274 A1 5/2013
WO WO-2013066427 A1 5/2013
WO WO-2013066866 A1 5/2013
WO WO-2013066903 A1 5/2013
WO WO-2013067355 A1 5/2013
WO WO-2013067530 A2 5/2013
WO WO-2013067537 A1 5/2013
WO WO-2013068413 A1 5/2013
WO WO-2013068431 A1 5/2013
WO WO-2013068432 A1 5/2013
WO WO-2013068847 A2 5/2013
WO WO-2013070653 A1 5/2013
WO WO-2013070872 A1 5/2013
WO WO-2013071047 A1 5/2013
WO WO-2013072392 A1 5/2013
WO WO-2013072929 A2 5/2013
WO WO-2013074696 A1 5/2013
WO WO-2013075068 A1 5/2013
WO WO-2013077907 A1 5/2013
WO WO-2013078199 A2 5/2013
WO WO-2013079604 A1 6/2013
WO WO-2013082111 A2 6/2013
WO WO-2013082418 A1 6/2013
WO WO-2013082427 A1 6/2013
WO WO-2013082470 A1 6/2013
WO WO-2013082529 A1 6/2013
WO WO-2013082590 A1 6/2013
WO WO-2013084000 A2 6/2013
WO WO-2013085951 A1 6/2013
WO WO-2013086008 A1 6/2013
WO WO-2013086322 A1 6/2013
WO WO-2013086354 A1 6/2013
WO WO-2013086373 A1 6/2013
WO WO-2013086486 A1 6/2013
WO WO-2013086502 A1 6/2013
WO WO-2013086505 A1 6/2013
WO WO-2013086526 A1 6/2013
WO WO-2013087083 A1 6/2013
WO WO-2013087791 A1 6/2013
WO WO-2013087911 A1 6/2013
WO WO-2013087912 A1 6/2013
WO WO-2013088250 A1 6/2013
WO WO-2013090294 A1 6/2013
WO WO-2013090601 A2 6/2013
WO WO-2013090648 A1 6/2013
WO WO-2013090841 A2 6/2013
WO WO-2013090861 A1 6/2013
WO WO-2013090897 A1 6/2013
WO WO-2013091001 A1 6/2013
WO WO-2013093648 A2 6/2013
WO WO-2013096626 A1 6/2013
WO WO-2013096812 A1 6/2013
WO WO-2013098589 A1 7/2013
WO WO-2013100869 A2 7/2013
WO WO-2013103842 A1 7/2013
WO WO-2013112778 A1 8/2013
WO WO-2013112780 A1 8/2013
WO WO-2013113326 A1 8/2013
WO WO-2013113501 A1 8/2013
WO WO-2013113502 A1 8/2013
WO WO-2013113736 A1 8/2013
WO WO-2013126776 A1 8/2013
WO WO-2013128027 A1 9/2013
WO WO-2013129935 A1 9/2013
WO WO-2013129936 A1 9/2013
WO WO-2013130161 A1 9/2013
WO WO-2013130535 A1 9/2013
WO WO-2013134349 A1 9/2013
WO WO-2013135359 A1 9/2013
WO WO-2013136234 A1 9/2013
WO WO-2013138343 A1 9/2013
WO WO-2013138346 A1 9/2013
WO WO-2013142349 A1 9/2013
WO WO-2013143555 A1 10/2013
WO WO-2013143683 A1 10/2013

(56) References Cited

FOREIGN PATENT DOCUMENTS

WO WO-2013143698 A1 10/2013
WO WO-2013143699 A1 10/2013
WO WO-2013143700 A2 10/2013
WO WO-2013148186 A1 10/2013
WO WO-2013148541 A1 10/2013
WO WO-2013149141 A1 10/2013
WO WO-2013151650 A1 10/2013
WO WO-2013151663 A1 10/2013
WO WO-2013151664 A1 10/2013
WO WO-2013151665 A2 10/2013
WO WO-2013151666 A2 10/2013
WO WO-2013151667 A1 10/2013
WO WO-2013151668 A2 10/2013
WO WO-2013151669 A1 10/2013
WO WO-2013151670 A2 10/2013
WO WO-2013151671 A1 10/2013
WO WO-2013151672 A2 10/2013
WO WO-2013151736 A2 10/2013
WO WO-2013151771 A1 10/2013
WO WO-2013152351 A2 10/2013
WO WO-2013153550 A2 10/2013
WO WO-2013154766 A1 10/2013
WO WO-2013154774 A1 10/2013
WO WO-2013155487 A1 10/2013
WO WO-2013155493 A1 10/2013
WO WO-2013155513 A1 10/2013
WO WO-2013158127 A1 10/2013
WO WO-2013158141 A1 10/2013
WO WO-2013158579 A1 10/2013
WO WO-2013166385 A1 11/2013
WO WO-2013166498 A1 11/2013
WO WO-2013173582 A1 11/2013
WO WO-2013173657 A1 11/2013
WO WO-2013173693 A1 11/2013
WO WO-2013174409 A1 11/2013
WO WO-2013177421 A2 11/2013
WO WO-2013182683 A1 12/2013
WO WO-2013184945 A1 12/2013
WO WO-2013185069 A1 12/2013
WO WO-2013188979 A1 12/2013
WO WO-2014004436 A2 1/2014
WO WO-2014012479 A1 1/2014
WO WO-2014012994 A1 1/2014
WO WO-2014012996 A1 1/2014
WO WO-2014014613 A2 1/2014
WO WO-2014014890 A1 1/2014
WO WO-2014015334 A1 1/2014
WO WO-2014015422 A1 1/2014
WO WO-2014016439 A1 1/2014
WO WO-2014018675 A1 1/2014
WO WO-2014024193 A1 2/2014
WO WO-2014025312 A1 2/2014
WO WO-2014025795 A1 2/2014
WO WO-2014025890 A1 2/2014
WO WO-2014026044 A2 2/2014
WO WO-2014026284 A1 2/2014
WO WO-2014027006 A1 2/2014
WO WO-2014028209 A1 2/2014
WO WO-2014028429 A2 2/2014
WO WO-2014028487 A1 2/2014
WO WO-2014028763 A1 2/2014
WO WO-2014039185 A1 3/2014
WO WO-2014042920 A1 3/2014
WO WO-2014043618 A1 3/2014
WO WO-2014047649 A1 3/2014
WO WO-2014052634 A1 4/2014
WO WO-2014053622 A1 4/2014
WO WO-2014053624 A1 4/2014
WO WO-2014053628 A1 4/2014
WO WO-2014053629 A1 4/2014
WO WO-2014053634 A1 4/2014
WO WO-2014053654 A1 4/2014
WO WO-2014053879 A1 4/2014
WO WO-2014053880 A1 4/2014
WO WO-2014053881 A1 4/2014
WO WO-2014053882 A1 4/2014
WO WO-2014054026 A1 4/2014
WO WO-2014059022 A1 4/2014
WO WO-2014062697 A2 4/2014
WO WO-2014063059 A1 4/2014
WO WO-2014064258 A1 5/2014
WO WO-2014064534 A2 5/2014
WO WO-2014064543 A1 5/2014
WO WO-2014064687 A1 5/2014
WO WO-2014066811 A1 5/2014
WO WO-2014066898 A1 5/2014
WO WO-2014066912 A1 5/2014
WO WO-2014067551 A1 5/2014
WO WO-2014068542 A1 5/2014
WO WO-2014071072 A2 5/2014
WO WO-2014071219 A1 5/2014
WO WO-2014071963 A1 5/2014
WO WO-2014072061 A1 5/2014
WO WO-2014072468 A1 5/2014
WO WO-2014072481 A1 5/2014
WO WO-2014072747 A1 5/2014
WO WO-2014072997 A1 5/2014
WO WO-2014072999 A1 5/2014
WO WO-2014074218 A1 5/2014
WO WO-2014074289 A1 5/2014
WO WO-2014074299 A1 5/2014
WO WO-2014074597 A1 5/2014
WO WO-2014074823 A1 5/2014
WO WO-2014074905 A1 5/2014
WO WO-2014074912 A1 5/2014
WO WO-2014075047 A2 5/2014
WO WO-2014076709 A1 5/2014
WO WO-2014078399 A1 5/2014
WO WO-2014078636 A1 5/2014
WO WO-2014081299 A1 5/2014
WO WO-2014081300 A1 5/2014
WO WO-2014081303 A1 5/2014
WO WO-2014081507 A1 5/2014
WO WO-2014081849 A1 5/2014
WO WO-2014093574 A1 6/2014
WO WO-2014093924 A1 6/2014
WO WO-201414476 A1 9/2014
WO WO-2014144039 A1 9/2014
WO WO-2014144711 A1 9/2014
WO WO-2014152027 A1 9/2014
WO WO-2014152030 A1 9/2014
WO WO-2014152031 A1 9/2014
WO WO-2014152211 A1 9/2014
WO WO-2014152540 A1 9/2014
WO WO-2014158795 A1 10/2014
WO WO-2014159813 A1 10/2014
WO WO-2014164253 A1 10/2014
WO WO-2015006747 A2 1/2015
WO WO-2015034925 A1 3/2015
WO WO-2015034928 A1 3/2015
WO WO-2015038892 A1 3/2015
WO WO-2015048744 A2 4/2015
WO WO-2015051214 A1 4/2015
WO WO-2015058069 A1 4/2015
WO WO-2015105926 A1 7/2015

OTHER PUBLICATIONS

Abciximab (ReoPro)FDA Description, Jan. 4, 1997, No Volume number, pp. 1-17.

Abramova, T., "Frontiers and Approaches to Chemical Synthesis of Oligodeoxyribonucleotides," Molecules 18(1):1063-1075, MDPI, Switzerland (2013).

Abuchowski, A., et al., "Immunosuppressive Properties and Circulating Life of Achromobacter Glutaminase-Asparaginase Covalently Attached to Polyethylene Glycol in Man," Cancer Treatment Reports 65(11-12):1077-1081, U.S. National Cancer Institute, United States (1981).

Abuchowski, A., et al., "Reduction of Plasma Urate Levels in the Cockerel with Polyethylene Glycol-Uricase," The Journal of Pharmacology and Experimental Therapeutics 219(2):352-354, American Society for Pharmacology and Experimental Therapeutics, United States (1981).

(56) References Cited

OTHER PUBLICATIONS

Adcetris, brentuximab vedotin, Product Label, 2011,No Volume, pp. 1-15.
Adis R&D Profile, Belimumab, Drugs R D, 2010; vol. 10 , No. 1, pp. 55-65.
Aduri, R., et al., "Amber Force Field Parameters for the Naturally Occurring Modified Nucleosides in RNA," Journal of Chemical Theory and Computation 3(4):1464-1475, American Chemical Society, United States (2007).
Agadjanyan, M.G., et al., "Prototype Alzheimer's Disease Vaccine Using the Immunodominant B Cell Epitope from Beta-Amyloid and Promiscuous T Cell Epitope Pan HLA DR-Binding Peptide," Journal of Immunology 174(3):1580-1586, American Association of Immunologists, United States (2005).
Agaisse, H. and Lereclus D., "STAB-SD: A Shine-Dalgarno Sequence in the 5' Untranslated Region is a Determinant of mRNA Stability," Molecular Microbiology 20(3):633-643, Blackwell Scientific Publications, England (1996).
Aissani, B. and Bernardi, G., "CpG Islands, Genes and Isochores in the Genomes of Vertebrates," Gene 106(2):185-195, Elsevier, Netherlands (1991).
Akashi, H., "Gene Expression and Molecular Evolution," Current Opinion in Genetics & Development 11(6):660-666, Elsevier, England (2001).
Akinc, A., et al., "Development of Lipidoid-siRNA Formulations for Systemic Delivery to the Liver," Molecular Therapy : The Journal of the American Society of Gene Therapy 17(5):872-879, Academic Press, United States (2009).
Akinc, A., et al., "Targeted Delivery of RNAi Therapeutics with Endogenous and Exogenous Ligand-Based Mechanisms," Molecular Therapy : The Journal of the American Society of Gene Therapy 18(7):1357-1364, Academic Press, United States (2010).
Aksenova, N.N., et al., "Influence of Ribonucleic Acids from the Liver on Implantation and Growth of Transplantable Tumours," Nature 196:443-444, Nature Publishing Group, England (1962).
Alberts, et al., Molecular Biology of the Cell, 3rd ed. Garland Publishing, Inc. New York, NY, 1994, pp. 368-369.
Aleku, M., et al., "Atu027, a Liposomal Small Interfering RNA Formulation Targeting Protein Kinase N3, Inhibits Cancer Progression," Cancer Research 68(23):9788-9798, American Association for Cancer Research, United States (2008).
Alexandrakis, M.G., et al., "Relationship Between Circulating BAFF Serum Levels with Proliferating Markers in Patients with Multiple Myeloma," BioMed Research International 2013:1-7, Hindawi Pub. Co., United States (2013).
Alfonso, M., et al., "An Anti-Idiotype Vaccine Elicits a Specific Response to N-Glycolyl Sialic Acid Residues of Glycoconjugates in Melanoma Patients," The Journal of Immunology 168(5):2523-2529, American Association of Immunologists, United States (2002).
Alonso, R., et al., "Towards the Definition of a Chimpanzee and Human Conserved CD6 Domain 1 Epitope Recognized by T1 Monoclonal Antibody," Hybridoma 27(4):291-301, Mary Ann Liebert, Inc., United States (2008).
Alpha Galactosidase A; alpha-galactosidase a precursor [ *Homo sapiens*] NCBI, 2010, pp. 1-4.
Alprolix, Highlights of Prescribing Information, Full Prescribing Information, Biogen Idec,2013, No Vol, pp. 1-19.
Alten, R., et al., "The Human Anti-IL-1 Beta Monoclonal Antibody ACZ885 is Effective in Joint Inflammation Models in Mice and in a Proof-of-Concept Study in Patients with Rheumatoid Arthritis," Arthritis Research & Therapy 10(3):R67, BioMed Central, England (2008).
Anderson, B.R., et al., "Incorporation of Pseudouridine into mRNA Enhances Translation by Diminishing PKR Activation," Nucleic Acids Research 38(17):5884-5892, Oxford University Press, England (2010).
Anderson, B.R., et al., "Nucleoside Modifications in RNA Limit Activation of 2'-5'-Oligoadenylate Synthetase and Increase Resistance to Cleavage by RNase L," Nucleic Acids Research 39(21):9329-9338, Oxford University Press, England (2011).
Anderson, D.M., et al., "Stability of mRNA/Cationic Lipid Lipoplexes in Human and Rat Cerebrospinal Fluid: Methods and Evidence for Nonviral mRNA Gene Delivery to the Central Nervous System," Human Gene Therapy 14(3):191-202, M.A. Liebert, United States (2003).
Anderson, et al. The Bridge, National Academy of Engineering of the National Academies, Fall 2006, vol. 36., No. 3, pp. 1-55.
Andrews-Pfannkoch, C., et al., "Hydroxyapatite-Mediated Separation of Double-Stranded DNA, Single-Stranded DNA, and RNA Genomes from Natural Viral Assemblages," Applied and Environmental Microbiology 76(15):5039-5045, American Society for Microbiology, United States (2010).
Andries, O., et al., "Comparison of the gene transfer efficiency of mRNA/GL67 and pDNA/GL67 complexes in respiratory cells," Molecular Pharmaceutics 9(8):2136-2145, American Chemical Society, United States (2012).
Angevin, E., et al., "A Phase I/II, Multiple-Dose, Dose-Escalation Study of Siltuximab, an Anti-Interleukin-6 Monoclonal Antibody, in Patients with Advanced Solid Tumors," Clinical Cancer Research 20(8):2192-2204, The Association, United States (2014).
Anichini, A., et al., "Cytotoxic T Cells Directed to Tumor Antigens Not Expressed on Normal Melanocytes Dominate HLA-A2.1-Restricted Immune Repertoire to Melanoma," Journal of Immunology 156(1):208-217, American Association of Immunologists, United States (1996).
Anonymous: "Messenger RNA", Internet: Wikipedia. Jun. 19, 2013, XP002699196, Retrieved from the Internet: URL: http://en.wikipedia_org/wiki/Messenger RNA.
Aoi, T., et al., "Generation of Pluripotent Stem Cells from Adult Mouse Liver and Stomach Cells," Science 321(5889):699-702, American Association for the Advancement of Science, United States (2008).
Aota, S. and Ikemura, T., "Diversity in G + C Content at the Third Position of Codons in Vertebrate Genes and its Cause," Nucleic Acids Research 14(16):6345-6355, Oxford University Press, England (1986).
Apostolopoulos, V., et al., "Cellular Mucins: Targets for Immunotherapy," Critical Reviews in Immunology 14(3-4):293-309, Begell House, United States (1994).
Apostolopoulos, V., et al., "Targeting Antigens to Dendritic Cell Receptors for Vaccine Development," Journal of Drug Delivery 2013:1-22, Hindawi Pub. Corp., Egypt (2013).
Arce-Fonseca, M., et al., "Specific Humoral and Cellular Immunity Induced by Trypanosoma Cruzi DNA Immunization in a Canine Model.," Veterinary Research 44:15, BioMed Central, England (2013).
Archer, S.J., "Induction of a T-cell Specific Antigen on Bone Marrow Lymphocytes with Thymus RNA.," Immunology 34(1):123-129, Blackwell Scientific Publications, England (1978).
Argininosuccinate Synthetase; Argininosuccinate Synthetase, isoform CRA_b (*Homo sapiens*) NCBI, Dec. 18, 2006, No Vol., pp. 1-3.
Armstrong, Deborah, et al., Farletuzumab (MORAb-003) in platinum-sensitive ovarian cancer patients experiencing a first relapse, Community Oncology, 2010, vol. 7, No. 2, Supp 1., pp. 1-4.
Ashely, D.M., et al., "Bone Marrow-generated Dendritic Cells Pulsed with Tumor Extracts or Tumor Rna Induce Antitumor Immunity Against Central Nervous System Tumors," The Journal of Experimental Medicine 186(7):1177-1182, Rockefeller University Press, United States (1997).
Ast, G., "How Did Alternative Splicing Evolve?," Nature Reviews. Genetics 5(10):773-782, Nature Pub. Group, England (2004).
Aurup, H., et al., "Translation of 2'-Modified mRNA in Vitro and in Vivo," Nucleic Acids Research 22(23):4963-4968, Oxford University Press, England (1994).
Austyn, J.M., "New Insights into the Mobilization and Phagocytic Activity of Dendritic Cells.," The Journal of Experimental Medicine 183(4):1287-1292, Rockefeller University Press, United States (1996).
Avastin, Bevacizumab, Labeling Text, 2013, No Volume, pp. 1-27.

(56) References Cited

OTHER PUBLICATIONS

Avid Radiopharmaceuticals, Dominantly Inherited Alzheimer Network Trial: An Opportunity to Prevent Dementia. A Study of Potential Disease Modifying Treatments in Individuals at Risk for or With a Type of Early Onset Alzheimer's Disease Caused by a Genetic.
Baars, A., et al., "A Phase II Study of Active Specific Immunotherapy and 5-FU/Leucovorin as Adjuvant Therapy for Stage III Colon Carcinoma," British Journal of Cancer 86(8):1230-1234, Nature Publishing Group on behalf of Cancer Research UK, England (2002).
Babich, F.R., et al., "Cross-Species Transfer of Learning: Effect of Ribonucleic Acid from Hamsters on Rat Behavior," Proceedings of the National Academy of Sciences USA 54(5):1299-1302, National Academy of Sciences, United States (1965).
Bachellerie, J.P., et al., "Antisense SnoRNAs: A Family of Nucleolar RNAs with Long Complementarities to rRNA," Trends in Biochemical Sciences 20(7):261-264, Elsevier Trends Journals, England (1995).
Badawi, A.H. and Siahaan, T.J., "Immune Modulating Peptides for the Treatment and Suppression of Multiple Sclerosis," Clinical Immunology 144(2):127-138, Academic Press, United States (2012).
Badis, G., et al., "A SnoRNA that Guides the two Most Conserved Pseudouridine Modifications within rRNA Confers a Growth Advantage in Yeast," RNA 9(7):771-779, Cold Spring Harbor Laboratory Press, United States (2003).
Baeten, D., et al., "Anti-Interleukin-17A Monoclonal Antibody Secukinumab in Treatment of Ankylosing Spondylitis: A Randomised, Double-Blind, Placebo-Controlled Trial," Lancet 382(9906):1705-1713, Elsevier, England (2013).
Bag, J., "Recovery of Normal Protein Synthesis in Heat-Shocked Chicken Myotubes by Liposome-Mediated Transfer of mRNAs," Canadian Journal of Biochemistry and Cell Biology 63(3):231-235, National Research Council of Canada, Canada (1985).
Bagnall, et al., Rat strain differences on performance in the Morris water maze. Animal Technology, 1999, 50 (2):69-77.
Bai, D.L., et al., "Huperzine A, a Potential Therapeutic Agent for Treatment of Alzheimer's Disease," Current Medicinal Chemistry 7(3):355-374, Bentham Science Publishers, Netherlands (2000).
Bain, J.D. and Switzer, C., "Regioselective Ligation of Oligoribonucleotides using DNA Splints," Nucleic Acids Research 20(16):4372, Oxford University Press, England (1992).
Baker, D.L., et al., "RNA-Guided RNA Modification: Functional Organization of the Archaeal H/ACA RNP," Genes & Development 19(10):1238-1248, Cold Spring Harbor Laboratory Press, United States (2005).
Baker, K.P., et al., "Generation and Characterization of Lymphostat-B, a Human Monoclonal Antibody that Antagonizes the Bioactivities of B Lymphocyte Stimulator," Arthritis and Rheumatism 48(11):3253-3265, Wiley-Blackwell, United States (2003).
Bakker, J.M. et al., "Therapeutic Antibody Gene Transfer: An Active Approach to Passive Immunity," Molecular Therapy : The Journal of the American Society of Gene Therapy 10(3):411-416, Academic Press, United States (2004).
Balakin, A.G. et al., "The RNA World of the Nucleolus: Two Major Families of Small RNAs Defined by Different Box Elements with Related Functions," Cell 86(5):823-834, Cell Press, United States (1996).
Balazs, A.B., et al., "Vectored Immunoprophylaxis Protects Humanized Mice From Mucosal HIV Transmission," Nature Medicine 20(3):296-300, Nature Publishing Company, United States (2014).
Ballatore, C., et al., "Microtubule Stabilizing Agents as Potential Treatment for Alzheimer's Disease and Related Neurodegenerative Tauopathies," Journal of Medicinal Chemistry 55(21):8979-8996, American Chemical Society, United States (2012).
Bamias, G., et al., "Leukocyte Traffic Blockade as a Therapeutic Strategy in Inflammatory Bowel Disease," Current Drug Targets 14(12):1490-1500, Bentham Science Publishers, Netherlands (2013).
Bandala-Sanchez, E., et al., "T Cell Regulation Mediated by Interaction of Soluble CD52 with the Inhibitory Receptor Siglec-10," Nature Immunology 14(7):741-748, Nature America Inc., United States (2013).
Bandbon Balenga, N. A., et al., "Bicistronic Expression Plasmid Encoding Allergen and Anti-IgE Single Chain Variable Fragmentantibody as a Novel DNA Vaccine for Allergy Therapy and Prevention," Medical Hypotheses 67(1):71-74, Eden Press, United States (2006).
Banerjee, A.K., "5'-Terminal Cap Structure in Eucaryotic Messenger Ribonucleic Acids," Microbiological Reviews 44(2):175-205, American Society for Microbiology, United States (1980).
Barber, R., "The Chromatographic Separation of Ribonucleic Acids," Biochimica Et Biophysica Acta 114(2):422-424, Elsevier Pub. Co., Netherlands (1966).
Bargemann, C.I., et al., "The Neu Oncogene Encodes an Epidermal Growth Factor Receptor-Related Protein," Nature 319(6050):226-230, Nature Publishing Group, England (1986).
Barker, E., et al., "Effect of a Chimeric Anti-Ganglioside GD2 Antibody on Cell-Mediated Lysis of Human Neuroblastoma Cells," Cancer Research 51(1):144-149, American Association for Cancer Research, United States (1991).
Barlow, P.G., et al., "The Human Cathelicidin LL-37 Preferentially Promotes Apoptosis of Infected Airway Epithelium," American Journal of Respiratory Cell and Molecular Biology 43(6):692-702, American Thoracic Society, United States (2010).
Barouch, D., et al., "Therapeutic Efficacy of Potent Neutralizing HIV-1-Specific Monoclonal Sntibodies in SHIV-Infected Rhesus Monkeys," Nature 503(7475):224-228, Nature Publishing Group, England (2013).
Barr, I.G., et al., "Epidemiological, Antigenic and Genetic Characteristics of Seasonal Influenza A(H1N1), A(H3N2) and B Influenza Viruses: Basis for the WHO Recommendation on the Composition of Influenza Vaccines for use in the 2009-2010 Northern Hemisphere Season," Vaccine 28(5):1156-1167, Elsevier Science, Netherlands (2010).
Basarkar, A. and Singh, J., "Nanoparticulate Systems for Polynucleotide Delivery," International Journal of Nanomedicine 2(3):353-360, DOVE Medical Press, New Zealand (2007).
Baserga, R., et al., "the LGF-I Receptor in Cell Growth, Transformation and Apoptosis," Biochimica et biophysica acta 1332(3):F105-F126, Elsevier Publisher Co, Netherlands (1997).
Bates, T.R., et al., "Detection of Familial Hypercholesterolaemia: A Major Treatment Gap in Preventative Cardiology," Heart, Lung & Circulation 17(5):411-413, Elsevier Australia, Australia (2008).
Batshaw, M.L., et al., "Risk of Serious Illness in Heterozygotes for Ornithine Transcarbamylase Deficiency," The Journal of Pediatrics 108(2):236-241, Mosby, United States (1986).
Batshaw, M.L., et al., "Treatment of Inborn Errors of Urea Synthesis: Activation of Alternative Pathways of Waste Nitrogen Synthesis and Excretion," The New England Journal of Medicine 306(23):1387-1392, Massachusetts Medical Society, United States (1982).
Bechler, K., "Influence of Capping and Polyadenylation on mRNA Expression and on Antisense RNA Mediated Inhibition of Gene Expression," Biochemical and Biophysical Research Communications 241(1):193-199, Academic Press, United States (1997).
Beigneux, A., et al., "Human CYP7A1 Deficiency: Progress and Enigmas," The Journal of Clinical Investigation 110(1):29-31, American Society for Clinical Investigation, United States (2002).
Bekker, P.J., et al., "A Single-Dose Placebo-Controlled Study of AMG 162, a Fully Human Monoclonal Antibody to RANKL, in Postmenopausal Women," Journal of Bone and Mineral Research19(7):1059-1066, American Society for Bone and Mineral Research, United States (2004).
Bekker, P.J., et al., "The Effect of a Single Dose of Osteoprotegerin in Postmenopausal Women," Journal of Bone and Mineral Research 16(2):348-360, American Society for Bone and Mineral Research, United States (2001).
Beljanski, M., et al., "Iron Stimulated RNA-Dependent DNA Polymerase Activity from Goldfish Eggs," Cellular and Molecular Biology 34(1):17-25, Pergamon Press, England (1988).

(56) References Cited

OTHER PUBLICATIONS

Bell, D.W., et al., "Predisposition to Cancer Caused Fy Genetic and Functional Defects of Mammalian Atad5," PLoS Genetics 7(8):e1002245, Public Library of Science, United States (2011).
Belliveau, N.M., et al., "Microfluidic Synthesis of Highly Potent Limit-Size Lipid Nanoparticles for in Vivo Delivery of siRNA," Molecular Therapy. Nucleic Acids 1:e37, Public Library of Science, United States (2012).
Bermudez, L.E., et al., "Treatment with Recombinant Granulocyte Colony-Stimulating Factor (Filgrastin) Stimulates Neutrophils and Tissue Macrophages and Induces an Effective Non-Specific Response Against *Mycobacterium avium* in Mice," Immunology 94(3):297-303, Blackwell Scientific Publications, England (1998).
Bernardi, G., "The Vertebrate Genome: Isochores and Evolution," Molecular Biology and Evolution 10(1):186-204, Oxford University Press, United States (1993).
Bernhard, H., et al., "Generation of Immunostimulatory Dendritic Cells from Human CD34+ Hematopoietic Progenitor Cells of the Bone Marrow and Peripheral Blood.," Cancer Research 55(5):1099-1104, American Association for Cancer Research, United States (1995).
Bernstein, E., et al., "Role for a Bidentate Ribonuclease in the Initiation Step of RNA Interference," Nature 409(6818):363-366, Nature Publishing Group, England (2001).
Bernstein, P. and Ross, J., "Poly(A), Poly(A) Binding Protein and the Regulation of mRNA Stability," Trends in Biochemical Sciences 14(9):373-377, Elsevier Trends Journals, England (1989).
Bertolini, M.C. and De Lucca, F.L., "Fractionation of Immune RNA Isolated from the Spleens of Mice Infected with Trypanosoma Cruzi," The Journal of Infectious Diseases 143(6):827-831, Oxford University Press, United States (1981).
Bertolini, M.C. and De Lucca, F.L., "In Vitro Effect of 18S Immune RNA on Macrophage Resistance to Trypanosoma Cruzi," Cellular and Molecular Biology 32(2):167-171, Pergamon Press, England (1986).
Bertolini, M.C., and De Lucca, F.L., "The Protective Effect of the 4-5S Immune RNA Against Trypanosoma Cruzi Infection in Mice," Tropical Medicine and Parasitology 36(3):131-134, Georg Thieme Verlag, Germany (1985).
Bertrand, E. and Bordonne, R., "Assembly and Traffic of Small Nuclear RNPs," Progress in Molecular and Subcellular Biology 35:79-97, Springer-Verlag, United States (2004).
Bertrand, E., and Fournier, M.J., "The snoRNPs and Related Machines: Ancient Devices that Mediate Maturation of rRNA," The Nucleolus 223-257, Springer Science & Business Media (2004).
Bettinger, T., et al., "Peptide-Mediated RNA Delivery: A Novel Approach for Enhanced Transfection of Primary and Post-Mitotic Cells," Nucleic Acids Research 29(18):3882-3891, Oxford University Press, England (2001).
Bevan, M.J., "Antigen Presentation to Cytotoxic T Lymphocytes in Vivo," The Journal of Experimental Medicine 182(3):639-641, Rockefeller University Press, United States (1995).
Bevilazqua A., et al., "Post-Transcriptional Regulation of Gene Expression by Degradation of Messenger RNAs," Journal of Cellular Physiology 195(3):356-372, Wiley-Liss, United States (2003).
Bhattacharya, B.K. et al., "A Practical Synthesis of N1-Methyl-2'-deoxy-ψ-uridine (ψ-Thymidine) and its Incorporation into G-Rich Triple Helix Forming Oligonucleotides," Nucleosides and Nucleotides 14(6):1269-1287 (1995).
Bieler, K. et al., Plasmids for Therapy and Vaccination. Wiley-VCH GmbH, Weinheim, Feb. 2001.
Bikard, D., et al., "Programmable Repression and Activation of Bacterial Gene Eexpression Using an Engineered CRISPR-Cas System," Nucleic Acids Research 41(15):7429-7437, Information Retrieval ltd, England (2013).
Binder, M., et al., "The Epitope Recognized by Rituximab," Blood 108(6):1975-1978, American Society of Hematology, United States (2006).
Binder, R., et al., "Evidence that the Pathway of Transferrin Receptor mRNA Degradation Involves an Endonucleolytic Cleavage within the 3' UTR and does not Involve Poly(A) Tail Shortening," The EMBO Journal 13(8):1969-1980, Wiley Blackwell, England (1994).
Biocca, S., et al., "Intracellular Expression of Anti-p21 ras Single Chain FY Fragments Inhibits Meiotic Maturation of Xenopus Oocytes," Biochemical and Biophysical Research Communications 197(2):422-427, Academic Press, United States (1993).
Bionaz, M. and Loor, J.J., "ACSL1, AGPAT6, FABP3, LPIN1, and SLC27A6 are the Most Abundant Isoforms in Bovine Mammary Tissue and their Expression is Affected by Stage of Lactation," The Journal of Nutrition 138(6):1019-1024, American Society for Nutrition, United States (2008).
Biopharma, Sample Synagis, Medlmmune, Inc., 2013, No Vol. pp. 1-19.
Bird, A.P., "CpG-Rich Islands and the Function of DNA Methylation," Nature 321(6067):209- 213, Nature Publishing Group, England (1986).
Black, D.D. and Griffin, A.C., "Similarity of the Transfer Factors in Novikoff Ascites Tumor and Other Amino Acid-Incorporating Systems," Cancer Research 30(5):1281-1286, American Association for Cancer Research, United States (1970).
Blelloch, R., et al., "Generation of Induced Pluripotent Stem Cells in the Absence of Drug Selection," Cell Stem Cell 1(3):245-247, American Association for Cancer Research, United States (2007).
Bloch, G., et al., "Sequence-Dependence of the Conformational Changes Induced by the 5-Methyl Cytosine in Synthetic RNA Oligomers," FEBS Letters 219(2):464-468, John Wiley & Sons Ltd, England (1987).
Blom, D.J., et al., "A 52-Week Placebo-Controlled Trial of Evolocumab in Hyperlipidemia," The New England Journal of Medicine 370(19):1809-1819, The New England Journal of Medicine, United States (2014).
Bococizumab, Statement on a Nonproprietary Name Adopted by the USAN Council, 2013, No Vol. pp. 1-2.
Boczkowski, D., et al., "Dendritic Cells Pulsed with RNA are Potent Antigen-Presenting Cells in Vitro and in Vivo," The Journal of Experimental Medicine 184(2):465-472, Rockefeller University Press, United States (1996).
Boczkowski, D., et al., "Induction of Tumor Immunity and Cytotoxic T Lymphocyte Responses using Dendritic Cells Transfected with Messenger RNA Amplified from Tumor Cells," Cancer Research 60(4):1028-1034, American Association for Cancer Research, United States (2000).
Body, J.J., et al., "A Study of the Biological Receptor Activator of Nuclear Factor-Kappab Ligand Inhibitor, Denosumab, in Patients with Multiple Myeloma or Bone Metastases from Breast Cancer," Clinical Cancer Research 12(4):1221-1228, The Association, United States (2006).
Bohrmann, B., et al., "Gantenerumab: A Novel Human Anti-Aβ Antibody Demonstrates Sustained Cerebral Amyloid-β Binding and Elicits Cell-Mediated Removal of Human Amyloid-β," Journal of Alzheimer's Disease 28(1):49-69, IOS Press, Netherlands (2012).
Bolhassani, A., et al., "Improvement of Different Vaccine Delivery Systems for Cancer Therapy," Molecular Cancer 10(3):1-20, BioMed Central, England (2011).
Bolukbasi, M.F., et al., "MiR-1289 and "Zipcode"-Like Sequence Enrich mRNAs in Microvesicles," Molecular Therapy Nucleic Acids 1:e10, Nature Pub. Group, United States (2012).
Bonehill, A., et al., "Single-Step Antigen Loading and Activation of Dendritic Cells by mRNA Electroporation for the Purpose of Therapeutic Vaccination in Melanoma Patients," Clinical Cancer Research 15(10):3366-3375, The Association, United States (2009).
Bonham, K.S., et al., "A Promiscuous Lipid-Binding Protein Diversifies the Subcellular Sites of Toll-Like Receptor Signal Transduction," Cell 156(4):705-716, Cell Press, United States (2014).
Bonora, G.M., et al., "HELP (High Efficiency Liquid Phase) New Oligonucleotide Synthesis on Soluble Polymeric Support," Nucleic Acids Research18(11):3155-3159, Oxford University Press, England (1990).
Boon, T., et al., "Genes Coding for Tumor Rejection Antigens: Perspectives for Specific Immunotherapy," Important Advances in Oncology 53-69, Lippincott, United States (1994).

(56) References Cited

OTHER PUBLICATIONS

Borghaei, H., et al., "Phase I Dose Escalation, Pharmacokinetic and Pharmacodynamic Study of Naptumomab Estafenatox Alone in Patients with Advanced Cancer and with Docetaxel in Patients with Advanced Non-Small-Cell Lung Cancer," Journal of Clinical Oncology 27(25):4116-4123, American Society of Clinical Oncology, United States (2009).
Borovkov, A.Y., et al., "High-Quality Gene Assembly Directly from Unpurified Mixtures of Microarray-Synthesized Oligonucleotides," Nucleic Acids Research 38(19):e180, Oxford University Press, England (2010).
Bose, S., et al., "Role of Nucleolin in Human Parainfluenza Virus Type 3 Infection of Human Lung Epithelial Cells," Journal of Virology 78(15):8146-8158, American Society for Microbiology, United States (2004).
Bosma, P.J., "Inherited Disorders of Bilirubin Metabolism," Journal of Hepatology 38(1):107-117, Elsevier, Netherlands (2003).
Bottero, F., et al., "Gene Transfection and Expression of the Ovarian Carcinoma Marker Folate Binding Protein on NIH/3T3 Cells Increases Cell Growth in Vitro and in Vivo," Cancer Research 53(23):5791-5796, American Association for Cancer Research, United States (1993).
Bouloy, M., et al., "Both the 7-Methyl and the 2'-O-Methyl Groups in the Cap of mRNA Strongly Influence its Ability to Act as Primer for Influenza Virus RNA Transcriptio," Proceedings of the National Academy of Sciences USA 77(7):3952-3956, National Academy of Sciences, United States (1980).
Bousquet, J., et al., "Eosinophilic Inflammation in Asthma," The New England Journal of Medicine 323(15):1033-1039, Massachusetts Medical Society, United States (1990).
Bouxsein, N.F., et al., "Structure and Gene Silencing Activities of Monovalent and Pentavalent Cationic Lipid Vectors Complexed with SiRNA," Biochemistry 46(16):4785-4792, American Chemical Society, United States (2007).
Bowen, M.A., et al., "Functional Effects of CD30 on a Large Granular Lymphoma Cell Line, YT. Inhibition of Cytotoxicity, Regulation of CD28 and IL-2R, and Induction of Homotypic Aggregation," Journal of Immunology 151(11):5896-5906, American Association of Immunologists, United States (1993).
Braissant, O., "Current Concepts in the Pathogenesis of Urea Cycle Disorders," Molecular Genetics and Metabolism 100:S3-S12, Academic Press, United States (2010).
Brandenburg, B., et al., "Mechanisms of Hemagglutinin Targeted Influenza Virus Neutralization," Immunology Letters 8(12):e80034, Elsevier, Netherlands (2016).
Brandt, B., et al., "Detection of the Metastatic Potential of Blood-Borne and Immunomagnetically Enriched Epithelial Cells by Quantitative ERBB-2 RT-PCR," Clinical & Experimental Metastasis 14(4):399-408, Kluwer Academic Publishers, Netherlands (1996).
Braun, S.E., et al., "Preclinical Studies of Lymphocyte Gene Therapy for Mild Hunter Syndrome (Mucopolysaccharidosis Type II)," Human Gene Therapy 7(3):283-290, M.A. Liebert, United State (1996).
Brieba, L.G., et al., "Role of T7 RNA Polymerase His784 in Start Site Selection and Initial Transcription," Biochemistry 41(16):5144-5149, American Chemical Society, United States (2002).
Brockton, N.T., "UGT1A1 Polymorphisms and Colorectal Cancer Susceptibility," Gut 50(6):748-749, American Chemical Society, United States (2002).
Brossart, P., et al., "Her-2/Neu-Derived Peptides are Tumor-Associated Antigens Expressed by Human Renal Cell and Colon Carcinoma Lines and are Recognized by in Vitro Induced Specific Cytotoxic T Lymphocytes," Cancer Research 58(4):732-736, American Association for Cancer Research, United States (1998).
Brossart, P., et al., "Identification of HLA-A2-Restricted T-Cell Epitopes Derived from the MUC1 Tumor Antigen for Broadly Applicable Vaccine Therapies," Blood 93(12):4309-4317, American Society of Hematology, United States (1999).
Brossart, P., et al., "Induction of Cytotoxic T-Lymphocyte Responses in Vivo After Vaccinations with Peptide-Pulsed Dendritic Cells," Blood 96(9):3102-3108, American Society of Hematology, United States (2000).
Brossart, P., et al., "Virus-Mediated Delivery of Antigenic Epitopes into Dendritic Cells as a Means to Induce CTL," Journal of Immunology 158(7):3270-3276, American Association of Immunologists, United States (1997).
Brown, C.E. And Sachs, a.B., "Poly(A) Tail Length Control in *Saccharomyces cerevisiae* Occurs by Message-Specific Deadenylation," Molecular and Cellular Biology 18(11):6548-6559, American Society for Microbiology, United States (1998).
Broz, P. and Monack, D.M., "Newly Described Pattern Recognition Receptors Team Up Against Intracellular Pathogens," Nature Reviews Immunology 13(8):551-565, Nature Publishing Group, England (2013).
Buccoliero, R., et al., "Elevation of Lung Surfactant Phosphatidylcholine in Mouse Models of Sandhoff and of Niemann-Pick a Disease," Journal of Inherited Metabolic Disease 27(5):641-648, Kluwer, Netherlands (2004).
Burgess, T.L., et al., "Biochemical Characterization of AMG 102: A Neutralizing, Nully Human Monoclonal Antibody to Human and Nonhuman Primate Hepatocyte Growth Factor," Molecular Cancer Therapeutics 9(2):400-409, American Association for Cancer Research, United States (2010).
Burke, B. and Warren, G., "Microinjection of mRNA Coding for an Anti-Golgi Antibody Inhibits Intracellular Transport of a Viral Membrane Protein," Cell 36(4):847-856, Cell Press, United States (1984).
Burks, E.A., et al., "In vitro Scanning Saturation Mutagenesis of an Antibody Binding Pocket," Proceedings of the National Academy of Sciences USA 94(2):412-417, Plenum Publishing Corporation , United States (1997).
Burton, D.R., et al., "A Large Array of Human Monoclonal Antibodies to Type 1 Human Immunodeficiency Virus from Combinatorial Libraries of Asymptomatic Seropositive Individuals," Proceedings of the National Academy of Sciences USA 88(22):10134-10137., National Academy of Sciences, United States (1991).
Burton, D.R, et al., "Efficient Neutralization of Primary Isolates of HIV-1 by a Recombinant Human Monoclonal Antibody," Science 266(5187):1024-1027, American Association for the Advancement of Science, United States (1994).
Busse, W.W., et al., "Safety Profile, Pharmacokinetics, and Biologic Activity of MEDI-563, an Anti-IL-5 Receptor Alpha Antibody, in a Phase I Study of Subjects with Mild Asthma," The Journal of Allergy and Clinical Immunology 125(6):1237-1244.e2, Mosby, United States (2010).
Butler, E.T. and Chamberlin M.J., "Bacteriophage SP6-Specific RNA polymerase. I Isolation and Characterization of the Enzyme," The Journal of Biological Chemistry 257(10):5772-5778, American Society for Biochemistry and Molecular Biology, United States (1982).
By hAQP5 (*Homo sapiens* aquaporin 5 (AQP5) mRNA; NCBI, pp. 1-5, published Dec. 27, 2010, No. Vol.
Califf, R.M., et al., "Use of a Monoclonal Antibody Directed Against the Platelet Glycoprotein IIb/IIIa Receptor in High-Risk Coronary Angioplasty," The New England Journal of Medicine 330(14):956-961, Massachusetts Medical Society, United States (1994).
Canakinumab FDA Label, 2009, No Volume # pp. 1-11.
Cang, S., et al., "Novel CD20 Monoclonal Antibodies for Lymphoma Therapy," Journal of Hematology and Oncology 5(64):1-9, Biomed Central, England (2012).
Cannon, G. and Weissman, D., "RNA Based Vaccines," DNA and Cell Biology 21(12):953-961, Mary Ann Liebert, United States (2002).
Capoccia, B.J., et al., "G-CSF and AMD3100 Mobilize Monocytes into the Blood that Stimulate Angiogenesis in Vivo through a Paracrine Mechanism," Blood 108(7):2438-2445, American Society of Hematology, United States (2006).
Caput, D., et al., "Identification of a Common Nucleotide Sequence in the 3'-Untranslated Region of MRNA Molecules Specifying

(56) References Cited

OTHER PUBLICATIONS

Inflammatory Mediators," Proceedings of the National Academy of Sciences USA 83(6):1670-1674, National Academy of Sciences, United States (1986).
Carboxypeptidas N, Carboxypeptidas N caralytic Chanin precursor [*Homo sapiens*] NCBI, 2010, pp. 1-4.
Carnahan, J., et al., "Epratuzumab, a Humanized Monoclonal Antibody Targeting CD22: Characterization of in Vitro Properties," Clinical Cancer Research 9(10 Pt 2):3982S-3990S, The Association, United States (2003).
Caron, H., et al., "The Human Transcriptome Map: Clustering of Highly Expressed Genes in Chromosomal Domains," Science 291(5507):1289-1292, American Association for the Advancement of Science, United States (2001).
Carralot, J.P., et al., "Polarization of Immunity Induced by Direct Injection of Naked Sequence-Stabilized mRNA Vaccines," Cellular and Molecular Life Sciences 61(18):2418- 2424, Springer, Switzerland (2004).
Carrington, J.C. and Freed, D.D., "Cap-Independent Enhancement of Translation by a Plant Potyvirus 5' Nontranslated Region," Journal of Virology 64(4):1590-1597, American Society for Microbiology, United States (1990).
Castro, M., et al., "Reslizumab for Poorly Controlled, Eosinophilic Asthma: A Randomized, Placebo-Controlled Study," American Journal of Respiratory and Critical Care Medicine 184(10):1125-1132, American Thoracic Society, United States (2011).
Caudy, A.A., et al., "Fragile X-Related Protein and VIG Associate With the RNA Interference Machinery," Genes and development 16(19):2491-2496, Cold Spring Harbor Laboratory Press, United States (2002).
Cavaille, J., et al., "Identification of Brain-Specific and Imprinted Small Nucleolar RNA Genes Exhibiting an unusual Genomic Organization.," Proceedings of the National Academy of Sciences USA 97(26):14311-14316, National Academy of Sciences, United States (2000).
Cavaille, J., et al., "Targeted Ribose Methylation of RNA In Vivo Directed by Tailored Antisense RNA Guides," Nature 383(6602):732-735, Nature Publishing Group, England (1996).
Cavelti-Weder, C., et al., "Effects of Gevokizumab on Glycemia and Inflammatory Markers in Type 2 Diabetes," Diabetes Care 35(8):1654-1662, American Diabetes Association, United States (2012).
Celluzzi, C.M., et al., "Peptide-Pulsed Dendritic Cells Induce Antigen-Specific CTL-Mediated Protective Tumor Immunity," The Journal of Experimental Medicine 183(1):283-287, Rockefeller University Press, United States (1996).
Chan, E.M., et al., "Live Cell Imaging Distinguishes Bona Fide Human Ips Cells from Partially Reprogrammed Cells," Nature Biotechnology 27(11):1033-1037, Nature America Publishing, United States (2009).
Chang, C.C., et al., "Tolerization of Dendritic Cells by T(S) Cells: the Crucial Role of Inhibitory Receptors ILT3 and ILT4," Nature Immunology 3(3):237-243, Nature America, United States (2002).
Chang, C.W., et al., "Non-Ionic Amphiphilic Biodegradable PEG-PLGA-PEG Copolymer Enhances Gene Delivery Efficiency in Rat Skeletal Muscle," Journal of Controlled Release 118(2):245-253, Elsevier B.V., Netherlands (2007).
Chang, Y.C., et al., "Synthesis and Solution Conformation Studies of 3-substituted Uridine and Pseudouridine Derivatives," Bioorganic & Medicinal Chemistry 16(5):2676-2686, Elsevier Science, England (2008).
Chapman, A.P., et al., "Therapeutic Antibody Fragments With Prolonged In Vivo Half-Lives," Nature Biotechnology 17(8):780-783, Nature America Publishing, United States (1999).
Chappell, S.A., et al., "Ribosomal Tethering and Clustering as Mechanisms for Translation Initiation," Proceedings of the National Academy of Sciences USA 103(48):18077-18082, National Academy of Sciences, United States (2006).
Charette, M. and Gray, M.W., "Pseudouridine in RNA: What, Where, How, and Why," IUBMB Life 49(5):341-351, Taylor & Francis, England (2000).
Chelius, D., et al., "Structural and Functional Characterization of the Trifunctional Antibody Catumaxomab," Mabs 2(3):309-319, Taylor & Francis, England (2010).
Chen, C., et al., "A Flexible RNA Backbone within the Polypyrimidine Tract is Required for U2AF65 Binding and Pre-Mrna Splicing in Vivo," Molecular and Cellular Biology 30(17):4108-4119, American Society for Microbiology, United States (2010).
Chen, D., et al., "Rapid Discovery of Potent Sirna-Containing Lipid Nanoparticles Enabled by Controlled Microfluidic Formulation," Journal of the American Chemical Society 134(16):6948-6951, American Chemical Society, United States (2012).
Chen, H., et al., "TGF-Beta 1 Attenuates Myocardial Ischemia-Reperfusion Injury via Inhibition of Upregulation of MMP-1," American Journal of Physiology. Heart and Circulatory Physiology 284(5):H1612-H1617, American Physiological Society,, United States (2003).
Chen, H.X., "Expanding the Clinical Development of Bevacizumab," Oncologist 9(Suppl. 1):27-35, Alphamed Press, United States (2004).
Chen, J.R., et al., "Vaccination of Monoglycosylated Hemagglutinin Induces Cross-Strain Protection Against Influenza Virus Infections," Proceedings of the National Academy of Sciences USA 111(7):2476-2481, National Academy of Sciences, United States (2014).
Chen, X.L., et al., "Expression of Human Factor IX in Retrovirus-Transfected Human Umbilical Cord Tissue Derived Mesenchymal Stem Cells," Journal of Experimental Hematology 17(1):184-187, Zhongguo Shi Yan Xue Za Zhi She, China (2009).
Chen, Y., et al., "Self-Assembled Rosette Nanotubes Encapsulate and Slowly Release Dexamethasone," International Journal of Nanomedicine 6:1035-1044, Dove Medical Press, New Zealand (2011).
Chen, Z., et al., "Enhanced Protection Against a Lethal Influenza Virus Challenge by Immunization With Both Hemagglutinin- and Neuraminidase-Expressing DNAs," Vaccine 17(7-8):653-659, Elsevier Science, Netherlands (1999).
Cheng, C., et al., "Multifunctional Triblock Copolymers for Intracellular Messenger RNA Delivery," Biomaterials 33(28):6868-6876, Elsevier Science, Netherlands (2012).
Cheng, E.C., and Lin, H., "Repressing the Repressor: A Lincrna as a MicroRNA Sponge in Embryonic Stem Cell Self-Renewal," Developmental Cell 25(1):1-2, Cell Press, United States (2013).
Cheng, G., et al., "T-Cell Tolerance and the Multi-Functional Role of IL-2R Signaling in T-regulatory cells," Immunological Reviews 241(1):63-76, Blackwell, England (2011).
Cheng, S., et al., "Effective Amplification of Long Targets Form Cloned Inserts and Human Genomic DNA," Proceedings of the National Academy of Sciences USA 91(12):5695-5699, National Academy of Sciences, United States (1994).
Cheng, W.F., et al., "Enhancement of Sindbis Virus Self-Replicating RNA Vaccine Potency by Linkage of Herpes Simplex Virus Type 1 VP22 Protein to Antigen," Journal of Virology 75(5):2368-2376, American Society for Microbiology, United States (2001).
Cheng, W.F., et al., "Enhancement of Sindbis Virus Self-Replicating RNA Vaccine Potency by Linkage of Mycobacterium Tuberculosis Heat Shock Protein 70 Gene to an Antigen Gene," Journal of Immunology 166(10):6218-6226, American Association of Immunologists, United States (2001).
Cho, E.J., et al., "MRNA Capping Enzyme is recruited to the Transcription Complex by Phosphorylation of the RNA Polymerase II Carboxy-Terminal Domain," Genes and Development 11(24):3319-3326, Cold Spring Harbor Laboratory Press, United States (1997).
Cho, H.H., et al., "A Mutation in Human CMP-Sialic Acid Hydroxylase Occurred After the Homo-Pan Divergence," Proceedings of the National Academy of Sciences USA 95(20):11751-11756, National Academy of Sciences, United States (1998).
Cho, J.H., et al., "Enhanced Cellular Immunity to Hepatitis C Virus Nonstructural Proteins by Codelivery of Granulocyte Macrophage-

(56) References Cited

OTHER PUBLICATIONS

Colony Stimulating Factor Gene in Intramuscular DNA Immunization ," Vaccine 17(9-10):1136-1144, Elsevier Science, Netherlands (1999).
Chowdhury, J.R., et al., "Bilirubin Mono-and Diglucuronide Formation by Human Liver in Vitro: Assay by High-Pressure Liquid Chromatography," Hepatology 1(6):622-627, Wiley, United States (1981).
Choy, E.H., et al., "Efficacy of a Novel PEGylated Humanized Anti-TNF Fragment (CDP870) in Patients with Rheumatoid Arthritis: A Phase II Double-Blinded, Randomized, Dose-Escalating Trial," Rheumatology 41(10)1133-1137, Oxford University Press, England (2002).
Chui, H.M., et al., "Synthesis of Helix 69 of *Escherichia coli* 23S rRNA Containing Its Natural Modified Nucleosides, M(3)Psi and Psi," The Journal of Organic Chemistry 67(25):8847-8854, American Chemical Society, United States (2002).
Church, L.D. and McDermott, M.F., "Canakinumab, a Fully-Human mAB against IL-1beta for the Potential Treatment of Inflammatory Disorders," Current Opinion in Molecular Therapeutics 11(1):81-89, Thomson Reuters, England (2009).
Cimzia, Product Label, Reference ID: 3217327, UCB, Inc., 2008, No. Vol #, pp. 1-26.
Clawson, G.A. and Smuckler, E.A., "Increased Amounts of Double-Stranded RNA in the Cytoplasm of Rat Liver Following Treatment with Carcinogens," Cancer Research 42(8):3228-3231, American Association for Cancer Research, United States (1982).
Cleary, M.A., et al., "Production of Complex Nucleic Acid Libraries using Highly Parallel in Situ Oligonucleotide Synthesis," Nature Methods 1(3):241-248, Nature Publishing Group, United States (2004).
Cohen, I., et al., "Differential Release of Chromatin-Bound IL-1 alpha Discriminates Between Necrotic and Apoptotic Cell Death by the Ability to Induce Sterile Inflammation," Proceedings of the National Academy of Sciences USA 107(6):2574-2579, National Academy of Sciences, United States (2010).
Cohen, P.J., et al., "Murine Epidermal Langerhans Cells and Splenic Dendritic Cells Present Tumor-Associated Antigens to Primed T Cells," European Journal of Immunology 24(2):315-319, Wiley-VCH, Germany (1994).
Collas, P. and Taranger, C.K., "Epigenetic Reprogramming of Nuclei Using Cell Extracts," Stem Cell Reviews 2(4):309-317, Humana Press, United States (2006).
Collas, P., "Dedifferentiation of Cells: New Approaches," Cytotherapy 9(3):236-244, Elsevier, England (2007).
Coller Bs., "A New Murine Monoclonal Antibody Reports an Activation-Dependent Change in the Conformation and/or Microenvironment of the Platelet Glycoprotein IIb/IIIa Complex," The Journal of Clinical Investigation 76(1):101-108, American Society for Clinical Investigation, United States (1985).
Coller, B.S. and Scudder, L.E., "Inhibition of Dog Platelet Function by In Vivo Infusion of F(ab')2 Fragments of a Monoclonal Antibody to the Platelet Glycoprotein IIb/IIIa Receptor," Blood 66(6):1456-1459, American Society of Hematology, United States (1985).
Colot, V. and Rossignol, J.L., "Eukaryotic DNA Methylation as an Evolutionary Device," Bioessays 21(5):402-411, Wiley, United States (1999).
Colter, J.S., et al., "Infectivity of Ribonucleic Acid from Ehrlich Ascites Tumour Cells Infected with Mengo Encephalitis," Nature 179(4565):859-860, Nature Publishing Group, England (1957).
Colter, J.S., et al., "Infectivity of Ribonucleic Acid Isolated from Virus-Infected Tissues," Virology 4(3):522-532, Academic Press., United States (1957).
Compton, J., "Nucleic Acid Sequence-Based Amplification," Nature 350(6313):91-92, Nature Publishing Group, England (1991).
Conde, F.P., et al., "The Aspergillus Toxin Restriction is a Suitable Cytotoxic Agent for Generation of Immunoconjugates with Monoclonal Antibodies Directed Against Human Carcinoma Cells," European Journal of Biochemistry / FEBS 178(3):795-802, Federation of European Biochemical Societies, England (1989).
Condon, C., et al., "DNA-Based Immunization by in vivo Transfection of Dendritic cells," Nature Medicine 2(10):1122-1128, Nature Publishing Company, United States (1996).
Coney, L.R., et al., "Cloning of a Tumor-associated Antigen: MOv18 and MOv19 Antibodies Recognize a Folate-binding Protein," Cancer Research 51(22):6125-6132, American Association for Cancer Research, United States (1991).
Cong, L., et al., "Multiplex Genome Engineering Using CRISPR/Cas Systems," Science 339(6121):819-823, American Association for the Advancement of Science, United States (2013).
Conry, R.M., et al., "A Carcinoembryonic Antigen Polynucleotide Vaccine has in Vivo Antitumor Activity," Gene Therapy 2(1):59-65, Nature Publishing Group, England (1995).
Conry, R.M., et al., "Characterization of a Messenger RNA Polynucleotide Vaccine Vector," Cancer Research 55(7):1397-1400, American Association for Cancer Research, United States (1995).
Conry, R.M., et al., "Immune Response to a Carcinoembryonic Antigen Polynucleotide Vaccine," Cancer Research 54(5):1164-1168, American Association for Cancer Research, United States (1994).
Cools, N., et al., "Balancing Between Immunity and Tolerance: An Interplay Between Dendritic Cells, Regulatory T Cells, and Effector T Cells," Journal of Leukocyte Biology 82(6):1365-1374, Society for Leukocyte Biology, United States (2007).
Copreni, E., et al., "Lentivirus-Mediated Gene Transfer to the Respiratory Epithelium: A Promising Approach to Gene Therapy of Cystic Fibrosis," Gene Therapy 11(Suppl. 1):S67-S75, Nature Publishing Group, England (2004).
Corneti, Jeff et al. Update of Clinicla Trials to Cure Hemophilia, Hemophilia of Georgia, Dec. 12, 2013, No Vol. pp. 1-2.
Corren, J., et al., "Lebrikizumab Treatment in Adults with Asthma," The New England Journal of Medicine 365(12):1088-1098, Massachusetts Medical Society, United States (2011).
Cortes, J.J., et al., "Mutations in the Conserved Loop of Human U5 SnRNA generate Use of Novel Cryptic 5' Splice Sites In Vivo," The EMBO Journal 12(13):5181-5189, Wiley Blackwell, England (1993).
Cosman, D., et al., "ULBPS, Novel MHC Class I-Related Molecules, Bind to CMV Glycoprotein UL16 and Stimulate NK Cytotoxicity through the NKG2D Receptor," Immunity 14(2):123-133, Cell Press, United States (2001).
Coughlin, C.M. and Vonderheide, R.H., "Targeting Adult and Pediatric Cancers via Cell-Based Vaccines and the Prospect of Activated B Lymphocytes as a Novel Modality," Cancer Biology and Therapy 2(5):466-470, Taylor & Francis, United States (2003).
Cousens, L.P., et al., "Application of IgG-Derived Natural Treg Epitopes (Igg Tregitopes) to Antigen-Specific Tolerance Induction in a Murine Model of Type 1 Diabetes," Journal of Diabetes Research 2013:621693, Hindawi Publishing Corporation, Egypt (2013).
Cousens, L.P., et al., "In Vitro and In Vivo Studies of IgG-Derived Treg Epitopes (Tregitopes): A Promising New Tool for Tolerance Induction and Treatment of Autoimmunity," Journal of Clinical Immunology 33(Suppl. 1):S43-S49, Springer, Netherlands (2013).
Cousens, L.P., et al., "Tregitope Update: Mechanism of Action Parallels IVIg," Autoimmunity Reviews 12(3):436-443, Elsevier, Netherlands (2013).
Cowling, V.H., "Regulation of mRNA Cap Methylation," The Biochemical Journal 425(2):295-302, Portland Press on behalf of the Biochemical Society, England (2010).
Cox, G.J., et al., "Bovine Herpesvirus 1: immune Responses in Mice and Cattle Injected with Plasmid DNA," Journal of Virology 67(9):5664-5667, American Society for Microbiology, United States (1993).
Craig, J.M. and Bickmore, W.A., "The Distribution of CpG Islands in Mammalian Chromosomes," Nature Genetics 7(3):376-382, Nature Publishing Company, United States (1994).
Cramer, P., et al., "Functional Association between Promoter Structure and Transcript Alternative Splicing," Proceedings of the National Academy of Sciences USA 94(21):11456-11460, National Academy of Sciences, United States (1997).

(56) References Cited

OTHER PUBLICATIONS

Cree, B. et al., Tolerability and effects of rituxamab (anti CD20 antibody) in neuromyelitis optica (NMO) and rapidly worsening multiple sclerosis (MS). Neurology. 2004; 62(S5):A492.
Cribbs, D.H., et al., "Adjuvant-Dependent Modulation of TH1 and TH2 Responses to immunization with Beta-Amyloid," International Immunology 15(4):505-514, Oxford University Press, England (2003).
Crigler, John et al. Society Transactions, Society for Pediatric Research, 31st Annual Meeting, Atlantic City, Congenital Familial Nonhemolytic Jaundice with Kernicterus: A New Clinical Entity, 1951, 3rd session, no Vol. pp. 1-3.
Croft, M., et al., "TNF Superfamily in Inflammatory Disease: Translating Basic Insights," Trends in Immunology 33(3):144-152, Elsevier Science, England (2012).
Crowe, J.S., et al., "Humanized Monoclonal Antibody CAMPATH-1H: Myeloma Cell Expression of Genomic Constructs, Nucleotide Sequence of cDNA Constructs and Comparison of Effector Mechanisms of Myeloma and Chinese Hamster Ovary Cell-Derived Material," Clinical and Experimental Immunology 87(1):105-110, Blackwell Scientific Publications, England (1992).
Cu, Y., et al., "Enhanced Delivery and Potency of Self-Amplifying mRNA Vaccines by Electroporation in Situ," Vaccines 1(3):367-383, MDPI AG, Switzerland (2013).
Cuburu, N., et al., "Intravaginal Immunization with HPV Vectors Induces Tissue-Resident CD8+ T Cell Responses," The Journal of Clinical Investigation 122(12):4606-4620, American Society for Clinical Investigation, United States (2012).
Culver, K.W. et al., Gene Therapy, a Handbook for Physicians. Mary Ann Lieber, Inc, New York. 1994; 63-77.
Cun, D., et al., "Preparation and Characterization of Poly (DL-Lactide-Co-Glycolide) Nanoparticles for Sima Delivery," International Journal of Pharmaceutics 390(1):70-75, Elsevier/North-Holland Biomedical Press., Netherlands (2010).
Cunningham, S.C., et al., "AAV2/8-Mediated Correction of OTC Deficiency is Robust in Adult but not Neonatal Spf(ash) Mice," The Journal of the American Society of Gene Therapy 17(8):1340-1346, Academic Press, United States (2009).
Cystic Fibrosis Transmembrane Conductance Regulator; cystic fibrosis transmembrane conductance regulator [*Homo sapiens*]; NCBI, 2010, No Vol., pp. 1-5.
Daguer, J.P., et al., "Increasing the Stability of SacB Transcript Improves Levansucrase Production in Bacillus Subtilis," Letters in Applied Microbiology 41(2):221-226, Blackwell Scientific Publications, England (2005).
Dahlman, J.E., et al., "In Vivo Endothelial siRNA Delivery using Polymeric Nanoparticles with Low Molecular Weight," Nature Nanotechnology 9(8):648-655, Nature Publishing Group, England (2014).
Dai, M.S., et al., "Introduction of Human Erythropoietin Receptor Complementary DNA by Retrovirus-Mediated Gene Transfer into Murine Embryonic Stem Cells Enhances Erythropoiesis in Developing Embryoid Bodies," Biology of Blood and Marrow Transplantation 6(4):395-407, Carden Jennings Publishing, United States (2000).
Danke, N.A., et al., "Comparative Study of GAD65-Specific CD4+ T Cells in Healthy and Type 1 Diabetic Subjects," Journal of Autoimmunity 25(4):303-311, Academic Press, England (2005).
Daridon, Capucine et al., Epratuzumab Affects B Cells Trafficking in Systemic Lupus Erythematosus, Ann Rheum Dis, 2011, vol. 70, No #, pp. 1-2.
David McAuley, Pharm.D., Alzheimers Disease—Therapeutic agents, 2012, No Vol. #, pp. 1-3.
Davidson, E.H., An Analysis of Niu Menchang's Research on Transformation by RNA. Biotechnology in China, 1989, 92-102.
Davis, Dr., "Stabilization of RNA Stacking by Pseudouridine," Nucleic Acids Research 23(24):5020-5026, Oxford University Press, England (1995).
Davis, H.L., et al., "DNA-Based Immunization Induces Continuous Secretion of Hepatitis B Surface Antigen and High Levels of Circulating Antibody," Human Molecular Genetics 2(11):1847-1851, IRL Press at Oxford University Press, England (1993).
Davtyan, H., et al., "Immunogenicity, Efficacy, Safety, and Mechanism of Action of Epitope Vaccine (Lu AF20513) for Alzheimer's Disease: Prelude to a Clinical Trial," The Journal of Neuroscience 33(11):4923-4934, Society for Neuroscience, United States (2013).
De Carvalho, S., "Angiokines, Angiogenesis and Angiolymphoproliferative Syndromes (ALPS)," Angiology 34(4):231-243, Sage Publications, United States (1983).
De Carvalho, S., "Biologic Properties of Human Leukemic and Tumoral RNA. III. The Effect of Different Media on the Cytopathogenicitv in Tissue Culture," The Journal of Laboratory and Clinical Medicine 55:694-705, Elsevier, United States (1960).
De Carvalho, S., "Cancer 1974: An Analytical Vademecum of Oncologic Relevance," Oncology 28(4):289-298, Karger., Switzerland (1973).
De Carvalho, S., "Effect of RNA from Normal Human Bone Marrow on Leukaemic Marrow in vivo," Nature 197:1077-1080, Nature Publishing Group, England (1963).
De Carvalho, S., "Epigenetic Transformation by RNA from Human Neoplastic Cells," Oncology 27(1):3-29, Karger, Switzerland (1973).
De Carvalho, S., et al., "Differences in Information Ccontent of Ribonucleic Acids from Malignant Tissues and Homologous Organs as Expressed by their Biological Activities," Experimental and Molecular Pathology 1:96-103, Academic Press, United States (1962).
De Carvalho, S., "In vitro Angiogenic Activity of RNA from Leukemic Lymphocytes," Angiology 29(7):497-505, Sage Publications, United States (1978).
De Carvalho, S., "Natural History of Congenital Leukemia. An Experiment of Nature Revealing Unexplored Features of Fetal-maternal Isoimmunity, Longest Recorded Survival Following Use of Leukemostatic Maternal Isoantibody," Oncology 27(1):52-63, Karger, Switzerland (1973).
De Groot, A.S., et al., "Activation of natural regulatory T cells by IgG Fc-derived peptide "Tregitopes"," Blood 112(8):3303-3311, The American Society of Hematology, United States (2008).
De Lucca, F.L., et al., "Effect of the Calcium Phosphate-mediated RNA Uptake on the Transfer of Cellular Immunity of a Synthetic Peptide of HIV-1 to Human Lymphocytes by Exogenous RNA," Molecular and Cellular Biochemistry 228(1-2):9-14, Kluwer Academic, Netherlands (2001).
De Marco, D., et al., "A Non-VH1-69 Heterosubtypic Neutralizing Human Monoclonal Antibody Protects Mice against H1N1 and H5N1 Viruses," PLoS One 7(4):e34415, Public Library of Science, United States (2012).
Decarvalho, S., and Rand, H.J., "Comparative Effects of Liver and Tumour Ribonucleic Acids on the Normal Liver and the Novikoff Hepatoma Cells of the Rat," Nature 189:815-817, Nature Publishing Group, England (1961).
Decatur, W.A. And Fournier, M.J., "RNA-guided nucleotide modification of ribosomal and other RNAs.," The Journal of Biological Chemistry 278(2):695-698, American Society for Biochemistry and Molecular Biology, United States (2003).
Deering, R.P., "Nucleic Acid Vaccines: Prospects for Non-viral Delivery of mRNA Vaccines," Expert Opinion on Drug Delivery 11(6):885-899, Informa Healthcare, England (2014).
Delafontaine, P., et al., "Regulation of Vascular Smooth Muscle Cell Insulin-like Growth Factor I Receptors by Phosphorothioate Oligonucleotides. Effects on Cell Growth and Evidence that Sense Targeting at the ATG Site Increases Receptor Expression," The Journal of Biological Chemistry 270(24):14383-14388, American Society for Biochemistry and Molecular Biology, United States (1995).
Delehanty, J.B., et al., "Peptides for Specific Intracellular Delivery and Targeting of Nanoparticles: Implications for Developing Nanoparticle-mediated Drug Delivery," Therapeutic Delivery 1(3):411-433, Future Science, England (2010).
Department of Chemistry, University of Maine. 2008, Structure and Properties of Nucleosides and Nucleotides, p. 1-5.

(56) References Cited

OTHER PUBLICATIONS

Deres, K., et al., "In vivo Priming of Virus-specific Cytotoxic T Lymphocytes with Synthetic Lipopeptide Vaccine," Nature 342(6249):561-564, Nature Publishing Group, England (1989).
Desaulniers, J.P., et al., "Synthesis of 15N-enriched Pseudouridine Derivatives," Organic Letters 5(22):4093-4096, American Chemical Society, United States (2003).
Deshayes, S., et al., "Cell Penetrating Peptides: Tools for Intracellular Delivery of Therapeutics," Cellular and Molecular Life Sciences 62(16):1839-1849, Springer, Switzerland (2005).
Desrosiers, R., et al., "Identification of Methylated Nucleosides in Messenger RNA from Novikoff Hepatoma Cells," Proceedings of the National Academy of Sciences USA 71(10):3971-3975, National Academy of Sciences, United States (1974).
Devine, P.L., et al., "The Breast Tumor-associated Epitope Defined by Monoclonal Antibody 3E1.2 is an O-linked Mucin Carbohydrate Containing N-glycolylneuraminic Acid," Cancer Research 51(21):5826-5836, American Association for Cancer Research, United States (1991).
Dharap, S.S., et al., "Tumor-specific Targeting of an Anticancer Drug Delivery System by LHRH Peptide," Proceedings of the National Academy of Sciences USA 102(36):12962-12967, National Academy of Sciences, United States (2005).
Di Caro, V., et al., "In vivo Delivery of Nucleic Acid-formulated Microparticles as a Potential Tolerogenic Vaccine for Type 1 Diabetes," The Review of Diabetic Studies 9(4):348-356, Society for Biomedical Diabetes Research, Germany (2012).
Di Meglio, P., and Nestle, F.O., "The Role of IL-23 in the Immunopathogenesis of Psoriasis," F1000 biology reports 2(40):1-5, Faculty of 1000, England (2010).
Diebold, S.S., et al., "Innate Antiviral Responses by Means of TLR7-mediated Recognition of Single-stranded RNA," Science 303(5663):1529-1531, American Association for the Advancement of Science, United States (2004).
Dijoseph, J.F., et al., "Antibody-targeted Chemotherapy with CMC-544: A CD22-targeted Immunoconjugate of Calicheamicin for the Treatment of B-lymphoid Malignancies," Blood 103(5):1807-1814, American Society of Hematology, united States (2004).
Dimari, J.F., and Bechhofer, D.H., "Initiation of mRNA Decay in Bacillus Subtilis," Molecular Microbiology 7(5):705-717, Blackwell Scientific Publications, England (1993).
Ding, Z., et al., "State-of-the-art 2003 on PKU Gene Therapy," Molecular Genetics and Mmetabolism 81(1):3-8, Academic Press, United States (2004).
Dingman, W., and Sporn, M.B., "Molecular Theories of Memory," Science 144(3614):26-29, American Association for the Advancement of Science, United States (1964).
Disbrow, G.L., et al., "Codon Optimization of the HPV-16 E5 Gene Enhances Protein Expression," Virology 311(1):105-114, Academic Press., United States (2003).
Dodart, J.C., et al., "Immunization Reverses Memory Deficits without Reducing Brain Abeta Burden in Alzheimer's Disease Model," Nature Neuroscience 5(5):452-457, Nature Publishing Group, United States (2002).
Doffek, K., et al., "Phosphatidylserine Inhibits NFκB and p38 MAPK Activation in Human Monocyte Derived Dendritic Cells," Molecular Immunology 48(15-16):1771-1777, Pergamon Press, England (2011).
Dong, X.Y., et al., "Identification of Genes Differentially Expressed in Human Hepatocellular Carcinoma by a Modified Suppression Subtractive Hybridization Method," International Journal of Cancer 112(2):239-248, Wiley-Liss, United States (2004).
Dong, Y., and Feng, S.S., "Poly(d,l-lactide-co-glycolide)/montmorillonite Nanoparticles for Oral Delivery of Anticancer Drugs," Biomaterials 26(30):6068-6076, Elsevier Science, Netherlands (2005).
Donnelly, J., et al., "Technical and Regulatory Hurdles for DNA Vaccines," International Journal for Parasitology 33(5-6):457-467, Elsevier Science, England (2003).
Doody, R.S., et al., "Phase 3 Trials of Solanezumab for Mild-to-Moderate Alzheimer's Disease," The New England Journal of Medicine 370(4):311-321, Massachusetts Medical Society, United States (2014).
Dreyer, H.C., et al., "Leucine-enriched Essential Amino Acid and Carbohydrate Ingestion Following Resistance Exercise Enhances Mtor Signaling and Protein Synthesis in Human Muscle," American Journal of Physiology. Endocrinology and Metabolism 294(2):E392-400, American Physiological Society, United States (2008).
Du, H., et al., "Lysosomal Acid Lipase Deficiency: Correction of Lipid Storage by Adenovirus-mediated Gene Transfer in Mice," Human Gene Therapy 13(11):1361-1372, M.A. Liebert, United States (2002).
Du, L., et al., "Arginine-rich Cell-penetrating Peptide Dramatically Enhances Amo-mediated Atm Aberrant Splicing Correction and Enables Delivery to Brain and Cerebellum," Human Molecular Genetics 20(16):3151-3160, IRL Press, England (2011).
Dubes, G.R. and Klingler, E.A. Jr., "Facilitation of Infection of Monkey Cells with Poliovirus "Ribonucleic Acid"," Science 133(3446):99-100, American Association for the Advancement of Science, United States (1961).
Dumont, J.A., et al., "Prolonged Activity of a Recombinant Factor VIII-Fc Fusion Protein in Hemophilia A Mice and Dogs," Blood 119(13):3024-3030, The American Society of Hematology, United States (2012).
Dunham, S.P., "The Application of Nucleic Acid Vaccines in Veterinary Medicine," Research in Veterinary Science 73(1):9-16, British Veterinary Association, England (2002).
Dunn, J.J., et al., "Different Template Specificities of Phage T3 and T7 RNA Polymerases," Nature: New Biology 230(11):94-96, Macmillan Journals, England (1971).
Duret, L., and Mouchiroud, D., "Expression Pattern and, Surprisingly, Gene Length Shape Codon Usage in Caenorhabditis, *Drosophila*, and *Arabidopsis*," Proceedings of the National Academy of Sciences of the United States of America 96(8):4482-4487, National Academy of Sciences, United States (1999).
Duret, L., "Evolution of Synonymous Codon Usage in Metazoans.," Current Opinion in Genetics & Development 12(6):640-649, Elsevier, England (2002).
Earl, R.A., et al., "A Chemical Synthesis of the Nucleoside 1-methylpseudouridine," Journal of Heterocyclic Chemistry 14(4):699-700 (1977).
Easton, L.E., et al., "Rapid, Nondenaturing Rna Purification Using Weak Anion-exchange Fast Performance Liquid Chromatography," RNA 16(3):647-653, Cold Spring Harbor Laboratory Press, United States (2010).
Ebel, W., et al., "Preclinical Evaluation of MORAb-003, a Humanized Monoclonal Antibody Antagonizing Folate Receptor-Alpha," Cancer Immunity 7:6, Cancer Research Institute, United States (2007).
Ebert, A.D., et al., "Induced Pluripotent Stem Cells from a Spinal Muscular Atrophy Patient," Nature 457(7227):277-280, Nature Publishing Group, England (2009).
Ebert, M.S., et al., "Microrna Sponges: Competitive Inhibitors of Small Rnas in Mammalian Cells," Nature Methods 4(9):721-726, Nature Publishing Group, England (2007).
Eberwine, J. et al., "Analysis of Gene Expression in Single Live Neurons," Proceedings of the National Academy of Sciences of the United States of America 89(7):3010-3014, National Academy of Sciences, United States (1992).
Edelheit, S. et al., "Transcriptome-wide Mapping of 5-methylcytidine Rna Modifications in Bacteria, Archaea, and Yeast Reveals M5c Within Archaeal Mrnas," PLoS Genetics 9(6):e1003602, Public Library of Science, United States (2013).
Edelstein, M. L., et al., "Gene Therapy Clinical Trials Worldwide 1989-2004—an Overview," The Journal of Gene Medicine 6(6):597-602, John Wiley & Sons, England (2004).
Edery, I., et al., "An Efficient Strategy to Isolate Full-Length CDNAs Based on an MRNA Cap Retention Procedure (CAPture)," Molecular and Cellular Biology 15(6):3363-3371, American Society for Microbiology, United States (1995).

(56) References Cited

OTHER PUBLICATIONS

Edmonds, M., "Polyadenylate Polymerases," Methods in Enzymology 181:161-170, Academic Press, United States (1990).
Egeter, O., et al., "Eradication of Disseminated Lymphomas with Cpg-dna Activated T Helper Type 1 Cells from Nontransgenic Mice," Cancer Research 60(6):1515-1520, American Association for Cancer Research, United States (2000).
Eisen, T., et al., "Naptumomab Estafenatox: Targeted Immunotherapy with a Novel Immunotoxin," Current Oncology Reports 16(2):370, Current Science, United States (2014).
El Ouahabi, A., et al., "Double Long-chain Amidine Liposome-mediated Self Replicating Rna Transfection," FEBS Letters 380(1-2):108-112, John Wiley & Sons Ltd, England (1996).
Elango, N., et al., "Optimized Transfection of Mrna Transcribed From A D(a/t)100 Tail-containing Vector," Biochemical and Biophysical Research Communications 330(3):958-966, Academic Press, United States (2005).
Elbashir, S.M., et al., Duplexes of 21-nucleotide RNAs mediate RNA interference in cultured mammalian cells, Nature 411(6836):494-498, Nature Publishing Group, United States (2001).
Eli Lilly and Company, A Study in Second Line Metastatic Colorectal Cancer, ClinicalTrials.gov , Apr. 2, 2014, http://clinicaltrials.govict2/show/NCT011837807term=ramucirumab &rank=20&submit_fld_opt., pp. 1-4.
Eli Lilly and Company, A Study of Chemotherapy and Ramucirumab vs. Chemotherapy Alone in Second Line Nonsmall Cell Lung Cancer Participants Who Received Prior First Line Platinum Based Chemotherapy, ClinicalTrials.gov , Apr. 2, 2014, http://clinicaltrials.gov.
Eli Lilly and Company, A Study of Paclitaxel With or Without Ramucirumab in Metastatic Gastric Adenocarcinoma, ClinicalTrials.gov, Apr. 2, 2014, http://clinicaltrials.govict2/show/NCT01170663? term=rannucirumab&rank=5&submit_fid_opt, pp. 1-4.
Eli Lilly and Company, A Study of Ramucirumab (IMC-1121B) Drug Product (DP) and Best Supportive Care (BSC) Versus Placebo and BSC as 2nd-Line Treatment in Patients With Hepatocellular Carcinoma After 1st-Line Therapy With Sorafenib (REACH), ClinicalTrials.
Eli Lilly and Company, Clinical Trial of Solanezumab for Older Individuals Who May be at Risk for Memory Loss (A4), ClinicalTrials.gov, Apr. 2, 2014, http://clinicaltrials.govict2/show/NCT02008357, pp. 1-3.
Eli Lilly and Company, Progress of Mild Alzheimer's Disease in Participants on Solanezumab Versus Placebo (EXPEDITION 3), ClinicalTrials.gov, Apr. 2, 2014, http://clinicaltrials.govict2/show/NCT01900665, pp. 1-3.
Eli Lilly and Company, ReoPRo, Abciximab, Product Label, 2005, No volume number, pp. 1-4.
Ellem., K.A. and Colter., J.S., "The Interaction of Infections Ribonucleic Acid with a Mammalian Cell Line. I. Relationship Between the Osmotic Pressure of the Medium and the Production of Infectious Centers," Virology 11:434-443, Academic Press, United States (1960).
Ellem., K.A. and Colter., J.S., "The Interaction of Infectious Ribonucleic Acid with a Mammalian Cell Line. II. Kinetics of the Formation of Infectious Centers," Virology 12:511-520, Academic Press, United States (1960).
Ellem., K.A. and Colter., J.S., "The Intzraction of Infectious Ribonucleic Acids with Mammalian Cells. III. Comparison of Infection and Rna Uptake in the Hela Cell-polio Rna and L Cell-mengo Rna Systems," Virology 15:113-126, Academic Press, United States (1961).
Ellem., K.A. and Colter., J.S., "The Isolation of Three Variants of Mengo Virus Differing in Plaque Morphology and Hemagglutinating Characteristics," Virology 15:340-347, Academic Press, United States (1961).
Ellis, S.G., et al., "Safety and Antiplatelet Effect of Murine Monoclonal Antibody 7e3 Fab Directed Against Platelet Glycoprotein lib/iiia in Patients Undergoing Elective Coronary Angioplasty," Coronary Artery Disease 4(2):167-175, Lippincott Williams & Wilkins, England (1993).
El-Sagheer, A.H., and Brown, T., "Click Nucleic Acid Ligation: Applications in Biology and Nanotechnology," Accounts of Chemical Research 45(8):1258-1267, American Chemical Society, United States (2012).
EMEA, Committee for Medicinal Products for Human Use, European Medicines Agency, 2008, No Vol. pp. 1-13.
Endo, F., et al., "A Nonsense Mutation in the 4-hydroxyphenylpyruvic Acid Dioxygenase Gene (hpd) Causes Skipping of the Constitutive Exon and Hypertyrosinemia in Mouse Strain III," Genomics 25(1):164-169, Academic Press, United States (1995).
EP11830061, Supplementary Search Report, dated Mar. 18, 2014.
Epicentre Forum. Tools and Techniques for Genomics and RNA Research. 2006; 13(2): 1-8.
Epicentre Forum. Tools and Techniques for Genomics and RNA Research. 2007; 14(1): 1-24.
Erlandsson, E., et al., "Identification of the Antigenic Epitopes in Staphylococcal Enterotoxins A and E and Design of a Superantigen for Human Cancer Therapy," Journal of Molecular Biology 333(5):893-905, Elsevier, England (2003).
Esposito, S., "Effect on Leukaemic Cells of Ribonucleic Acid Extracted from Calf's Spleen," Nature 203:1078-1079, Nature Publishing Group, England (1964).
Esvelt, K.M., et al., "A System for the Continuous Directed Evolution of Biomolecules," Nature 472(7344):499-503, Nature Publishing Group, England (2011).
European Public Assessment Report (EPAR), Removab, European Medicines Agency, 2009, No Vol. # pp. 1-2.
European Supplementary Search Report, EP11815407, dated Jun. 13, 2014, pp. 1-13.
Evel-Kabler, K., et al., "Socs1 Restricts Dendritic Cells' Ability to Break Self Tolerance and Induce Antitumor Immunity by Regulating II-12 Production and Signaling," The Journal of Clinical Investigation 116(1):90-100, American Society for Clinical Investigation, United States (2006).
Ezzat, K., et al., "Pepfect 14, a Novel Cell-penetrating Peptide for Oligonucleotide Delivery in Solution and as Solid Formulation," Nucleic Acids Research 39(12):5284-5298, Oxford University Press, England (2011).
Fahy, E., et al., "Self-sustained Sequence Replication (3sr): An Isothermal Transcription-based Amplification System Alternative to Pcr," PCR Methods and Applications 1(1):25-33, Cold Spring Harbor Laboratory Press, United States (1991).
Faissner, A., et al., "Analysis of Polypeptides of the Tree Shrew (tupaia) Herpesvirus by Gel Electrophoresis," The Journal of General Virology 58Pt1:139-148, Microbiology Society, England (1982).
Falugi, F., et al., "Role of Protein A in the Evasion of Host Adaptive Immune Responses by *Staphylococcus aureus*," MBio 4(5):e00575-13, American Society for Microbiology, England (2013).
Fan, X.C., and Steitz J.A., et al., "Overexpression of Hur, a Nuclear-cytoplasmic Shuttling Protein, Increases the in Vivo Stability of Are-containing Mrnas," The EMBO Journal 17(12):3448-3460, Wiley Blackwell, England (1998).
Fandrich, F., et al., "Preimplantation-stage Stem Cells Induce Long-term Allogeneic Graft Acceptance Without Supplementary Host Conditioning," Nature Medicine 8(2):171-178, Nature Publishing Company, United States (2002).
Fang, S.H., et al., "Functional Measurement of Hepatitis C Virus Core-specific Cd8(+) T-cell Responses in the Livers or Peripheral Blood of Patients by Using Autologous Peripheral Blood Mononuclear Cells as Targets or Stimulators," Journal of Clinical Microbiology 39(11):3895-3901, Journal of Clinical Microbiology, United States (2001).
Fang, S.L., et al., "A Novel Cell-penetrating Peptide Derived from Human Eosinophil Cationic Protein," PloS one 8(3):e57318, Public Library of Science, United States (2013).

(56) References Cited

OTHER PUBLICATIONS

Fattori, E., et al., "Gene Electro-transfer of an Improved Erythropoietin Plasmid in Mice and Non-human Primates," The Journal of Gene Medicine 7(2):228-236, John Wiley & Sons, England (2005).
FDA Guide, Herceptin (trastuzumab), Highlights of Prescribing Information, 2010, Genentech, Inc., pp. 1-33.
FDA Guide, Tysabri, Elan Pharmaceuticals, Inc., Reference ID: 3308057, Biogen Idec, Inc. 2013, No Volume #, pp. 1-6.
FDA, Highlights of Prescribing Information Lucentis(ranibizumab injection), Genentech, Inc., 2006, No Vol., pp. 1-9.
FDA Label, Actemra (tocilizumab) , Risk Evaluation and Mitigation Strategy (REMS) 2013, Genentech, Inc., Reference ID: 3394610, No Vol. #, pp. 1-53.
FDA Label, Arzerra, Prescribing Info, 2009, GlaxoSmithKline, No. Vol, pp. 1-13.
FDA Label, Bexxar, Tositumomab and Iodine I 131 Tositumomab 2003, Corixa Corp. and GlaxoSmithKline, No Vol #, pp. 1-49.
FDA Label, Ibritumomab Tiuxetan, Zevalin, 2001, IDEC Pharmaceuticals Corporation, No Vol. pp. 1-38.
FDA Label, Rituxan, Rituximab, IDEC Pharmaceuticals Corporation and Genetech, Inc., No Vol #, pp. 1-2.
FDA Label—Synagiso (Palivizumab)—1999, MedImmune, Inc., No. Vol. pp. 1-7.
FDA Label—VectibixO (panitumumab), Amgen Inc., 2006-2008, No Vol. , pp. 1-13.
FDA, Medication Guide Xolair, (omalizumab), 2013, No Vol. pp. 1-2.
Feagan, B.G., et al. "Vedolizumab as Induction and Maintenance Therapy for Ulcerative Colitis," The New England Journal of Medicine 369(8):699-710, Massachusetts Medical Society, United States (2013).
Fearnley, D.B., et al., "Monitoring Human Blood Dendritic Cell Numbers in Normal Individuals and in Stem Cell Transplantation," Blood 93(2):728-736, American Society of Hematology, United States (1999).
Felden, B., et al., "Presence and Location of Modified Nucleotides in *Escherichia coli* Tmrna: Structural Mimicry with Trna Acceptor Branches," The EMBO Journal 17(11):3188-3196, Wiley Blackwell, England (1998).
Felgner, P.L. Cationic lipid/polynucleotide condensates for in vitro and in vivo polynucleotide delivery—the cytofectins. J. of Liposome Research. 1993; 3(1): 3-16.
Felgner, P.L., et al., "Lipofection: A Highly Efficient, Lipid-mediated Dna-transfection Procedure," Proceedings of the National Academy of Sciences of the United States of America 84(21):7413-7417, National Academy of Sciences, United States (1987).
Felgner, P.L. Particulate systems and polymers for in vitro and in vivo delivery of polynucleotides. Adv. Drug Delivery Rev. 1990; 5(3): 163-187.
Fellner, C., et al., "Ipilimumab (yervoy) Prolongs Survival in Advanced Melanoma: Serious Side Effects and a Hefty Price Tag May Limit Its Use," P & T : A Peer-reviewed Journal for Formulary Management 37(9):503-530, MediMedia, United States (2012).
Feng, R., et al., "Pu.1 and C/ebpalpha/beta Convert Fibroblasts into Macrophage-like Cells," Proceedings of the National Academy of Sciences of the United States of America 105(16):6057-6062, National Academy of Sciences, United States (2008).
Fernandez, I.S., et al., "Unusual Base Pairing During the Decoding of a Stop Codon by the Ribosome," Nature 500(7460):107-110, Nature Publishing Group, England (2013).
Ferrara, C., et al., "Unique Carbohydrate-carbohydrate Interactions are Required for High Affinity Binding Between Fcgammariii and Antibodies Lacking Core Fucose," Proceedings of the National Academy of Sciences of the United States of America 108(31):12669-12674, National Academy of Sciences, United States (2011).
Ferrara, J.L., et al., "Graft-versus-host Disease," Lancet 373(9674):1550-1561, Elsevier, England (2009).
Ficz, G., et al., "Dynamic Regulation of 5-hydroxymethylcytosine in Mouse Es Cells and During Differentiation," Nature 473(7347):398-402, Nature Publishing Group, England (2011).
Figini, M., et al., "Reversion of Transformed Phenotype in Ovarian Cancer Cells by Intracellular Expression of Anti Folate Receptor Antibodies," Gene Therapy 10(12):1018-1025, Nature Publishing Group, England (2003).
Finn, J.D., et al., "Eradication of Neutralizing Antibodies to Factor VIII in Canine Hemophilia A After Liver Gene Therapy," Blood 116(26):5842-5848, American Society of Hematology, United States (2010).
Fisch, P., et al., "Generation of Antigen-presenting Cells for Soluble Protein Antigens Ex Vivo from Peripheral Blood Cd34+ Hematopoietic Progenitor Cells in Cancer Patients," European Journal of Immunology 26(3):595-600, Wiley-VCH, Germany (1996).
Fisher, K.J. and Wilson, J.M., "The Transmembrane Domain of Diphtheria Toxin Improves Molecular Conjugate Gene Transfer," The Biochemical Journal 321(Pt1):49-58, Published by Portland Press on behalf of the Biochemical Society, England (1997).
Fishman, M., et al., "In Vitro Transfer of Macrophage Rna to Lymph Node Cells," Nature 198:549-551, Nature Publishing Group, England (1963).
Fisk, B., et al., "Identification of an Immunodominant Peptide of Her-2/neu Protooncogene Recognized by Ovarian Tumor-specific Cytotoxic T Lymphocyte Lines," The Journal of Experimental Medicine 181(6):2109-2117, Rockefeller University Press, United States (1995).
Forsberg, G., et al., "Naptumomab Estafenatox, an Engineered Antibody-superantigen Fusion Protein with Low Toxicity and Reduced Antigenicity," Journal of immunotherapy 33(5):492-499, Rockefeller University Press, United States (2010).
Forsberg, G., et al., "Therapy of Human Non-small-cell Lung Carcinoma Using Antibody Targeting of a Modified Superantigen," British Journal of Cancer 85(1):129-136, Nature Publishing Group on Behalf of Cancer Research UK, England (2001).
Francisco, J.A., et al., "Cac10-vcmmae, an Anti-cd30-monomethyl Auristatin E Conjugate with Potent and Selective Antitumor Activity," Blood 102(4):1458-1465, American Society of Hematology, United States (2003).
Frank, B., et al., "Interanimal "Memory" Transfer: Results from Brain and Liver Homogenates," Science 169(3943):399-402, American Association for the Advancement of Science (1970).
Franklin, R.M., et al., "Purification and Properties of the Replicative Intermediate of the Rna Bacteriophage R17," Proceedings of the National Academy of Sciences of the United States of America 55(6):1504-1511, National Academy of Sciences, United States (1966).
Freeman, W.M., et al., "Quantitative Rt-pcr: Pitfalls and Potential," BioTechniques 26(1):112-122, 124-125, Informs Healthcare USA Inc, England (1999).
Freudenberg., J.M., et al., "Acute Depletion of Tet1-dependent 5-hydroxymethylcytosine Levels Impairs Lif/stat3 Signaling and Results in Loss of Embryonic Stem Cell Identity," Nucleic Acids research 40(8):3364-3377, Oxford University Press, England (2012).
Frey, M.R., and Matera, A.G., "Rna-Mediated Interaction of Cajal Bodies and U2 Snrna Genes," The Journal of Cell Biology 154(3):499-509, Rockefeller University Press, United States (2001).
Friese, M.A., et al., "Mica/nkg2d-mediated Immunogene Therapy of Experimental Gliomas," Cancer Research 63(24):8996-9006, American Association for Cancer Research, United States (2003).
Fuke, H., and Ohno M., "Role of Poly (a) Tail as an Identity Element for Mrna Nuclear Export," Nucleic Acids Research 36(3):1037-1049, Oxford University Press, England (2008).
Fukuda, I., et al., "In Vitro Evolution of Single-chain Antibodies Using Mrna Display," Nucleic Acids Research 34(19):e127, Oxford University Press, England (2006).
Furie, R., et al., "A Phase Iii, Randomized, Placebo-controlled Study of Belimumab, a Monoclonal Antibody That Inhibits B Lymphocyte Stimulator, in Patients with Systemic Lupus Erythematosus," Arthritis and Rheumatism 63(12):3918-3930, Wiley-Blackwell, United States (2011).

(56) References Cited

OTHER PUBLICATIONS

Fusaki, N., et al., "Efficient Induction of Transgene-free Human Pluripotent Stem Cells Using a Vector Based on Sendai Virus, an Rna Virus that Does Not Integrate into the Host Genome," Proceedings of the Japan Academy. Series B, Physical and Biological Sciences 85(8):348-362, Japan Academy, Japan (2009).
Fynan, E.F., et al., "Dna Vaccines: Protective Immunizations by Parenteral, Mucosal, and Gene-gun Inoculations," Proceedings of the National Academy of Sciences of the United States of America 90(24):11478-11482, National Academy of Sciences, United States (1993).
Gall, J.G., "A Role for Cajal Bodies in Assembly of the Nuclear Transcription Machinery," FEBS letters 498(2-3):164-167, John Wiley & Sons Ltd, England (2001).
Gall, J.G., "The Centennial of the Cajal Body," Nature Reviews. Molecular Cell Biology 4(12):975-980, Nature Publishing Group, England (2003).
Gallie, D.R., "A Tale of Two Termini: a Functional Interaction Between the Termini of an Mrna is a Prerequisite for Efficient Translation Initiation," Gene 216(1):1-11, Elsevier/North-Holland, Netherlands (1998).
Gallie, D.R., "The 5'-leader of Tobacco Mosaic Virus Promotes Translation Through Enhanced Recruitment of Eif4f," Nucleic Acids Research 30(15):3401-3411, Oxford University Press, England (2002).
Gallie, D.R., "The Cap and Poly(a) Tail Function Synergistically to Regulate Mrna Translational Efficiency," Genes & Development 5(11):2108-2116, Cold Spring Harbor Laboratory Press, United States (1991).
Ganot, P., et al., "Site-specific Pseudouridine Formation in Preribosomal Rna is Guided by Small Nucleolar Rnas," Cell 89(5):799-809, Cell Press, United States (1997).
Gao, G., et al., "Erythropoietin Gene Therapy Leads to Autoimmune Anemia in Macaques," Blood 103(9):3300-3302, American Society of Hematology, United States (2004).
Gao, M., et al., "A Novel Mma-decapping Activity in Hela Cytoplasmic Extracts is Regulated by Au-rich Elements," The EMBO Journal 20(5):1134-1143, Wiley Blackwell, England (2001).
Gao, X., et al., "Nonviral Gene Delivery: What we Know and what is Next," The AAPS Journal 9(1):E92-104, American Association of Pharmaceutical Scientists, United States (2007).
Garbe, C. and Orfanos, C.E., "Epidemiology of Malignant Melanoma in West Germany in an International Comparison," Onkologie 12(6):253-262, Karger, Switzerland (1989).
Garber, D.W., et al., "A Sensitive and Convenient Method for Lipoprotein Profile Analysis of Individual Mouse Plasma Samples," Journal of Lipid Research 41(6):1020-1026, American Society for Biochemistry and Molecular Biology, United States (2000).
Garcia, Gilles et al., Anti-interleukin-5 Therapy in Serve Asthma, Rare Diseases and Orphan Drugs, 2013, vol. 22, No. #, pp. 251-257.
Garcia, Maria et al., Patient Consideration in the Management of Rheumatoid Arthritis: Role of Once-A-Month Golimumab Injection, Clinical Medical Insights: Therapeutics, Libertas Academica, 2011, vol. 3, No #, pp. 415-423.
Gardiner-Garden, M. and Frommer, M., "CpG Islands in Vertebrate Genomes," Journal of Molecular Biology 196(2):261-282, Elsevier, England (1987).
Garin-Chesa, P., et al., "Trophoblast and Ovarian Cancer Antigen Lk26. Sensitivity and Specificity in Immunopathology and Molecular Identification as a Folate-binding Protein," The American Journal of Pathology 142(2):557-567, Elsevier, United States (1993).
Gasche C., et al., "Sequential Treatment of Anemia in Ulcerative Colitis with Intravenous Iron and Erythropoietin," Digestion 60(3):262-267, Karger, Switzerland (1999).
Geijtenbeek, T.B., et al., "Identification of Dc-sign, a Novel Dendritic Cell-specific Icam-3 Receptor that Supports Primary Immune Responses," Cell 100(5):575-585, Cell Press, United States (2000).
Genbank: *Homo sapiens* 15 kDa Selenoprotein (September 15), Transcript Variant 1, mRNA. NCBI Reference Sequence: NM_004261.3, pp. 1-4.
Genbank NP_000651.3, Transforming Growth Factor Beta-1 Precursor [*Homo sapiens*], Nov. 13, 2011; online.
Genentech, A Study of the Efficacy and Safety of Ocrelizumab in Patients with Relapsing-Remitting Multiple Sclerosis, ClinicalTrials.gov, Apr. 1, 2014, http://clinicaltrials.govict2/show/NCT00676715, pp. 1-3.
Genovese, M.C., et al., "A Phase 2 Dose-ranging Study of Subcutaneous Tabalumab for the Treatment of Patients with Active Rheumatoid Arthritis and an Inadequate Response to Methotrexate," Annals of the Rheumatic Diseases 72(9):1453-1460, BMJ, England (2013).
Genovese, M.C., et al., "Efficacy and Safety of Secukinumab in Patients with Rheumatoid Arthritis: A Phase Ii, Dose-finding, Double-blind, Randomised, Placebo Controlled Study," Annals of the Rheumatic Diseases 72(6):863-869, BMJ, England (2013).
Genovese, M.C., et al., "Ocrelizumab, a Humanized Anti-cd20 Monoclonal Antibody, in the Treatment of Patients with Rheumatoid Arthritis: a Phase I/ii Randomized, Blinded, Placebo-controlled, Dose-ranging Study," Arthritis and Rheumatism 58(9):2652-2661, Wiley-Blackwell, United States (2008).
Gerbi, S.A. and Lange, T.S., "All Small Nuclear Rnas (snrnas) of the [u4/u6.u5] Tri-snrnp Localize to Nucleoli; Identification of the Nucleolar Localization Element of U6 Snrna," Molecular Biology of the Cell 13(9):3123-3137, American Society for Cell Biology, United States (2002).
Gershon, P.D., "(A)-tail of Two Polymerase Structures," Nature Structural Biology 7(10):819-821, Nature Publishing Group, United States (2000).
Gevaert, P., et al., "Mepolizumab, a Humanized Anti-il-5 Mab, as a Treatment Option for Severe Nasal Polyposis," The Journal of Allergy and Clinical Immunology 128(5):989-995.e1-8, Mosby, United States (2011).
Gevokizumab, Statement on a Nonproprietary Name Adopted by the Usan Council, No Year No Volume p. 1.
Ghazi, A., et al., "Benralizumab—a Humanized Mab to Il-5rα with Enhanced Antibody-dependent Cell-mediated Cytotoxicity—a Novel Approach for the Treatment of Asthma," Expert Opinion on Biological Therapy 12(1):113-118, Taylor & Francis, England (2012).
Giblin, M.F., et al., "Selective Targeting of *E. coli* Heat-stable Enterotoxin Analogs to Human Colon Cancer Cells," Anticancer Research 26(5A):3243-3251, International Institute of Anticancer Research, Greece (2006).
Gibson, D.G., et al., "Chemical Synthesis of the Mouse Mitochondrial Genome," Nature Methods 7(11):901-903, Nature Publishing Group, United States (2010).
Gibson, D.G., et al., "Creation of a Bacterial Cell Controlled by a Chemically Synthesized Genome," Science 329(5987):52-56, American Association for the Advancement of Science, United States (2010).
Gierer, A. and Schramm, G., "Infectivity of Ribonucleic Acid from Tobacco Mosaic Virus," Nature 177(4511):702-703, Nature Publishing Group, England (1956).
Gilboa, E. and Vieweg, J., "Cancer Immunotherapy with Mrna-transfected Dendritic Cells," Immunological Reviews 199:251-263, Blackwell, England (2004).
Giljohann, D.A., et al., "Gene Regulation with Polyvalent Sirna-nanoparticle Conjugates," Journal of the American Chemical Society 131(6):2072-2073, American Chemical Society, United States (2009).
Gilkeson, G.S., et al., "Induction of Cross-reactive Anti-dsdna Antibodies in Preautoimmune Nzb/nzw Mice by Immunization with Bacterial Dna," The Journal of Clinical Investigation 95(3):1398-1402, American Society for Clinical Investigation, United States (1995).
Gillies, S.D., et al., "Antibody-targeted Interleukin 2 Stimulates T-cell Killing of Autologous Tumor Cells," Proceedings of the National Academy of Sciences of the United States of America 89(4):1428-1432, National Academy of Sciences, United States (1992).

(56) References Cited

OTHER PUBLICATIONS

Gillies, S.D., et al., "Expression of Human Anti-Tetanus Toxoid Antibody in Transfected Murine Myeloma Cells," Journal of Biotechnology 7:799-804, Nature Publishing Company (1989).
Ginsberg, S.D., et al., "Predominance of Neuronal MRNAs in Individual Alzheimer's Disease Senile Plaques," Annals of Neurology 45(2):174-181, Wiley-Liss, United States (1999).
Glucosylceramidase, Glucosylceramidase Isoform Iprecursor [*Homo sapiens*]; NCBI, 2010, No Vol., pp. 1-4.
Goel, N. and Stephens, S., "Certolizumab Pegol," MAbs 2(2):137-147, Taylor & Francis, United States (2010).
Golatowski, C., et al., "Comparative Evaluation of Saliva Collection Methods for Proteome Analysis," International Journal of Clinical Chemistry 419:42-46,Elsevier., Netherlands (2013).
Goldberg, I.H. and Rabinowitz, M., "The Incorporation of 5-Ribosyluracil Triphosphate into Rna in Nuclear Extracts of Mammalian Cells," Biochemical and Biophysical Research Communications 6:394-398, Academic Press, United States (1961).
Goldstein, J.L. and Brown, M.S., "The LDL Receptor," Arteriosclerosis, Thrombosis, and Vascular Biology 29(4):431-438, Lippincott Williams &lNilkins, United States (2009).
Goldstein, N.I., et al., "Biological Efficacy of a Chimeric Antibody to the Epidermal Growth Factor Receptor in a Human Tumor Xenograft Model," Clinical Cancer Research 1(11):1311-1318, Denville, United States (1995).
Golimumbab—Product Label—Janssen Biotech, Inc., 2013, No Volume number, pp. 1-19.
Gomes, A.Q., et al., "Non-Classical Major Histocompatibility Complex Proteins as Determinants of Tumour Immunosurveillance," EMBO Reports 8(11):1024-1030, Wiley Blackwell, London (2007).
Gonzalez, F., et al., "Generation of Mouse-Induced Pluripotent Stem Cells by Transient Expression of a Single Nonviral Polycistronic Vector," Proceedings of the National Academy of Sciences of the United States of America 106(22):8918-8922, National Academy of Sciences, United States (2009).
Goodchild, J., "Conjugates of Oligonucleotides and Modified Oligonucleotides: A Review of Their Synthesis and Properties," Bioconjugate Chemistry 1(3):165-187, American Chemical Society, United States (1990).
Gordon, F.H., et al., "A Pilot Study of Treatment of Active Ulcerative Colitis with Natalizumab, a Humanized Monoclonal Antibody to Alpha-4 Integrin," Alimentary Pharmacology & Therapeutics 16(4):699-705, Oxford : Wiley-Blackwell (England) (2002).
Gordon, S.N., et al., "Targeting the vaginal mucosa with human papillomavirus pseudovirion vaccines delivering simian immunodeficiency virus DNA," Journal of Immunology 188(2):714-723, American Association of Immunologists, United States (2012).
Grabbe, S., "Dendritic Cells as Initiators of Tumor Immune Responses: A Possible Strategy for Tumor Immunotherapy?," Immunology Today 16(3):117-121, Elsevier Science Publishers, England (1995).
Grabbe, S., et al., "Tumor Antigen Presentation by Epidermal Antigen-Presenting Cells in the Mouse: Modulation by Granulocyte-Macrophage Colony-Stimulating Factor, Tumor Necrosis Factor Alpha, and Ultraviolet Radiation," Journal of Leukocyte Biology 52(2):209-217, Society for Leukocyte Biology, United States (1992).
Grabbe, S., et al., "Tumor Antigen Presentation by Murine Epidermal Cells," Journal of immunology 146(10):3656-3661, American Association of Immunologists, United States (1991).
Graf, M., et al., "Codon-Optimized Genes that Enable Increased Heterologous Expression in Mammalian Cells and Elicit Efficient Immune Responses in Mice after Vaccination of Naked DNA," Methods in Molecular Medicine 94:197-210, Humana Press, United States (2004).
Graf, T. And Enver, T., "Forcing Cells to Change Lineages," Nature 462(7273):587-594, Nature Publishing Group, England (2009).
Graham, F.L. and Van Der Eb, J., "A New Technique for the Assay of Infectivity of Human Adenovirus 5 DNA," Virology 52(2):456-467, Academic Press, United States (1973).
Graham, F.L. and Vandereb, A.J., "A New Technique for the Assay of Infectivity of Human Adenovirus 5 DNA," Virology 52(2):456-467, Academic Press, United States (1973).
Gram, G.J., et al., "Immunological Analysis of a Lactococcus Lactis-Based DNA Vaccine Expressing HIV gp120," Genetic Vaccines and Therapy 5:3, BioMed Central, England (2007).
Granstein, R.D., et al., "Induction of Anti-Tumor Immunity with Epidermal Cells Pulsed with Tumor-Derived RNA or Intradermal Administration of RNA," The Journal of Investigative Dermatology 114(4):632-636, Elsevier, United States (2000).
Grant, R.W. and Dixit,V.D., "Mechanisms of Disease: Inflammasome Activation and the Development of Type 2 Diabetes," Frontiers in Immunology 4:50, Lausanne, Switzerland (2013).
Greenblatt, M.S., et al., "Mutations in the P53 Tumor Suppressor Gene: Clues to Cancer Etiology and Molecular Pathogenesis," Cancer Research 54(18):4855-4878, American Association for Cancer Research, United States (1994).
Greenfeder, S., et al., "Th2 Cytokines and Asthma. The Role of interleukin-5 in Allergic Eosinophilic Disease," Respiratory Research 2(2):71-79, BioMed Central Ltd, England (2001).
Grentzmann, G., et al., "A Dual-Luciferase Reporter System for Studying Recoding Signals," RNA 4(4):479-486, Cold Spring Harbor Laboratory Press, United States (1998).
Grunig, G., et al., "Interleukin 13 and the Evolution of Asthma Therapy," American Journal of Clinical and Experimental Immunology 1(1):20-27, E-Century Publishing Corporation, United States (2012).
Grunwald, V. and Hidalgo, M., "Developing Inhibitors of the Epidermal Growth Factor Receptor for Cancer Treatment," Journal of the National Cancer Institute 95(12):851-867, Oxford University Press, United States (2003).
Grosjean, H., DNA and RNA Modification Enzymes Structure, Mechanisms, Functions and Evolution. Molecular Biology Intelligence Unit. Estimated Publication Date: May 2009. pp. 1-2.
Grosjean, H., et al. Fine-Tuning of RNA Functions by Modification and Editing. Topics in Current Genetics, vol. 12, 2005, XXiV, p. 442.
Grosjean, H., et al. How Nucleic Acids Cope with High Temperature. Physiology and Biochemistry of Extremophiles. 2007. Chapter 4, pp. 39-58.
Grosjean, H., Modification and editing of RNA: historical overview and important facts to remember. Fine-tuning of RNA functions by modification and editing. Topics Curr Gen. Jan. 2005; 12: 1-22.
Grosjean, H., Nucleic Acids Are Not Boring Long Polymers of Only Four Types of Nucleotides: A Guided Tour. Chapter 1. Landes Bioscience. 2009. pp. 1-18.
Gross, G. and Hauser, H., "Heterologous Expression as a Tool for Gene Identification and Analysis," Journal of Biotechnology 41(2-3):91-110, Elsevier Science Publishers, Netherlands (1995).
Grudzien, E., et al., "Novel Cap Analogs for in Vitro Synthesis of mRNAs with High Translational Efficiency," RNA 10(9):1479-1487, Cold Spring Harbor Laboratory Press, United States (2004).
Grudzien-Nogalska, E., et al., "Phosphorothioate Cap Analogs Stabilize mRNA and Increase Translational Efficiency in Mammalian Cells," RNA 13(10):1745-1755, Cold Spring Harbor Laboratory Press, United States (2007).
Grundy, S.M., "Promise of Low-Density Lipoprotein-Lowering Therapy for Primary and Secondary Prevention," Circulation 117(4):569-573, Lippincott Williams & Wilkins, United States (2008).
Gryaznov, S.M., "Oligonucleotide N3'—>P5' Phosphoramidates as Potential Therapeutic Agents," Biochimica et Biophysica acta 1489(1):131-140, Elsevier, Netherlands (1999).
Gu, M., et al., "Combinatorial Synthesis with High Throughput Discovery of Protein-Resistant Membrane Surfaces," Biomaterials 34(26):6133-6138, Elsevier Science, Netherlands (2013).
Guagnozzi, D. and Caprilli, R., "Natalizumab in the Treatment of Crohn'S Disease," Biologics : Targets & Therapy 2(2):275-284, Dove Medical Press, New Zealand (2008).
Guerrero-Cázares, H., et al., "Biodegradable Polymeric Nanoparticles Show High Efficacy and Specificity at DNA Delivery to Human Glioblastoma in Vitro and in Viv.," ACS nano 8(5):5141-5153, American Chemical Society, United States (2014).

(56) References Cited

OTHER PUBLICATIONS

Guhaniyogi, J. and Brewer, G., "Regulation of mRNA Stability in Mammalian Cells," Gene 265(1-2):11-23, Elsevier, Netherlands (2001).
Gunn C.K., "Hereditary Acholuric Jaundice in the Rat," Canadian Medical Association Journal 50(3):230-237, Canadian Medical Association, Canada (1944).
Guo, L., et al., "Structure and Function of a Cap-Independent Translation Element That Functions in Either the 3' or the 5' Untranslated Region," RNA 6(12):1808-1820, Cold Spring Harbor Laboratory Press, United States (2000).
Guo, Z.S., et al., "Life After Death: Targeting High Mobility Group Box 1 in Emergent Cancer Therapies," American Journal of cancer Research 3(1):1-20, e-Century Pub. Corp, United States (2013).
Gupta et al., Project Reporl Condon Opitimization, 2003, pp. 1-13.
Gupta, S. and Garg, N.J., "Tcvac3 Induced Control of Trypanosoma Cruzi Infection and Chronic Myocarditis in Mice," PloS one 8(3):e59434, Public Library of Science, United States (2013).
Haas, J., et al., "Codon Usage Limitation in the Expression of Hiv-1 Envelope Glycoprotein," Current Biology 6(3):315-324, Cell Press, England (1996).
Haft, D.H., et al., "A Guild of 45 CRISPR-Associated (Cas) Protein Families and Multiple Crispr/Cas Subtypes Exist in Prokaryotic Genomes," PLoS Computational Biology 1(6):e60, Public Library of Science, United States (2005).
Hainsworth, J.D., "Monoclonal Antibody Therapy in Lymphoid Malignancies," The Oncologist 5(5):376-384, AlphaMed Press, United States (2000).
Hale, G., et al., "Removal of T Cells From Bone Marrow for Transplantation: A Monoclonal Antilymphocyte Antibody that Fixes Human Complement," Blood 62(4):873-882, American Society of Hematology, United States of America (1983).
Hambraeus, G. et al., "A 5' Stem-Loop and Ribosome Binding but not Translation are Important for the Stability of Bacillus Subtilis AprE Leader mRNA," Microbiology 148(Pt 6):1795-1803, Microbiology Society, London (2002).
Hamid, O., et al., "Safety and Tumor Responses with Lambrolizumab (Anti-Pd-1) in Melanoma," The New England Journal of Medicine 369(2):134-144, Massachusetts Medical Society, United States of America (2013).
Hamrick, M.W., "The Skeletal Muscle Secretome: An Emerging Player in Muscle-Bone Crosstalk," BoneKEy Reports 1:60, Nature Publishing Group, England (2012).
Han, S., et al., "Novel Autoantigens in Type 1 Diabetes," American Journal of Translational Research 5(4):379-392, e-Century Pub. Corp, United States of America (2013).
Hancock, J.F., "Reticulocyte Lysate Assay for in Vitro Translation and Posttranslational Modification of Ras Proteins," Methods in Enzymology 255:60-65, Academic Press, United States (1995).
Hanessian, S. et al., A highly stereocontrolled and efficient synthesis of alpha- and beta-pseudouridines. Tetrahedron Letters. 2003; 44: 8321-8323.
Hank, J.A., et al., "Immunogenicity of the Hu14.18-IL2 Immunocytokine Molecule in Adults with Melanoma and Children with Neuroblastoma," Clinical Cancer Research 15(18):5923-5930, The Association, United States of America (2009).
Hannon, G.J., et al., "Trans Splicing of Nematode Pre-Messenger RNA in Vitro," Cell 61(7):1247-1255, Cell Press, United States of America (1990).
Hansen, T.B., et al., "Natural RNA Circles Function as Efficient Microrna Sponges," Nature 495(7441):384-388, Nature Publishing Group, England (2013).
Harel, J., et al., "[Action of Polyribonucleotides, Extracted by the Phenol Method, on the Growth of Mouse Tumor Cells]," Comptes Rendus Hebdomadaires Des séances de l'Académie des sciences 254:4390-4392, Académie des Sciences, France (1962).
Harris, J., et al., "An Improved Rna Amplification Procedure Results in Increased Yield of Autologous RNA Transfected Dendritic Cell-Based Vaccine," Biochimica et Biophysica Acta 1724(1-2):127-136, Elsevier, Netherlands (2005).
Hart, T.K., et al., "Preclinical Efficacy and Safety of Mepolizumab (Sb-240563), a Humanized Monoclonal Antibody to IL-5, in Cynomolgus Monkeys," The Journal of Allergy and Clinical Immunology 108(2):250-257, St Louis, Mosby, United States of America (2001).
Hausmann, R., "Bacteriophage T7 Genetics," Current Topics in Microbiology and Immunology 75:77-110, Springer Verlag, Germany (1976).
Hays, E.F., et al., "Induction of Mouse Leukaemia with Purified Nucleic Acid Preparations," Nature 180(4599):1419-1420, Nature Publishing Group, England (1957).
He, K., et al., "Synthesis and Separation of Diastereomers of Ribonucleoside 5'-(Alpha-P-Borano)Triphosphates," The Journal of Organic Chemistry 63(17):5769-5773, American Chemical Society, United States (1998).
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hedlund, G., et al., "The Tumor Targeted Superantigen ABR-217620 Selectively Engages TRBV7-9 and Exploits TCR-pMHC Affinity Mimicry in Mediating T Cell Cytotoxicity," PloS one 8(10):e79082, Public Library of Science, United States (2013).
Hedman, M., et al., "Safety and Feasibility of Catheter-Based Local Intracoronary Vascular Endothelial Growth Factor Gene Transfer in the Prevention of Postangioplasty and In-Stent Restenosis and in the Treatment of Chronic Myocardial Ischemia: Phase II Results of the Kuopio Angiogenesis Trial," Circulation 107(21):2677-2683, Lippincott Williams & Wilkins, United States (2003).
Heidenreich, O., et al., "Chemically Modified RNA: Approaches and Applications," FASEB Journal 7(1):90-96, The Federation, United States (1993).
Heidenreich, O., et al., "High Activity and Stability of Hammerhead Ribozymes Containing 2'-Modified Pyrimidine Nucleosides and Phosphorothioates," The Journal of Biological Chemistry 269(3):2131-2138, American Society for Biochemistry and Molecular Biology, United States (1994).
Heil, F., et al., "Species-Specific Recognition of Single-Stranded RNA Via Toll-Like Receptor 7 and 8," Science 303(5663):1526-1529, American Association for the Advancement of Science, United States (2004).
Heilman, K.L., et al., "Internal 6-Methyladenine Residues Increase the in Vitro Translation Efficiency of Dihydrofolate Reductase Messenger RNA," The International Journal of Biochemistry & Cell Biology 28(7):823-829, Elsevier, Netherlands (1996).
Heiser, A., et al., "Autologous Dendritic Cells Transfected with Prostate-Specific Antigen Rna Stimulate CTL Responses Against Metastatic Prostate Tumors," The Journal of Clinical Investigation 109(3):409-417, American Society for Clinical Investigation, United States (2002).
Heiser, A., et al., "Human Dendritic Cells Transfected with Renal Tumor RNA Stimulate Polyclonal T-Cell Responses Against Antigens Expressed by Primary and Metastatic Tumors," Cancer research 61(8):3388-3393, American Association for Cancer Research, United States (2001).
Heiser, A., et al., "Human Dendritic Cells Transfected with RNA Encoding Prostate-Specific Antigen Stimulate Prostate-Specific CTL Responses in Vitro," Journal of Immunology 164(10):5508-5514, American Association of Immunologists, United States (2000).
Heiser, A., et al., "Induction of Polyclonal Prostate Cancer-Specific CTL Using Dendritic Cells Transfected with Amplified Tumor RNA," Journal of immunology 166(5):2953-2960, American Association of Immunologists, United States (2001).
Helbock, H.J., et al., "N2-Methyl-8-0xoguanine: A tRNA Urinary Metabolite—Role of Xanthine Oxidase," Free Radical Biology & Medicine 20(3):475-481, Elsevier Science, United States (1996).
Helm, M., "Post-transcriptional Nucleotide Modification and Alternative Folding of RNA," Nucleic Acids Research 34(2):721-733, Oxford University Press, England (2006).
Hemmi, H., et al., "A Toll-Like Receptor Recognizes Bacterial DNA," Nature 408(6813):740-745, Nature Publishing Group, England (2000).

(56) References Cited

OTHER PUBLICATIONS

Hentze, M.W. and Preiss, T., "Circular RNAs: Splicing'S Enigma Variations," The EMBO Journal 32(7):923-925, Wiley Blackwell, England (2013).
Herbst, R.S. and Sandler, A.B., "Non-Small Cell Lung Cancer and Antiangiogenic Therapy: What Can Be Expected of Bevacizumab?," The Oncologist 9:19-26, AlphaMed Press, United States (2004).
Hernandez, A.M., et al., "Anti-NeuGcGM3 Antibodies, Actively Elicited by Idiotypic Vaccination in Nonsmall Cell Lung Canc er patients, Induce Tumor Cell Death by an Oncosis-like Mechanism," Journal of Immunology 186(6):3735-3744, American Association of Immunologists, United States (2011).
Herweijer, H. and Wolff, J.A. "Gene Therapy Progress and Prospects: Hydrodynamic Gene Delivery," Gene Therapy 14(2):99-107, Nature Publishing Group, England (2007).
Hess, M., et al., "The Effects of Nucleic Acids on Pituitary ACTH Content," Endocrinology 68:548-552, Endocrine Society, United States (1961).
High, K.A., "The Gene Therapy Journey for Hemophilia: Are We there Yet?," Blood 120(23):4482-4487, American Society of Hematology, United States (2012).
Higman, M.A., et al., "The mRNA (Guanine-7-)Methyltransferase Domain of the Vaccinia Virus mRNA Capping Enzyme. Expression in *Escherichia coli* and Structural and Kinetic Comparison to the intact Capping Enzyme.," The Journal of Biological Chemistry 269(21):14974-14981, American Society for Biochemistry and Molecular Biology, United States (1994).
Higman, M.A., et al., "The Vaccinia Virus mRNA (Guanine-N7-)-Methyltransferase Requires Both Subunits of the mRNA Capping Enzyme for Activity," The Journal of Biological Chemistry 267(23)1 6430-16437, American Society for Biochemistry and Molecular Biology, United States (1992).
Hilleren, P. and Parker, R., "Mechanisms of mRNA Surveillance in Eukaryotes," Annual Review of Genetics 33:229-260, Annual Reviews, United States (1999).
Hillman,N.W and Niu, M.C., "Chick Cephalogenesis.l. The Effect of RNA on Early Cephalic Development," Proceedings of the National Academy of Sciences of the United States of America 50:486-493, National Academy of Sciences, United States (1963).
Hillmen P., et al., "Effect of Eculizumab on Hemolysis and Transfusion Requirements in Patients with Paroxysmal Nocturnal Hemoglobinuria," The New England Journal of Medicine 350(6):552-559, Massachusetts Medical Society, United States (2004).
Håkelien, A.M. and Collas, P., "Novel Approaches to Transdifferentiation," Cloning and Stem Cells 4(4):379-387, Mary Ann Liebert, United States (2002).
Håkelien, A.M., et al., "Reprogramming Fibroblasts to Express T-Cell Functions Using Cell Extracts," Nature Biotechnology 20(5):460-466, Nature America Publishing, United States (2002).
Ho, C.S., et al., "Electrospray Ionisation Mass Spectrometry: Principles and Clinical Applications," The Clinical Biochemist 24(1):3-12, Australasian Association of Clinical Biochemists, Australia (2003).
Hoath, S.B. and Leahy, D.G. "The organization of Human Epidermis: Functional Epidermal Units and Phi Proportionality," The Journal of Investigative Dermatology 121(6):1440-1446, Elsevier, United States (2003).
Hochreiter-Hufford, A., and Ravichandran, K.S., "Clearing the Dead: Apoptotic Cell Sensing, Recognition, Engulfment, and Digestion," Cold Spring Harbor Perspectives in Biology 5(1):a008748, Cold Spring Harbor Laboratory Press, United States (2013).
Hodges, P.E and Rosenberg, L.E., "The Spfash Mouse: A Missense Mutation in the ornithine Transcarbamylase Gene Also Causes Aberrant mRNA Splicing," Proceedings of the National Academy of Sciences of the United States of America 86(11):4142-4146, National Academy of Sciences, United States (1989).
Hoerr, I., et al., "In Vivo Application of RNA Leads to induction of Specific Cytotoxic T Lymphocytes and Antibodies," European Journal of Immunology 30(1):1-7, Wiley-VCH, Germany (2000).
Hoerr, I. et al., Stabilized Messenger RNA (RNActiveTM) as a Tool for Innovative Gene Delivery. Tissue Engineering. Apr. 2007; 13(4): 865-925.
Hoffman, B.E., et al., "Nonredundant Roles of Il-10 and TGF-B in Suppression of Immune Responses to Hepatic Aav-Factor Ix Gene Transfer," Molecular Therapy 19(7):1263-1272, Academic Press, United States (2011).
Hoffmann-La Roche, A Study of Obinutuzumab (R05072759) in Combination With CHOP Chemotherapy Versus MabThera/Rituxan (Rituximab) With CHOP in Patients With CD2O-Positive Diffuse Large B-Cell Lymphoma (GOYA), ClinicalTrials.gov, Apr. 2, 2014, http://clinicaltr.
Hoffmann-La Roche, A Study of Obinutuzumab (R05072759) Plus Chemotherapy in Comparison With MabThera/ Rituxan (Rituximab) Plus Chemotherapy Followed by GA101 or MabThera/ Rituxan Maintenance in Patients With Untreated Advanced Indolent Non-Hodgkin's Lympho.
Hofman M.K., et al., "Cyp7A1 A-278C Polymorphism Affects the Response of Plasma Lipids Alter Dietary Cholesterol or Cafestol Interventions in Humans," The Journal of Nutrition 134(9):2200-2204, American Society for Nutrition, United States (2004).
Holcik, M. And Liebhaber, S.A., "Four Highly Stable Eukaryotic Mrnas Assemble 3' Untranslated Region RNA-Protein Complexes Sharing Cis and Trans Components," Proceedings of the National Academy of Sciences of the United States of America 94(6):2410-2414, National Academy of Sciences, United States (1997).
Hole, N., and Stern, P.L., "A 72 Kd Trophoblast Glycoprotein Defined by a Monoclonal Antibody," British Journal of Cancer 57(3):239-246, Nature Publishing Group on behalf of Cancer Research UK, London (1988).
Holmes, D. et al., Cell positioning and sorting using dielectrophoresis. Eur Cell Mater. 2002; 4(2):120-2.
Holtkamp, S., et al., "Modification of Antigen-Encoding RNA Increases Stability, Translational Efficacy, and T-Cell Stimulatory Capacity of Dendritic Cells," Blood 108(13):4009-4017, American Society of Hematology, United States (2006).
Hooks, M.A., et al., "Muromonab Cd-3: A Review of its Pharmacology, Pharmacokinetics, and Clinical Use in Transplantation," Pharmacotherapy 11(1):26-37, Wiley-Blackwell, United States (1991).
Hopkins, B.D., et al., "A Secreted PTEN Phosphatase That Enters Cells to Alter Signaling and Survival," Science 341(6144):399-402, American Association for the Advancement of Science, United States (2013).
Hornung, V., et al., "5'-Triphosphate RNA is the Ligand for RIG-I," Science 314(5801):994-997, American Association for the Advancement of Science, United States (2006).
Houghton, A.N., "Cancer Antigens: Immune Recognition of Self and Altered Self," The Journal of Experimental Medicine 180(1):1-4, Rockefeller University Press, United States (1994).
Hovingh, G.K., et al., "Diagnosis Treatment of Familial Hypercholesterolaemia," European Heart Journal 34(13):962-971, Oxford University Press, England (2013).
Hsu, F.J., et al., "Vaccination of Patients with B-Cell Lymphoma using Autologous Antigen-Pulsed Dendritic Cells," Nature medicine 2(1):52-58, Nature Publishing Company, United States (1996).
Hu, B.Y., et al., "Neural Differentiation of Human Induced Pluripotent Stem Cells Follows Developmental Principles but with Variable Potency," Proceedings of the National Academy of Sciences of the United States of America 107(9):4335-4340, National Academy of Sciences, United States (2010).
Hu, S., et al., "Codon Optimization, Expression, Characterization of an Internalizing Anti-Erbb2 Single-Chain Antibody in Pichia Pastoris," Protein Expression and Purification 47(1):249-257, Academic Press, United States (2006).
Huang, K., et al., "Respiratory Syncytial Virus-Neutralizing Monoclonal Antibodies Motavizumab and Palivizumab Inhibit Fusion," Journal of Virology 84(16):8132-8140, American Society for Microbiology, United States (2010).

(56) References Cited

OTHER PUBLICATIONS

Huangfu, D., et al., "Induction of Pluripotent Stem Cells by Defined Factors is Greatly Improved by Small-Molecule Compounds," Nature Biotechnology 26(7):795-797, Nature America Publishing, United States (2008).
Huangfu, D., et al., "Induction of Pluripotent Stem Cells From Primary Human Fibroblasts with Only Oct4 Sox2," Nature Biotechnology 26(11):1269-1275, Nature America Publishing, United States (2008).
Huddleston, J.A. and Brownlee, G.G.,, "The Sequence of the Nucleoprotein Gene of Human Influenza A Virus, Strain A/NT/60/68," Nucleic Acids Research 10(3):1029-1038, Oxford University Press, England (1982).
Hue, K.K., et al., "A Polypurine Sequence That Acts as a 5' mRNA Stabilizer in Bacillus Subtilis," Journal of Bacteriology 177(12):3465-3471, American Society for Microbiology, United States (1995).
Hueber, W., et al., "Effects of AIN457, a Fully Human Antibody to Interleukin-17A, on Psoriasis, Rheumatoid Arthritis, Uveitis," Science Translational Medicine 2(52):52ra72, American Association for the Advancement of Science, United States (2010).
Huizinga, T.W., et al., "Sarilumab, a Fully Human Monoclonal Antibody Against Il-6Rα in Patients with Rheumatoid Arthritis an Inadequate Response to Methotrexate: Efficacy Safety Results from the Romised SARIL-RA-MOBILITY, Part A Trial," Annals of the Rheumatic Diseases 73(9):1626-1634, BMJ, England (2014).
Humbert, M., et al., "Relationship Between IL-4 IL-5 mRNA Expression and Disease Severity in Atopic Asthma," American Journal of Respiratory and Critical Care edicine 156(3Pt1):704-708, American Thoracic Society, United States (1997).
Hung, C.F., et al., "Ovarian Cancer Gene Therapy Using HPV-16 Pseudovirion Carrying the HSV-TK Gene," PloS one 7(7):e40983, Public Library of Science, United States (2012).
Hunt, D.M., et al., "The L Protein of Vesicular Stomatitis Virus Modulates the Response of the Polyadenylic Acid Polymerase to S-Adenosylhomocysteine," The Journal of General Virology 69(Pt10):2555-2561, Microbiology Society, England (1988).
Hutas, G., "Ocrelizumab, a Humanized Monoclonal Antibody Against CD20 for Inflammatory Disorders B-Cell Malignancies," Current Opinion in Investigational Drugs 9(11):1206-1215, Thomson Reuters (Scientific) Ltd, England (2008).
Hwang, W.Y., et al., "Efficient Genome Editing in Zebrafish Using a CRISPR-Cas System," Nature Biotechnology 31(3):227-229, Nature America Publishing, United States (2013).
Iduronate 2-Sulfatase; iduronate 2-sulfatase isofrom a preproprotein [ *Homo sapiens*]; NCBI, 2010, pp. 1-4.
Imbimbo, B.P., et al., "Solanezumab for the Treatment of Mild-To-Moderate Alzheimer'S Disease," Expert Review of Clinical Immunology 8(2):135-149, Taylor & Francis, England (2012).
ImClone Systems Incorporated and Bristol-Myers Squibb Company, ERBITUX, Cetuximab, 2004, No Vol number, pp. 1-18.
Inaba, K., et al., "Dendritic Cells Pulsed with Protein Antigens in Vitro Can Prime Antigen-Specific, MHC-Restricted T Cells In Situ," The Journal of Experimental Medicine 172(2):631-640, Rockefeller University Press, United States (1990).
Inaba, K., et al., "Direct Activation of CD8+ Cytotoxic T Lymphocytes by Dendritic Cells," The Journal of Experimental Medicine 166(1):182-194, Rockefeller University Press, United States (1987).
Inaba, K., et al., "Generation of Large Numbers of Dendritic Cells From Mouse Bone Marrow Cultures Supplemented with Granulocyte/Macrophage Colony-Stimulating Factor," The Journal of Experimental Medicine 176(6):1693-1702, Rockefeller University Press, United States (1992).
Innis, M.A., et al., "DNA Sequencing with thermus Aquaticus Dna Polymerase Direct Sequencing of Polymerase Chain Reaction-Amplified DNA," Proceedings of the National Academy of Sciences of the United States of America 85(24):9436-9440, National Academy of Sciences, United States (1988).
International Preliminary Report on Patentability for International Application No. PCT/US2012/031781, The International Bureau of WIPO, Switzerland, dated Oct. 1, 2013, 11 pages.
International Search Report and Written Opinion for International Application No. PCT/US11/46861, ISA/US, Alexandria, Virginia, United States, dated Apr. 13, 2012, 5 pages.
International Search Report and Written Opinion for International Application No. PCT/US11/54636, ISA/US, Alexandria, Virginia, United States, dated Apr. 17, 2012, 12 pages.
International Search Report and Written Opinion for International Application No. PCT/US2013/030067, ISA/US, Alexandria, Virginia, United States, dated Dec. 20, 2013, 14 pages.
International Search Report and Written Opinion for International Application No. PCT/US2013/062943, European Patent Office, Netherlands, dated Jan. 7, 2014, 19 pages.
"International Search Report and Written Opinion for International Application No. PCT/US2014/055394, ISA/US Alexandria, Virginia, dated Jan. 2, 2015, 9 pages."
International Search Report and Written Opinion for International Application Serial No. PCT/US2013/030070, ISA/US, Alexandria, Virginia, United States, dated Dec. 23, 2013, 17 pages.
International Search Report for International Application No. PCT/US12/054574 ISA/US, Alexandria, Virginia, United States, dated Jul. 1, 2013.
International Search Report for International Application No. PCT/US12/54561, ISA/US, Alexandria, Virginia, United States, dated Feb. 26, 2013.
International Search Report for International Application No. PCT/US12/58519, ISA/US, Alexandria, Virginia, United States, dated Feb. 28, 2013.
International Search Report for International Application No. PCT/US12/68732, ISA/US, Alexandria, Virginia, United States, dated Feb. 22, 2013.
International Search Report for International Application No. PCT/US12/69610, ISA/US, Alexandria, Virginia, United States, dated Feb. 27, 2013.
International Search Report for International Application No. PCT/US12/71105, ISA/US, Alexandria, Virginia, United States, dated Mar. 5, 2013.
International Search Report for International Application No. PCT/US12/71118, ISA/US, Alexandria, Virginia, United States, dated Apr. 5, 2013.
International Search Report for International Application No. PCT/US13/20921, ISA/US, Alexandria, Virginia, United States, dated Mar. 26, 2013.
International Search Report for International Application No. PCT/US13/54635, ISA/US, Alexandria, Virginia, United States, dated Mar. 3, 2014.
International Search Report for International Application No. PCT/US2010/059305, Korean Intellectual Property Office, Republic of Korea, dated Aug. 23, 2011.
International Search Report for International Application No. PCT/US2010/059317, Korean Intellectual Property Office, Republic of Korea, dated Aug. 22, 2011.
International Search Report for International Application No. PCT/US2012/031781, European Patent Office, Netherlands, dated Jan. 11, 2013.
International Search Report for International Application No. PCT/US2012/068714, ISA/US, Alexandria, Virginia, United States, dated Aug. 6, 2013.
International Search Report for International Application No. PCT/US2013/030062, European Patent Office, Netherlands, dated Oct. 21, 2013.
International Search Report for International Application No. PCT/US2013/75177, ISA/US, Alexandria, Virginia, United States, dated May 5, 2014.
International Search Report for International Application No. PCT/US2014/020206, ISA/US, Alexandria, Virginia, United States, dated May 23, 2014.
International Search Report for International Application No. PCT/US2013/030064, European Patent Office, Netherlands, dated Oct. 21, 2013.

(56) References Cited

OTHER PUBLICATIONS

International Search Report for International Application Serial No. PCT/US2013/030070, ISA/US, Alexandria, Virginia, United States, dated Dec. 23, 2013.
International Search Report from International Application No. PCT/US11/54617 dated Oct. 3, 2011.
International Search Report from International Application No. PCT/US12/38028 dated Aug. 14, 2012.
Issa, G.C., et al., "Novel Agents in Waldenstrom Macroglobulinemia," Clinical investigation 1(6):815-824, Future Science, England (2011).
Ito, A., et al., "Defucosylated Anti-CCR4 Monoclonal Antibody Exercises Potent ADCC-Mediated Antitumor Effect in the Novel Tumor-Bearing Humanized NOD/Shi-scid, IL-2Rgamma(null) Mouse Model," Cancer Immunology, Immunotherapy : CII 58(8):1195-1206, Springer Verlag, Germany (2009).
Ito, M.K., "ISIS 301012 Gene Therapy for Hypercholesterolemia: Sense, Antisense, or Nonsense'?," The Annals of Pharmacotherapy 41(10):1669-1678, Thousand Oaks, United States (2007).
Ito, S., et al., "Role of Tet Proteins in 5mC to 5hmC Conversion, ES-Cell Self-Renewal and inner Cell Mass Specification," Nature 466(7310):1129-1133, Nature Publishing Group, England (2010).
Ivanovska, N., et al., "Immunization with a DNA Chimeric Molecule Encoding a Hemagglutinin Peptide and a Scfv CD21-Specific Antibody Fragment induces Long-Lasting IgM and CTL Responses to influenza Virus," Vaccine 24(11):1830-1837, Elsevier Science, Netherlands (2006).
Iwasaki, A., et al., "Enhanced CTL Responses Mediated by Plasmid Dna Immunogens Encoding Costimulatory Molecules and Cytokines," Journal of Immunology 158(10):4591-4601, American Association of Immunologists, United States (1997).
Iwase, R., et al., "Molecular Design of a Eukaryotic Messenger RNA and Its Chemical Synthesis," Nucleic Acids Research 20(7):1643-1648, Oxford University Press, England (1992).
Iyanagi, T., "Molecular Basis of Multiple UDP-Glucuronosyltransferase Isoenzyme Deficiencies in the Hyperbilirubinemic Rat (Gunn Rat)," The Journal of Biological Chemistry 266(35):24048-24052, American Society for Biochemistry and Molecular Biology, United States (1991).
Jachertz, D. et al., Treatment of P815 mastocytoma in DBA/2 mice with RNA. J Immunogen. 1974; 1: 355-362.
Jacobsen, L., et al., "Allergen-Specific Immunotherapy Provides Immediate, Long-Term and Preventive Clinical Effects in Children and Adults: The Effects of Immunotherapy Can Be Categorised by Level of Benefit—The Centenary of Allergen Specific Subcutaneous Immunotherapy," Clinical and Translational Allergy 2:8, BioMed Central, England (2012).
Jady, B.E. and Kiss, T., "A Small Nucleolar Guide RNA Functions Both in 2'-O-Ribose Methylation and Pseudouridylation of the U5 Spliceosomal RNA," The EMBO Journal 20(3):541-551, Wiley Blackwell, England (2001).
Jaffers, G.J., et al., "Monoclonal Antibody Therapy. Anti-Idiotypic and Non-Anti-Idiotypic Antibodies to OKT3 Arising Despite intense Immunosuppression," Transplantation 41(5):572-578, Lippincott Williams & Wilkins, United States (1986).
Jaglowski, S.M., et al., "The Clinical Application of Monoclonal Antibodies in Chronic Lymphocytic Leukemia," Blood 116(19):3705-3714, American Society of Hematology, United States (2010).
Janeway, C. et al., Immunobiology: the immune system in health and disease. Garland Publishing, Inc, London. 1997; 13:12-13:21.
Jansen, P.L., "Diagnosis and Management of Crigler-Najjar Syndrome," European journal of pediatrics 158:S89-S94, Springer-Verlag, Germany (1999).
Janssens, Ann et al., Rixuximab for Chronic Lymphocytic Leukemia in Treatment-NaTve and Treatment-Experienced, OneLive, Bringing Oncology Together, Apr. 2, 2014, No Vol. , pp. 1-7.
Janssens, S. and Beyaert, R., "Role of Toll-Like Receptors in Pathogen Recognition," Clinical Microbiology Reviews 16(4):637-646, American Society for Microbiology, United States (2003).
Jeck, W.R., et al., "Circular RNAs are Abundant, Conserved, and Associated with ALU Repeats," RNA 19(2):141-157, Cold Spring Harbor Laboratory Press, United States (2013).
Jemielity, J., et al., "Novel "Anti-Reverse" Cap Analogs with Superior Translational Properties," RNA 9(9):1108-1122, Cold Spring Harbor Laboratory Press, United States (2003).
Jia, F., et al., "A Nonviral Minicircle Vector for Deriving Human Ips Cells," Nature methods 7(3):197-199, Nature Pub. Group, United States (2010).
Jia, G., et al., "Periostin Is a Systemic Biomarker of Eosinophilic Airway inflammation in Asthmatic Patients," The Journal of allergy and clinical immunology 130(3):647-654, St Louis, Mosby, United States (2012).
Jia, Z. And Danko, I., "Long-Term Correction of Hyperbilirubinemia in the Gunn Rat by Repeated intravenous Delivery of Naked Plasmid DNA into Muscle," Molecular Therapy 12(5):860-866, Academic Press, United States (2005).
Jiang, J., et al., "Topical Application of Ketoconazole Stimulates Hair Growth in C3H/Hen Mice," The Journal of dermatology 32(4):243-247, Wiley-Blackwell, England (2005).
Jin, Wei et al., IL-17 cytokines in immunity and inflammation, Emerging Microbes and Infections, 2013, vol. 2, No. #, pp. 1-5.
Jinek, M., et al., "A Programmable Dual-RNA-Guided DNA Endonuclease in Adaptive Bacterial Immunity," Science 337(6096):816-821, American Association for the Advancement of Science, United States (2012).
Jinek, M., et al., "RNA-Programmed Genome Editing in Human Cells," eLife 2:e00471, eLife Sciences Publications, England (2013).
Jirikowski, G.F., et al., "Reversal of Diabetes Insipidus in Brattleboro Rats: Intrahypothalamic Injection of Vasopressin mRNA," Science 255(5047):996-998, American Association for the Advancement of Science, United States (1992).
Johnson, K.M., et al., "Role of Heparan Sulfate in Attachment to and Infection of the Murine Female Genital Tract by Human Papillomavirus," Journal of Virology 83(5):2067-2074, American Society for Microbiology, United States (2009).
Jones, P.C., "An Alteration in Cell Morpholoy Under the Influence of a Tumour RNA," Nature 202:1226-1227, Nature Publishing Group, England (1964).
Juliano, R.L., et al., "Cell-Targeting and Cell-Penetrating Peptides for Delivery of therapeutic and Imaging Agents," Wiley Interdisciplinary Reviews 1(3):324-335, John Wiley & Sons, United States (2009).
Julien, J.P., et al., "Broadly Neutralizing Antibody PGT121 Allosterically Modulates CD$ Binding via Recognition of theHIV-1 Gp120 V3 Base and Multiple Surrounding Glycans," PLoS Pathogens 9(5):e1003342, Public Library of Science, United States (2013).
Kabanov, A.V., et al., "A New Class of Antivirals: Antisense Oligonucleotides Combined with a Hydrophobic Substituent Effectively Inhibit Influenza Virus Reproduction and Synthesis of Virus-Specific Proteins in Mdck Cells," FEBS letters 259(2):327-330, John Wiley & Sons Ltd, England (1990).
Kadakol, A., et al., "Genetic Lesions of Bilirubin Uridine-Diphosphoglucuronate Glucuronosyltransferase (UGT1A1) causing Crigler-najjar and Gilbert Syndromes: Correlation of Genotype to Phenotype," Human Mutation 16(4):297-306, Wiley-Liss, United States (2000).
Kahan, F.M. And Hurwitz, J., "The Role of Deoxyribonucleic Acid in Ribonucleic Acid Synthesis. Iv. the Incorporation of Pyrimidine and Purine Analogues Into Ribonucleic Acid.," The Journal of Biological Chemistry 237:3778-3785, American Society for Biochemistry and Molecular Biology, United States (1962).
Kaji, K., et al., "Virus-Free Induction of Pluripotency and Subsequent Excision of Reprogramming Factors," Nature 458(7239):771-775, Nature Publishing Group, England (2009).
Kalnins, A., et al., "Sequence of the Lacz Gene of *Escherichia coli*," The EMBO Journal 2(4):593-597, Wiley Blackwell, England (1983).
Kanapathipillai, M., et al., "Nanoparticle Targeting of Anti-Cancer Drugs that Alter Intracellular Signaling or Influence the Tumor

(56) References Cited

OTHER PUBLICATIONS

Microenvironment," Advanced Drug Delivery Reviews 107-118, Elsevier Science Publishers, Netherlands (2014).
Kanaya, S., et al., "Codon Usage and tRNA Genes in Eukaryotes: Correlation of Codon Usage Diversity with Translation Efficiency and with Cg-Dinucleotide Usage as Assessed by Multivariate Analysis," Journal of molecular evolution 53(4-5):290-298, Springer-Verlag, Germany (2001).
Kandimalla, E.R., et al., "Design, Synthesis and Biological Evaluation of Novel Antagonist Compounds of Toll-Like Receptors 7, 8 and 9," Nucleic Acids Research 41(6):3947-3961, Oxford University Press, England (2013).
Kandimalla, E.R., et al., "Divergent Synthetic Nucleotide Motif Recognition Pattern: Design and Development of Potent immunomodulatory Oligodeoxyribonucleotide Agents with Distinct Cytokine Induction Profiles," Nucleic Acids Research 31(9):2393-2400, Oxford University Press, England (2003).
Kandimalla, E.R., et al., "Immunomodulatory Oligonucleotides Containing a Cytosine-Phosphate-2'-Deoxy-7-Deazaguanosine Motif as Potent Toll-Like Receptor 9 Agonists," Proceedings of the National Academy of Sciences of the United States of America 102(19):6925-6930, National Academy of Sciences, United States (2005).
Kane, L.P., "T Cell Ig and Mucin Domain Proteins and Immunity," Journal of Immunology 184(6):2743-2749, American Association of Immunologists, United States (2010).
Kang, H., et al., "Inhibition of Mdr1 Gene Expression by Chimeric HNA Antisense Oligonucleotides," Nucleic Acids Research 32(14):4411-4419, Oxford University Press, England (2004).
Kappos, L., et al., "Ocrelizumab in Relapsing-Remitting Multiple Sclerosis: A Phase 2, Randomised, Placebo-Controlled, Multicentre Trial," Lancet 378(9805):1779-1787, Elsevier, London (2011).
Karande, A.A., et al., "In Vitro induction of Chronic Myeloid Leukemia Associated Immune Reactivity in Normal Human Lymphocytes by Xenogeneic Immune RNA," Neoplasma 30(4):403-409, Slovak Academic Press, Slovakia (1983).
Kariko, K. and Weissman, D., "Naturally Occurring Nucleoside Modifications Suppress the Immunostimulatory Activity of RNA: Implication for Therapeutic Rna Development," Current Opinion in Drug Discovery & Development 10(5):523-532, Thomson Reuters, London (2007).
Kariko, K., et al., "Generating the Optimal MRNA for Therapy: HPLC Purification Eliminates Immune Activation and Improves Translation of Nucleoside-Modified, Protein-Encoding MRNA," Nucleic Acids Research 39(21):Oxford University Press, London (2011).
Kariko, K., et al., "In Vivo Protein Expression from MRNA Delivered into Adult Rat Brain," Journal of Neuroscience Methods 105(1):77-86, Elsevier, Netherlands (2001).
Kariko, K., et al., "Incorporation of Pseudouridine into MRNA Yields Superior Nonimmunogenic Vector with Increased Translational Capacity and Biological Stability," Molecular Therapy 16(11):1833-1840, Academic Press, United States (2008).
Kariko, K., et al., "Increased Erythropoiesis in Mice injected with Submicrogram Quantities of Pseudouridine-Containing MRNA Encoding Erythropoietin," Molecular Therapy 20(5):948-953, Academic Press, United States (2012).
Kariko, K., et al., "MRNA Is an Endogenous Ligand for Toll-Like Receptor 3," The Journal of Biological Chemistry 279(13):12542-12550, American Society for Biochemistry and Molecular Biology, United States (2004).
Kariko, K., et al., "Phosphate-Enhanced Transfection of Cationic Lipid-Complexed MRNA and Plasmid DNA," Biochimica Et Biophysica Acta 1369(2):320-334, Elsevier, Netherlands (1998).
Kariko, K., et al., "Suppression of RNA Recognition by Toll-Like Receptors: the Impact of Nucleoside Modification and the Evolutionary Origin of RNA," Immunity 23(2):165-175, Cell Press, United States (2005).
Kariko, Katalin, et al., Impacts of Nucleoside Modification on RNA-mediated activation of toll-like receptors, 2008, Nucleic Acides in Innate Immunity, No Vol., pp. 171-188.
Karlin, S, and Altschul, S.F., "Applications and Statistics for Multiple High-Scoring Segments in Molecular Sequences," Proceedings of the National Academy of Sciences USA 90(12):5873-5877, National Academy of Sciences, United States (1993).
Kassim, S.H., et al., "Gene Therapy in a Humanized Mouse Model of Familial Hypercholesterolemia Leads to Marked Regression of Atherosclerosis," PLoS One 5(10):e13424,Public Library of Science, United States (2010).
Katre, N.V., et al., "Chemical Modification of Recombinant Interleukin 2 by Polyethylene Glycol Increases its Potency in the Murine Meth A Sarcoma Model," Proceedings of the National Academy of Sciences of the United States of America 84(6):1487-1491, National Academy of Sciences, United States (1987).
Katz, N.P., et al., "Rapid Onset of Cutaneous Anesthesia with Emla Cream After Pretreatment with a New Ultrasound-Emitting Device," Anesthesia and Analgesia 98(2):371-376, Lippincott Williams & Wilkins, United States (2004).
Kaur, S., et al., "Mucins in Pancreatic Cancer and its Microenvironment," Nature reviews. Gastroenterology & Hepatology 10(10):607-620, Nature Pub, England (2013).
Kausar, F., et al., "Ocrelizumab: A Step Forward in the Evolution of B-Cell Therapy," Expert opinion on Biological Therapy 9(7):889-895, Taylor & Francis, England (2009).
Kawai, T. and Akira, S., "Antiviral Signaling Through Pattern Recognition Receptors," Journal of Biochemistry 141(2):137-145, Oxford University Press, England (2007).
Kawamura, T., et al., "Linking the P53 Tumour Suppressor Pathway to Somatic Cell Reprogramming," Nature 460(7259):1140-1144, Nature Publishing Group, England (2009).
Kazmierczak, K.M., et al., "The Phage N4 Virion RNA Polymerase Catalytic Domain is Related to Single-Subunit RNA Polymerases," The EMBO Journal 21(21):5815-5823, Wiley Blackwell, England (2002).
Keegen, L.P., et al., "The Many Roles of an RNA Editor," Nature Reviews. Genetics 2(11):869-878, Nature Publishing Group, England (2001).
Keith, B., et al., "HIF1α and HIF2α: Sibling Rivalry in Hypoxic Tumour Growth and Progression," Nature reviews. Cancer 12(1):9-22, Nature Publishing Group, England (2011).
Keller, E.B. and Noon, W.A., "Intron Splicing: A Conserved Internal Signal in Introns of Animal Pre-mRNAs," Proceedings of the National Academy of Sciences of the United States of America 81(23):7417-7120, National Academy of Sciences, United States (1984).
Kelly, K.A. and Jones, D.A., "isolation of a Colon Tumor Specific Binding Peptide Using Phage Display Selection," Neoplasia 5(5):437-444, BC Decker, Canada (2003).
Kempeni, J., "Preliminary Results of Early Clinical Trials with the Fully Human Anti-TNFalpha Monoclonal Antibody D2E7," Annals of the Rheumatic Diseases 58:170-172, BMJ, England (1999).
Keown, W.A., et al., "Methods for Introducing DNA into Mammalian Cells," Methods in Enzymology 185:527-537, Academic Press, United States (1990).
Keshishian, H., et al., "Quantification of Cardiovascular Biomarkers in Patient Plasma by Targeted Mass Spectrometry and Stable Isotope Dilution," Molecular & Cellular Proteomics : MCP 8(10):2339-2349, American Society for Biochemistry and Molecular Biology, United States (2009).
Kesselheim, A.S., "An Empirical Review of Major Legislation Affecting Drug Development: Past Experiences, Effects, and Unintended Consequences," The Milbank Quarterly 89(3):450-502, Blackwell Publishers, United States (2011).
Khare, P.D., et al. "Tumor Growth Suppression by a Retroviral Vector Displaying ScFv Antibody to CEA and Carrying the iNOS Gene," Anticancer Research 22(4):2443-2446, International Institute of Anticancer Research, Greece (2002).
Khullar, N., et al., "Comparative Evaluation of the Protective Effect of Immune Spleen Cells and Immune RNA against Plasmodium Berghei," Annals of Tropical Medicine and Parasitology 82(6):519-526, Maney Pub, England (1988).

(56) References Cited

OTHER PUBLICATIONS

Kim, B., et al., "The Interleukin-1α Precursor is Biologically Active and is Likely a Key Alarmin in the IL-1 Family of Cytokines," Frontiers in Immunology 4:391, Frontiers Research Foundation, Switzerland (2013).
Kim, C.H., et al., "Codon Optimization for High-Level Expression of Human Erythropoietin (EPO) in Mammalian Cells," Gene 199(1-2):293-301, Elsevier, Netherlands (1997).
Kim, D., et al., "Generation of Human Induced Pluripotent Stem Cells by Direct Delivery of Reprogramming Proteins," Cell Stem Cell 4(6):472-476, Cell Press, United States (2009).
Kim, H.K., et al., "Nontoxigenic Protein a Vaccine for Methicillin-Resistant *Staphylococcus aureus* Infections in Mice," The Journal of Experimental Medicine 207(9):1863-1870, Rockefeller University Press, United States (2010).
Kim, S., et al., "Transcriptional Suppression of Interleukin-12 Gene Expression Following Phagocytosis of Apoptotic Cells," Immunity 21(5):643-653, Cell Press, United States (2004).
Kim, S.H., et al., "Opsonized Erythrocyte Ghosts for Liver-Targeted Delivery of Antisense Oligodeoxynucleotides," Biomaterials 30(5):959-967, Elsevier Science, Netherlands (2009).
Kines, R.C., et al., "The Initial Steps Leading to Papillomavirus infection Occur on the Basement Membrane Prior to Cell Surface Binding," Proceedings of the National Academy of Sciences of the United States of America 106(48):20458-20463, National Academy of Sciences, United States (2009).
Kinjyo, I., et al., "SOCS1/JAB is a Negative Regulator of LPS-Induced Macrophage Activation.," Immunity 17(5):583-591, Cell Press, United States (2002).
Kinosita, K.Jr., et al., "Formation and Resealing of Pores of Controlled Sizes in Human Erythrocyte Membrane," Nature 268(5619):438-441, Nature Publishing Group, England (1977).
Kips, J.C., et al., "Effect of SCH55700, a Humanized Anti-Human Interleukin-5 Antibody, in Severe Persistent Asthma: A Pilot Study," American Journal of Respiratory and Critical Care Medicine 167(12):1655-1659, American Thoracic Society, United States (2003).
Kirby K.S., "A New Method for the Isolation of Ribonucleic Acids from Mammalian Tissues," The Biochemical Journal 64(3):405-408, Portland Press, England (1956).
Kirpotin, D.B., et al., "Antibody Targeting of Long-Circulating Lipidic Nanoparticles does not Increase Tumor Localization but does Increase Internalization in Animal Models," Cancer Research 66(13):6732-6740, American Association for Cancer Research, United States (2006).
Kirshenbaum, K., et al., "Designing Polymers that Mimic Biomolecules," Current Opinion in Structural Biology 9(4):530-535, Elsevier Science, England (1999).
Kiss, T., "Small Nucleolar Rna-Guided Post-Transcriptional Modification of Cellular RNAs," The EMBO Journal 20(14):3617-3622, Wiley Blackwell, England (2001).
Kiss, T., "Small Nucleolar RNAs: An Abundant Group of Noncoding RNAs with Diverse Cellular Functions," Cell 109(2):145-148, Cell Press, United States (2002).
Kitaguchi, K., et al., "Immune Deficiency Enhances Expression of Recombinant Human Antibody in Mice After Nonviral in Vivo Gene Transfer," International Journal of Molecular Medicine 16(4):683-688, D.A. Spandidos, Greece (2005).
Kiwaki, K., et al., "Correction of Ornithine Transcarbamylase Deficiency in Adult spf(ash) Mice and in OTC-Deficient Human Hepatocytes with Recombinant Adenoviruses Bearing the CAG promoter," Human Gene Therapy 7(7):821-830, M.A. Liebert, United States (1996).
Klinman, D.M., et al., "DNA Vaccines: Safety and Efficacy Issues," Springer Seminars in Immunopathology 19(2):245-256, Springer International, Germany (1997).
Knowles, L.M., et al., "CLT1 Targets Angiogenic Endothelium Through CLIC1 and Fibronectin," Angiogenesis 15(1):115-129, Springer, Germany (2012).
Kobayashi, T., et al., "Roles of the WHHL Rabbit in Translational Research on Hypercholesterolemia and Cardiovascular Diseases," Journal of Biomedicine & Biotechnology 2011:406473, Hindawi Pub. Corp, United States (2011).
Koch, G. and Bishop, J.M., "The Effect of Polycations on the Interaction of VIRAL Rna with Mammalian Cells: Studies on the Infectivity of Single- and Double-Stranded Poliovirus RNA," Virology 35(1):9-17, Academic Press, United States (1968).
Koch, G., et al., "An Agar Cell-Suspension Plaque Assay for Isolated Viral RNA," Biochemical and Biophysical Research Communications 24(3):304-309, Academic Press, United States (1966).
Koch, G., et al., "Quantitative Studies on the Infectivity of Ribonucleic Acid from Partially Purified and Highly Purified Poliovirus Preparations," Virology 10(3):329-343, Academic Press, United States (1960).
Koenigsknecht-Talboo, J., et al., "Rapid Microglial Response Around Amyloid Pathology After Systemic Anti-Abeta Antibody Administration in PDAPP Mice," The Journal of Neuroscience 28(52):14156-14164, Society for Neuroscience, United States (2008).
Koh, K.P., et al., "Tet1 and Tet2 Regulate 5-Hydroxymethylcytosine Production and Cell Lineage Specification in Mouse Embryonic Stem Cells," Cell Stem Cell 8(2):200-213, Cell Press, United States (2011).
Kohler, G. and Milstein, C., "Continuous Cultures of Fused Cells Secreting Antibody of Predefined Specificity," Nature 256(5517):495-497, Macmillan Journals Ltd., England (1975).
Koide, Y. et al., DNA vaccines. Jpn J Pharmacol. Jul. 2000;83(3):167-74.
Koido, S., et al., "Induction of Antitumor Immunity by Vaccination of Dendritic Cells Transfected with MUC1 RNA," Journal of Immunology 165(10):5713-5719, American Association of Immunologists, United States (2000).
Kolb, A.F, and Whitelaw, C.B., "A Virus-Neutralising Antibody is not Cytotoxic in Vitro," Molecular Immunology 43(6):677-689, Pergamon Press, England (2006).
Kolbeck, R., et al., "MEDI-563, a Humanized Anti-IL-5 Receptor Alpha mAb with Enhanced Antibody-Dependent Cell-Mediated Cytotoxicity Function," The Journal of Allergy and Clinical Immunology 125(6):1344-1353.e2, St Louis, Mosby, United States (2010).
Komar, A.A., et al., "Synonymous Codon Substitutions Affect Ribosome Traffic and Protein Folding During In Vitro Translation," FEBS Letters 462(3):387-391, John Wiley & Sons Ltd, England (1999).
Kontermann, R.E., et al., "Recombinant Bispecific Antibodies for Cancer Therapy," Acta Pharmacologica Sinica 26(1):1-9, Nature Publishing Group, United States (2005).
Kore, a.R., et al., "Synthesis and Biological Validation of NL-(4-Chlorophenoxyethyl) Substituted Dinucleotide Cap Analogs for mRNA Translation," Bioorganic & Medicinal Chemistry 21(15):4570-4574, Elsevier Science, England (2013).
Koren, M.J., et al., "Efficacy and Safety of Longer-Term Administration of Evolocumab (AMG 145) in Patients with Hypercholesterolemia: 52-Week Results from the Open-Label Study of Long-Term Evaluation Against LDL-C (OSLER) Randomized Trial," Circulation 129(2):234-243, Lippincott Williams & Wilkins, United States (2014).
Kormann, M.S., et al., "Expression of therapeutic proteins after delivery of chemically modified mRNA in mice," Nature Biotechnology 29(2):154-157, Nature America Publishing, United States (2011).
Korsten, K.H., et al., "The Strategy of Infection as a Criterion for Phylogenetic Relationships of Non-Coli Phages Morphologically Similar to Phage T7," The Journal of General Virology 43(1):57-73, Microbiology Society, England (1979).
Koski, G.K., et al. "Cutting Edge: Innate Immune System Discriminates Between RNA Containing Bacterial Versus Eukaryotic Structural Features that Prime for High-Level IL-12 Secretion by Dendritic Cells," Journal of Immunology 172(7):3989-3993, Williams & Wilkins, United States (2004).

(56) References Cited

OTHER PUBLICATIONS

Kozak, M., "Regulation of Translation Via mRNA Structure in Prokaryotes and Eukaryotes," Gene 361:13-37, Elsevier, Netherlands (2005).
Kozielski, K.L., et al., "Bioreducible Cationic Polymer-Based Nanoparticles for Efficient and Environmentally Triggered Cytoplasmic siRNA Delivery to Primary Human Brain Cancer Cells," ACS Nano 8(4):3232-3241, American Chemical Society, United States (2014).
Kreiter, S., et al., "Intranodal Vaccination with Naked Antigen-Encoding RNA Elicits Potent Prophylactic and therapeutic Antitumoral Immunity," Cancer Research 70(22):9031-9040, American Association for Cancer Research, United States (2010).
Kreiter, S., et al., "Tumor Vaccination using Messenger RNA: Prospects of a Future Therapy," Current Opinion in Immunology 23(3):399-406, Elsevier, England (2011).
Kreitman, R.J. and Pastan, I., "Antibody Fusion Proteins: Anti-CD22 Recombinant Immunotoxin Moxetumomab Pasudotox," Clinical Cancer Research 17(20):6398-6405, The Association, United States (2011).
Kreitman, R.J., et al., "Phase I Trial of Anti-CD22 Recombinant Immunotoxin Moxetumomab Pasudotox (CAT-8015 or HA22) in Patients with Hairy Cell Leukemia," Journal of Clinical Oncology 30(15):1822-1828, American Society of Clinical Oncology, United States (2012).
Krieg, P.A. and Melton, D.A., "Functional Messenger RNAs are Produced by SP6 in Vitro Transcription of Cloned cDNAs," Nucleic Acids Research 12(18):7057-7070, Oxford University Press, England (1984).
Krieg, P.A. and Melton, D.A., "In Vitro RNA Synthesis with SP6 RNA Polymerase," Methods in Enzymology 155:397-415, Academic Press, United States (1987).
Krueger, G.G., et al., "A Human Interleukin-12/23 Monoclonal Antibody for the Treatment of Psoriasis," The New England Journal of Medicine 356(6):580-592, Massachusetts Medical Society, United States (2007).
Kudla, G., et al., "High Guanine and Cytosine Content Increases mRNA Levels in Mammalian Cells," PLoS Biology 4(6):e180, Public Library of Science, United States (2006).
Kuenen, B., et al., "A Phase I Pharmacologic Study of Necitumumab (IMC-11F8), a Fully Human IgG1 Monoclonal Antibody Directed against EGFR in Patients with Advanced Solid Malignancies," Clinical Cancer Research 16(6):1915-1923, The Association, United States (2010).
Kufe, D.W. et al., Holland-Frei cancer medicine, 6th edition. Hamilton (ON): BC Decker; 2003; Table 12-1.
Kugler, A., et al. "Regression of Human Metastatic Renal Cell Carcinoma After Vaccination with Tumor Cell-Dendritic Cell Hybrids," Nature Medicine 6(3):332-336, Nature Publishing Company, United States (2000).
Kuhn, A.N., et al., "mRNA as a Versatile Tool for Exogenous Protein Expression," Current Gene Therapy 12(5):347-361, Bentham Science Publishers, Netherlands (2012).
Kuhn, E., et al. "Developing Multiplexed Assays for Troponin I and Interleukin-33 in Plasma by Peptide Immunoaffinity Enrichment and Targeted Mass Spectrometry," Clinical Chemistry 55(6):1108-1117, American Association for Clinical Chemistry, United States (2009).
Kuijpers, T.W., et al., "CD20 Deficiency in Humans Results in Impaired T Cell-Independent Antibody Responses," The Journal of Clinical Investigation 120(1):214-222, American Society for Clinical Investigation, United States (2010).
Kundu, T.K. and Rao, M.R., "CpG Islands in Chromatin Organization and Gene Expression," Journal of Biochemistry 125(2):217-222, Oxford University Press, England (1999).
Kurzrock, R., et al., "A Phase I, Open-Label Study of Siltuximab, an Anti-II-6 Monoclonal Antibody, in Patients with B-Cell Non-Hodgkin Lymphoma, Multiple Myeloma, or Castleman Disease," Clinical Cancer Research 19(13):3659-3670, The Association, United States (2013).
Kusakabe, K., et al., "The Timing of GM-CSF Expression Plasmid Administration influences the Th1/Th2 Response induced by an HIV-1-Specific DNA Vaccine," Journal of Immunology 164(6):3102-3111, American Association of Immunologists, United States (2000).
Kvasnica, M., et al., "Platinum(II) Complexes with Steroidal Esters of L-Methionine and L-Histidine: Synthesis, Characterization and Cytotoxic Activity," Bioorganic & Medicinal Chemistry 16(7):3704-3713, Elsevier Science, England (2008).
Kwissa, M., et al., "Cytokine-Facilitated Priming of Cd8+ T Cell Responses by DNA Vaccination," Journal of Molecular Medicine 81(2):91-101, Springer International, Germany (2003).
Kwoh, D.Y., et al., "Transcription-Based Amplification System and Detection of Amplified Human Immunodeficiency Virus Type 1 with a Bead-Based Sandwich Hybridization Format," Proceedings of the National Academy of Sciences of the United States of America 86(4):1173-1177, National Academy of Sciences, United States (1989).
Kwon, H.J., et al., "Molecular Basis for LDL Receptor Recognition by PCSK9," Proceedings of the National Academy of Sciences of the United States of America 105(6)1 820-1825, National Academy of Sciences, United States (2008).
Kwong, P.D., et al., "Broadly neutralizing antibodies and the search for an HIV-1 vaccine: the end of the beginning," Nature Reviews. Immunology 13(9):693-701, Nature Pub. Group, England (2013).
Laakkonen, P. and Vuorinen, K., "Homing Peptides as Targeted Delivery Vehicles," Integrative Biology : Quantitative Biosciences from Nano to Macro 2(7-8):326-337, RSC Publishing, England (2010).
Lachmann, H.J., et al., "In Vivo Regulation of interleukin 1Beta in Patients with Cryopyrin-Associated Periodic Syndromes," The Journal of Experimental Medicine 206(5):1029-1036, Rockefeller University Press, United States (2009).
Lachmann, H.J., et al., "Use of Canakinumab in the Cryopyrin-Associated Periodic Syndrome," The New England Journal of Medicine 360(23):2416-2425, Massachusetts Medical Society, United States (2009).
Lach-Trifilieff, E., et al., "An Antibody Blocking Activin Type II Receptors Induces Strong Skeletal Muscle Hypertrophy and Protects from Atrophy," Molecular and Cellular Biology 34(4):606-618, American Society for Microbiology, United States (2014).
Lacour, F., et al., "Transplantable Malignant Tumors in Mice Induced by Preparations Containing Ribonucleic Acid Extracted from Human and Mouse Tumors," Journal of the National Cancer Institute 24:301-327, Oxford University Press, United States (1960).
Lai, C.J., et al., "Patterning of the Neural Ectoderm of Xenopus Laevis by the Amino-Terminal Product of Hedgehog Autoproteolytic Cleavage," Development 121(8):2349-2360, Company of Biologists Limited, England (1995).
Lai, S.K., et al., "Mucus-Penetrating Nanoparticles for Drug and Gene Delivery to Mucosal Tissues," Advanced Drug Delivery Reviews 61(2):158-171, Elsevier Science Publishers, Netherlands (2009).
Lai, S.K., et al., "Rapid Transport of Large Polymeric Nanoparticles in Fresh Undiluted Human Mucus," Proceedings of the National Academy of Sciences of the United States of America 104(5):1482-1487, National Academy of Sciences, United States (2007).
Lalatsa, A., et al., "Amphiphilic Poly(L-Amino Acids)—New Materials for Drug Delivery," Journal of Controlled Release 161(2):523-536, Elsevier Science Publishers, Netherlands (2012).
Lambert et al., Thematic Review Series: New Lipid and Lipoprotein Targets for the Treatment of Cardiometabolic Diseases the PCSK9 decade, Journal of Lipid Research vol. 53, 2012 pp. 2515-2524.
Lanca, T., et al., "The MHC Class Ib Protein ULBP1 is a Nonredundant Determinant of Leukemia/Lymphoma Susceptibility to Gammadelta T-Cell Cytotoxicity," Blood 115(12):2407-2411, American Society of Hematology, United States (2010).
Lange, T.S. and Gerbi, S.A., "Transient Nucleolar Localization of U6 Small Nuclear RNA in Xenopus Laevis Oocytes," Molecular Biology of the Cell 11(7):2419-2428, American Society for Cell Biology, United States (2000).

(56) References Cited

OTHER PUBLICATIONS

Langer, R., New methods of drug delivery. Science. Sep. 28, 1990;249(4976):1527-33.
Langford, C.J. and Gallwitz, D., "Evidence for an Intron-Contained Sequence Required for the Splicing of Yeast RNA Polymerase II Transcripts," Cell 33(2):519-527, Cell Press, United States (1983).
Larregina, A.T. and Falo L.D. Jr., "Changing Paradigms in Cutaneous Immunology: Adapting with Dendritic Cells," The Journal of Investigative Dermatology 124(1):1-12, Elsevier, United States (2005).
Latarjet, R., et al., "[Production of Multiple Cancers in Mice Having Received Nucleic Acid Extract from Isologous & Homologous Leukemic Tissues]," Comptes Rendus Hebdomadaires Des Seances De l'Academie Des Sciences 246(5):853-855, Academy of Sciences, France (1958).
Lathe, R., "Synthetic Oligonucleotide Probes Deduced from Amino Acid Sequence Data. Theoretical and Practical Considerations," Journal of Molecular Biology 183(1):1-12, Elsevier, England (1985).
Laursen, N.S. and Wilson, I.A., "Broadly Neutralizing Antibodies against Influenza Viruses," Antiviral Research 98(3):476-483, Elsevier, Netherlands (2013).
Lavrik, I,N., et al., "Translational Properties of mHNA, a Messenger RNA Containing Anhydrohexitol Nucleotides," Biochemistry 40(39):11777-11784, American Chemical Society, United States (2001).
Le, T.P., et al., "Safety, Tolerability and Humoral Immune Responses After Intramuscular Administration of a Malaria DNA Vaccine to Healthy Adult Volunteers," Vaccine 18(18):1893-1901, Elsevier Science, Netherlands (2000).
Leader, B., et al., "Protein Therapeutics: A Summary and Pharmacological Classification," Nature Reviews. Drug Discovery 7(1):21-39, Nature Pub. Group, England (2008).
Leda, M., et al., "Direct Reprogramming of Fibroblasts into Functional Cardiomyocytes by Defined Factors," Cell 142(3):375-386, Cell Press, United States of America (2010).
Ledford, H., "Circular RNAs Throw Genetics for a Loop," Nature 494(7438):415, Nature Publishing Group, England (2013).
Ledford, H., Supercharged Antibodies Fight HIV-Related Virus in Monkeys, Nature, 2013, No Volume, pp. 1-2.
Lee, B., et al., "Hepatocyte Gene therapy in a Large Animal: A Neonatal Bovine Model of Citrullinemia," Proceedings of the National Academy of Sciences of the United States of America 96(17):3981-3986, National Academy of Sciences, United States (1999).
Lee, G., et al., "Modelling Pathogenesis and Treatment of Familial Dysautonomia Using Patient-Specific iPSCs," Nature 461(7262):402-406, Nature Publishing Group, England (2009).
Lee, J., et al., "Molecular Basis for the Immunostimulatory Activity of Guanine Nucleoside Analogs: Activation of Toll-Like Receptor 7," Proceedings of the National Academy of Sciences of the United States of America 100(11):6646-6651, National Academy of Sciences, United States (2003).
Lee, J.B., et al., "Lipid Nanoparticle siRNA Systems for Silencing the Androgen Receptor in Human Prostate Cancer in Vivo," International Journal of Cancer 131(5):781-790, Wiley-Liss, United States (2012).
Lee, J.T. And Nussbaum, R.L., "An Arginine to Glutamine Mutation in Residue 109 of Human Ornithine Transcarbamylase Completely Abolishes Enzymatic Activity in Cos1 Cells," The Journal of Clinical Investigation 84(6):1762-1766, American Society for Clinical Investigation, United States (1989).
Lee, Judong et al., TIM Polymorphisms—Genetics and Function, Genes Immun. 2011, vol. 12, No. 8, pp. 595-604.
Lee, P.Y., et al., "Thermosensitive Hydrogel as a Tgf-Beta1 Gene Delivery Vehicle Enhances Diabetic Wound Healing," Pharmaceutical Research 20(12):1995-2000, Kluwer Academic/Plenum Publishers, United States (2003).
Lee, S. and Margolin, K., "Cytokines in Cancer Immunotherapy," Cancers 3(4):3856-3893, MDPI, Switzerland (2011).
Legleiter, J., et al., "Effect of Different Anti-Abeta Antibodies on Abeta Fibrillogenesis as Assessed by Atomic force Microscopy," Journal of Molecular Biology 335(4):997-1006, Elsevier, England (2004).
Lehto, T., et al., "Cell-Penetrating Peptides for the Delivery of Nucleic Acids," Expert Opinion on Drug Delivery 9(7):823-836, Informa Healthcare, England (2012).
Leitner, W.W., et al., "DNA and RNA-Based Vaccines: Principles, Progress and Prospects," Vaccine 18(9-10):765-777, Elsevier Science, Netherlands (1999).
Lenz, A., et al., "Human and Murine Dermis Contain Dendritic Cells isolation by Means of a Novel Method and Phenotypical and Functional Characterization," The Journal of Clinical Investigation 92(6):2587-2596, American Society for Clinical Investigation, United States (1993).
Leonard, J.P. and Goldenberg, D.M., "Preclinical and Clinical Evaluation of Epratuzumab (Anti-CD22 IgG) in B-Cell Malignancies," Oncogene 26(25):3704-3713, Nature Publishing Group, England (2007).
Leonardi, C., et al., "Anti-Interleukin-17 Monoclonal Antibody Ixekizumab in Chronic Plaque Psoriasis," The New England Journal of Medicine 366(13):1190-1199, Massachusetts Medical Society, United States (2012).
Lerner, M.R., et al., "Are snRNPs involved in Splicing?," Nature 283(5743):220-224, Nature Publishing Group, England (1980).
Lesaffre, B., et al., "Direct Non-Cell Autonomous Pax6 Activity Regulates Eye Development in the Zebrafish," Neural Development 2:2, BioMed Central, England (2007).
Leung, D.W., "The Structure and Functions of Human Lysophosphatidic Acid Acyltransferases," Frontiers in Bioscience 6:D944-953, Frontiers in Bioscience Publications, United States (2001).
Lewandowski, L.J., et al., "Separation of the infectious Ribonucleic Acid of Potato Spindle Tuber Virus from Double-Stranded Ribonucleic Acid of Plant Tissue Extracts," Journal of Virology 8(5):809-812, American Society for Microbiology, United States (1971).
Lewis, David, Dynamic Polyconjugates (DPC) Technology: An elegant solution to the siRNA delivery problem. Arrowhead Research Corp (Nasdaq: ARWR). Nov. 2011.
Lewis, J.D., et al., "The influence of 5' and 3' End Structures on Pre-mRNA Metabolism," Journal of Cell Science 19:13-19, Company of Biologists, England (1995).
Lewis, J.K., et al., "Matrix-assisted Laser Desorption/Ionization Mass Spectrometry in Peptide and Protein Analysis," in: Encyclopedia of Analytical Chemistry, Meyers, R.A., ed., pp. 5880-5894, John Wiley & Sons, Chichester, England (2000).
Li, J., et al., "Methylation Protects miRNAs and siRNAs from a 3'-End Uridylation Activity in *Arabidopsis*," Current biology : CB 15(16):1501-1507, Cell Press, England (2005).
Li, L., et al., "Preparation and Gene Delivery of Alkaline Amino Acids-Based Cationic Liposomes," Archives of Pharmacal Research 31(7):924-931, Pharmaceutical Society of Korea, Korea (South) (2008).
Li, X., et al., "Generation of Destabilized Green Fluorescent Protein as a Transcription Reporter," The Journal of Biological Chemistry 273(52):34970-34975, American Society for Biochemistry and Molecular Biology, United States (1998).
Li, Z., et al., "Controlled Gene Delivery System Based on thermosensitive Biodegradable Hydrogel," Pharmaceutical Research 20(6):884-888, Kluwer Academic/Plenum Publishers, United States (2003).
Li, Z.J. and Cho, C.H., "Peptides as Targeting Probes against Tumor Vasculature for Diagnosis and Drug Delivery," Journal of Translational Medicine 10(Suppl.1):1-9, BioMed Central, England (2012).
Lian, T. and Ho, R.J., "Trends and Developments in Liposome Drug Delivery Systems," Journal of Pharmaceutical Sciences 90(6):667-680, Elsevier, United States (2001).
Liang, X.H., et al., "The Spliced Leader-Associated RNA is a Trypanosome-Specific sn(o) RNA that has the Potential to Guide Pseudouridine Formation on the SL RNA," RNA 8(2):237-246, Cold Spring Harbor Laboratory Press, United States (2002).

(56) References Cited

OTHER PUBLICATIONS

Licatalosi, D.D. and Darnell, R.B., "Splicing Regulation in Neurologic Disease," Neuron 52(1):93-101, Cell Press, United States (2006).
Li,L. and Shen, Y., "Overcoming Obstacles to Develop Effective and Safe siRNA therapeutics," Expert Opinion on Biological Therapy 9(5):609-619, Taylor & Francis, England (2009).
Limbach, P.A., et al., "Summary: the Modified Nucleosides of RNA," Nucleic Acids Research 22(12):2183-2196, Oxford University Press, England (1994).
Limberis, M.P., et al., "Intranasal Antibody Gene Transfer in Mice and Ferrets Elicits Broad Protection against Pandemic influenza," Science Translational Medicine 5(187):1-8, American Association for the Advancement of Science, United States (2013).
Lin, J.E., et al., "Bacterial Heat-Stable Enterotoxins: Translation of Pathogenic Peptides into Novel Targeted Diagnostics and Therapeutics," Toxins 2(8):2028-2054, MDPI, Switzerland (2010).
Linden, O., et al., "Dose-Fractionated Radioimmunotherapy in Non-Hodgkin'S Lymphoma using Dota-Conjugated, 90Y-Radiolabeled, Humanized Anti-CD22 Monoclonal Antibody, Epratuzumab.," Clinical Cancer Research 11(14):5215-5222, The Association, United States (2005).
Linder, H., et al., "Peripheral Blood Mononuclear Cells Induce Programmed Cell Death in Human Endothelial Cells and may Prevent Repair: Role of Cytokines," Blood 89(6):1931-1938, American Society of Hematology, United States (1997).
Linehan, D.C., et al., "Tumor-Specific and HLA-A2-Restricted Cytolysis by Tumor-Associated Lymphocytes in Human Metastatic Breast Cancer," Journal of Immunology 155(9):4486-4491, American Association of Immunologists, United States (1995).
Linke, R., et al., "Catumaxomab: Clinical Development and Future Directions," mAbs 2(2):129-136, Taylor & Francis, United States (2010).
Lipari, M.T., et al., "Furin-Cleaved Proprotein Convertase Subtilisin/Kexin Type 9 (PCSk9) is Active and Modulates Low Density Lipoprotein Receptor and Serum Cholesterol Levels," The Journal of Biological Chemistry 287(52):43482-43491, American Society for Biochemistry and Molecular Biology, United States (2012).
Liu, A.Y., et al., "Production of a Mouse-Human Chimeric Monoclonal Antibody to CD20 with Potent Fc-Dependent Biologic Activity," Journal of Immunology 139(10):3521-3526, American Association of Immunologists, United States (1987).
Liu, C., et al., "Peptidoglycan Recognition Proteins: A Novel Family of Four Human Innate Immunity Pattern Recognition Molecules," The Journal of Biological Chemistry 276(37):34686-34694, American Society for Biochemistry and Molecular Biology, United States (2001).
Lizardi, P.M., et al., "Mutation Detection and Single-Molecule Counting Using isothermal Rolling-Circle Amplification," Nature Genetics 19(3):225-232, Nature Pub. Co, United States (1998).
Lo, A., et al., "Hepatocellular Carcinoma Cell-Specific Peptide Ligand for Targeted Drug Delivery," Molecular Cancer Therapeutics 7(3):579-589, American Association for Cancer Research, United States (2008).
Lo Surdo, P., et al., "Mechanistic Implications for LDL Receptor Degradation from the PCSK9/LDLR Structure at Neutral pH," EMBO Reports 12(12):1300-1305, Wiley Blackwell, England (2011).
Lobenberg, R., et al., "Improved Body Distribution of 14C-Labelled AZT Bound to Nanoparticles in Rats Determined by Radioluminography," Journal of Drug Targeting 5(3):171-179, Informa Healthcare, England (1998).
Loduca, P.A., et al., "Hepatic Gene Transfer as a Means of Tolerance induction to Transgene Products," Current Gene Therapy 9(2):104-114, Bentham Science Publishers, Netherlands (2009).
Loging, Wt., et al., "Identifying Potential Tumor Markers and Antigens by Database Mining and Rapid Expression Screening," Genome Research 10(9):1393-1402, Cold Spring Harbor Laboratory Press, United States (2000).
Lonez, C., et al., "Cationic Liposomal Lipids: From Gene Carriers to Cell Signaling," Progress in Lipid Research 47(5):340-347, Pergamon, England (2008).
Lonial, S., et al., "Elotuzumab in combination with lenalidomide and low-dose dexamethasone in relapsed or refractory multiple myeloma," Journal of Clinical Oncology 30(16):1953-1959, American Society of Clinical Oncology, United States (2012).
Lopez, M.F., et al., "Selected Reaction Monitoring-Mass Spectrometric Immunoassay Responsive to Parathyroid Hormone and Related Variants," Clinical Chemistry 56(2):281-290, American Association for Clinical Chemistry, United States (2010).
Lopez-Berestein, G,. et al., "Treatment of Systemic Fungal infections with Liposomal Amphotericin B," Archives of Internal Medicine 149(11):2533-2536, American Medical Assn, United States (1989).
Lorenz, C., et al., "Protein Expression from Exogenous mRNA: Uptake by Receptor-mediated Endocytosis and Trafficking via the Lysosomal Pathway," RNA Biology 8(4):627-636, Taylor & Francis, United States (2011).
Lorenzi, J.C., et al., "Intranasal Vaccination with Messenger RNA as a New Approach in Gene Therapy: Use against Tuberculosis," BMC Biotechnology 10(77):1-11, BioMed Central, England (2010).
Love, K.T., et al., "Lipid-Like Materials for Low-Dose, In Vivo Gene Silencing," Proceedings of the National Academy of Sciences of the United States of America 107(5):1864-1869, National Academy of Sciences, United States (2010).
Lowe, T.M. and Eddy, S.R., "A Computational Screen for Methylation Guide snoRNAs in Yeast," Science 283(5405):1168-1171, American Association for the Advancement of Science, United States (1999).
Lowry, W.E., et al., "Generation of Human Induced Pluripotent Stem Cells from Dermal Fibroblasts," Proceedings of the National Academy of Sciences of the United States of America 105(8):2883-2888, National Academy of Sciences, United States (2008).
Lozier, J.N., "Gene Therapy Factor IX Padua: them that have, give," Blood 120(23):4452-4453, American Society of Hematology, United States (2012).
Lu, B., et al., "Cloning and Characterization of Murine 1-acyl-sn-glycerol 3-phosphate Acyltransferases and their Regulation by PPARalpha in Murine Heart," The Biochemical Journal 385:469-477, Portland Press, England (2005).
Lu, C., et al., "miR-221 and miR-155 Regulate Human Dendritic Cell Development, Apoptosis, and Il-12 Production Through Targeting of P27Kip1 , Kpc1 , and Socs-1," Blood 117(16):4293-4303, American Society of Hematology, United States (2011).
Lu, D., et al., "Tailoring in Vitro Selection for a Picomolar Affinity Human Antibody Directed against Vascular Endothelial Growth Factor Receptor 2 for Enhanced Neutralizing Activity," The Journal of Biological Chemistry 278(44):43496-43507, American Society for Biochemistry and Molecular Biology, United States (2003).
Lu, L.F., et al., "Foxp3-Dependent MicroRNA155 Confers Competitive Fitness to Regulatory T Cells by Targeting SOCS1 Protein," Immunity 30(1):80-91, Cell Press, United States (2009).
Lu, R.M., et al., "Targeted Drug Delivery Systems Mediated by a Novel Peptide in Breast Cancer Therapy and Imaging," PloS One 8(6):1-13, Public Library of Science, United States (2013).
Lu, X., et al., "Peptidoglycan Recognition Proteins are a New Class of Human Bactericidal Proteins," The Journal of Biological Chemistry 281(9):5895-5907, American Society for Biochemistry and Molecular Biology, United States (2006).
Lubberts, E., et al., "Treatment with a Neutralizing Anti-Murine Interleukin-17 Antibody after the Onset of Collagen-Induced Arthritis Reduces Joint Inflammation, Cartilage Destruction, and Bone Erosion," Arthritis and Rheumatism 50(2):650-659, Wiley-Blackwell, United States (2004).
Lund, P.E., et al., "Pseudovirions as Vehicles for the Delivery of siRNA," Pharmaceutical Research 27(3):400-420, Kluwer Academic/Plenum, United States (2010).
Luo, D. and Saltzman, W.M., "Synthetic DNA Delivery Systems," Nature Biotechnology 18(1):33-37, Nature America Publishing, United States (2000).

(56) References Cited

OTHER PUBLICATIONS

Luo, X., et al., "Dendritic Cells with TGF-Beta1 Differentiate Naive CD4+CD25-T Cells into islet-Protective Foxp3+ Regulatory T Cells," Proceedings of the National Academy of Sciences of the United States of America 104(8):2821-2826, National Academy of Sciences, United States (2007).
Luukkonen, B.G. and Seraphin, B., "A Conditional U5 snRNA Mutation Affecting Pre-mRNA Splicing and Nuclear Pre-mRNA Retention Identifies SSD1/SRK1 as a General Splicing Mutant Suppressor," Nucleic Acids Research 27(17):3455-3465, Oxford University Press, England (1999).
Lysosomal Acid Lipase (lysosomal acid lipase/ cholesteryl ester hydrolase isoform 1 precursor [*Homo sapiens*]; NCBI, 2010, No Vol., pp. 1-3.
Ma, B., et al., "HPV Pseudovirions as DNA Delivery Vehicles," Therapeutic Delivery 2(4):427-430, Future Science, England (2011).
Ma, X., et al., "Pseudouridylation (PSI) of U2 snRNA in S. Cerevisiae is Catalyzed by an RNA-Independent Mechanism," The EMBO Journal 22(8):1889-1897, Wiley Blackwell, England (2003).
Mackie, G.A., "Vectors for the Synthesis of Specific RNAs in Vitro," Biotechnology 10:253-267, Butterworth-Heinemann, United States (1988).
Maclean, C., et al., "Systematic Review: Comparative Effectiveness of Treatments to Prevent Fractures in Men and Women with Low Bone Density or Osteoporosis," Annals of Internal Medicine 148(3):197-217, American Society of Internal Medicine, United States (2008).
Maden, B.E., et al. "Classical and Novel Approaches to the Detection and Localization of the Numerous Modified Nucleotides in Eukaryotic Ribosomal RNA," Biochimie 77(1-2):22-29, Editions Scientifiques Elsevier, France (1995).
Maehr, R., et al., "Generation of Pluripotent Stem Cells from Patients with Type 1 Diabetes," Proceedings of the National Academy of Sciences of the United States of America 106(37):15768-15773, National Academy of Sciences, United States (2009).
Magee, W.E., et al., "Marked Stimulation of Lymphocyte-Mediated Attack on Tumor Cells by Target-Directed Liposomes Containing Immune RNA," Cancer Research 38(4):1173-1176, American Association for Cancer Research, United States (1978).
Mali, P., et al., "Rna-Guided Human Genome Engineering via Cas9," Science 339(6121):823-826, American Association for the Advancement of Science, United States (2013).
Malone, R.W., et al., "Cationic Liposome-Mediated RNA Transfection," Proceedings of the National Academy of Sciences of the United States of America 86(16):6077-6081, National Academy of Sciences, United States (1989).
Mannick, J.A. and Egdahl, R.H., "Transformation of Nonimmune Lymph Node Cells to State of Transplantation Immunity by RNA a Preliminary Report," Annals of Surgery 156:356-366, Lippincott Williams & Wilkins, United States (1962).
Mansour, A.M. and Niu, M.C., "Functional Studies with Uterine RNA," Proceedings of the National Academy of Sciences of the United States of America 94(31):764-770, National Academy of Sciences, United States (1965).
Mansour, S.L., et al., "Disruption of the Proto-Oncogene Int-2 in Mouse Embryo-Derived Stem Cells: A General Strategy for Targeting Mutations to Non-Selectable Genes," Nature 336(6197):348-352, Nature Publishing Group, England (1988).
Marini, J.C., at al., "Phenylbutyrate Improves Nitrogen Disposal via an Alternative Pathway Without Eliciting an Increase in Protein Breakdown and Catabolism in Control and ornithine Transcarbamylase-Deficient Patients," The American Journal of Clinical Nutrition 93(6):1248-1254, American Society of Clinical Nutrition, United States (2011).
Marquina, G., et al., "Gangliosides Expressed in Human Breast Cancer,"Cancer Research 56(22):5165-5171,American Association for Cancer Research, United States (1996).
Marson, a., et al., "WNT Signaling Promotes Reprogramming of Somatic Cells to Pluripotency," Cell Stem Cell 3(2):132-135, Cell Press, United States (2008).
Martin, S.A., et al., "Purification of mRNA Guanylyltransferase and mRNA (Guanine-7-) Methyltransferase from Vaccinia Virions," The Journal of Biological Chemistry 250(24):9322-9329, American Society for Biochemistry and Molecular Biology, United States (1975).
Martinelli, R.A., et al., "Chemiluminescent Hybridization-Ligation Assays for Delta F508 and Delta I507 Cystic Fibrosis Mutations," Clinical Chemistry 42(1):14-18, American Association for Clinical Chemistry, United States (1996).
Martinon, F., et al., "Induction of Virus-Specific Cytotoxic T Lymphocytes in Vivo by Liposome-Entrapped mRNA," European Journal of Immunology 23(7):1719-1722, Wiley-VCH, Germany (1993).
Massenet, S., et al., "Pseudouridine Mapping in the *Saccharomyces cerevisiae* Spliceosomal U Small Nuclear RNAS (SnRNAs) Reveals that Pseudouridine Synthase Pus1P Exhibits a Dual Substrate Specificity for U2 SnRNA and tRNA," Molecular and Cellular Biology 19(3):2142-2154, American Society for Microbiology, United States (1999).
Mathers, A.R. and Larregina, A.T., "Professional Antigen-Presenting Cells of the Skin," Immunologic Research 36(1-3):127-136, Humana Press, United States (2006).
Matray,T.J. and Gryaznov, S.M., "Synthesis and Properties of RNA Analogs-Oligoribonucleotide N3'—>P5' Phosphoramidates," Nucleic Acids Research 27(20):3976-3985, Oxford University Press, England (1999).
Matsuda, A. et al., "Nucleosides. 120. Syntheses of 2'-deoxy-ψ-isocytidine and 2'-deoxy-1-methyl-ψ-uridine from ψ-uridine," Journal of Organic Chemistry 46(18):3603-3609 (1981).
Matsuda, a., et al., "Synthesis of 3-Methylpseudouridine and 2'-Deoxy-3-Methyl-Pseudouridine," Carbohydrate Research 100:297-302, Elsevier, Netherlands (1982).
Matsuda, D. and Mauro, V.P., "Determinants of Initiation Codon Selection During Translation in Mammalian Cells," PloS one 5(11):e15057, Oxford University Press, England (2010).
Matsue, H., et al., "Folate Receptor Allows Cells to Grow in Low Concentrations of 5-Methyltetrahydrofolate," Proceedings of the National Academy of Sciences of the United States of America 89(13):6006-6009, National Academy of Sciences, United States (1992).
Maurer, N., et al., "Spontaneous Entrapment of Polynucleotides Upon Electrostatic Interaction with Ethanol-Destabilized Cationic Liposomes," Biophysical Journal 80(5):2310-2326, Cell Press, United States (2001).
Mayfield, S.P., et al., "Expression and Assembly of a Fully Active Antibody in Algae," Proceedings of the National Academy of Sciences of the United States of America 100(2):438-442, National Academy of Sciences, United States (2003).
Mayo Clinic, Factor Ix Complex (Intravenous Route, Injection Route) Description and Brand Names—Drugs and Supplements, http://www.mayoclinic.org/drugs-supplements/factor-ix-complex-intravenous-route-injection-route/ description/drg-20063804, Apr. 1, 2014, N.
Mazumdar, S. and Greenwald, D., "Golimumab," mAbs 1(5):422-431, Taylor & Francis, United States (2009).
McCafferty, J., et al., "Phage Antibodies: Filamentous Phage Displaying Antibody Variable Domains," Nature 348(6301):552-554, Nature Publishing Group, London (1990).
McCormack, A.L., et al., "Alpha-Synuclein Suppression by Targeted Small Interfering RNA in the Primate Substantia Nigra," PloS one 5(8):e12122, Nature Publishing Group, England (2010).
McCormack, M.P. and Rabbitts, T.H., "Activation of the T-Cell Oncogene LMO2 After Gene Therapy for X-Linked Severe Combined Immunodeficiency," The New England Journal of Medicine 350(9):913-922, Massachusetts Medical Society., United States (2004).
McDonald, J.D. and Charlton, C.K., "Characterization of Mutations at the Mouse Phenylalanine Hydroxylase Locus," Genomics 39(3):402-405, Academic Press, United States (1997).

(56) References Cited

OTHER PUBLICATIONS

McElwee, K.J., et al., "Transfer of Cd8(+) Cells Induces Localized Hair Loss Whereas Cd4(+)/Cd25(−) Cells Promote Systemic Alopecia Areata and Cd4(+)/Cd25(+) Cells Blockade Disease Onset in the C3H/Hej Mouse Model," The Journal of Investigative Dermatology 124(5):947-957, Elsevier, United States (2005).
McGary, E.C., et al., "Post-Transcriptional Regulation of Erythropoietin mRNA Stability by Erythropoietin mRNA-Binding Protein," The Journal of Biological Chemistry 272(13):8628-8634, American Society for Biochemistry and Molecular Biology, United States (1997).
McGee, M.M., et al., "The Quantitative Determination of Phenylalanine Hydroxylase in Rat Tissues its Developmental Formation in Liver," The Biochemical Joumal 127(4):669-674, Published by Portland Press on behalf of the Biochemical Society, England (1972).
McGlynn, R., et al., "Differential Subcellular Localization of Cholesterol, Gangliosides, and Glycosaminoglycans in Murine Models of Mucopolysaccharide Storage Disorders," The Journal of Comparative Neurology 480(4):415-426, Wiley-Liss, United States (2004).
McInnes, I.B., et al., "Efficacy and Safety of Secukinumab, a Fully Human Anti-Interleukin-17A Monoclonal Antibody, in Patients with Moderate-To-Severe Psoriatic Arthritis: a 24-Week, Randomised, Double-Blind, Placebo-Controlled, Phase Ii Proof-of-Concept Trial," Annals of the Rheumatic Diseases 73(2):349-356, BMJ, England (2014).
McKenney, J.M., et al., "Safety and Efficacy of a Monoclonal Antibody to Proprotein Convertase Subtilisin/Kexin Type 9 Serine Protease, SAR236553/REGN727, in Patients with Primary Hypercholesterolemia Receiving Ongoing Stable Atorvastatin Therapy," Journal of the American College of Cardiology 59(25):2344-2353, Elsevier Biomedical, United States (2012).
McKenzie, B.S., et al., "Nucleic Acid Vaccines: Tasks and Tactics," Immunologic Research 24(3):225-244, Humana Press, United States (2001).
McLean, L.P., et al., "Vedolizumab for the Treatment of Ulcerative Colitis and Crohn'S Disease," Immunotherapy 4(9):883-898, Humana Press, United States (2012).
McLean, M.J., et al., "Membrane Differentiation of Cardiac Myoblasts Induced in Vitro by an RNA-Enriched Fraction from Adult Heart," Experimental Cell Research 110(1):1-14, Academic Press, United States (1977).
McNutt, M.C., et al., "Antagonism of Secreted PCSK9 Increases Low Density Lipoprotein Receptor Expression in HepG2 Cells," The Journal of biological chemistry 284(16):10561-10570, American Society for Biochemistry and Molecular Biology, United States (2009).
Mease, P.J., et al., "Effect of Certolizumab Pegol on Signs and Symptoms in Patients with Psoriatic Arthritis: 24-Week Results of a Phase 3 Double-Blind Randomised Placebo-Controlled Study (RAPID-PsA)," Annals of the Rheumatic Diseases 73(1):48-55, BMJ, England (2014).
MEGAscript Kit Product Manual, Ambion/Invitrogen website: http://tools.invitrogen.com/content/sfs/manuals/ cms_072987.pdf, Publication Date: Oct. 27, 2009 (last accessed Mar. 17, 2013)("Ambion").
Mellits, K.H., et al., "Removal of Double-Stranded Contaminants from RNA Transcripts: Synthesis of Adenovirus VA RNAI From a T7 Vector," Nucleic Acids Research 18(18):5401-5406, Oxford University Press, England (1990).
Memczak, S., et al., "Circular RNAs are a Large Class of Animal RNAs with Regulatory Potency," Nature 495(7441):333-338, Nature Publishing Group, England (2013).
Mendelsohn, J., "Epidermal Growth Factor Receptor Inhibition by a Monoclonal Antibody as Anticancer Therapy," Clinical Cancer Research 3(12 Pt 2):2703-2707, The Association, United States (1997).
Merelli, B., et al., "Targeting the PD1/PD-L1 Axis in Melanoma: Biological Rationale, Clinical Challenges and Opportunities," Critical Reviews in Oncology/Hematology 89(1):140-165, Elsevier Scientific Publishers, Netherlands (2014).
Messer, W.B., et al., "Dengue Virus Envelope Protein Domain I/II Hinge Determines Long-Lived Serotype-Specific Dengue Immunity," Proceedings of the National Academy of Sciences of the United States of America 111(5):1939-1944, National Academy of Sciences, United States (2014).
Metz, B., et al. "Identification of Formaldehyde-Induced Modifications in Proteins: Reactions with Model Peptides," The Journal of Biological Chemistry 279(8):6235-6243, American Society for Biochemistry and Molecular Biology, United States (2004).
Meunier, L., et al., "Heterogeneous Populations of Class II MHC+ Cells in Human Dermal Cell Suspensions. Identification of a Small Subset Responsible for Potent Dermal Antigen-Presenting Cell Activity with Features Analogous to Langerhans Cells," The Journal of Immunology 151(8):4067-4080, American Association of Immunologists, United States (1993).
Micic, O.I., et al., "Synthesis and Characterization of InP, GaP, and GaInP2 Quantum Dots," Journal of Physical Chemistry 99(19):7754-7759, American Chemical Society, United States (1995).
Mieszawska, A.J., et al., "Synthesis of Polymer-Lipid Nanoparticles for Image-Guided Delivery of Dual Modality Therapy," Bioconjugate Chemistry 24(9):1429-1434, American Chemical Society, United States (2013).
Mignone, F. et al., Untranslated regions of mRNAs. Genome Biol. 2002;3(3):REVIEWS2004. Epub Feb. 28, 2002. pp. 1-10.
Minagar, A., "Current and Future Therapies for Multiple Sclerosis," Scientifica 2013:1-11, BioMed Central Ltd, England (2013).
Mingozzi, F., et al., "Pharmacological Modulation of Humoral Immunity in a Nonhuman Primate Model of AAC Gene Transfer for Hemophilia B," Molecular Therapy 20(7):1410-1416, Academic Press, United States (2012).
Ministry of Health, Labour and Welfare, Report on the Deliberation Results, Soliris for Intravenous Infusion 300 mg, 2010, No Vol., pp. 1-105.
Minks, M.A., et al., "Structural Requirements of Double-Stranded RNA for the Activation of 2',5'-Oligo(A) Polymerase and Protein Kinase of Interferon-Treated HeLa Cells," The Journal of Biological Chemistry 254(20):10180-10183, American Society for Biochemistry and Molecular Biology, United States (1979).
Miotti, S., et al., "Characterization of Human Ovarian Carcinoma-associated Antigens Defined by Novel Monoclonal Antibodies with Tumor-restricted Specificity," International Journal of Cancer 39(3):297-303, Wiley-Liss, United States (1987).
Miranda, P.S. and Bosma, P.J., "Towards Liver-Directed Gene Therapy for Crigler-Najjar Syndrome," Current Gene Therapy 9(2):72-82, Bentham Science Publishers, Netherlands (2009).
Mishra, N.C., et al., "Induction by RNA of Inositol independence in Neurospora Crassa," Proceedings of the National Academy of Sciences of the United States of America 72(2):642-645, National Academy of Sciences, United States (1975).
Mishra, R.K., et al., "Improved Leishmanicidal Effect of Phosphorotioate Antisense Oligonucleotides by LDL-Mediated Delivery," Biochimica et Biophysica Acta 1264(2):229-237, Elsevier, Netherlands (1995).
Mitchell, D.A. and Nair, S.K., "RNA Transfected Dendritic Cells as Cancer Vaccines," Current Opinion in Molecular Therapeutics 2(2):176-181, Thomson Reuters (Scientific) Ltd, England (2000).
Mitchell, D.A. and Nair, S.K., "RNA-Transfected Dendritic Cells in Cancer Immunotherapy," The Journal of Clinical Investigation 106(9):1065-1069, American Society for Clinical Investigation, United States (2000).
Mitchell, P. and Tollervey, D., "mRNA Turnover," Current Opinion in Cell Biology 13(3):320-325, Elsevier, England (2001).
Mitragotri, S., "Devices for Overcoming Biological Barriers: The Use of Physical forces to Disrupt the Barriers," Advanced Drug Delivery Reviews 65(1):100-103, Elsevier Science Publishers, Netherlands (2013).
Miura, K., et al., "Variation in the Safety of Induced Pluripotent Stem Cell Lines," Nature Biotechnology 27(8):743-745, Nature America Publishing, United States (2009).

(56) References Cited

OTHER PUBLICATIONS

Miyagi, S.J. and Collier, A.C., "The Development of UDP-Glucuronosyltransferases 1A1 and 1A6 in the Pediatric Liver," Drug Metabolism and Disposition 39(5):912-929, American Society for Pharmacology and Experimental Therapeutics, United States (2011).
Mockey, M., et al., "mRNA-Based Cancer Vaccine: Prevention of B16 Melanoma Progression and Metastasis by Systemic Injection of MART1 mRNA Histidylated Lipopolyplexes," Cancer Gene Therapy 14(9):802-814, Nature Publishing Group, England (2007).
Mohamadzadeh, M., et al., "Dendritic Cell Targeting of Bacillus Anthracis Protective Antigen Expressed by Lactobacillus Acidophilus Protects Mice from Lethal Challenge," Proceedings of the National Academy of Sciences of the United States of America 106(11):4331-4336, National Academy of Sciences, United States (2009).
Monobe, M., et al. "Beta-Pseudouridine, a Beer Component, Reduces Radiation-Induced Chromosome Aberrations in Human Lymphocytes," Mutation Research 538(1-2):93-99, Elsevier, Netherlands (2003).
Moore, J.E., et al., "The Corneal Epithelial Stem Cell," DNA and Cell Biology 21(5-6):443-451, Mary Ann Liebert, United States (2002).
Moore, M.J. and Sharp, P.A., "Site-Specific Modification of PRE-mRNA: the 2'-Hydroxyl Groups at the Splice Sites," Science 256(5059):992-997, American Association for the Advancement of Science, United States (1992).
Moreaux, J., et al., "BAFF and APRIL Protect Myeloma Cells from Apoptosis Induced by interleukin 6 Deprivation and Dexamethasone," Blood 103(8):3148-3157, American Society of Hematology, United States (2004).
Morgan, D., "Immunotherapy for Alzheimer'S Disease," Journal of Internal Medicine 269(1):54-63, Blackwell Scientific Publications, England (2011).
Morgan, H.D., et al., "Molecular Basis of Cell and Developmental Biology:Activation-induced Cytidine Dreaminase Deaminates 5-Methylcytosine in DNA and Is Expressed in Pluripotent Tissues: Implications for Epigenetic Reprogramming," Journal of Biological Chemistry 279(50):52353-52360, American Society for Biochemistry and Molecular Biology, United States (2004).
Morinaga, T., et al., "Primary Structures of Human Alpha-Fetoprotein and its mRNA," Proceedings of the National Academy of Sciences of the United States of America 80(15):4604-4608, National Academy of Sciences, United States (1983).
Morphotek, Efficacy and Safety of MORAb-003 in Subjects With Platinum-sensitive Ovarian Cancer in First Relapse, ClinicalTrials.gov, Apr. 2, 2014, http://clinicaltrials.govict2/show/NCT00849667?term=Farletuzumab&rank=4&submit_fld_opt, pp. 1-3.
Morse, M.A., et al., "Generation of Dendritic Cells in Vitro from Peripheral Blood Mononuclear Cells with Granulocyte-Macrophage-Colony-Stimulating Factor, Interleukin-4, and Tumor Necrosis Factor-Alpha for Use in Cancer Immunotherapy," Annals of Surgery 226(1):6-16, Lippincott Williams & Wilkins, United States (1997).
Morton, S.W., et al., "Scalable Manufacture of Built-to-order Nanomedicine: Spray-Assisted Layer-by-Layer Functionalization of Print Nanoparticles," Advanced materials 25(34):4707-4713, Weinheim : Wiley-VCH, Germany (2013).
Mossner, E., et al., "Increasing the Efficacy of CD20 Antibody Therapy through the Engineering of a New Type II anti-CD20 Antibody with Enhanced Direct and Immune Effector Cell-Mediated B-Cell Cytotoxicity," Blood 115(22):4393-4402, American Society of Hematology, United States (2010).
Mount, S.M., "A Catalogue of Splice Junction Sequences," Nucleic Acids Research 10(2):459-472, Oxford University Press, England (1982).
Mujoo, K., et al., "Disialoganglioside Gd2 on Human Neuroblastoma Cells: Target Antigen for Monoclonal Antibody-Mediated Cytolysis and Suppression of Tumor Growth," Cancer Research 47(4):1098-1104, American Association for Cancer Research, United States (1987).
Mujoo, K., et al., "Functional Properties and Effect on Growth Suppression of Human Neuroblastoma Tumors by Isotype Switch Variants of Monoclonal Antiganglioside GD2 Antibody 14.18," Cancer Research 49(11): 2857-2861, American Association for Cancer Research, United States (1989).
Mukherji, S., et al., "MicroRNAs Can Generate Thresholds in Target Gene Expression," Nature Genetics 43(9):854-859, Nature Pub. Co, United States (2011).
Mulkearns, et al., "FCHO2 Organizes Clathrin-coated Structures and Interacts with Dab2 for LDLR Endocytosis," Molecular Biology of the Cell, pp. 1-28 (2012).
Muller, M.R., et al., "Transfection of Dendritic Cells with RNA induces CD4- and CD8-Mediated T Cell Immunity Against Breast Carcinomas and Reveals the Immunodominance of Presented T Cell Epitopes," Journal of Immunology 170(12):5892-5896, American Association of Immunologists, United States (2003).
Murakawa, G.J., et al., "Direct Detection of HIV-1 RNA From AIDS and ARC Patient Samples," DNA 7(4):287-295, Mary Ann Liebert, United States (1988).
Myette, J.R. and Niles, E.G., "Domain Structure of the Vaccinia Virus mRNA Capping Enzyme Expression in *Escherichia coli* of a Subdomain Possessing the RNA 5'-Triphosphatase and Guanylyltransferase Activities and a Kinetic Comparison to the Full-Size Enzyme," The Journal of Biological Chemistry 271(20):11936-11944, American Society for Biochemistry and Molecular Biology, United States (1996).
Nagata, S., et al., "Codon Optimization Effect on Translational Efficiency of DNA Vaccine in Mammalian Cells: Analysis of Plasmid DNA Encoding a CTL Epitope Derived from Microorganisms," Biochemical and Biophysical Research Communications 261(2):445-451, Academic Press, United States (1999).
Nagata, S., et al., "Molecular Cloning and Expression of cDNA for Human Granulocyte Colony-Stimulating Factor," Nature 319(6052):415-418, Nature Publishing Group, England (1986).
Nagata, S., et al., "The Chromosomal Gene Structure and Two Mrnas for Human Granulocyte Colony-Stimulating Factor," The EMBO Journal 5(3):575-581, Wiley Blackwell, England (1986).
Nagata, S., et al., "Synthesis and Biological Activity of Artificial mRNA Prepared with Novel Phosphorylating Reagents," Nucleic Acids Research 38(21):7845-7857, Oxford University Press, England (2010).
Nair, P., et al., "CD6 Synergistic Co-Stimulation Promoting Proinflammatory Response is Modulated without interfering with the Activated Leucocyte Cell Adhesion Molecule Interaction," Clinical and Experimental Immunology 162(1):116-130, Blackwell Scientific Publications, England (2010).
Nair, S., et al., "Soluble Proteins Delivered to Dendritic Cells Via PH-Sensitive Liposomes Induce Primary Cytotoxic T Lymphocyte Responses in Vitro," The Journal of Experimental Medicine 175(2):609-612, Rockefeller University Press, United States (1992).
Nair, S.K., et al., "Antigen-Presenting Cells Pulsed with Unfractionated Tumor-Derived Peptides are Potent Tumor Vaccines," European Journal of Immunology 27(3):589-597, Weinheim : Wiley-VCH, Germany (1997).
Nair, S.K., et al., "Induction of Cytotoxic T Cell Responses and Tumor Immunity Against Unrelated Tumors Using Telomerase Reverse Transcriptase RNA Transfected Dendritic Cells," Nature Medicine 6(9): 1011-1017, Nature Publishing Company, United States (2000).
Nair, S.K., et al., "Induction of Primary Carcinoembryonic Antigen (Cea)-Specific Cytotoxic T Lymphocytes in Vitro Using Human Dendritic Cells Transfected with RNA," Nature Biotechnology 16(4):364-369, Nature America Publishing, United States (1998).
Nakagawa, M., et al., "Generation of Induced Pluripotent Stem Cells without Myc From Mouse and Human Fibroblasts," Nature Biotechnology 26(1):101-106, Nature America Publishing, United States (2008).
Nakamura, K. and Knight, R.A., "Intranuclear Incorporation of Thymic Low Molecular Weight RNA by Murine Bone Marrow Immunoblasts and Inhibition of Plasma Cell Formation by a Deriva-

(56) References Cited

OTHER PUBLICATIONS tive of Rifampicin," Microbiology and Immunology 26(1):41-57, Richmond : Wiley-Blackwell, Australia (1982).
Nakamura, K., "Conversion of Immune Response Patterns From High to Low and Low to High by an RNase-Sensitive Thymocyte Extract," Immunology 41(1):25-35, Blackwell Scientific Publications, England (1980).
Nakamura, K., et al., "A Model for the Autosensitization Autoantibody Production Associated with Xenogeneic Thymic RNA," Journal of Immunology 121(2):702-709, American Association of Immunologists, United States (1978).
Nakamura, K., et al., "Antigen Restricted Hybridization between Antigen Primed Macrophage and Thymic RNA," Immunological communications 10(4-5):367-382, Marcel Dekker, United States (1981).
Nakamura, K., et al., "Generation of Anti-Nzb Red Blood Cell antibody-Forming Plasma Cells from Bone Marrow Cultures of Syngeneic and Allogeneic Mice: Functional Modulation of Helper T-Cell Subsets in Autosensitization," Immunology 48(3):579-586, Blackwell Scientific Publications, England (1983).
Nakamura, K., et al., "Mechanism of Anti-DNA Antibody Formation the Functional Modulation of Helper T-Subset Plays the Key Role in Both Murine and Human B-Cell Autosensitization," Microbiology and Immunology 30(7):703-715, Richmond : Wiley-Blackwell, Australia (1986).
Nakamura, K., et al., "The Proliferation of Plasma Cells from Mouse Bone Marrow in Vitro III Primary and Secondary Immune Responses Associated with Thymic RNA," Immunological Communications 8(5-6):511-529, Marcel Dekker, United States (1979).
Nakamura, K., "The Proliferation of Plasma Cells from Mouse Bone Marrow in Vitro. II—Stimulation of IgG-Producing Cells by a RNase-Sensitive Thymocyte Homogenate," Cellular Immunology 25(2):163-177, Academic Press, United States (1976).
Nakamura, O. and Takakura, K., "The Role of Immune RNA in the Immunotherapy of Malignant Brain Tumor," Brain and Nerve 34(4):333-339, Igaku Shoin, Tokyo (1982).
Nallagatla, S.R., et al., "A Brilliant Disguise for Self RNA: 5'-End and Internal Modifications of Primary Transcripts Suppress Elements of Innate Immunity," RNA Biology 5(3):140-144, Taylor & Francis, United States (2008).
Narayanan, A., et al., "Role of the Box C/D Motif in Localization of Small Nucleolar RNAs to Coiled Bodies and Nucleoli," Molecular Biology of the Cell 10(7):2131-2147, American Society for Cell Biology, United States (1999).
National Cancer Institute, Drugs Approved for Ovarian Cancer, Aug. 16, 2013, No Vol.,pp. 1-2.
Naz, R.K., et al. "Novel Human Prostate-Specific cDNA: Molecular Cloning, Expression, and Immunobiology of the Recombinant Protein," Biochemical and Biophysical Research Communications 297(5):1075-1084, Academic Press, United States (2002).
NCBI BLAST, Accession No. BE136127.1, Retrieved from https://www.ncbi.nlm.nih.gov/nucest/8598627, 2007.
Neal, Z.C., et al., "Enhanced Activity of Hu14.18-IL2 Immunocytokine against Murine Nxs2 Neuroblastoma when Combined with interleukin 2 Therapy," Clinical Cancer Research 10(14):4839-4847, The Association, United States (2004).
Needleman, S.B. and Wunsch, C.D., "A General Method Applicable to the Search for Similarities in the Amino Acid Sequence of Two Proteins," Journal of Molecular Biology 48(3):443-453, Academic Press, England (1970).
Neer, R.M., et al., "Effect of Parathyroid Hormone (1-34) on Fractures and Bone Mineral Density in Postmenopausal Women with Osteoporosis," The New England Journal of Medicine 344(19):1434-1441, Massachusetts Medical Society, United States (2001).
Negrier, C., et al., "Enhanced Pharmacokinetic Properties of a GlycoPEGylated Recombinant Factor IX: A First Human Dose Trial in Patients with Hemophilia B," Blood 118(10):2695-2701, The American Society of Hematology, United States (2011).
Nelson, C.E., et al., "Tunable Delivery of siRNA from a Biodegradable Scaffold to Promote Angiogenesis in Vivo," Advanced Materials 26(4):607-614, Weinheim : Wiley-VCH, Germany (2014).
Neninger, E., et al., "Active Immunotherapy with 1E10 Anti-Idiotype Vaccine in Patients with Small Cell Lung Cancer: Report of a Phase I Trial," Cancer Biology & Therapy 6(2):145-150, Taylor & Francis, United States (2007).
Nestle, F.O., et al., "Vaccination of Melanoma Patients with Peptide- or Tumor Lysate-Pulsed Dendritic Cells," Nature Medicine 4(3):328-332, Nature Publishing Company, United States (1998).
Neumann, E., et al., "Fundamentals of Electroporative Delivery of Drugs and Genes," Bioelectrochemistry and Bioenergetics 48(1):3-16, Elsevier Sequoia, Netherlands (1999).
Neve, S., et al., "Tissue Distribution, Intracellular Localization and Proteolytic Processing of Rat 4-Hydroxyphenylpyruvate Dioxygenase," Cell biology International 27(8):611-624, John Wiley Sons Chichester, England (2003).
New, K. and Brechbiel, M.W., "Growing Applications of "Click Chemistry" for Bioconjugation in Contemporary Biomedical Research," Cancer biotherapy & Radiopharmaceuticals 24(3):289-302, Mary Ann Liebert, United States (2009).
Newby, M.I. and Greenbaum, N.L., "Sculpting of the Spliceosomal Branch Site Recognition Motif by a Conserved Pseudouridine," Nature Structural Biology 9(12):958-965, Nature Pub. Co, United States (2002).
Newman, A. and Norman, C., "Mutations in Yeast U5 SnRNA Alter the Specificity of 5' Splice-Site Cleavage," Cell 65(1):115-123, Cell Press, United States (1991).
Newman, A.J. and Norman, C., "U5 SnRNA interacts with Exon Sequences at 5' and 3' Splice Sites," Cell 68(4):743-754, Cell Press, United States (1992).
Newmark, J. et al., Preparation and properties of adducts of streptokinase and streptokinase-plasmin complex with poly ethylene glycol and pluronic polyol F38. J Appl Biochem. 1982; 4:185-9.
Ngai, P.H., et al., "Agrocybin, an Antifungal Peptide from the Edible Mushroom Agrocybe Cylindracea," Peptides 26(2):191-196, Elsevier Science, United States (2005).
Nguyen, A., et al., "Quantitative Assessment of the Use of Modified Nucleoside Triphosphates in Expression Profiling: Differential Effects on Signal intensities and Impacts on Expression Ratios," BMC Biotechnology 2:14, BioMed Central, England (2002).
Nguyen, M.K. and Lee, D.S., "Injectable Biodegradable Hydrogels," Macromolecular Bioscience 10(6):563-579, Wiley-VCH, Germany (2010).
Ni, J., et al., "Small Nucleolar RNAs Direct Site-Specific Synthesis of Pseudouridine in Ribosomal RNA," Cell 89(4):565-573, Cell Press, United States (1997).
Ni, Y.G., et al., "A PCSK9-Binding Antibody that Structurally Mimics the Egf(A) Domain of LDL-Receptor Reduces LDL Cholesterol in Vivo," Journal of Lipid Research 52(1):78-86, American Society for Biochemistry and Molecular Biology, United States (2011).
Nicholas, J., et al., "New and Emerging Disease-Modifying Therapies for Relapsing-Remitting Multiple Sclerosis: What is New and What is to Come," Journal of Central Nervous System Disease 4: 81-103, Libertas Academica, New Zealand (2012). 0.
Nicholson, A.W., et al., "Accurate in Vitro Cleavage by RNAse III of Phosphorothioate-Substituted RNA Processing Signals in Bacteriophage T7 Early mRNA," Nucleic Acids Research 16(4):1577-1591, Oxford University Press, England (1988).
Nielsen, D.A. and Shapiro, D.J., "Preparation of Capped RNa Transcripts Using T7 RNA Polymerase," Nucleic Acids Research 14(14):5936, Oxford University Press, England (1986).
Nielsen, P., et al., "Peptide Nucleic Acids as Therapeutic Agents," Current opinion in Structural Biology 9(3):353-357, Elsevier Science, England (1999).
Nikolin, V.P., et al., "Resistance of Mice Exposed to Whole-Body Irradiation to Transplanted Hemopoietic Cells Modified with RNA Preparations," Bulletin of Experimental Biology and Medicine 129(6):571-574, Springer, United States (2000).

(56) References Cited

OTHER PUBLICATIONS

Nitin, N., et al., "Peptide-Linked Molecular Beacons for Efficient Delivery and Rapid mRNA Detection in Living Cells," Nucleic Acids Research 32(6):e58, Oxford University Press, England (2004).
Niu, M.C. and Sasaki, N., "Causal Analysis of Embryonic Differentiation I Responsiveness of Presumptive Ectoderm as a Regulating Factor in RNA Function," Experimental Cell Research 64(1):57-64, Academic Press, United States (1971).
Niu, M.C. and Sasaki, N., "Causal Analysis of Embryonic Differentiation II Dual Function of Exogenous RNA in Differentiation of Presumptive Ectoderm," Experimental Cell Research 64(1):65-76, Academic Press, United States (1971).
Niu, M.C. and Deshpande, A.K., "The Development of Tubular Heart in RNA-Treated Post-Nodal Pieces of Chick Blastoderm," Journal of Embryology and Experimental Morphology 29(2):485-501, Cambridge Univ, England (1973).
Niu, M.C. and Leikola, A., "The Developmental Potentiality of the Liver-RNA-Treated Posterior Primitive Streak in the Chick Embryo," The Biological Bulletin 135(1):200-207, Marine Biological Laboratory, United States (1968).
Niu, M.C. and Mulherkar, L., "The Role of Exogenous Heart-RNA in Development of the Chick Embryo Cultivated in Vitro," Journal of Embryology and Experimental Morphology 24(1):33-42, Cambridge Univ, England (1970).
Niu, M.C. and Niu, L.C., "Re-Examination of the DNA-Mediated Transformation in Goldfish," Scientia Sinica. Series B 26(7):700-707, Academia Sinica, China (1983).
Niu, M.C. and Tung, T.C., "Genetic Manipulation in Higher organisms. I. Goldfish Ova as Materials of Operation, mRNA Mediated Alteration of the Liver Specific Isozymes," Scientia Sinica 20(6):803-806, Academia Sinica, China (1977).
Niu, M.C., Current Evidence Concerning Chemical Inducers. Evolution of Nervous Control from Primitive Organisms. 1959, 7-30.
Niu, M.C., et al "Antagonistic Action of Exogenous Histone and RNA in Mouse Ascites," Proceedings of the Society for Experimental Biology and Medicine 140(1):256-262, Blackwell Science, United States (1972).
Niu, M.C. et al., Genetic Manipulation in Higher Organisms; III. Detection of Soya Protein in Seeds Derived from Soya mRNA-Treated Rice. Scientia Sinica, 1980, 23:119-23.
Niu, M.C., et al "Poly(A)-Attached RNA as Activator in Embryonic Differentiation," Proceedings of the Society for Experimental Biology and Medicine 147(1):318-322, Blackwell Science, United States (1974).
Niu, M.C., et al,, "Presence of Liver-Forming Fraction in Fish Egg mRNAs Detected by its Ability to Encode Albumin Synthesis," Scientia Sinica 23(4):510-516, Academia Sinica, China (1980).
Niu, M.C., et al "Ribonucleic Acid-Induced Changes in Mammalian Cells," Proceedings of the National Academy of Sciences USA 47(10):1689-1700, National Academy of Sciences, United States (1961).
Niu, M.C., et al "RNA-Induced Biosynthesis of Specific Enzymes," Proceedings of the National Academy of Sciences of the United States of America 48(11):1964-1969, National Academy of Sciences, United States (1962).
Niu, M.C., et al "The Entrance of Exogenous RNA into the Mouse Ascites Cell," Proceedings of the Society for Experimental Biology and Medicine 128(2):550-555, Blackwell Science, United States (1968).
Niu, M.C., et al "Transfer of Information from mRNA to Chromosomes by Reverse Transcription in Early Development of Goldfish Eggs," Cellular and Molecular Biology 35(3):333-345, Pergamon Press, England (1989).
Niu, M.C., "Functional Potentiality of Ribonucleic Acid," Acta—Unio Internationalis Contra Cancrum 20:995-996, Union Internationale Centre le Cancer, Belgium (1964).
Niu, M.C., "Glucose-6-Phosphatase: Reexamination of the RNA-Induced Activity in Mouse Ascites Tumor Cells," Science 148(3669):513-516, American Association for the Advancement of Science, United States (1965).
Niu, M.C., "Mode of Action of the Exogenous Ribonucleic Acid in Cell Function," National Cancer Institute monograph 13:167-177, National Cancer Institute, United States (1964).
Niu, M.C., The Effect of mRNA on Nuclear Activity in Developing Systems. 1980, 415-33.
Niu, M.C., "Thymus Ribonucleic Acid and Embryonic Differentiation," Proceedings of the National Academy of Sciences of the United States of America 44(12):1264-1274, National Academy of Sciences, United States (1958).
Niu, M.C., VII. New Approaches to the Problem of Embryonic Induction. Cellular Mechanisms, Differentiation and Growth. 1956, 155-71.
No authors, "A Randomized Clinical Trial of OKT3 Monoclonal Antibody for Acute Rejection of Cadaveric Renal Transplants. Ortho Multicenter Transplant Study Group," The New England Journal of Medicine 313(6):337-342, Massachusetts Medical Society, United States (1985).
Nogueira, R.T., et al., "Recombinant Yellow Fever Viruses Elicit Cd8+ T Cell Responses and Protective Immunity Against Trypanosoma Cruzi," PloS one 8(3):e59347, Academia Sinica, China (2013).
Norbury, C.J., "Cytoplasmic RNA: A Case of the Tail Wagging the Dog," Nature reviews, Molecular cell biology 14(10):643-653, Nature Pub. Group, England (2013).
Novakovic, D., et al.,"Profile of Gantenerumab and its Potential in the Treatment of Alzheimer'S Disease," Drug Design, Development and Therapy 7:1359-1364, Dove Press Limited, New Zealand (2013).
Novartis, Product Label, Simulect, Basiliximab, 1998, No Vol. pp. 1-7.
Oberg (Aquaporins, Production Optimization and Characterization; Thesis for the Degree of Doctor of Philosophy in Natural Science; University of Gothenburg, Department of Chemistry—Biochemistry; pp. 1-69, published May 27, 2011. No Vol.
Oberhauser, B. and Wagner, E., "Effective Incorporation of 2'-O-Methyl-Oligoribonucleotides into Liposomes and Enhanced Cell Association Through Modification with Thiocholesterol," Nucleic Acids Research 20(3):533-538, Oxford University Press, England (1992).
Occhiogrosso, G., et al., "Prolonged Convection-Enhanced Delivery into the Rat Brainstem," Neurosurgery 52(2):388-394, Lippincott Williams & Wilkins, United States (2003).
Ochman, H., et al., "Genetic Applications of an Inverse Polymerase Chain Reaction," Genetics 120(3):621-623, Genetics Society of America, United States (1988).
Odens, M., "Prolongation of the Life Span in Rats," Journal of the American Geriatrics Society 21(10):450-451, Blackwell Science, United States (1973).
Odoherty, U., et al,, "Human Blood Contains Two Subsets of Dendritic Cells, One Immunologically Mature and the Other Immature," Immunology 82(3):487-493, Blackwell Scientific Publications, England (1994).
Ofengand, J. and Henes, C., "The Function of Pseudouridylic Acid in Transfer Ribonucleic Acid II Inhibition of Amino acyl Transfer Ribonucleic Acid-Ribosome Complex formation by Ribothymidylyl-Pseudouridylyl-Cytidylyl-Guanosine 3'-Phosphate," The Journal of Biological Chemistry 244(22):6241-6253, American Society for Biochemistry and Molecular Biology, United States (1969).
Office Action dated Jan. 27, 2015, in related Japanese Patent Application No. 2014-502899, filed on Apr. 2, 2012.
Ohashi, H., et al., "Efficient Protein Selection Based on Ribosome Display System with Purified Components," Biochemical and Biophysical Research Communications 352(1):270-276, Academic Press, United States (2007).
Ohmichi, T., et al., "Efficient Bacterial Transcription of DNA Nanocircle Vectors with Optimized Single-Stranded Promoters," Proceedings of the National Academy of Sciences of the United

(56) References Cited

OTHER PUBLICATIONS

States of America 99(1):54-59, Washington, DC : National Academy of Sciences, United States (2002).
Okita, K., et al., "Generation of Mouse Induced Pluripotent Stem Cells without Viral Vectors," Science 322(5903):949-953, American Association for the Advancement of Science, United States (2008).
Okumura, K., et al., "Bax mRNA Therapy Using Cationic Liposomes for Human Malignant Melanoma," The journal of Gene Medicine 10(8):910-917, John Wiley & Sons, England (2008).
Oldhoff, J.M., et al., "Anti-II-5 Recombinant Humanized Monoclonal Antibody (Mepolizumab) for the Treatment of atopic Dermatitis," Allergy 60(5):693-696, Wiley-Blackwell, Denmark (2005).
Ornithine Carbamoyltransferase; ornithine carbamoyltransferase, nnitochondrial precursor [*Homo sapiens*}; NCBI, 2010, No Vol., pp. 1-3.
Oster, C.G. and Kissel, T., "Comparative Study of DNA Encapsulation Into PLGA Microparticles Using Modified Double Emulsion Methods and Spray Drying Techniques," Journal of Microencapsulation 22(3):235-244, Informa Healthcare, England (2005).
Ostrowitzki, S., et al., "Mechanism of Amyloid Removal in Patients with Alzheimer Disease Treated with Gantenerumab," Archives of Neurology 69(2):198-207, American Medical Assn, United States (2012).
Ottone, F., et al., "Relationship Between Folate-Binding Protein Expression and Cisplatin Sensitivity in Ovarian Carcinoma Cell Lines," British Journal of Cancer 76(1):77-82, Nature Publishing Group, England (1997).
Owen, M. and Friedenstein, A.J., "Stromal Stem Cells: Marrow-Derived Osteogenic Precursors," Ciba Foundation symposium 136:42-60, Associated Scientific Publishers, Netherlands (1988).
Ozawa, T., et al., "Amplification and Analysis of cDNA Generated From a Single Cell by 5'-Race: Application to Isolation of Antibody Heavy and Light Chain Variable Gene Sequences from Single B Cells," BioTechniques 40(4):469-470, Informa Healthcare USA, England (2006).
Padhi, D., et al., "Single-dose, Placebo-controlled, Randomized Study of AMG 785, a Sclerostin Monoclonal Antibody," Journal of Bone and Mineral Research 26(1):19-26, American Society for Bone and Mineral Research, United States (2011).
Padilla, R. and Sousa, R., "A Y639F/H784A T7 RNA Polymerase Double Mutant Displays Superior Properties for Synthesizing RNAs with Non-Canonical NTPS," Nucleic Acids Research 30(24):e138, Oxford University Press, England (2002).
Paglia, P., et al., "Murine Dendritic Cells Loaded in Vitro with Soluble Protein Prime Cytotoxic T Lymphocytes against Tumor Antigen in Vivo," The Journal of Experimental Medicine 183(1):317-322, Rockefeller University Press, United States (1996).
Painter, H., et al., 494. Topical delivery of mRNA to the murine lung and nasal epithelium. Mol Ther. 2004; 9: S187.
Palese, P., "Making Better influenza Virus Vaccines?," Emerging Infectious Diseases 12(1):61-65, National Center for Infectious Diseases, Centers for Disease Control and Prevention (CDC), United States (2006).
Palu, G., et al., "In Pursuit of New Developments for Gene Therapy of Human Diseases," Journal of Biotechnology 68(1):1-13, Elsevier Science Publishers, Netherlands (1999).
Palucka, A.K., et al., "Taming Cancer by inducing Immunity via Dendritic Cells," Immunological Reviews 220:129-150, Blackwell, England (2007).
Pangburn, T.O., et al., "Peptide-and Aptamer-Functionalized Nanovectors for Targeted Delivery of Therapeutics," Journal of Biomechanical Engineering 131(7):74005, American Society of Mechanical Engineers, United States (2009).
Papapetrou, E.P., et al., "Stoichiometric and Temporal Requirements of Oct4, Sox2, Klf4, and C-Myc Expression for Efficient Human iPSC induction and Differentiation," Proceedings of the National Academy of Sciences of the United States of America 106(31):12759-12764, National Academy of Sciences, United States (2009).

Papp, K.A., et al., "Anti-IL-17 Receptor Antibody AMG 827 Leads to Rapid Clinical Response in Subjects with Moderate to Severe Psoriasis: Results from a Phase I, Randomized, Placebo-Controlled Trial," The Journal of Investigative Dermatology 132(10):2466-2469, Elsevier, United States (2012).
Papp, K.A., et al., "Brodalumab, an Anti-interleukin-17-Receptor Antibody for Psoriasis," The New England Journal of Medicine 366(13):1181-1189, Massachusetts Medical Society, United States (2012).
Papp, K.A., et al., "Efficacy and Safety of Secukinumab in the Treatment of Moderate-To-Severe Plaque Psoriasis: a Randomized, Double-Blind, Placebo-Controlled Phase II Dose-Ranging Study," The British Journal of Dermatology 168(2): 412-421, Blackwell Scientific Publications, England (2013).
Paradi, E. et al., Changes in the content of modified nucleotides in wheat rRNA during greening. Biologia Plantarum. Apr. 2003; 47(1):33-8.
Park, I.H., et al., "Reprogramming of Human Somatic Cells to Pluripotency with Defined Factors," Nature 451(7175):141-146, Nature Publishing Group, England (2008).
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Parker, R., et al., "Recognition of the TACTAAC Box During mRNA Splicing in Yeast Involves Base Pairing to the U2-Like snRNA," Cell 49(2):229-239, Cell Press, United States (1987).
Pasadhika, S. and Rosenbaum, J.T., "Update on the Use of Systemic Biologic Agents in the Treatment of Noninfectious Uveitis," Biologics 8:67-81, Dove Medical Press, New Zealand (2014).
Pascolo, S., "Vaccination with Messenger RNA (mRNA)," Handbook of Experimental Pharmacology 183:221-235, Springer-Verlag, Germany (2008).
Passini, M.A., et al., "AAV Vector-Mediated Correction of Brain Pathology in a Mouse Model of Niemann-Pick a Disease," Molecular Therapy 11(5):754-762, Academic Press, United States (2005).
Passos, G.A. and De Lucca, F.L., "In Vivo Induction of Immunological Memory to Human Tumor Extract with Poly (A)-Containing Immune RNA," Cellular and Molecular Biology 34(2):157-164, Pergamon Press, England (1988).
Pastore, N., et al., "Sustained Reduction of Hyperbilirubinemia in Gunn Rats after Adeno-Associated Virus-Mediated Gene Transfer of Bilirubin UDP-Glucuronosyltransferase Isozyme 1A1 to Skeletal Muscle," Human Gene Therapy 23(10): 1082-1089, Liebert, United States (2012).
Paul, S.M., et al., "How to Improve R&D Productivity: The Pharmaceutical Industry'S Grand Challenge," Nature Reviews. Drug discovery 9(3):203-214, Nature Pub Group, England (2010).
Pavord, I.D., et al., "Mepolizumab for Severe Eosinophilic Asthma (Dream): A Multicentre, Double-Blind, Placebo-Controlled Trial," Lancet 380(9842):651-659, Elsevier, England (2012).
Pays, E., "Characterization of Double-Stranded Ribonucleic Acid Sequences Present in the Initial Transcription Products of Rat Liver Chromatin," The Biochemical Journal 165(2):237-245, Portland Press on behalf of the Biochemical Society, England (1977).
PCT Invitation to pay additional fees and, where applicable, protest fee for International application No. PCT/US2013/030061, dated Aug. 22, 2013.
PCT Invitation to pay additional fees and, where applicable, protest fee for International application No. PCT/US2013/030062, dated Jul. 19, 2013.
PCT Invitation to pay additional fees and, where applicable, protest fee for International application No. PCT/US2013/030064, dated Jul. 5, 2013.
Peakman, M., "Can We Vaccinate Against Type 1 Diabetes?," F1000 Biology Reports 4:19, Faculty of 1000, England (2012).
Pearson, W.R. and Lipman, D.J., "Improved Tools for Biological Sequence Comparison," Proceedings of the National Academy of Sciences USA 85(8):2444-2448, National Academy of Sciences, United States (1988).
Peculis, B., "RNA Processing: Pocket Guides to Ribosomal RNA," Current Biology 7(8):R480-R482, Cell Press, England (1997).

(56) References Cited

OTHER PUBLICATIONS

Peng, Z.H., et al. "Synthesis and Application of a Chain-Terminating Dinucleotide mRNA Cap Analog," Organic letters 4(2):161-164, American Chemical Society, United States (2002).
Penheiter, S.G., et al., "Type II Transforming Growth Factor-Beta Receptor Recycling is Dependent Upon the Clathrin Adaptor Protein Dab2," Molecular Biology of the Cell 21(22):4009-4019, American Society for Cell Biology, United States (2010).
Peoples, G.E., et al. "Breast and Ovarian Cancer-Specific Cytotoxic T Lymphocytes Recognize the Same Her2/Neu-Derived Peptide," Proceedings of the National Academy of Sciences of the United States of America 92(2):432-436, National Academy of Sciences, United States (1995).
Perche, F., et al., "Enhancement of Dendritic Cells Transfection In Vivo and of Vaccination against B16F10 Melanoma with Mannosylated Histidylated Lipopolyplexes Loaded with Tumor Antigen Messenger RNA," Nanomedicine 7(4): 445-453, Elsevier, United States (2011).
Perez-Velez, M.E., et al., "Induction of Neutralization Antibodies in Mice by Dengue-2 Envelope DNA Vaccines," Puerto Rico Health Sciences Journal 28(3):239-250, University of Puerto Rico Medical Sciences Campus, Puerto Rico (2009).
Pesole, G., et al., "Structural and Functional Features of Eukaryotic mRNA Untranslated Regions," Gene 276(1-2):73-81, Elsevier, Netherlands (2001).
Pesole, G., et al., "UTRdb and UTRsite: Specialized Databases of Sequences and Functional Elements of 5' and 3' Untranslated Regions of Eukaryotic mRNAs Update 2002," Nucleic Acids Research 30(1):335-340, Oxford University Press, England (2002).
Peters, R.T., et al., "Biochemical and Functional Characterization of a Recombinant Monomeric Factor VIII-Fc Fusion Protein," Journal of Thrombosis and Haemostasis 11(1):132-141, Blackwell Pub, England (2013).
Petit, I., et al., "G-Csf Induces Stem Cell Mobilization by Decreasing Bone Marrow SDF-1 and Up-Regulating CXCR4," Nature Immunology 3(7):687-694, Nature America Inc, United States (2002).
Phelan, A., et al., "Intercellular Delivery of Functional p53 by the Herpesvirus Protein VP22," Nature biotechnology 16(5):440-443, Nature America Publishing, United States (1998).
Phillips, M.I., "Somatic Gene Therapy for Hypertension," Brazilian Journal of Medical and Biological Research 33(6):715-721, Brazilian Association of Science Communication, Brazil (2000).
Phizicky, E.M., et al., "Biochemical Genomics Approach to Map Activities to Genes," Methods in Enzymology 350:546-559, Academic Press, United States (2002).
Piganis, R.A., et al., "Suppressor of Cytokine Signaling (SOCS) 1 Inhibits Type I Interferon (IFN) Signaling via the Interferon Alpha Receptor (IFNAR1)-Associated Tyrosine Kinase Tyk2," The Journal of Biological Chemistry 286(39):33811-33818, American Society for Biochemistry and Molecular Biology, United States (2011).
Podbregar, M., et al., "Cytokine Response of Cultured Skeletal Muscle Cells Stimulated with Proinflammatory Factors Depends on Differentiation Stage," The Scientific World Journal 2013:617170, Hindawi Publishing Corporation, Egypt (2013).
Polidoros, A.N., et al., "Rolling Circle Amplification-Race: A Method for Simultaneous Isolation of 5' and 3' cDNA Ends from Amplified cDNA Templates," BioTechniques 41(1):35-42, Informa Healthcare USA, England (2006).
Pollard, C., et al., "Type I IFN Counteracts the Induction of Antigen-Specific Immune Responses by Lipid-Based Delivery of mRNA Vaccines," Molecular Therapy 21(1):251-259, Academic Press, United States (2013).
Pon, R.T., et al., "Multiple Oligodeoxyribonucleotide Syntheseson a Reusable Solid-Phase CPG Support via the Hydroquinone-O,O'-Diacetic Acid (Q-Linker) Linker Arm," Nucleic Acids Research 27(6):1531-1538, Oxford University Press, England (1999).
Ponsaerts, P., et al. "Cancer Immunotherapy Using RNA-Loaded Dendritic Cells," Clinical and Experimental Immunology 134(3):378-384, Blackwell Scientific Publications, England (2003).
Ponsaerts, P., et al. "Highly Efficient mRNA-Based Gene Transfer in Feeder-Free Cultured H9 Human Embryonic Stem Cells," Cloning and Stem Cells 6(3):211-216, Mary Ann Liebert, United States (2004).
Ponsaerts, P., et al. "Messenger RNA Electroporation is Highly Efficient in Mouse Embryonic Stem Cells: Successful Flpe- and Cre-Mediated Recombination," Gene therapy 11(21):1606-1610, Nature Publishing Group, England (2004).
Ponsaerts, P., et al. "Messenger RNA Electroporation of Human Monocytes, followed by Rapid in Vitro Differentiation, Leads to Highly Stimulatory Antigen-Loaded Mature Dendritic Cells," Journal of Immunology 169(4):1669-1675, American Association of Immunologists, United States (2002).
Porgador, A., et al., "Induction of Antitumor Immunity Using Bone Marrow-Generated Dendritic Cells," Journal of Immunology 156(8):2918-2926, American Association of Immunologists, United States (1996).
Powell, J.S., et al., "Safety and Prolonged Activity of Recombinant Factor VIII Fc Fusion Protein in Hemophilia a Patients," Blood 119(13):3031-3037, The American Society of Hematology, United States (2012).
Pradilla, G., et al., "Prevention of Vasospasm by Anti-CD11/CD18 Monoclonal Antibody Therapy following Subarachnoid Hemorrhage in Rabbits," Journal of Neurosurgery 101(1):88-92, American Association of Neurological Surgeons, United States (2004).
Preisler, H.D. and Jacobs, S.K., "Sensitization in Vitro to Murine Myeloblastic Leukemia Cells by Xenogeneic Immune RNA," Journal of the National Cancer Institute 62(1):133-137, Oxford University Press, United States (1979).
Preiss, T. and Hentze, M.W., "Dual Function of the Messenger RNA Cap Structure in Poly(A)-Tail-Promoted Translation in Yeast," Nature 392(6675):516-520, Nature Publishing Group, England (1998).
Presta, L.G., et al., "Humanization of an Anti-Vascular Endothelial Growth Factor Monoclonal Antibody for the therapy of Solid Tumors and Other Disorders," Cancer Research 57(20):4593-4599, American Association for Cancer Research, United States (1997).
Prevvett, M., et al., "Antivascular Endothelial Growth Factor Receptor (Fetal Liver Kinase 1) Monoclonal Antibody Inhibits Tumor Angiogenesis and Growth of Several Mouse and Human Tumors," Cancer Research 59(20): 5209-5218, American Association for Cancer Research, United States (1999).
Pridgen, E.M., et al., "Transepithelial Transport of FC-Targeted Nanoparticles by the Neonatal FC Receptor for Oral Delivery," Science Translational Medicine 5(213):213ra167, American Association for the Advancement of Science, United States (2013).
Probst, J., et al., "Spontaneous Cellular Uptake of Exogenous Messenger RNA in Vivo is Nucleic Acid-Specific, Saturable and Ion Dependent," Gene therapy 14(15):1175-1180, Nature Publishing Group, England (2007).
Prokaria Ltd, Tsc DNA ligase, 2013, No Vol., pp. 1-3.
Prokazyme Ltd., ThermoPhage, ssDNA ligase,2013, No Vol. pp. 1-3.
Puga, A., et al., "Difference Between Functional and Structural Integrity of Messenger RNA," Proceedings of the National Academy of Sciences of the United States of America 70(7):2171-2175, National Academy of Sciences, United States (1973).
Pulford, B., et al., "Liposome-siRNA-Peptide Complexes Cross the Blood-Brain Barrier and Significantly Decrease PrP on Neuronal Cells and Prp in Infected Cell Cultures," PloS one 5(6):e11085, Public Library of Science, United States (2010).
Pullinger, C.R., et al., "Human Cholesterol 7Alpha-Hydroxylase (CYP7A1) Deficiency has a Hypercholesterolemic Phenotype," The Journal of Clinical Investigation 110(1):109-117, American Society for Clinical Investigation, United States (2002).
Purchio, A.F. and Fareed, G.C., "Methods for Molecular Cloning in Eukaryotic Cells," Methods in Enzymology 68:357-375, Academic Press, United States (1979).
Qi, L.S., et al., "Repurposing Crispr as an RNA-Guided Platform for Sequence-Specific Control of Gene Expression," Cell 152(5):1173-1183, Cell Press, United States (2013).

(56) References Cited

OTHER PUBLICATIONS

Queen, C., et al., "A Humanized Antibody That Binds to the interleukin 2 Receptor," Proceedings of the National Academy of Sciences USA 86(24):10029-10033, National Academy of Sciences, United States (1989).
Query, C.C., et al. "Branch Nucleophile Selection in Pre-mRNA Splicing: Evidence for the Bulged Duplex Model," Genes & Development 8(5):587-597, Cold Spring Harbor Laboratory Press, United States (1994).
Raal, F., et al., "Elevated PCSK9 Levels in Untreated Patients with Heterozygous or Homozygous Familial Hypercholesterolemia and the Response to High-Dose Statin therapy," Journal of the American Heart Association 2(2):1-8, Wley-Blackwell, England (2013).
Raal, F., et al., "Low-Density Lipoprotein Cholesterol-Lowering Effects of AMG 145, a Monoclonal Antibody to Proprotein Convertase Subtilisin/Kexin Type 9 Serine Protease in Patients with Heterozygous Familial Hypercholesterolemia: the Reduction of LDL-C with PCSK9 inhibition in Heterozygous Familial Hypercholesterolemia Disorder (Rutherford) Randomized Trial," Circulation 126(20):2408-2417, Lippincott Williams & Wilkins, United States (2012).
Rabinovich, P.M., et al. "Chimeric Receptor mRNA Transfection as a Tool to Generate Antineoplastic Lymphocytes," Human Gene Therapy 20(1):51-61, M.A. Liebert, United States (2009).
Rabinovich, P.M., et al. "Synthetic Messenger RNA as a Tool for Gene therapy," Human Gene Therapy 17(10):1027-1035, M.A. Liebert, United States (2006).
Racila, D., et al., "Transient Expression of OCT4 is Sufficient to Allow Human Keratinocytes to Change their Differentiation Pathway," Gene Therapy 18(3):294-303, Nature Publishing Group, England (2011).
Rader, D.J., et al., "Monogenic Hypercholesterolemia: New insights in Pathogenesis and Treatment," The Journal of Clinical Investigation 111(12):1795-1803, American Society for Clinical Investigation, United States (2003).
Raff, M., "Adult Stem Cell Plasticity: Fact or Artifact?," Annual Review of Cell and Developmental Biology 19:1-22, Annual Reviews, United States (2003).
Raghavan, M., et, al., "Effects of Receptor Dimerization on the Interaction Between the Class I Major Histocompatibility Complex-Related Fc Receptor and Igg," Proceedings of the National Academy of Sciences of the United States of America 92(24):11200-11204, National Academy of Sciences, United States (1995).
Rajagopalan, L.E., et al., "Turnover and Translation of In Vitro Synthesized Messenger RNAs in Transfected, Normal Cells," The Journal of Biological Chemistry 271(33):19871-19876, American Society for Biochemistry and Molecular Biology, United States (1996).
Ramanathan, M.P., et al., "Development of a Novel DNA Syncon Tetravalent Dengue Vaccine that Elicits Immune Responses against Four Serotypes," Vaccine 27(46):6444-6453, Elsevier Science, Netherlands (2009).
Ramazeilles, C., et al., "Antisense Phosphorothioate Oligonucleotides: Selective Killing of the Intracellular Parasite Leishmania Amazonensis.," Proceedings of the National Academy of Sciences of the United States of America 91(17):7859-7863, National Academy of Sciences, United States (1994).
Rammensee, H.G., et al., "Peptides Naturally Presented by MHC Class I Molecules," Annual Review of Immunology 11:213-244, Annual Reviews, United States (1993).
Rascati, R.J., et al., "Characterization of Fv-1 Gene-Product-Mediated Resistance Transfer," Intervirology 15(2):87-96, Karger, Switzerland (1981).
Raschke, S. and Eckel, J., "Adipo-Myokines: Two Sides of the Same Coin—Mediators of Inflammation and Mediators of Exercise," Mediators of Inflammation 2013:1-16, Article ID 320724,Hindawi Publishing Corporation, United States (2013).
Ratajczak, J., et al., "Embryonic Stem Cell-Derived Microvesicles Reprogram Hematopoietic Progenitors: Evidence for Horizontal Transfer of mRNA and Protein Delivery," Leukemia 20(5):847-856, Nature Publishing Group, England (2006).
Ratajczak, J., et al., "Membrane-Derived Microvesicles: Important and Underappreciated Mediators of Cell-to-Cell Communication," Leukemia 20(9):1487-1495, Nature Publishing Group, England (2006).
Ravichandran, K.S., "Find-Me and Eat-Me Signals in Apoptotic Cell Clearance: Progress and Conundrums," The Journal of Experimental Medicine 207(9):1807-1817, Rockefeller University Press, United States (2010).
Ray, D., et al., "A Compendium of RNA-Binding Motifs for Decoding Gene Regulation," Nature 499(7457):172-177, Nature Publishing Group, England (2013).
Read, M.L., et al., "A Versatile Reducible Polycation-Based System for Efficient Delivery of a Broad Range of Nucleic Acids," Nucleic Acids Research 33(9):e86, Oxford University Press, England (2005).
Reddy, A., et al., "The Effect of Labour and Placental Separation on the Shedding of Syncytiotrophoblast Microparticles, Cell-Free DNA and mRNA in Normal Pregnancy and Pre-Eclampsia," Placenta 29(11):942-949, W.B. Saunders, England (2008).
Reed, R. and Maniatis, T., "Intron Sequences involved in Lariat Formation During Pre-mRNA Splicing," Cell 41(1):95-105, Cell Press, United States (1985).
Regberg, J., et al., "Applications of Cell-Penetrating Peptides for Tumor Targeting and Future Cancer therapies," Pharmaceuticals 5(9):991-1007, Cell Press, United States (2012).
Regnier, P., et al., "Degradation of mRNA in Bacteria: Emergence of Ubiquitous Features," BioEssays : News and Reviews in Molecular, Cellular and Developmental Biology 22(3):235-244, Wiley, United States (2000).
Reichert, J.M., "Which are the Antibodies to Watch in 2013?," mAbs 5(1):1-4, Taylor & Francis, United States (2013).
Rejman, J., et al., "mRNA Transfection of Cervical Carcinoma and Mesenchymal Stem Cells Mediated by Cationic Carriers," Journal of Controlled Release 147(3):385-991, Elsevier Science Publishers, Netherlands (2010).
Ren, W., et al., "Molecular Cloning and Characterization of 4-Hydroxyphenylpyruvate Dioxygenase Gene from Lactuca Sativa," Journal of Plant Physiology 168(10):1076-1083, Urban & Fischer, Germany (2011).
Renkvist, N., et al., "A Listing of Human Tumor Antigens Recognized by T Cells," Cancer Immunology, Immunotherapy : CII 50(1):3-15, Springer Verlag, Germany (2001).
Reyes-Sandoval, A., et al., "DNA Vaccines," Current Molecular Medicine 1(2):217-243, Bentham Science Publishers, Netherlands (2001).
Reynolds, B.A., et al., , "Generation of Neurons and Astrocytes from Isolated Cells of the Adult Mammalian Central Nervous System," Science 255(5052):1707-1710, American Association for the Advancement of Science, United States (1992).
Rich, P., et al., "Secukinumab induction and Maintenance therapy in Moderate-to-Severe Plaque Psoriasis: A Randomized, Double-Blind, Placebo-Controlled, Phase II Regimen-Finding Study.," The British Journal of Dermatology 168(2):402-411, Blackwell Scientific Publications, England (2013).
Richter, J.D., "Cytoplasmic Polyadenylation in Development and Beyond," Microbiology and Molecular Biology Reviews : MMBR 63(2):446-456, American Society for Microbiology, United States (1999).
Riechmann, L., et al., "Reshaping Human Antibodies for Therapy," Nature 332(6162):323-327, Nature Publishing Group, United States (1988).
Rob, C., et al., "IgG4 Breaking the Rules," Immunology 105(1):9-19, Blackwell Scientific Publications, England (2002).
Robak, T., et al., "Current and Emerging Treatments for Chronic Lymphocytic Leukaemia," Drugs 69(17):2415-2449, Springer International, New Zealand (2009).
Robbins, M., et al., "2'-O-Methyl-Modified RNAs act As TLR7 Antagonists," Molecular Therapy 15(9):1663-1669, Academic Press, United States (2007).

(56) References Cited

OTHER PUBLICATIONS

Robbins, P.D., et al., "Retroviral Vectors for Use in Human Gene therapy for Cancer, Gaucher Disease, and Arthritis," Annals of the New York Academy of Sciences 716:72-88, New York Academy of Sciences, United States (1994).
Robbins, P.F., et al., "Human Tumor Antigens Recognized by T Cells," Current Opinion in Immunology 8(5):628-636, Elsevier, England (1996).
Roberts, J.N., et al., "Genital Transmission of HPV in a Mouse Model is Potentiated by Nonoxynol-9 and inhibited by Carrageenan," Nature Medicine 13(7):857-861, Nature Publishing Company, United States (2007).
Robinson, F., et al., "Expression of Human nPTB is Limited by Extreme Suboptimal Codon Content," PloS one 3(3):e1801, Public Library of Science, United States (2008).
Robinson, H.L., et al., "Protection against a Lethal influenza Virus Challenge by Immunization with a Haemagglutinin-Expressing Plasmid DNA," Vaccine 11(9):957-960, Elsevier Science, Netherlands (1993).
Robles, a.I., et al., "Reduced Skin Tumor Development in Cyclin D1-Deficient Mice Highlights the oncogenic ras Pathway in Vivo," Genes & Development 12(16):2469-2474, Cold Spring Harbor Laboratory Press, United States (1998).
Roche Pharma AG, A Study to Evaluate Two Doses of Ocrelizumab in Patients With Active Systemic Lupus Erythematosus (BEGIN), ClinicalTrials.gov , Apr. 1, 2014, No Vol #, hftp://clinicaltrials.govict2/show/NCT00539838, pp. 1-4.
Roche Pharma AG, A Study to Investigate the Efficacy and Safety of Bendamustine Compared With Bendamustine +R05072759 (GA101) in Patients With Rituximab-Refractory, Indolent Non-Hodgkin's Lymphoma (GADOLIN), ClinicalTrials.gov, Apr. 2, 2014, http://clinicaltr.
Roche, Zenapax (daclizumabl) Sterile Concentrate for Injection,2013, No Vol., pp. 1-11.
Rock, K.L., "A New Foreign Policy: MHC Class I Molecules Monitor the Outside World," Immunology Today 17(3):131-137, Elsevier Science Publishers, England (1996).
Rodriguez, P.L., et al., "Minimal "Self" Peptides that inhibit Phagocytic Clearance and Enhance Delivery of Nanoparticles," Science 339(6122):971-975, American Association for the Advancement of Science, United States (2013).
Roep, B.O. and Peakman, M., "Antigen Targets of Type 1 Diabetes Autoimmunity," Cold Spring Harbor Perspectives in Medicine 2(4):1-15, Cold Spring Harbor Laboratory Press, United States (2012 ).
Roger S. Riley, MD, Ph.D., Apr. 2005, http://www.pathology.vcu.edu/clinical/coag/FIX °/020Deficiency.pdf, no volume, no pages, no publisher, no journal, 2 pages long.
Rohloff, C.M., et al. "DUROS Technology Delivers Peptides and Proteins at Consistent Rate Continuously for 3 to 12 Months," Journal of Diabetes Science and Technology 2(3):461-467, Sage, United States (2008).
Romani, N., et al., "Generation of Mature Dendritic Cells from Human Blood an Improved Method with Special Regard to Clinical Applicability," Journal of Immunological Methods 196(2):137-151, Elsevier, Netherlands (1996).
Romani, N., et al., "Presentation of Exogenous Protein Antigens by Dendritic Cells to T Cell Clones Intact Protein is Presented Best by Immature, Epidermal Langerhans Cells," The Journal of Experimental Medicine 169( 3):1169-1178, Rockefeller University Press, United States (1989).
Romosozumab, Statement on a Nonproprietary Name Adopted by the USAN Council, No Year , No Volume, p. 1.
Rosa, A. and Brivanlou, A.H., "Synthetic mRNAs: Powerful tools for Reprogramming and Differentiation of Human Cells," Cell Stem Cell 7(5):549-550, Cell Press, United States (2010).
Rose, Jason, MicroRNA "Sponge": Proof of Concept for a Novel MicroRNA Target Identification Technique, a Major Qualifying Project Report, Submitted to the Faculty of Worcester Polytechnic Institute, 2010, No Volume, pp. 1-26.
Rosenberg, L.E., et al., "Biogenesis of Ornithine Transcarbamylase in spfash Mutant Mice: Two Cytoplasmic Precursors, one Mitochondrial Enzyme," Science 222(4622):426-428, American Association for the Advancement of Science, United States (1983).
Rosenberg, S.A., et al., "Cancer Immunotherapy: Moving Beyond Current Vaccines," Nature Medicine 10(9):909-915, Nature Publishing Company, United States (2004).
Rosman, Z., et al., "Biologic therapy for Autoimmune Diseases: An Update.," BMC Medicine 11(88):1-12, BioMed Central, England (2013).
Ross, B.S. et al., Synthesis and incorporation of 2'-0-methyl-pseudouridine into oligonucleotides. Nucleosides and Nucleotides. 1997; 16(7/9):1547-9.
Ross, J., "Control of Messenger RNA Stability in Higher Eukaryotes," Trends in Genetics : TIG 12(5):171-175, Elsevier Trends Journals, England (1996).
Rossi, Derrick. Open letter Entitled "Change to mRNA Reprogramming Protocol" Publication Date: Aug. 13, 2011 ("Rossi")(available at Addgene website: http://www.addgene.org/static/data183/87/3686c0f2-c9a2-11e0- b8a9-003048dd6500.pdf, last retrieved Mar. 1.
Rossi, E.A., et al., "Trogocytosis of Multiple B-Cell Surface Markers by CD22 Targeting with Epratuzumab," Blood 122(17):3020-3029, American Society of Hematology, United States (2013).
Rossjohn, J., et al., "Structure of the Activation Domain of the GM-CSF/IL-3/IL-5 Receptor Common Beta-Chain Bound to an Antagonist," Blood 95(8):2491-2498, American Society of Hematology, United States (2000).
Roth, E.M., et al., "Atorvastatin with or without an Antibody to PCSK9 in Primary Hypercholesterolemia," The New England Journal of Medicine 367(20):1891-1900, Massachusetts Medical Society, United States (2012).
Roufosse, F.E., et al., "Long-Term Safety of Mepolizumab for the Treatment of Hypereosinophilic Syndromes," The Journal of Allergy and Clinical Immunology 131(2):461-467, Mosby, United States (2013).
Roy-Chowdhury, J., et al., "Molecular Basis for the Lack of Bilirubin-Specific and 3-Methylcholanthrene-Inducible UDP-Glucuronosyltransferase Activities in Gunn Rats. The Two Isoforms Are Encoded by Distinct MRNA Species That Share an Identical Single Base Deletion," The Journal of Biological Chemistry 266(27):18294-18298, American Society for Biochemistry and Molecular Biology, United States (1991).
Roy-Chowdhury, N., et al., "Isolation of Multiple Normal and Functionally Defective forms of Uridine Diphosphate-Glucuronosyltransferase From Inbred Gunn Rats," The Journal of Clinical Investigation 79(2):327-334, American Society for Clinical Investigation, United States (1987).
Rozenski, J., et al., "The RNA Modification Database: 1999 Update," Nucleic Acids Research 27(1):196-197, Oxford University Press, England (1999).
Ruetschi, U., et al., "Human 4-Hydroxyphenylpyruvate Dioxygenase Gene (HPD)," Genomics 44(3):292-299, Academic Press, United States (1997).
Ruf, P., et al., "Characterisation of the New EpCAM-Specific Antibody HO-3: Implications for Trifunctional Antibody Immunotherapy of Cancer," British Journal of Cancer 97(3):315-321, Nature Publishing Group, England (2007).
Ruhnke, M., et al., "Long-Term Culture and Differentiation of Rat Embryonic Stem Cell-Like Cells into Neuronal, Glial, Endothelial, and Hepatic Lineages," Stem Cells 21(4):428-436, Nature Publishing Group, England (2003).
Ryser, M., et al., "S1 P(1) Overexpression Stimulates S1P-Dependent Chemotaxis of Human Cd34+ Hematopoietic Progenitor Cells but Strongly Inhibits SDF-1/CXCR4-Dependent Migration and in Vivo Homing," Molecular Immunology 46(1):166-171, Pergamon Press, England (2008).
Saenz-Badillos, J., et al., "RNA as a Tumor Vaccine: A Review of the Literature," Experimental Dermatology 10(3):143-154, Munksgaard, Denmark (2001).

(56) References Cited

OTHER PUBLICATIONS

Saison-Behmoaras, T., et al., "Short Modified Antisense Oligonucleotides Directed against Ha-ras Point Mutation Induce Selective Cleavage of the mRNA and Inhibit T24 Cells Proliferation.," The EMBO Journal 10(5):1111-1118, Wiley Blackwell, England (1991).
Saito, K., et al., "Cell Participation in Immune Response by Immune Ribonucleic Acid I the Role of T Lymphocytes in Immune Response by Immune RNA Against T-Dependent Antigens," Immunology 41(4):937-945, Blackwell Scientific Publications, England (1980).
Saito, R., et al., "Distribution of Liposomes into Brain and Rat Brain Tumor Models by Convection-Enhanced Delivery Monitored with Magnetic Resonance Imaging," Cancer Research 64(7):2572-2579, American Association for Cancer Research, United States (2004).
Sakuma, S., et al., "Mucoadhesion of Polystyrene Nanoparticles having Surface Hydrophilic Polymeric Chains in the Gastrointestinal Tract," International Journal of Pharmaceutics 177(2):161-172, Elsevier, Netherlands (1999).
Salles, G., et al., "Phase 1 Study Results of the Type II Glycoengineered Humanized Anti-CD20 Monoclonal Antibody Obinutuzumab (GA101) in B-cell lymphoma Patients," Blood 119(22):5126-5132, American Society of Hematology, United States (2012).
Sallusto, F., et al., "Dendritic Cells Use Macropinocytosis and the Mannose Receptor to Concentrate Macromolecules in the Major Histocompatibility Complex Class II Compartment: Downregulation by Cytokines and Bacterial Products," The Journal of Experimental Medicine 182(2):389-400, Rockefeller University Press, United States (1995).
Sallusto, F., et al., "Efficient Presentation of Soluble Antigen by Cultured Human Dendritic Cells Is Maintained by Granulocyte/macrophage Colony-stimulating Factor Plus Interleukin 4 and Downregulated by Tumor Necrosis Factor Alpha," The Journal of Experimental Medicine 179(4):1109-1118, Rockefeller University Press, United States (1994).
Salzman, J., et al., "Circular RNAs are the Predominant Transcript Isoform from Hundreds of Human Genes in Diverse Cell Types," PloS one 7(2):1-12, Public Library of Science, United States (2012).
Samarsky, D.A., et al., "The snoRNA Box C/D Motif Directs Nucleolar Targeting and also Couples snoRNA Synthesis and Localization," The EMBO Journal 17(13):3747-3757, Wiley Blackwell, England (1998).
Sandborn, W.J., et al., "Vedolizumab as Induction and Maintenance Therapy for Crohn's Disease," The New England Journal of Medicine 369(8):711-721, Massachusetts Medical Society, United States (2013).
Sanofi, Fact Sheet, PCSK9 and Alirocumab Backgrounder, Regeneron, 2013, No Vol. pp. 1-3.
Santi, D.V., "Mechanistic Studies of RNA Modifying Enzymes RNA Pseudouridine Synthase and m5Cytosine Methyl Transferase," Nucleic Acids Symposium Series 44:147-148, Oxford University Press, England (2000).
Santini, S.M., et al., "Type I Interferon as a Powerful Adjuvant for Monocyte-Derived Dendritic Cell Development and Activity in Vitro and in Hu-PBL-SCID Mice," The Journal of Experimental Medicine 191(10):1777-1788, Rockefeller University Press, United States (2000).
Sanyal, S. and Niu, M.C., "Effects of RNA on the Developmental Potentiality of the Posterior Primitive Streak of the Chick Blastoderm," Proceedings of the National Academy of Sciences of the United States of America 55(4):743-750, National Academy of Sciences, United States (1966).
Saponara, A.G. and Enger, M.D., "The Isolation from Ribonucleic Acid of Substituted Uridines Containing Alpha-Aminobutyrate Moieties Derived from Methionine," Biochimica Et Biophysica Acta 349(1):61-77, Elsevier, Netherlands (1974).
Satoh, M., et al., "X-Linked Immunodeficient Mice Spontaneously Produce Lupus-Related Anti-RNA Helicase a Autoantibodies, but are Resistant to Pristane-Induced Lupus," International Immunology 15(9):1117-1124, Oxford University Press, England (2003).
Satthaporn, S. and Eremin, O., "Dendritic Cells (II): Role and therapeutic Implications in Cancer," Journal of the Royal College of Surgeons of Edinburgh 46(3):159-167, Edinburgh, Scotland (2001).
Satz, M.L., et al., "Mechanism of Immune Transfer by RNA Extracts Immune RNA Induces the Synthesis of Idiotype-Bearing Antigen Receptors in Noncommitted Cells," Molecular and Cellular Biochemistry 33(3):105-113, The Hague, Netherlands (1980).
Scheel, B., et al., "Immunostimulating Capacities of Stabilized RNA Molecules," European Journal of Immunology 34(2):537-547, Wiley-VCH, Germany (2004).
Scheid, J.F., et al., "Sequence and Structural Convergence of Broad and Potent HIV Antibodies that Mimic CD4 Binding," Science 333(6049):1633-1637, American Association for the Advancement of Science, United States (2011).
Schirrmacher, V., et al., "Intra-Pinna Anti-Tumor Vaccination with Self-Replicating infectious RNA or with DNA Encoding a Model Tumor Antigen and a Cytokine," Gene Therapy 7(13):1137-1147, Nature Publishing Group, England (2000).
Schmidt, A.E. and Bajaj, S.P., "Structure-Function Relationships in Factor IX and Factor Ixa," Trends in Cardiovascular Medicine 13(1):39-45, Elsevier Science, United States (2003).
Schmidt, W.M., et al., "Capselect: A Highly Sensitive Method for 5' CAP-Dependent Enrichment of Full-Length cDNA in PCR-Mediated Analysis of mRNAs," Nucleic Acids Research 27(21):e31,Oxford University Press, England (1999).
Schmitt, F., et al., "Lentiviral Vectors that Express UGT1A1 in Liver and Contain miR-142 Target Sequences Normalize Hyperbilirubinemia in Gunn Rats," Gastroenterology 139(3):999-1007, W.B. Saunders, United States (2010).
Schmitt, W.E., et al., "In Vitro induction of a Bladder Cancer-Specific T-Cell Response by mRNA-Transfected Dendritic Cells," Journal of Cancer Research and Clinical Oncology 127(3):203-206, Springer-Verlag, Germany (2001).
Scholte, B.J., et al., "Animal Models of Cystic Fibrosis," Journal of Cystic Fibrosis 183-190, Elsevier, Netherlands (2004).
Schott, J.W., et al., "Viral and Non-Viral Approaches for Transient Delivery of mRNA and Proteins," Current Gene Therapy 11(5):382-398, Bentham Science Publishers, Netherlands (2011).
Schroeder, U., et al., "Peptide Nanoparticles Serve as a Powerful Platform for the Immunogenic Display of Poorly Antigenic Actin Determinants," Journal of Molecular Biology 386(5):1368-1381, Elsevier, England (2009).
Schuelke, M., et al., "Myostatin Mutation associated with Gross Muscle Hypertrophy in a Child," The New England Journal of Medicine 350(26):2682-2688, Massachusetts Medical Society, United States (2004).
Schuler, G. et al., "Murine Epidermal Langerhans Cells Mature into Potent Immunostimulatory Dendritic Cells in Vitro," The Journal of Experimental Medicine 161(3):526-546, Rockefeller University Press, United States (1985).
Schuler-Thurner, B. et al., "Mage-3 and Influenza-Matrix Peptide-Specific Cytotoxic T Cells are Inducible in Terminal Stage HLA-A2.1+ Melanoma Patients by Mature Monocyte-Derived Dendritic Cells.," Journal of Immunology 165(6):3492-3496, American Association of Immunologists, United States (2000).
Scursoni, A.M., et al., "Detection of N-Glycolyl GM3 Ganglioside in Neuroectodermal Tumors by Immunohistochemistry: An Attractive Vaccine Target for Aggressive Pediatric Cancer.," Clinical & Developmental Immunology 2011:245181, Hindawi Pub. Corporation, Egypt (2011).
Seabury, C.M., et al., "Analysis of Sequence Variability and Protein Domain Architectures for Bovine Peptidoglycan Recognition Protein 1 and Toll-Like Receptors 2 and 6," Genomics 92(4):235-245, Academic Press, United States (2008).
Segura, J., et al., "Monitoring Gene therapy by External Imaging of mRNA: Pilot Study on Murine Erythropoietin," Therapeutic Drug Monitoring 29(5):612-618, Lippincott Williams & Wilkins, United States (2007).
Seldin, M.M. and Wong, G.W., "Regulation of Tissue Crosstalk by Skeletal Muscle-Derived Myonectin and Other Myokines," Adipocyte 1(4):200-202, Lippincott Williams & Wilkins, United States (2012).

(56) References Cited

OTHER PUBLICATIONS

Semenov, M., et al., "SOST Is a Ligand for LRP5/LRP6 and a Wnt Signaling Inhibitor," The Journal of Biological Chemistry 280(29):26770-26775, American Society for Biochemistry and Molecular Biology, United States (2005).

Semple, S.C., et al., "Efficient Encapsulation of Antisense Oligonucleotides in Lipid Vesicles Using Ionizable Aminolipids: Formation of Novel Small Multilamellar Vesicle Structures.," Biochimica Et Biophysica Acta 1510(1-2):152-166, Elsevier, Netherlands (2001).

Semple, S.C., et al., "Rational Design of Cationic Lipids for siRNA Delivery," Nature Biotechnology 28(2):172-176, Nature America Publishing, United States (2010).

SEQ Search Result 1(U.S. Appl. No. 13/897,362) dated Oct. 11, 2013.

Serrate, S., et al., "Transfer of Cellular Immunity In Vivo with Immune RNA in an Allogeneic Murine Model," Clinical Immunology and Immunopathology 22(1):75-82, Academic Press, United States (1982).

Shapiro, A.D., et al., "Recombinant Factor IX-Fc Fusion Protein (rFIXFc) Demonstrates Safety and Prolonged Activity in a Phase 1/2a Study in Hemophilia B Patients," Blood 119(3):666-672, American Society of Hematology, United States (2012).

Sharp, J.S. and Bechhofer, D.H., "Effect of Translational Signals on mRNA Decay in Bacillus Subtilis," Journal of Bacteriology 185(18):5372-5379, American Society for Microbiology, United States (2003).

Sharp, P.M., et al., "DNA Sequence Evolution: The Sounds of Silence," Philosophical Transactions of the Royal Society of London 349(1329):241-247, Royal Society, England (1995).

Shea, R.G., et al., "Synthesis, Hybridization Properties and antiviral Activity of Lipid-Oligodeoxynucleotide Conjugates," Nucleic Acids Research 18(13):3777-3783, Oxford University Press, England (1990).

Shealy, D.J., et al., "Characterization of Golimumab, a Human Monoclonal Antibody Specific for Human Tumor Necrosis Factor α," mAbs 2(4):428-439, Taylor & Francis, United States (2010).

Shen, B., et al., "Generation of Gene-Modified Mice via Cas9/RNA-Mediated Gene Targeting," Cell Research 23(5):720-723, Nature Publishing Group, England (2013).

Sheridan, W., et al., "Effect of Peripheral-Blood Progenitor Cells Mobilised by Filgrastim (G-CSF) on Platelet Recovery after High-Dose Chemotherapy," Lancet 339(8794):640-644, Elsevier, England (1992).

Shi, Y., et al., "A Combined Chemical and Genetic Approach for the Generation of Induced Pluripotent Stem Cells," Cell Stem Cell 2(6):525-528, American Society for Microbiology, United States (2008).

Shi, Y., et al., "Identification and Characterization of Pancreatic Eukaryotic initiation Factor 2 Alpha-Subunit Kinase, PEK, Involved in Translational Control," Molecular and Cellular Biology 18(12):7499-7509, American Society for Microbiology, United States (1998).

Shiba, Y., et al., "Chemical Synthesis of a Very Long Oligoribonucleotide with 2-Cyanoethoxymethyl (CEM) as the 2'-O-Protecting Group: Structural Identification and Biological Activity of a Synthetic 110mer Precursor-MicroRNA Candidate," Nucleic Acids Research 35(10):3287-3296, Information Retrieval Ltd, England (2007).

Shin, J.H., et al., "Positive Conversion of Negative Signaling of CTLA4 Potentiates Antitumor Efficacy of Adoptive T-Cell therapy in Murine Tumor Models," Blood 119(24):5678-5687, American Society of Hematology, United States (2012).

Shingai, M., et al., "Antibody-Mediated Immunotherapy of Macaques Chronically infected with SHIV Suppresses Viraemia," Nature 503(7475):277-280, Nature Publishing Group, England (2013).

Shingo, T., et al., "Erythropoietin Regulates the In Vitro and In Vivo Production of Neuronal Progenitors by Mammalian Forebrain Neural Stem Cells," The Journal of Neuroscience 21(24):9733-9743, Society for Neuroscience, United States (2001).

Shuman, S., "Capping Enzyme in Eukaryotic mRNA Synthesis," Progress in Nucleic Acid Research and Molecular Biology 50:101-129, Academic Press., United States (1995).

Shuman, S., et al., "Purification and Characterization of a GTP-Pyrophosphate Exchange Activity from Vaccinia Virions Association of the GTP-Pyrophosphate Exchange Activity with Vaccinia mRNA Guanylyltransferase RNA (Guanine-7-)Methyltransferase Complex (Capping Enzyme)," The Journal of Biological Chemistry 255(23):11588-11598, American Society for Biochemistry and Molecular Biology, United States (1980).

Shuman, S., "Structure, Mechanism, and Evolution of the mRNA Capping Apparatus," Progress in Nucleic Acid Research and Molecular Biology 66:1-40, Academic Press, United States (2001).

Shusterrman, S., et al., "Antitumor Activity of hu14.18-IL2 in Patients with Relapsed/Refractory Neuroblastoma: A Children'S Oncology Group (COG) Phase II Study," Journal of Clinical Oncology 28(33):4969-4975, American Society of Clinical Oncology, United States (2010).

Sieger, N., et al., "CD22 Ligation Inhibits Downstream B Cell Receptor Signaling and Ca(2+) Flux Upon Activation," Arthritis and Rheumatism 65(3):770-779, Wiley-Blackwell, United States (2013).

Siena, S., et al., "Expansion of Immunostimulatory Dendritic Cells from Peripheral Blood of Patients with Cancer," The Oncologist 2(1):65-69, AlphaMed Press, United States (1997).

Simioni, P., et al., "X-Linked Thrombophilia with a Mutant Factor IX (Factor IX Padua)," The New England Journal of Medicine 361(17):1671-1675, Massachusetts Medical Society, United States (2009).

Simon, T., et al., "Consolidation Treatment with Chimeric anti-GD2-Antibody Ch14.18 in Children Older than 1 Year with Metastatic Neuroblastoma," Journal of Clinical Oncology 22(17):3549-3557, American Society of Clinical Oncology, United States (2004).

Simonaro, C.M., et al., "Joint and Bone Disease in Mucopolysaccharidoses VI and VII: Identification of New therapeutic Targets and Biomarkers Using animal Models," Pediatric Research 57(5Pt1):701-707, Nature Publishing Group, United States (2005).

Sindelar, L.E. and Jaklevic, J.M., "High-Throughput DNA Synthesis in a Multichannel format," Nucleic Acids Research 23(6):982-987, Oxford University Press, England (1995).

Slapikoff, S., et al., "Mechanism of Ribonucleic Acid Polymerase Action Effect of Nearest Neighbors on Competition Between Uridine Triphosphate and Uridine Triphosphate analogs for Incorporation into Ribonucleic Acid," Biochemistry 6(12):3654-3658, American Chemical Society, United States (1967).

Sleeman, J., et al., "Dynamic Interactions Between Splicing snRNPs, Coiled Bodies and Nucleoli Revealed Using snRNP Protein Fusions to the Green Fluorescent Protein," Experimental Cell Research 243(2):290-304, Academic Press, United States (1998).

Smith, C.M. and Steitz, J.A., "Sno Storm in the Nucleolus: New Roles for Myriad Small RNPs," Cell 89(5):669-672, Cell Press, United States (1997).

Smith, J.P., et al., "Drug Retention and Distribution after intratumoral Chemotherapy with Fluorouracil/Epinephrine Injectable Gel in Human Pancreatic Cancer Xenografts," Cancer Chemotherapy and Pharmacology 44(4):267-274, Springer Verlag, Germany (1999).

Smith, K.P. and Lawrence, J.B., "Interactions of U2 Gene Loci and their Nuclear Transcripts with Cajal (Coiled) Bodies: Evidence for PreU2 within Cajal Bodies," Molecular Biology of the Cell 11(9):2987-2998, American Society for Cell Biology, United States (2000).

Smith, W.S. et al., RNA modified uridines: VI: Conformations of 3-[3-(S)-Amino-3-Carboxypropyl]Uridine (acp3U) from tRNA and 1-Methyl-3-[3-(S)-Amino-3-Carboxypropyl]Pseudouridine (mlacp3?) from rRNA. Nucleosides and Nucleotides. 1992; 11(10):1683-94.

Smits, E., et al., "RNA-Based Gene Transfer for Adult Stem Cells and T Cells," Leukemia 18(11):1898-1902, Nature Publishing Group, England (2004).

(56) References Cited

OTHER PUBLICATIONS

Smull, C.E. and Ludwig, E.H., "Enhancement of the Plaque-forming Capacity of Poliovirus Ribonucleic Acid with Basic Proteins," Journal of Bacteriology 84(5)1 035-1040, American Society for Microbiology, United States (1962).
Sohn, R.L., et al., "In-Vivo Particle Mediated Delivery of mRNA to Mammalian Tissues: Ballistic and Biologic Effects," Wound Repair and Regeneration 9(4):287-296, Blackwell Science, United States (2001).
Soll, D., "Enzymatic Modification of Transfer RNA," Science 173(3994):293-299, American Association for the Advancement of Science, United States (1971).
Song, E., et al., "Antibody Mediated in vivo Delivery of Small Interfering RNAs via Cell-surface Receptors,"Nature Biotechnology 23(6):709-717, Nature America Publishing, United States (2005).
Song, K.H., et al., "A Putative Role of Micro RNA in Regulation of Cholesterol 7Alpha-Hydroxylase Expression in Human Hepatocytes," Journal of Lipid Research 51(8):2223-2233, American Society for Biochemistry and Molecular Biology, United States (2010).
Sontheimer, E.J. and Steitz, J.A., "The U5 and U6 Small Nuclear RNAs as Active Site Components of the Spliceosome," Science 262(5142):1989-1996, American Association for the Advancement of Science, United States (1993).
Sorrentino, V. and Zelcer, N., "Post-Transcriptional Regulation of Lipoprotein Receptors by the E3-Ubiquitin Ligase Inducible Degrader of the Low-Density Lipoprotein Receptor," Current Opinion in Lipidology 23(3):213-219, Lippincott Williams & Wilkins, England (2012).
Sousa, R. et al., T7 RNA polymerase. Prog Nucleic Acid Res Mol Biol. 2003;73:1-41.
Sousa, R., "Use of T7 RNA Polymerase and its Mutants for Incorporation of Nucleoside Analogs into RNA," Methods in Enzymology 317:65-74, Academic Press, United States (2000).
Spooner, R.A., et al., "DNA Vaccination for Cancer Treatment," Gene Therapy 2(3):173-180, Nature Publishing Group, England (1995).
Spratlin, J.L., et al., "Phase I Pharmacologic and Biologic Study of Ramucirumab (Imc-1121B), a Fully Human Immunoglobulin G1 Monoclonal Antibody Targeting the Vascular Endothelial Growth Factor Receptor-2," Journal of Clinical Oncology 28(5):780-787, American Society of Clinical Oncology, United States (2010).
Sproat, B.S., "Chemistry and Applications of Oligonucleotide Analogues," Journal of Biotechnology 41(2-3):221-238, Elsevier Science Publishers, Netherlands (1995).
Squires, J., et al., "Widespread Occurrence of 5-Methylcytosine in Human Coding and Non-Coding RNA," Nucleic Acids Research 40(11):5023-5033, Oxford University Press, England (2012).
Srinivasan, A. and Mukherji, S.K., "Tositumomab and Iodine I 131 Tositumomab (Bexaar)," American Joumal of Neuroradiology 32(4):637-638, American Society of Neuroradiology, United States (2011).
Stadtfeld, M., et al. "Induced Pluripotent Stem Cells Generated without Viral integration," Science 322(5903):945-949, American Association for the Advancement of Science, United States (2008).
Staley, J.P. and Guthrie, C., "Mechanical Devices of the Spliceosome: Motors, Clocks, Springs, and Things," Cell 92(3):315-326, Cell Press, United States (1998).
Stanek, D., et al., "Detection of snRNP Assembly intermediates in Cajal Bodies by Fluorescence Resonance Energy Transfer," The Journal of Cell Biology 166(7):1015-1025, Rockefeller University Press, United States (2004).
Stanley, K., "Design of Randomized Controlled Trials," Circulation 115(9):1164-1169, Lippincott Williams & Wilkins, United States (2007).
Stark, M.R., et al., "An RNA Ligase-Mediated Method for the Efficient Creation of Large, Synthetic Rnas," RNA 12(11):2014-2019, Cold Spring Harbor Laboratory Press, United States (2006).
Steege, D.A., "Emerging Features of mRNA Decay in Bacteria," RNA 6(8):1079-1090, Cold Spring Harbor Laboratory Press, United States (2000).
Steel, J., et al., "Influenza Virus Vaccine Based on the Conserved Hemagglutinin Stalk Domain," mBio 1(1):Cold Spring Harbor Laboratory Press, United States (2010).
Stein, E.A., et al., "Effect of a Monoclonal Antibody to PCSK9 on LDL Cholesterol," The New England Journal of Medicine 366(12):1108-1118, Massachusetts Medical Society, United States (2012).
Steinfeld, S.D. and Youinou, P., "Epratuzumab (Humanised Anti-CD22 Antibody) in Autoimmune Diseases," Expert Opinion on Biological Therapy 6(9):943-949, Taylor & Francis, England (2006).
Steinman, R.M. et al., "Dendritic Cells: Antigen Presentation, Accessory Function and Clinical Relevance," Advances in Experimental Medicine and Biology 329:1-9, Kluwer Academic/Plenum Publishers, United States (1993).
Steinman, R.M., "The Dendritic Cell System and its Role in Immunogenicity," Annual Review of Immunology 9:271-296, Annual Reviews, United States (1991).
Stelic Institute & Co., Contract Research Services Specialized in NASH-HCC, Ver.2012.11, 2012, 99.1-10.
Stepinski, J., et al., "Synthesis and Properties of mRNAs Containing the Novel "Anti-Reverse" Cap Analogs 7-Methyl(3'-O-Methyl)GpppG and 7-Methyl (3'-Deoxy)GpppG," RNA 7(10):1486-1495, Cold Spring Harbor Laboratory Press, United States (2001).
Sterner, D.E. and Berger, S.L., "Acetylation of Histones and Transcription-Related Factors," Microbiology and Molecular Biology Reviews : MMBR 64(2):435-459, American Society for Microbiology, United States (2000).
Stevenson, F.T., et al., "The N-Terminal Propiece of Interleukin 1 Alpha is a Transforming Nuclear Oncoprotein," Proceedings of the National Academy of Sciences of the United States of America 94(2):508-513, National Academy of Sciences, United States (1997).
Stiles, D.K., et al., "Widespread Suppression of Huntingtin with Convection-Enhanced Delivery of siRNA," Experimental Neurology 233(1):463-471, Academic Press, United States (2012).
Stinchcomb, D.T., et al., "Isolation and Characterisation of a Yeast Chromosomal Replicator," Nature 282(5734):39-43, Nature Publishing Group, England (1979).
Stockinger, W., et al., "The Px-Domain Protein SNX17 interacts with Members of the LDL Receptor Family and Modulates Endocytosis of the LDL Receptor," The EMBO Journal 21(16):4259-4267, Wiley Blackwell, England (2002).
Stohl, W., "Future Prospects in Biologic Therapy for Systemic Lupus Erythematosus," Nature Reviews Rheumatology 9(12):705-720, American Society for Microbiology, United States (2013).
Strassburg, C.P., "Hyperbilirubinemia Syndromes (Gilbert-Meulengracht, Crigler-Najjar, Dubin-Johnson, and Rotor Syndrome)," Best practice & Research. Clinical Gastroenterology 24(5):555-571, Elsevier, Netherlands (2010).
Strausberg et al., National Cancer Institute, Cancer Genome Anatomy Project, Tumor Gene Index, gene accession No. BE136127, 1997 pp ??.
Strobel, I., et al., "Human Dendritic Cells Transfected with Either RNA or DNA Encoding influenza Matrix Protein M1 Differ in their Ability to Stimulate Cytotoxic T Lymphocytes," Gene Therapy 7(23):2028-2035, Nature Publishing Group, England (2000).
Strong, T.V., et al., "Incorporation of Beta-Globin Untranslated Regions into a Sindbis Virus Vector for Augmentation of Heterologous mRNA Expression," Gene Therapy 4(6):624-627, Nature Publishing Group, England (1997).
Stroock, A.D., et al., "Chaotic Mixer for Microchannels," Science 295(5555):647-651, American Association for the Advancement of Science, United States (2002).
Stuart, L.M., et al., "Inhibitory Effects of Apoptotic Cell ingestion Upon Endotoxin-Driven Myeloid Dendritic Cell Maturation," Journal of Immunology 168(4):1627-1635, American Association of Immunologists, United States (2002).

(56) References Cited

OTHER PUBLICATIONS

Studier, F.W. and Moffatt, B.A., "Use of Bacteriophage T7 RNA Polymerase to Direct Selective High-Level Expression of Cloned Genes," Journal of Molecular Biology 189(1):113-130, Elsevier, England (1986).
Studier, F.W., et al., "Use of T7 RNA Polymerase to Direct Expression of Cloned Genes," Methods in Enzymology 185:60-89, Academic Press., United States (1990).
Su, Z., et al., "Enhanced induction of Telomerase-Specific CD4(+) T Cells Using Dendritic Cells Transfected with RNA Encoding a Chimeric Gene Product," Cancer Research 62(17):5041-5048, American Association for Cancer Research, United States (2002).
Su, Z., et al., "Immunological and Clinical Responses in Metastatic Renal Cancer Patients Vaccinated with Tumor RNA-Transfected Dendritic Cells," Cancer Research 63(9):2127-2133, American Association for Cancer Research, United States (2003).
Suchanek, G., et al., "Amino Acid Sequence of Honeybee Prepromelittin Synthesized in Vitro," Proceedings of the National Academy of Sciences of the United States of America 75(2):701-704, National Academy of Sciences, United States (1978).
Suciu-Foca, N., et al., "Soluble Ig-Like Transcript 3 inhibits Tumor Allograft Rejection in Humanized Scid Mice and T Cell Responses in Cancer Patients," Journal of Immunology 178(11):7432-7441, American Association of Immunologists, United States (2007).
Suda, T. and Liu, D., "Hydrodynamic Gene Delivery: Its Principles and Applications," Molecular Therapy 15(12):2063-2069, Academic Press, United States (2007).
Sugatani, J., et al., "Transcriptional Regulation of Human UGT1A1 Gene Expression: Activated Glucocorticoid Receptor Enhances Constitutive Androstane Receptor/Pregnane X Receptor-Mediated UDP-Glucuronosyltransferase 1A1 Regulation with Glucocorticoid Receptor-Interacting Protei," Molecular Pharmacology 67(3):845-855, American Society for Pharmacology and Experimental Therapeutics, United States (2005).
Sullenger, B.A. and Gilboa, E., "Emerging Clinical Applications of RNA," Nature 418(6894):252-258, Nature Publishing Group, England (2002).
Sullivan, D., et al., "Effect of a Monoclonal Antibody to PCSK9 on Low-Density Lipoprotein Cholesterol Levels in Statin-intolerant Patients: The Gauss Randomized Trial," JAMA 308(23):2497-2506, American Medical Association, United States (2012).
Sumathipala, N. and Jiang, H., "Involvement of Manduca Sexta Peptidoglycan Recognition Protein-1 in the Recognition of Bacteria and Activation of Prophenoloxidase System," Insect Biochemistry and Molecular Biology 40(6):487-495, Elsevier Science, England (2010).
Summar, M., "Current Strategies for the Management of Neonatal Urea Cycle Disorders," The Journal of Pediatrics 138:S30-S39, Mosby, United States (2001).
Sun, J., et al., "B Lymphocyte Stimulator: A New Target for Treating B Cell Malignancies," Chinese Medical Journal 121(14):1319-1323, Mosby, United States (2008).
Sutherland, C.L., et al., "ULBPs, Human Ligands of the NKG2D Receptor, Stimulate Tumor Immunity with Enhancement by IL-15," Blood 108(4):1313-1319, American Society of Hematology, United States (2006).
Svinarchuk, F.P., et al. "Inhibition of HIV Proliferation in MT-4 Cells by Antisense Oligonucleotide Conjugated to Lipophilic Groups," Biochimie 75(1-2):49-54, Elsevier, France (1993).
Szabo, E., et al., "Direct Conversion of Human Fibroblasts to Multilineage Blood Progenitors," Nature 468(7323):521-526, Nature Publishing Group, England (2010).
Tahiliani, M., et al., "Conversion of 5-Methylcytosine to 5-Hydroxymethylcytosine in Mammalian DNA by MII Partner TET1," Science 324(5929):930-935, American Association for the Advancement of Science, United States (2009).
Takahashi, K. and Yamanaka, S., "Induction of Pluripotent Stem Cells from Mouse Embryonic and Adult Fibroblast Cultures by Defined Factors," Cell 126(4):663-676, Cell Press, United States (2006).
Takahashi, K., et al., "Induction of Pluripotent Stem Cells from Adult Human Fibroblasts by Defined Factors," Cell 131(5): 861-872, Cell Press, United States (2007).
Takahashi, R., et al., "SOCS1 is Essential for Regulatory T Cell Functions by Preventing Loss of Foxp3 Expression as Well as IFN-{Gamma} and IL-17A Production," The Journal of Experimental Medicine 208(10):2055-2067, Rockefeller University Press, United States (2011).
Takahashi, T.T., et al., "mRNA Display: Ligand Discovery, Interaction Analysis and Beyond," Trends in Biochemical Sciences 28(3):159-165, Elsevier Trends Journals, England (2003).
Tam, C., et al., "Cytokeratins Mediate Epithelial Innate Defense Through their Antimicrobial Properties," The Journal of Clinical Investigation 122(10):3665-3677, American Society for Clinical Investigation, United States (2012).
Tanaka, M., et al., "Inhibition of Heart Transplant injury and Graft Coronary Artery Disease after Prolonged Organ Ischemia by Selective Protein Kinase C Regulators," The Journal of Thoracic and Cardiovascular Surgery 129(5):1160-1167, Mosby, United States (2005).
Tanaka, T. and Kishimoto, T., "Targeting Interleukin-6: All the Way to Treat Autoimmune and Inflammatory Diseases," International Journal of Biological Sciences 8(9):1227-1236, Ivyspring International, Australia (2012).
Tang, D.C., et al., "Genetic Immunization is a Simple Method for Eliciting an Immune Response," Nature 356(6365):152-154, Nature Publishing Group, England (1992).
Tanguay, R.L. and Gallie, D.R., "Translational Efficiency is Regulated by the Length of the 3' Untranslated Region," Molecular and Cellular Biology 16(1):146-156, American Society for Microbiology, United States (1996).
Taniguichi, T., et al., "Serum Levels of Galectin-3: Possible association with Fibrosis, Aberrant Angiogenesis, and Immune Activation in Patients with Systemic Sclerosis," the Journal of Rheumatology 39(3):539-544, Journal of Rheumatology Publishing Co, Canada (2012).
Taranger, C.K., et al., "induction of Dedifferentiation, Genomewide Transcriptional Programming, and Epigenetic Reprogramming by Extracts of Carcinoma and Embryonic Stem Cells," Molecular Biology of the Cell 16(12):5719-5735, American Society for Cell Biology, United States (2005).
Tavernier, G., et al., "mRNA as Gene therapeutic: How to Control Protein Expression," Journal of Controlled Release 150(3):238-247, Elsevier Science Publishers, Netherlands (2011).
Tazi, J. and Bird, A., "Alternative Chromatin Structure at CpG Islands," Cell 60(6):909-920, Cell Press, United States (1990).
Teckchandani, A., et al., "The Clathrin Adaptor Dab2 Recruits EH Domain Scaffold Proteins to Regulate Integrin β1 Endocytosis," Molecular Biology of the Cell 23(15):2905-2916, American Society for Cell Biology, United States (2012).
Teeling, J.L., et al., "Characterization of new human CD20 monoclonal antibodies with potent cytolytic activity against non-Hodgkin lymphomas," Blood 104(6):1793-1800, American Society of Hematology, United States (2004).
Teeling, J.L., et al., "The Biological Activity of Human CD20 Monoclonal Antibodies is Linked to Unique Epitopes on CD20," Journal of Immunology 177(1):362-371, American Association of Immunologists, United States (2006).
Teufel, R., et al., "Human Peripheral Blood Mononuclear Cells Transfected with Messenger RNA Stimulate Antigen-Specific Cytotoxic T-Lymphocytes In Vitro," Cellular and Molecular Life Sciences : CMLS 62(15):1755-1762, Springer, Switzerland (2005).
The Human Embryonic Stem Cell and the Human Embryonic Germ Cell. NIH Stem Cells: Scientific Progress and Future Research Directions, Department of Health and Human Services, Chapter 3, Jun. 2001.
The Stem Cell. NIH Stem Cells: Scientific Progress and Future Research Directions, Department of Health and Human Services, Chapter 1, Jun. 2001.
Thompson, M., et al., "Nucleolar Clustering of Dispersed tRNA Genes," Science 302(5649):1399-1401, American Association for the Advancement of Science, United States (2003).

(56) References Cited

OTHER PUBLICATIONS

Thomson, J.A., et al., "Isolation of a Primate Embryonic Stem Cell Line," Proceedings of the National Academy of Sciences of the United States of America 92(17):7844-7848, National Academy of Sciences, United States (1995).
Thomson, N.C. and Chaudhuri, R., "Omalizumab: Clinical Use for the Management of Asthma," Clinical Medicine Insights. Circulatory, Respiratory and Pulmonary Medicine 6:27-40, Libertas Academica, New Zealand (2012).
Thurner, B., et al., "Vaccination with Mage-3A1 Peptide-Pulsed Mature, Monocyte-Derived Dendritic Cells Expands Specific Cytotoxic T Cells and Induces Regression of Some Metastases in Advanced Stage IV Melanoma," The Journal of Experimental Medicine 190(11):1669-1678, Rockefeller University Press, United States (1999).
Toffoli, G., et al., "Overexpression of Folate Binding Protein in Ovarian Cancers," International Journal of Cancer 74(2):193-198, Wiley-Liss, United States (1997).
Torchilin, V., "Multifunctional and Stimuli-Sensitive Pharmaceutical Nanocarriers," European Journal of Pharmaceutics and Biopharmaceutics 71(3):431-444, Elsevier Science, Netherlands (2009).
Touriol, C., et al., "Generation of Protein Isoform Diversity by Alternative initiation of Translation at non-AUG Codons," Biology of the Cell 95(3-4):169-178, Elsevier Science, Netherlands (2003).
Tourriere, H., et al., "mRNA Degradation Machines in Eukaryotic Cells," Biochimie 84(8):821-837, Editions Scientifiques Elsevier, France (2002).
Towle, H.C., et al., "Purification and Characterization of Bacteriophage gh-I-Induced Deoxyribonucleic Acid-Dependent Ribonucleic Acid Polymerase from Pseudomonas Putida," The Journal of Biological Chemistry 250(5):1723-1733, American Society for Biochemistry and Molecular Biology, United States (1975).
Tracy, M., "Progress in the Development of LNP Delivery for siRNA Advancing LNPs to the Clinic," International Liposome Research Days Meeting, Vancouver, Canada. Aug. 2010, pp. 1-52.
Treat, J., et al., "Liposome Encapsulated Doxorubicin Preliminary Results of Phase I and Phase II Trials," in Liposomes in the Therapy of Infectious Diseases and Cancer, Lopez-Berestein, G.and Fidler, I.J., eds., pp. 353-365, Alan R. Liss, Inc.,United States(1989).
Trinchieri, G. and Sher, A., "Cooperation of Toll-Like Receptor Signals in Innate Immune Defence," Nature Reviews. Immunology 7(3):179-190, Nature Pub. Group, England (2007).
Tripathy, S.K., et al., "Long-Term Expression of Erythropoietin in the Systemic Circulation of Mice after Intramuscular injection of a Plasmid DNA Vector," Proceedings of the National Academy of Sciences of the United States of America 93(20):10876-10880, National Academy of Sciences, United States (1996).
Trojan, A., et al., "Immune Reactivity Against a Novel HLA-A3-Restricted Influenza Virus Peptide Identified by Predictive Algorithms and Interferon-Gamma Quantitative PCR," Journal of Immunotherapy 26(1):41-46, National Academy of Sciences, United States (2003).
Trollet, C., et al., "Delivery of DNA into Muscle for Treating Systemic Diseases: Advantages and Challenges," Methods in Molecular Biology 423:199-214, Humana Press, United States (2008).
Tsuchiya, M., et al., "Isolation and Characterization of the cDNA for Murine Granulocyte Colony-Stimulating Factor," Proceedings ofthe National Academy of Sciences of the United States of America 83(20):7633-7637, National Academy of Sciences, United States (1986).
Tung, T.C and Niu, M.C., "Organ Formation Caused by Nucleic Acid from Different Class—Urodele DNA Mediated Balancer Formation in Goldfish," Scientia Sinica 20(1):56-58, Academia Sinica, China (1977).
Tung, T.C and Niu, M.C., "The Effect of Carp EGG-mRNA on the Transformation of Goldfish Tail," Scientia Sinica 20(1):59-63, Academia Sinica, China (1977).
Tung, T.C and Niu, M.C., "Transmission of the Nucleic Acid-Induced Character, Caudal Fin, to the offspring in Goldfish," Scientia Sinica 18(2):223-231, Academia Sinica, China (1975).
Tuting, T., et al., "Gene-Based Strategies for the Immunotherapy of Cancer," Journal of Molecular Medicine 75(7):478-491, Academia Sinica, China (1997).
Tycowski, K.T., et al., "A Small Nucleolar RNA Requirement for Site-Specific Ribose Methylation of rRNA in Xenopus," Proceedings of the National Academy of Sciences of the United States of America 93(25):14480-14485, National Academy of Sciences, United States (1996).
Udenfriend, S., et al., "The Enzymatic Conversion of Phenylalanine to Tyrosine," The Journal of Biological Chemistry 194(2):503-511, American Society for Biochemistry and Molecular Biology, United States (1952).
Ueda, T., et al., "Phosphorothioate-Containing RNAs Show mRNA Activity in the Prokaryotic Translation Systems In Vitro," Nucleic Acids Research 19(3):547-552, Oxford University Press, England (1991).
Ulmer, J.B., "An Update on the State of the Art of DNA Vaccines," Current Opinion in Drug Discovery & Development 4(2):192-197, Thomson Reuters Ltd, England (2001).
Ulmer, J.B., et al., "Heterologous Protection against Influenza by injection of DNA Encoding a Viral Protein," Science 259(5102):1745-1749, American Association for the Advancement of Science, United States (1993).
Utikal, J., et al., "Immortalization Eliminates a Roadblock During Cellular Reprogramming into iPS Cells," Nature 460(7259):1145-1148, Nature Publishing Group, England (2009).
Uzgun, S., et al., "PEGylation Improves Nanoparticle Formation and Transfection Efficiency of Messenger RNA," Pharmaceutical Research 28(9):2223-2232, Kluwer Academic/Plenum Publishers, United States (2011).
Uzri, D. and Gehrke, L., "Nucleotide Sequences and Modifications that Determine RIG-I/RNA Binding and Signaling Activities," Journal of Virology 83(9):4174-4184, American Society for Microbiology, United States (2009).
Vaheri, A. and Pagano, J.S., "Infectious Poliovirus RNA: A Sensitive Method of assay," Virology 27(3):434-436, Academic Press, United States (1965).
Valcarcel, J., et al., "The Protein Sex-Lethal Antagonizes the Splicing Factor U2AF to Regulate Alternative Splicing of Transformer Pre-mRNA," Nature 362(6416):171-175, Nature Publishing Group, England (1993).
Valencia, P.M., et al., "Microfluidic Platform for Combinatorial Synthesis and Optimization of Targeted Nanoparticles for Cancer therapy," ACS Nano 7(12):10671-10680, American Chemical Society, United States (2013).
Van Bezooijen, R.L., et al., "Sclerostin is an Osteocyte-Expressed Negative Regulator of Bone Formation, But not a Classical BMP Antagonist," The Journal of Experimental Medicine 199(6):805-814, Rockefeller University Press, United States (2004).
Van Bezooijen, R.L., et al., "Wnt but not BMP Signaling is Involved in the Inhibitory Action of Sclerostin on Bmp-Stimulated Bone Formation," Journal of Bone and Mineral Research 22(1):19-28, American Society for Bone and Mineral Research, United States (2007).
Van Cruijsen, H., et al., "Tissue Micro Array Analysis of Ganglioside N-Glycolyl GM3 Expression and Signal Transducer and Activator of Transcription (Stat)-3 Activation in Relation to Dendritic Cell Infiltration and Microvessel Density in Non-Small Cell Lung Cancer," BMC Cancer 9:180, BioMed Central, England (2009).
Van Den Bosch, G.A., et al., "Simultaneous Activation of Viral Antigen-Specific Memory CD4+ and CD8+ T-Cells Using mRNA-Electroporated CD40-Activated Autologous B-Cells," Journal of Immunotherapy 29(5):512-523, Rockefeller University Press, United States (2006).
Van Gelder, R.N., et al., "Amplified RNA Synthesized from Limited Quantities of Heterogeneous cDNA," Proceedings of the National Academy of Sciences of the United States of America 87(5):1663-1667, National Academy of Sciences, United States (1990).

(56) References Cited

OTHER PUBLICATIONS

Van Tendeloo, V.F., et al., "Highly Efficient Gene Delivery by mRNA Electroporation in Human Hematopoietic Cells: Superiority to Lipofection and Passive Pulsing of mRNA and to Electroporation of Plasmid cDNA for Tumor Antigen Loading of Dendritic Cells," Blood 98(1):49-56, American Society of Hematology, United States (2001).
Van Tendeloo, V.F., et al., "mRNA-Based Gene Transfer as a Tool for Gene and Cell therapy," Current Opinion in Molecular Therapeutics 9(5):423-431, Thomson Reuters Ltd, England (2007).
Vaquero, C., et al., "Transient Expression of a Tumor-Specific Single-Chain Fragment and a Chimeric Antibody in Tobacco Leaves," Proceedings of the National Academy of Sciences of the United States of America 96(20)11128-11133, National Academy of Sciences, United States (1999).
Varambally, S., et al., "Genomic Loss of MicroRNA-101 Leads to Overexpression of Histone Methyltransferase EZH2 in Cancer," Science 322(5908):1695-1699, American Association for the Advancement of Science, United States (2008).
Vassilev, V.B., et al., "Microparticle-Mediated RNA Immunization against Bovine Viral Diarrhea Virus," Vaccine 19(15-16):2012-2019, Elsevier Science, Netherlands (2001).
Vazquez, A.M., et al., "Racotumomab: An Anti-Idiotype Vaccine Related to N-Glycolyl-Containing Gangliosides - Preclinical and Clinical Data," Frontiers in Oncology 2:1-6, Frontiers Research Foundation, Switzerland (2012).
Veres, G., et al., "The Molecular Basis of the Sparse Fur Mouse Mutation," Science 237(4813):415-417, American Association for the Advancement of Science, United States (1987).
Verheggen, C., et al., "Box CID Small Nucleolar RNA Trafficking Involves Small Nucleolar RNP Proteins, Nucleolar Factors and a Novel Nuclear Domain," The EMBO Journal 20(19):5480-5490, Wiley Blackwell, England (2001).
Verheggen, C., et al., "Mammalian and Yeast U3 snoRNPs are Matured in Specific and Related Nuclear Compartments," The EMBO Journal 21(11):2736-2745, Wiley Blackwell, England (2002).
Verma, I.M., et al., "Gene Therapy- Promises, Problems and Prospects," Nature 389(6648):239-242, Nature Publishing Group, England (1997).
Verma, I.M., et al., "Gene Therapy: Twenty-First Century Medicine," Annual Review of Biochemistry 74:711-738, Annual Reviews, United States (2005).
Verma, S. and Eckstein, F., "Modified Oligonucleotides: Synthesis and Strategy for Users," Annual Review of Biochemistry 67:99-134, Annual Reviews, United States (1998).
Verma, S., et al., "Functional Tuning of Nucleic Acids by Chemical Modifications: Tailored Oligonucleotides as Drugs, Devices, and Diagnostics.," Chemical Record 3(1): 51-60, Wiley, United States (2003).
Vichyanond, P., "Omalizumab in Allergic Diseases, a Recent Review," Asian Pacific Journal of Allergy and Immunology 29(3):209-219, Allergy and Immunology Society of Thailand, Thailand (2011).
Vierbuchen, T., et al., "Direct Conversion of Fibroblasts to Functional Neurons by Defined Factors," Nature 463(7284):1035-1041, Nature Publishing Group, England (2010).
Vilee, D.B., "Ribonucleic Acid: Control of Steroid Synthesis in Endocrine Tissue," Science 158(3801):652-653 (1967).
Villaret, D.B., et al., "Identification of Genes Overexpressed in Head and Neck Squamous Cell Carcinoma using a Combination of Complementary DNA Subtraction and Microarray Analysis," Laryngoscope 10(3Pt1):374-381,1Niley-Blackwell, United States (2000).
Virovic, L. et al., "Novel Delivery Methods for Treatment of Viral Hepatitis: an Update," Expert Opinion on Drug Delivery 2(4):707-717, Informa Healthcare, England (2005).
Viza, D., et al., "Human Lymphoblastoid Cells in Culture Replicate Immune Information Carried by Xenogeneic RNA," Differentiation; Research in Biological Diversity 11(3):181-184, Elsevier, England (1978).
Vlad, G., et al., "Immunoglobulin-Like Transcript 3-Fc Suppresses T-Cell Responses to Allogeneic Human islet Transplants in hu-NOD/SCID Mice," Diabetes 57(7):1878-1886, American Diabetes Association, United States (2008).
Wagner, E., "Polymers for siRNA Delivery: Inspired by Viruses to Be Targeted, Dynamic, and Precise," Accounts of Chemical Research 45(7):1005-1013, American Chemical Society, United States (2012).
Wagner, H.N., et al., "Administration Guidelines for Radioimmunotherapy of Non-Hodgkin'S Lymphoma with (90)Y-Labeled Anti-CD20 Monoclonal Antibody," Journal of Nuclear Medicine 43(2):267-272, Society of Nuclear Medicine, United States (2002).
Wahl, A.F., et al., "The Anti-CD30 Monoclonal Antibody SGN-30 Promotes Growth Arrest and DNA Fragmentation In Vitro and Affects Antitumor Activity in Models of Hodgkin's Disease," Cancer Research 62(13):3736-3742, American Association for Cancer Research, United States (2002).
Wahle, E., et al., "Poly(A) Tail Length Control is Caused by Termination of Processive Synthesis," The Journal of Biological Chemistry 270(6):2800-2808, American Society for Biochemistry and Molecular Biology, United States (1995).
Walker, A., et al., "Splitcore: An Exceptionally Versatile Viral Nanoparticle for Native Whole Protein Display Regardless of 3D Structure.," Scientific Reports 1:1-8, Nature Publishing Group, England (2011).
Walker, G.T., et al., "Isothermal In Vitro Amplification of DNA by a Restriction Enzyme/DNA Polymerase System," Proceedings of the National Academy of Sciences of the United States of America 89(1):392-396, National Academy of Sciences, United States (1992).
Walker, V., "Ammonia Toxicity and its Prevention in Inherited Defects of the Urea Cycle," Diabetes, Obesity & Metabolism 11(9):823-835, Wiley-Blackwell, England (2009).
Wallace, Daniel J. et al., Epratuzumab Demonstrates Clinically Meaningful Improvements in Patients with Moderate to Severe Systemic Lupus Erythematosus (SLE) Results from EMBLEM, a Phase IIB Study, ACR Concurrent Abstract Sessions, Systemic Lupus Enrthematosus-Clinical Aspects and Treatment: New Therapies, 2010, No Vol., pp. 1452.
Wallace, D.J., et al., "Efficacy and Safety of Epratuzumab in Patients with Moderate/Severe Active Systemic Lupus Erythematosus: Results from EMBLEM, a Phase IIb, Randomised, Double-Blind, Placebo-Controlled, Multicentre Study," Annals of the Rheumatic Diseases 73(1):183-190, BMJ, England (2014).
Wallet, M.A., et al., "Immunoregulation of Dendritic Cells," Clinical Medicine & Research 3(3):166-175, Marshfield Clinic, United States (2005).
Wang, B., et al., "Gene Inoculation Generates Immune Responses Against Human Immunodeficiency Virus Type 1," Proceedings of the National Academy of Sciences USA 90(9):4156-4160, National Academy of Sciences, United States (1993).
Wang, B., et al., "Immunization by Direct DNA Inoculation Induces Rejection of Tumor Cell Challenge," Human Gene Therapy 6(4):407-418, Liebert, United States (1995).
Wang, B.S., et al., "Fractionation of Immune RNA Capable of Transferring Tumor-Specific Cellular Cytotoxicity," Cellular Immunology 37(2):358-368, Elsevier, Netherlands (1978).
Wang, H., et al., "HMG-1 as a Late Mediator of Endotoxin Lethality in Mice," Science 285(5425):248-251, American Association for the Advancement of Science, United States (1999).
Wang, S.P., et al., "Phylogeny of mRNA Capping Enzymes," Proceedings of the National Academy of Sciences USA 94(18):9573-9578, National Academy of Sciences, United States (1997).
Wang, X., et al., "Re-Evaluating the Roles of Proposed Modulators of Mammalian Target of Rapamycin Complex 1 (mTORC1) Signaling," The Journal of Biological Chemistry 283(45):30482-30492, American Society for Biochemistry and Molecular Biology, United States (2008).

(56) References Cited

OTHER PUBLICATIONS

Wang, Y., et al., "Endogenous miRNA Sponge lincRNA-RoR Regulates Oct4, Nanog, and Sox2 in Human Embryonic Stem Cell Self-Renewal," Developmental Cell 25(1):69-80, Cell Press, United States (2013).
Wang, Y., et al., "Systemic Delivery of Modified mRNA Encoding Herpes Simplex Virus 1 Thymidine Kinase for Targeted Cancer Gene Therapy," Molecular Therapy 21(2):358-367, Academic Press, United States (2013).
Warren, L., et al., "Highly Efficient Reprogramming to Pluripotency and Directed Differentiation of Human Cells with Synthetic Modified mRNA," Cell Stem Cell 7(5):618-630, Cell Press, United States (2010).
Warren, T.L., et al., "Uses of Granulocyte-macrophage Colony-Stimulating Factor in Vaccine Development," Current Opinion in Hematolog 7(3):168-173, Lippincott Williams and Wilkins, United States (2000).
Watanabe, H., et al., "Conformational Stability and Warfarin-Binding Properties of Human Serum Albumin Studied by Recombinant Mutants," The Biochemical Journal 357(Pt1):269-274, Portland Press, England (2001).
Watanabe, H., et al., "Experimental Autoimmune Thyroiditis Induced by Thyroglobulin-Pulsed Dendritic Cells," Autoimmunity 31(4):273-282, Oxford : Taylor & Francis, England (1999).
Watanabe, T., et al., "Induction of Wild-Type p53 Activity in Human Cancer Cells by Ribozymes that Repair Mutant p53 Transcripts," Proceedings of the National Academy of Sciences USA 97(15):8490-8494, National Academy of Sciences, United States (2000).
Watts, G.F., et al., "Familial Hypercholesterolemia: A Missed Opportunity in Preventive Medicine.," Nature Clinical Practice. Cardiovascular Medicine 4(8): 404-405, Nature Pub. Group, England (2007).
Weaver, J.C., et al., "Electroporation Theory. Concepts and Mechanisms," Methods in Molecular Biology 55:3-28, Humana Press, United States (1995).
Weber, J., et al., "Granulocyte-macrophage-colony-stimulating Factor Added to a Multipeptide Vaccine for Resected Stage II Melanoma," Cancer 97(1):186-200, Wiley, United States (2003).
Wechsler, M.E., et al., "Novel Targeted therapies for Eosinophilic Disorders," The Journal of Allergy and Clinical Immunology 130(3):563-571, Mosby, United States (2012).
Wei, C.J., et al., "Induction of Broadly Neutralizing H1N1 Influenza Antibodies by Vaccination," Science 329(5995):1060-1064, American Association for the Advancement of Science, United States (2010).
Wei, X., et al., "Molecular Cloning and mRNA Expression of Two Peptidoglycan Recognition Protein (PGRP) Genes from Mollusk Solen Grandis," Fish & Shellfish Immunology 32(1):178-185, Academic Press, England (2012).
Weide, B., et al., "Direct Injection of Protamine-Protected mRNA: Results of a Phase 1/2 Vaccination Trial in Metastatic Melanoma Patients," Journal of Immunotherapy 32(5):498-507, Nature Publishing Group, England (2009).
Weide, B., et al., "Results of the First Phase I/II Clinical Vaccination Trial with Direct Injection of mRNA," Journal of Immunotherapy 31(2):180-188, Nature Publishing Group, England (2008).
Weisberger, A.S., "Induction of Alered Globin Synthesis in Human Immature Erythrocytes Incubated with Ribonucleoprotein," Proceedings of the National Academy of Sciences USA 48(1):68-80, National Academy of Sciences, United States (1962).
Weiss, S.B., et al., "Pseudouridine Formation: Evidence for RNA as an Intermediate," Science 149(3682):429-431, American Association for the Advancement of Science, United States (1965).
Weissman, D., et al., "Dendritic Cells Express and use Multiple HIV Coreceptors," Advances in Experimental Medicine and Biology 417:401-406, Kluwer Academic/Plenum Publishers, United States (1997).
Weissman, D., et al., "Hiv gag mRNA Transfection of Dendritic Cells (DC) Delivers Encoded Antigen to MHC Class I and II Molecules, Causes DC Maturation, and Induces a Potent Human in Vitro Primary Immune Response," Journal of Immunology 165(8):4710-4717, American Association of Immunologists, United States (2000).
Wells, J.M. and Dransfield, M.T., "Pathophysiology and Clinical Implications of Pulmonary Arterial Enlargement in COPD," International Journal of Chronic Obstructive Pulmonary Disease 8:509-521, Nature Pub. Group, United States (2013).
Wels, W., et al., "Construction, Bacterial Expression and Characterization of a Bifunctional Single-chain Antibody-Phosphatase Fusion Protein Targeted to the Human erbB-2 Receptor," Biotechnology 10(10):1128-1132, Nature Publishing Group, United States (1992).
Werman, A., et al., "The Precursor form of IL-1Alpha is an Intracrine Proinflammatory Activator of Transcription," Proceedings of the National Academy of Sciences of the United States of America 101(8):2434-2439, National Academy of Sciences, United States (2004).
West, J., et al., "Cloning and Expression of Two Human Lysophosphatidic Acid Acyltransferase cDNAs that Enhance Cytokine-Induced Signaling Responses in Cells," DNA and Cell Biology 16(6):691-701, Mary Ann Liebert, United States (1997).
Westenfeld, R., et al., "Anti-RANKL therapy—Implications for the Bone-Vascular-Axis in CKD? Denosumab in Post-Menopausal Women with Low Bone Mineral Density," Nephrology, Dialysis, Transplantation 21(8):2075-2077, Oxford University Press, England (2006).
Whitesides, G.M., "The Origins and the Future of Microfluidics," Nature 442(7101):368-373, Nature Pub. Group, United States (2006).
Whitington, P.F., et al., "Liver Transplantation for the Treatment of Urea Cycle Disorders," Journal of Inherited Metabolic Disease 112-118, Kluwer, Netherlands (1998).
WHO Drug Information, International Nonproprietary Names for Pharmaceutical Substances (INN), 1993, vol. 7, No. 4, pp. 1-16.
WHO Drug Information, International Nonproprietary Names for Pharmaceutical Substances (INN), 2011, vol. 25, No. 3, pp. 1-46.
WHO Drug Information, International Nonproprietary Names for Pharmaceutical Substances (INN), 2012, vol. 26, No. 2, pp. 1-79.
WHO Drug Information, International Nonproprietary Names for Pharmaceutical Substances (INN), 2012, vol. 26, No. 3, pp. 1-36.
WHO Drug Information, International Nonproprietary Names for Pharmaceutical Substances (INN), 2012, vol. 26, No. 4, pp. 1-71.
WHO Drug Information, International Nonproprietary Names for Pharmaceutical Substances (INN), Recommended INN, 2000, vol. 14, No. 1, pp. 39-76.
WHO Drug Information, International Nonproprietary Names for Pharmaceutical Substances (INN),2013, vol. 27, No. 4, pp. 1-60.
Wickens, M., et al., "A PUF Family Portrait: 3'UTR Regulation as a Way of Life," Trends in Genetics 18(3):150-157, Elsevier Trends Journals, England (2002).
Wiehe, J.M., et al., "mRNA-Mediated Gene Delivery Into Human Progenitor Cells Promotes Highly Efficient Protein Expression," Journal of Cellular and Molecular Medicine 11(3):521-530, Wiley-Blackwell, England (2007).
Wilcken, B., "Problems in the Management of Urea Cycle Disorders," Molecular Genetics and Metabolism 81(1):S86-S91, Academic Press, United States (2010).
Wilkie, G.S., et al., "Regulation of mRNA Translation by 5'- and 3'-UTR-Binding Factors," Trends in Biochemical Sciences 28(4):182-188, Elsevier Trends Journals, England (2003).
Wilkinson, R.A., et al., "Structure of the Fab Fragment of F105, a Broadly Reactive Anti-Human Immunodeficiency Virus (HIV) Antibody that Recognizes the CD4 Binding Site of HIV Type 1 GP120," Journal of Virology 79(20):13060-13069, American Society for Microbiology, United States (2005).
Williams, C.A., et al., "Apoptotic Cells Induce Dendritic Cell-Mediated Suppression via Interferon-Gamma-Induced IDO," Immunology 124(1):89-101, Blackwell Scientific Publications, England (2008).
Wilusz, C.J., et al., "Bringing the Role of mRNA Decay in the Control of Gene Expression Into Focus," Trends in genetics 20(10):491-497, Elsevier Trends Journals, England (2004).

(56) References Cited

OTHER PUBLICATIONS

Wilusz, J., et al., "A 64 kd Nuclear Protein Binds to RNA Segments that Include the AAUAAA Polyadenylation Motif," Cell 52(2):221-228, Cell Press, United States (1988).
Wing, K. and Sakaguchi, S., "Regulatory T Cells Exert Checks and Balances on Self Tolerance and Autoimmunity," Nature Immunology 11(1):7-13, Nature America Inc., United States (2010).
Winkler, D.G., et al., "Osteocyte Control of Bone Formation via Sclerostin, a Novel BMP Antagonist," The EMBO Journal 22(23):6267-6276, Wiley Blackwell, England (2003).
Winnicka, B., et al., "CD13 is Dispensable for Normal Hematopoiesis and Myeloid Cell Functions in the Mouse," Journal of Leukocyte Biology 88(2):347-359, Society for Leukocyte Biology, United States (2010).
Wolff, J.A., et al., "Direct Gene Transfer into Mouse Muscle in Vivo," Science 247(4949Pt1):1465-1468, American Association for the Advancement of Science, United States (1990).
Woltjen, K., et al, "PiggyBac Transposition Reprograms Fibroblasts to Induced Pluripotent Stem Cells," Nature 458(7239):766-770, Nature Publishing Group, England (2009).
Woodberry, T., et al., "Immunogenicity of a Human Immunodeficiency Virus (HIV) Polytope Vaccine Containing Multiple HLA A2 HIV CD8(+) Cytotoxic T-Cell Epitopes," Journal of Virology 73(7):5320-5325, American Society for Microbiology, United States (1999).
World Health Organization, Department of Communicable Disease Surveillance and Response, WHO/CSR, 2000, Chapter 7, pp. 1-7.
World Health Organization, Serological Diagnosis of Influenza by Microneutralization Assay, 2010, No Vol., pp. 1-25.
World Health Organization, WHO Manual on Animal Influenza Diagnosis and Surveillance, WHO Global Influenza Programme, CDS, CSR, NCS, 2002, vol. 5, No Number, pp. 1-99.
Wright, Timothy M.D., Transforming Molecules into Breakthrough Therapies, Novartis, Investor Day, London,2013, No Vol. pp. 1-16.
Wu, J. and Manley, J.L., "Mammalian Pre-mRNA Branch Site Selection by U2 SnRNP Involves Base Pairing," Genes and Development 3(10):1553-15561, Cold Spring Harbor Laboratory Press, United States (1989).
Wu, L., et al., "Fusion Protein Vectors to Increase Protein Production and Evaluate the Immunogenicity of Genetic Vaccines," Molecular Therapy 2(3):288-297, Academic Press, United States (2000).
Wu, X.C., et al., "Engineering a Bacillus Subtilis Expression-secretion System With a Strain Deficient in Six Extracellular Proteases," Journal of Bacteriology 173(16):4952-4958, American Society for Microbiology, United States (1991).
Wurm, F., et al., "Suppression of Melanoma Development and Regression of Melanoma in Xiphophorine Fish After Treatment with Immune RNA," Cancer research 41(9pt1):3377-3383, American Association for Cancer Research, United States (1981).
Wyatt, G.R., "Occurrence of 5-methylcytosine in nucleic acids," Nature 166(4214):237-238, Nature Publishing Group, England (1950).
Wyatt, J.R., et al., "Site-specific Cross-linking of Mammalian U5 Snrnp to the 5' Splice Site Before the First Step of Pre-mRNA Splicing," Genes and Development 6(12B):2542-2553, Cold Spring Harbor Laboratory Press, United States (1992).
Xgeva (denosumab) Product Label 2010-2013 pp. 1-16.
Xiang, B., et al., "Colorectal Cancer Immunotherapy," Discovery Medicine 15(84): 301-308, Discovery medicine, United States (2013).
Xu, C., et al., "Feeder-free Growth of Undifferentiated Human Embryonic Stem Cells," Nature Biotechnology 19(10):971-974, Nature America Publishing, United States (2001).
Xu, C., et al., "Identification of Differentially Expressed Genes in Human Prostate Cancer Using Subtraction and Microarray," Cancer Research 60(6):1677-1682, American Association for Cancer Research, United States (2000).
Yamamoto, A., et al., "Current Prospects for mRNA Gene Delivery," European Journal of Pharmaceutics and Biopharmaceutics 71(3):484-489, Elsevier Science, Netherlands (2009).
Yamashita, A., et al., "Concerted Action of Poly(A) Nucleases and Decapping Enzyme in Mammalian mRNA Turnover," Nature Structural and Molecular Biology 12(12):1054-1063, Nature Publishing Group, United States (2005).
Yang, J., et al., "CD4+ T Cells from Type 1 Diabetic and Healthy Subjects Exhibit Different Thresholds of Activation to a Naturally Processed Proinsulin Epitope," Journal of Autoimmunity 31(1):30-41, Academic Press, England (2008).
Yang, R.K. and Sondel, P.M., "Anti-GD2 Strategy in the Treatment of Neuroblastoma," Drugs of the Future 35(8):665, Thomson Reuters, United States (2010).
Yang, S.F., and Niu, M.C., "Albumin Synthesis in Mouse Uterus in Response to Liver mRNA,"Proceedings of the National Academy of Sciences USA74(5):1894-1898,National Academy of Sciences, United States (1977).
Yang, X., et al., "Effect of CD44 Binding Peptide Conjugated to an Engineered Inert Matrix on Maintenance of Breast Cancer Stem Cells and Tumorsphere formation," PLOS one 8(3):e59147, Public Library of Science, United States (2013).
Yang, X.D., et al., "Development of ABX-EGF, a Fully Human Anti-EGF Receptor Monoclonal Antibody, for Cancer Therapy," Critical Reviews in Oncology/Hematology 38(1):17-23, Elsevier Scientific Publishers, Netherlands (2001).
Yang, X.D., et al., "Eradication of Established Tumors by a Fully Human Monoclonal Antibody to the Epidermal Growth Factor Receptor without Concomitant Chemotherapy," Cancer Research 59(6):1236-1243, American Association for Cancer Research, United States (1999).
Yarovoi, H.V., et al., "Factor VIII Ectopically Expressed in Platelets: Efficacy in Hemophilia a Treatment," Blood 102(12):4006-4013, Grune & Stratton, United States (2003).
Ye, X., et al., "Prolonged Metabolic Correction in Adult Ornithine Transcarbamylase-Deficient Mice with Adenoviral Vectors," The Journal of Biological Chemistry 271(7):3639-3646, American Society for Biochemistry and Molecular Biology, United States (1996).
Yi, P., et al., "Betatrophin: A Hormone that Controls Pancreatic B Cell Proliferation," Cell 153(4):747-758, Cell Press, United States (2013).
Yi, Y., et al., "Current Advances in Retroviral Gene Therapy," Current Gene Therapy 11(3):218-228, Bentham Science Publishers, Netherlands (2011).
Ying, H., et al., "Cancer Therapy Using a Self-Replicating RNA Vaccine," Nature Medicine 5(7):823-827, Nature Publishing Company, United States (1999).
Yisraeli, J.K. and Melton, D.A., "Synthesis of Long, Capped Transcripts in Vitro by SP6 and T7 RNA Polymerases," Methods in Enzymology 180:42-50, Academic Press, United States (1989).
Yokoe, H. and Meyer, T., "Spatial Dynamics of GFP-Tagged Proteins Investigated by Local Fluorescence Enhancement," Nature Biotechnology 14(10):1252-1256, Nature America Publishing, United States (1996).
Yoshida, Y., et al., "Hypoxia Enhances the Generation of Induced Pluripotent Stem Cells," Cell Stem Cell 5(3):237-241, Nature America Publishing, United States (2009).
You, Z., et al., "A Retrogen Strategy for Presentation of an Intracellular Tumor Antigen as an Exogenous Antigen by Dendritic Cells Induces Potent Antitumor T Helper and CTL Responses," Cancer Research 61(1):197-205, American Association for Cancer Research, United States (2001).
Yu, AL., et al., "Anti-GD2 Antibody with GM-CSF, Interleukin-2, and Isotretinoin for Neuroblastoma," The New England Journal of Medicine 363(14):1324-1334, Massachusetts Medical Society, United States (2010).
Yu, AL., et al., "Phase I Trial of a Human-Mouse Chimeric Anti-Disialoganglioside Monoclonal Antibody Ch14.18 in Patients with Refractory Neuroblastoma and Osteosarcoma," Journal of Clinical Oncology 16(6):2169-2180, American Society of Clinical Oncology, United States (1998).
Yu, J. and Russell, J.E., "Structural and Functional Analysis of an mRNP Complex that Mediates the High Stability of Human Beta-

(56) References Cited

OTHER PUBLICATIONS

Globin mRNA," Molecular and Cellular Biology 21(17):5879-5888, American Society for Microbiology, United States (2001).
Yu, J., et al., "Human Induced Pluripotent Stem Cells Free of Vector and Transgene Sequences," Science 324(5928):797-801, American Association for the Advancement of Science, United States (2009).
Yu, J., et al., "Induced Pluripotent Stem Cell Lines Derived from Human Somatic Cells.," Science 318(5858):1917-1920, American Association for the Advancement of Science, United States (2007).
Yu, P.W., et al., "Sustained Correction of B-Cell Development and Function in a Murine Model of X-Linked Agammaglobulinemia (XLA) Using Retroviral-Mediated Gene Transfer," Blood 104(5):1281-1290, American Society of Hematology, United States (2004).
Yu, Y.T., et al., "Internal Modification of U2 Small Nuclear (sn)RNA Occurs in Nucleoli of Xenopus Oocytes," The Journal of Cell Biology 152(6):1279-1288, Rockefeller University Press, United States (2001).
Yu, Y.T., et al., "Modifications of U2 snRNA are Required for snRNP Assembly and Pre-mRNA Splicing," The Embo Journal 17(19):5783-5795, Wiley Blackwell, England (1998).
Zangi L., et al., "Modified mRNA Directs the Fate of Heart Progenitor Cells and Induces Vascular Regeneration after Myocardial Infarction," Nature Biotechnology 31(10):898-907, Nature America Publishing, United States (2013).
Zebarjadian, Y., et al., "Point Mutations in Yeast CBF5 can Abolish in Vivo Pseudouridylation of Rrna," Molecular and Cellular Biology 19(11):7461-7472, American Society for Microbiology, United States (1999).
Zeitlin, S. and Efstratiadis, A., "In Vivo Splicing Products of the Rabbit Beta-Globin pre-Mrna," Cell 39(3Pt2):589-602, Cell Press, United States (1984).
Zelcer, A., et al., "The Detection and Characterization of Viral-Related Double-Stranded RNAs in Tobacco Mosaic Virus-Infected Plants," Virology 113(2):417-427, Academic Press, United States (1981).
Zelcer, N., et al., "LXR Regulates Cholesterol Uptake through Idol-Dependent Ubiquitination of the LDL Receptor," Science 325(5936):100-104, American Association for the Advancement of Science, United States (2009).
Zeytin, H.E., et al., "Construction and Characterization of DNA Vaccines Encoding the Single-Chain Variable Fragment of the Anti-Idiotype Antibody 1A7 Mimicking the Tumor-Associated Antigen Disialoganglioside GD2," Cancer Gene Therapy 7(11):1426-1436, Nature Publishing Group, England (2000).
Zhang, D.W., et al., "Binding of Proprotein Convertase Subtilisin/Kexin Type 9 to Epidermal Growth Factor-Like Repeat a of Low Density Lipoprotein Receptor Decreases Receptor Recycling and increases Degradation," The Journal of Biological Chemistry 282(25):18602-18612, American Society for Biochemistry and Molecular Biology, United States (2007) with Supplemental Information.
Zhang, L., et al., "Both K63 and K48 Ubiquitin Linkages Signal Lysosomal Degradation of the LDL Receptor," Journal of Lipid Research 54(5):1410-1420, American Society for Biochemistry and Molecular Biology, United States (2013).
Zhang X., et al., "Advances in Dendritic Cell-Based Vaccine of Cancer," Cancer Biotherapy Radiopharmaceuticals 17(6):601-619, Mary Ann Liebert, Inc., United States (2002).
Zhang, Y., et al., "In Vivo Gene Delivery by Nonviral Vectors: Overcoming Hurdles?," Molecular Therapy 20(7):1298-1304, Academic Press, United States (2012).
Zhao, X. and Yu, Y.T., "Detection and Quantitation of RNA Base Modifications," RNA 10(6):996-1002, Cold Spring Harbor Laboratory Press, United States (2004).
Zhao, X. and Yu, Y.T., "Pseudouridines in and Near the Branch Site Recognition Region of U2 snRNA are Required for snRNP Biogenesis and pre-mRNA Splicing in Xenopus Oocytes," RNA 10(4):681-690, Cold Spring Harbor Laboratory Press, United States (2004).
Zhao, X., et al., "Regulation of Nuclear Receptor Activity by a Pseudouridine Synthase through Posttranscriptional Modification of Steroid Receptor RNA Activator," Molecular Cell 15(4): 549-558, Cell Press, United States (2004).
Zheng, Y., et al., "Intracellular Interleukin-1 Receptor 2 Binding Prevents Cleavage and Activity of Interleukin-1 a, Controlling Necrosis-Induced Sterile Inflammation," Immunity 38(2):285-295, Cell Press, United States (2013).
Zhigaltsev, I.V., et al., "Bottom-Up Design and Synthesis of Limit Size Lipid Nanoparticle Systems with Aqueous and Triglyceride Cores using Millisecond Microfluidic Mixing," Langmuir 28(7):3633-3640, American Chemical Society, United States (2012).
Zhou, H., et al., "Generation of Induced Pluripotent Stem Cells using Recombinant Proteins," Cell Stem Cell 4(5):381-384, Cell Press, United States (2009).
Zhou, J., et al., "Bilirubin Glucuronidation Revisited: Proper Assay Conditions to Estimate Enzyme Kinetics with Recombinant UGT1A1," Drug Metabolism and Disposition 38(11):1907-1911, American Society for Pharmacology and Experimental Therapeutics, United States (2010).
Zhou, W.Z., et al., "RNA Melanoma Vaccine: Induction of Antitumor Immunity by Human Glycoprotein 100 mRNA Immunization," Human Gene Therapy 10(16):2719-2724, M.A. Liebert, United States (1999).
Zhu, B., et al., "Syn5 RNA Polymerase Synthesizes Precise Run-Off RNA Products," Nucleic Acids Research 42(5):e33, Oxford University Press, England (2014).
Zhu, M., et al., "Population Pharmacokinetics of Rilotumumab, a Fully Human Monoclonal Antibody against Hepatocyte Growth Factor, in Cancer Patients," Journal of Pharmaceutical Sciences 103(1): 328-336, Elsevier, United States (2014).
Zhu, Z., et al., "Inhibition of Human Leukemia in an Animal Model with Human Antibodies Directed against Vascular Endothelial Growth Factor Receptor 2. Correlation Between Antibody Affinity and Biological Activity," Leukemia 17(3): 604-611, Nature Publishing Group, Specialist Journals, England (2003).
Zhu, Z., et al., "Inhibition of Vascular Endothelial Growth Factor-Induced Receptor Activation with Anti-Kinase Insert Domain-Containing Receptor Single-Chain Antibodies from a Phage Display Library," Cancer Research 58(15):3209-3214, American Association for Cancer Research, United States (1998).
Zhuang, Y. and Weiner, A.M., "A Compensatory Base Change in Human U2 snRNA can Suppress a Branch Site Mutation," Genes & Development 3(10):1545-1552, Cold Spring Harbor Laboratory Press, United States (1989).
Zia-Amirhosseini, P., et al., "Pharmacokinetics and Pharmacodynamics of SB-240563, a Humanized Monoclonal Antibody Directed to Human Interleukin-5, in Monkeys," The Journal of Pharmacology and Experimental Therapeutics 291(3):1060-1067, American Society for Pharmacology and Experimental Therapeutics, United States (1999).
Ziegler, R.J, et al., "AAV2 Vector Harboring a Liver-Restricted Promoter Facilitates Sustained Expression of Therapeutic Levels of Alpha-Galactosidase A and the Induction of Immune Tolerance in Fabry Mice," Molecular Therapy 9(2):231-240, Academic Press, United States (2004).
Zimmermann, E. and Muller, R.H., "Electrolyte- and pH-Stabilities of Aqueous Solid Lipid Nanoparticle (SLN) Dispersions in Artificial Gastrointestinal Media," European Journal of Pharmaceutics and Biopharmaceutics 52(2):203-210, Elsevier Science, Netherlands (2001).
Zitvogel, L., et al., "Therapy of Murine Tumors with Tumor Peptide-Pulsed Dendritic Cells: Dependence on T Cells, B7 Costimulation, and T Helper Cell 1-Associated Cytokines," The Journal of Experimental Medicine 183(1):87-97, Rockefeller University Press, United States (1996).
Zohra, F.T., et al., "Drastic Effect of Nanoapatite Particles on Liposome-Mediated mRNA Delivery to Mammalian Cells," Analytical Biochemistry 345(1):164-166, Academic Press, United States (2005).
Zohra, F.T., et al., "Effective Delivery with Enhanced Translational Activity Synergistically Accelerates mRNA-Based Transfection,"

(56) References Cited

OTHER PUBLICATIONS

Biochemical and Biophysical Research Communications 358(1):373-378, Academic Press, United States (2007).

Zonta, S., et al., "Uretero-Neocystostomy in a Swine Model of Kidney Transplantation: A New Technique," The Journal of Surgical Research 124(2):250-255, Academic Press, United States (2005).

Zorio, D.A. and Blumenthal, T., "Both Subunits of U2AF Recognize the 3' Splice Site in Caenorhabditis Elegans," Nature 402(6763):835-838, Nature Publishing Group, England (1999).

Zou Li-Li, et al., "Cell-Penetrating Peptide-Mediated Therapeutic Molecule Delivery into the Central Nervous System," Current Neuropharmacology 11(2):197-208, Bentham Science Publishers, United Arab Emirates (2013).

Zwick, M.B., et al., "Identification and Characterization of a Peptide that Specifically Binds the Human, Broadly Neutralizing Anti-Human Immunodeficiency Virus Type 1 Antibody B12," Journal of Virology 75(14):6692-6699, American Society for Microbiology, United States (2001).

Zwick, M.B., et al., "Molecular Features of the Broadly Neutralizing Immunoglobulin G1 B12 Required for Recognition of Human Immunodeficiency Virus Type 1 GP120," Journal of Virology 77(10):5863-5876, American Society for Microbiology, United States (2003).

GenBank, "Synthetic construct human G-CSF," Accession No. DQ914891, accessed at https://www.ncbi.nlm.nih.gov/nuccore/DQ914891, accessed on Aug. 24, 2017, 2 pages.

GenBank, "Pan paniscus EPO mRNA," Accession No. XM_003812904, accessed at https://www.ncbi.nlm.nih.gov/nuccore/XM_003812904, accessed on Aug. 24, 2017, 2 pages.

GenBank, "Human Factor IX mRNA," Accession No. AB186358, accessed at https://www.ncbi.nlm.nih.gov/nuccore/AB186358, accessed on Aug. 24, 2017, 2 pages.

GenBank, "Human VEGF mRNA," Accession No. AY047581, accessed at https://www.ncbi.nlm.nih.gov/nuccore/AY047581, accessed on Aug. 24, 2017, 2 pages.

Validi, I., et al., "Exosome-mediated transfer of mRNAS and microRNAs is a novel mechanism of generic exchange between cells," Nature Cell Biology 9:645-659, Nature Publishing Group, United Kingdom (2007).

* cited by examiner

98N12-5 (TETA5-LAP)

DLin DMA

DLin-K-DMA (2,2-Dilinoleyl-4-dimethylaminomethyl-[1,3]-dioxolane)

DLin-KC2-DMA

DLin-MC3-DMA

C12-200

PRIOR ART

Only single cutters are shown in the map

SEQUENCE LISTING

```
<160> NUMBER OF SEQ ID NOS: 23

<210> SEQ ID NO 1
<211> LENGTH: 624
<212> TYPE: DNA
<213> ORGANISM: Homo sapiens

<400> SEQUENCE: 1

atggctggac ctgccaccca gagccccatg aagctgatgg ccctgcagct gctgctgtgg     60

cacagtgcac tctggacagt gcaggaagcc acccccctgg gccctgccag ctccctgccc    120

cagagcttcc tgctcaagtg cttagagcaa gtgaggaaga tccagggcga tggcgcagcg    180

ctccaggaga agctggtgag tgagtgtgcc acctacaagc tgtgccaccc cgaggagctg    240

gtgctgctcg gacactctct gggcatcccc tgggctcccc tgagcagctg ccccagccag    300

gccctgcagc tggcaggctg cttgagccaa ctccatagcg gccttttcct ctaccagggg    360

ctcctgcagg ccctggaagg gatctccccc gagttgggtc ccaccttgga cacactgcag    420

ctggacgtcg ccgactttgc caccaccatc tggcagcaga tggaagaact gggaatggcc    480

cctgccctgc agcccaccca gggtgccatg ccggccttcg cctctgcttt ccagcgccgg    540

gcaggagggg tcctggttgc ctcccatctg cagagcttcc tggaggtgtc gtaccgcgtt    600

ctacgccacc ttgcccagcc ctga                                           624


<210> SEQ ID NO 2
<211> LENGTH: 829
<212> TYPE: DNA
<213> ORGANISM: Homo sapiens

<400> SEQUENCE: 2

ttggaccctc gtacagaagc taatacgact cactataggg aaataagaga gaaaagaaga     60

gtaagaagaa atataagagc caccatggct ggacctgcca cccagagccc catgaagctg    120

atggccctgc agctgctgct gtggcacagt gcactctgga cagtgcagga agccaccccc    180

ctgggccctg ccagctccct gccccagagc ttcctgctca agtgcttaga gcaagtgagg    240

aagatccagg gcgatggcgc agcgctccag gagaagctgg tgagtgagtg tgccacctac    300

aagctgtgcc accccgagga gctggtgctg ctcggacact ctctgggcat cccctgggct    360

cccctgagca gctgccccag ccaggccctg cagctggcag gctgcttgag ccaactccat    420

agcggccttt tcctctacca ggggctcctg caggccctgg aagggatctc cccgagttg     480

ggtcccacct tggacacact gcagctggac gtcgccgact ttgccaccac catctggcag    540
```

-continued

```
cagatggaag aactgggaat ggcccctgcc ctgcagccca cccagggtgc catgccggcc    600

ttcgcctctg ctttccagcg ccgggcagga ggggtcctgg ttgcctccca tctgcagagc    660

ttcctggagg tgtcgtaccg cgttctacgc caccttgccc agccctgaag cgctgccttc    720

tgcggggctt gccttctggc catgcccttc ttctctccct tgcacctgta cctcttggtc    780

tttgaataaa gcctgagtag gaaggcggcc gctcgagcat gcatctaga                829
```

<210> SEQ ID NO 3
<211> LENGTH: 772
<212> TYPE: DNA
<213> ORGANISM: Homo sapiens

<400> SEQUENCE: 3

```
ttggaccctc gtacagaagc taatacgact cactataggg aaataagaga gaaaagaaga     60

gtaagaagaa atataagagc caccatggcc ctgcagttgc tgctttggca ctcggccctc    120

tggacagtcc aagaagcgac tcctctcgga cctgcctcat cgttgccgca gtcattcctt    180

ttgaagtgtc tggagcaggt gcgaaagatt cagggcgatg gagccgcact ccaagagaag    240

ctctgcgcga catacaaact ttgccatccc gaggagctcg tactgctcgg gcacagcttg    300

gggattccct gggctcctct ctcgtcctgt ccgtcgcagg ctttgcagtt ggcagggtgc    360

ctttcccagc tccactccgg tttgttcttg tatcagggac tgctgcaagc ccttgaggga    420

atctcgccag aattgggccc gacgctggac acgttgcagc tcgacgtggc ggatttcgca    480

acaaccatct ggcagcagat ggaggaactg gggatggcac ccgcgctgca gcccacgcag    540

ggggcaatgc cggcctttgc gtccgcgttt cagcgcaggg cgggtggagt cctcgtagcg    600

agccaccttc aatcattttt ggaagtctcg taccgggtgc tgagacatct tgcgcagccg    660

tgagccttct gcggggcttg ccttctggcc atgcccttct tctctccctt gcacctgtac    720

ctcttggtct ttgaataaag cctgagtagg aaggcggccg ctcgagcatg ca            772
```

<210> SEQ ID NO 4
<211> LENGTH: 746
<212> TYPE: RNA
<213> ORGANISM: Homo sapiens

<400> SEQUENCE: 4

```
cucacuauag ggaaauaaga gagaaaagaa gaguaagaag aaauauaaga gccaccaaug     60

gcccugcagu ugcugcuuug gcacucggcc cucuggacag uccaagaagc gacuccucuc    120

ggaccugccu caucguugcc gcagucauuc cuuuugaagu gucuggagca ggugcgaaag    180

auucagggcg auggagccgc acuccaagag aagcucugcg cgacauacaa acuuugccau    240

cccgaggagc ucguacugcu cgggcacagc uuggggauuc ccugggcucc ucucucgucc    300

uguccgucgc aggcuuugca guuggcaggg ugccuuuccc agcuccacuc cgguuuguuc    360

uuguaucagg gacugcugca agcccuugag ggaaucucgc cagaauuggg cccgacgcug    420

gacacguugc agcucgacgu ggcggauuuc gcaacaacca ucuggcagca gauggaggaa    480

cuggggaugg cacccgcgcu gcagcccacg caggggggcaa ugccggccuu ugcguccgcg    540

uuucagcgca gggcgggugg aguccucgua gcgagccacc uucaaucauu uuuggaaguc    600

ucguaccggg ugcugagaca ucuugcgcag ccgugagccu ucugcggggc uugccuucug    660

gccaugcccu ucuucucucc cuugcaccug uaccucuugg ucuuugaaua aagccugagu    720

aggaaggcgg ccgcucgagc augcau                                         746
```

<210> SEQ ID NO 5
<211> LENGTH: 854
<212> TYPE: RNA
<213> ORGANISM: Homo sapiens

<400> SEQUENCE: 5
gggaaauaag agagaaaaga agaguaagaa gaaauauaag agccaccaug guauccaagg 60
gggaggagga caacauggcg aucaucaagg aguucaugcg auucaaggug cacauggaag 120
guucggucaa cggacacgaa uuugaaaucg aaggagaggg ugaaggaagg cccuaugaag 180
ggacacagac cgcgaaacuc aaggucacga aaggggggacc acuuccuuuc gccugggaca 240
uucuuucgcc ccaguuuaug uacgggucca aagcauaugu gaagcauccc gccgauauuc 300
cugacuaucu gaaacucagc uuucccgagg gauucaagug ggagcggguc augaacuuug 360
aggacggggg uguagucacc guaacccaag acucaagccu ccaagacggc gaguucaucu 420
acaaggucaa acugcggggg acuaacuuuc cgucggaugg gccggugaug cagaagaaaa 480
cgaugggaug ggaagcguca ucggagagga uguacccaga agauggugca uugaaggggg 540
agaucaagca gagacugaag uugaaagaug ggggacauua ugaugccgag gugaaaacga 600
cauacaaagc gaaaaagccg gugcagcuuc ccggagcgua uaaugugaau aucaaguugg 660
auauuacuuc acacaaugag gacuacacaa uugucgaaca guacgaacgc gcugagggua 720
gacacucgac gggaggcaug gacgaguugu acaaaugaua agcugccuuc ugcggggcuu 780
gccuucuggc caugcccuuc uucucucccu ugcaccugua ccucuugguc uuugaauaaa 840
gccugaguag gaag 854

<210> SEQ ID NO 6
<211> LENGTH: 924
<212> TYPE: DNA
<213> ORGANISM: Homo sapiens

<400> SEQUENCE: 6
tcaagctttt ggaccctcgt acagaagcta atacgactca ctatagggaa ataagagaga 60
aaagaagagt aagaagaaat ataagagcca ccatggtatc caagggggag gaggacaaca 120
tggcgatcat caaggagttc atgcgattca aggtgcacat ggaaggttcg gtcaacggac 180
acgaatttga aatcgaagga gagggtgaag gaaggcccta tgaagggaca cagaccgcga 240
aactcaaggt cacgaaaggg ggaccacttc ctttcgcctg ggacattctt tcgccccagt 300
ttatgtacgg gtccaaagca tatgtgaagc atcccgccga tattcctgac tatctgaaac 360
tcagctttcc cgagggattc aagtgggagc gggtcatgaa ctttgaggac gggggtgtag 420
tcaccgtaac ccaagactca agcctccaag acggcgagtt catctacaag gtcaaactgc 480
gggggactaa ctttccgtcg gatgggccgg tgatgcagaa gaaaacgatg ggatgggaag 540
cgtcatcgga gaggatgtac ccagaagatg gtgcattgaa gggggagatc aagcagagac 600
tgaagttgaa agatggggga cattatgatg ccgaggtgaa aacgacatac aaagcgaaaa 660
agccggtgca gcttcccgga gcgtataatg tgaatatcaa gttggatatt acttcacaca 720
atgaggacta cacaattgtc gaacagtacg aacgcgctga gggtagacac tcgacgggag 780
gcatggacga gttgtacaaa tgataagctg ccttctgcgg ggcttgcctt ctggccatgc 840
ccttcttctc tcccttgcac ctgtacctct tggtctttga ataaagcctg agtaggaagg 900
cggccgctcg agcatgcatc taga 924

<210> SEQ ID NO 7

<211> LENGTH: 725
<212> TYPE: RNA
<213> ORGANISM: Homo sapiens

<400> SEQUENCE: 7
gggaaauaag agagaaaaga agaguaagaa gaaauauaag agccaccaug ggagugcacg 60
agugucccgc gugguugugg uugcugcugu cgcucuugag ccucccacug ggacugccug 120 ugcuggggggc accacccaga uugaucugcg acucacgggu acuugagagg uaccuucuug 180
aagccaaaga agccgaaaac aucacaaccg gaugcgccga gcacugcucc cucaaugaga 240
acauuacugu accggauaca aaggucaauu ucuaugcaug gaagagaaug gaaguaggac 300
agcaggccgu cgaagugugg caggggcucg cgcuuuuguc ggaggcggug uugcggggguc 360 aggcccuccu cgucaacuca ucacagccgu gggagccccu ccaacuucau gucgauaaag 420
cggugucggg gcuccgcagc uugacgacgu ugcuucgggc ucugggcgca caaaaggagg 480
cuauuucgcc gccugacgcg gccuccgcgg caccccuccg aacgaucacc gcggacacgu 540
uuaggaagcu uuuuagagug uacagcaauu uccuccgcgg aaagcugaaa uuguauacug 600
gugaagcgug uaggacaggg gaucgcugau aagcugccuu cugcggggcu ugccuucugg 660
ccaugcccuu cuucucuccc uugcaccugu accucuuggu cuuugaauaa agccugagua 720
ggaag 725

<210> SEQ ID NO 8
<211> LENGTH: 1536
<212> TYPE: RNA
<213> ORGANISM: Homo sapiens

<400> SEQUENCE: 8
gggaaauaag agagaaaaga agaguaagaa gaaauauaag agccaccaau gcagcgcguc 60
aacaugauua uggccgaauc gccgggacuc aucacaaucu gccucuuggg uuaucucuug 120
ucggcagaau guaccguguu cuuggaucac gaaaacgcga acaaaauucu uaaucgcccg 180
aagcgguaua acuccgggaa acuugaggag uuugugcagg gcaaucuuga acgagagugc 240
auggaggaga aaugcuccuu ugaggaggcg agggaagugu uugaaaacac agagcgaaca 300
acggaguuuu ggaagcaaua cguagauggg gaccagugug agucgaaucc gugccucaau 360
gggggaucau guaaagauga caucaauagc uaugaaugcu ggugcccguu uggguuugaa 420
gggaagaacu gugagcugga ugugacgugc aacaucaaaa acggacgcug ugagcaguuu 480
uguaagaacu cggcugacaa uaagguagua ugcucgugca cagagggaua ccggcuggcg 540
gagaaccaaa aaucgugcga gcccgcaguc ccguucccuu gugggagggu gagcguguca 600
cagacuagca aguugacgag agcggagacu guauuccccg acguggacua cgucaacagc 660
accgaagccg aaacaauccu cgauaacauc acgcagagca cucaguccuu caaugacuuu 720
acgagggucg uaggugguga ggacgcgaaa cccggucagu uccccuggca ggugguauug 780
aacggaaaag ucgaugccuu uuguggaggu uccauuguca acgagaagug gauugucaca 840
gcggcacacu gcguagaaac aggagugaaa aucacgguag uggcgggaga gcauaacauu 900
gaagagacag agcacacgga acaaaagcga aaugucauca gaaucauucc acaccauaac 960
uauaacgcgg caaucaauaa guacaaucac gacaucgcac uuuuggagcu ugacgaaccu 1020
uuggugcuua auucguacgu caccccuauu uguauugccg acaaagagua uacaaacauc 1080
uucuugaaau ucggcuccgg guacguaucg ggcuggggca gaguguucca uaaggguaga 1140
uccgcacugg uguugcaaua ccucagggug ccccucgugg aucgagccac uugucugcgg 1200
uccaccaaau ucacaaucua caacaauaug uucugugcgg gauuccauga aggugggaga 1260
gauagcugcc agggagacuc agggggaccc cacgugacgg aagucgaggg gacgucauuu 1320
cugacgggaa uuaucucaug gggagaggaa ugugcgauga aggggaaaua uggcaucuac 1380
acuaaagugu cacgguaugu caauuggauc aaggaaaaga cgaaacucac gugaucagcc 1440
agcgcugccu ucugcggggc uugccuucug gccaugcccu ucuucucucc cuugcaccug 1500
uaccucuugg ucuuugaaua aagccugagu aggaag 1536

<210> SEQ ID NO 9
<211> LENGTH: 794
<212> TYPE: DNA
<213> ORGANISM: Homo sapiens

<400> SEQUENCE: 9
caagcttttg gaccctcgta cagaagctaa tacgactcac tatagggaaa taagagagaa 60
aagaagagta agaagaaata taagagccac catgggagtg cacgagtgtc ccgcgtggtt 120
gtggttgctg ctgtcgctct tgagcctccc actgggactg cctgtgctgg gggcaccacc 180
cagattgatc tgcgactcac gggtacttga gaggtacctt cttgaagcca aagaagccga 240
aaacatcaca accggatgcg ccgagcactg ctccctcaat gagaacatta ctgtaccgga 300
tacaaaggtc aatttctatg catggaagag aatggaagta ggacagcagg ccgtcgaagt 360
gtggcagggg ctcgcgcttt tgtcggaggc ggtgttgcgg ggtcaggccc tcctcgtcaa 420
ctcatcacag ccgtgggagc ccctccaact tcatgtcgat aaagcggtgt cggggctccg 480
cagcttgacg acgttgcttc gggctctggg cgcacaaaag gaggctattt cgccgcctga 540
cgcggcctcc gcggcacccc tccgaacgat caccgcggac acgtttagga agctttttag 600
agtgtacagc aatttcctcc gcggaaagct gaaattgtat actggtgaag cgtgtaggac 660
aggggatcgc tgataagctg ccttctgcgg ggcttgcctt ctggccatgc ccttcttctc 720
tcccttgcac ctgtacctct tggtctttga ataaagcctg agtaggaagg cggccgctcg 780
agcatgcatc taga 794

<210> SEQ ID NO 10
<211> LENGTH: 1869
<212> TYPE: DNA
<213> ORGANISM: Homo sapiens

<400> SEQUENCE: 10
agcttttgga ccctcgtaca gaagctaata cgactcacta tagggaaata agagagaaaa 60
gaagagtaag aagaaatata agagccacca tggaagatgc gaagaacatc aagaagggac 120
ctgccccgtt ttaccctttg gaggacggta cagcaggaga acagctccac aaggcgatga 180
aacgctacgc cctggtcccc ggaacgattg cgtttaccga tgcacatatt gaggtagaca 240
tcacatacgc agaatacttc gaaatgtcgg tgaggctggc ggaagcgatg aagagatatg 300
gtcttaacac taatcaccgc atcgtggtgt gttcggagaa ctcattgcag tttttcatgc 360
cggtccttgg agcacttttc atcggggtcg cagtcgcgcc agcgaacgac atctacaatg 420
agcgggaact cttgaatagc atgggaatct cccagccgac ggtcgtgttt gtctccaaaa 480
aggggctgca gaaaatcctc aacgtgcaga agaagctccc cattattcaa aagatcatca 540
ttatggatag caagacagat taccaagggt tccagtcgat gtataccttt gtgacatcgc 600
atttgccgcc agggtttaac gagtatgact tcgtccccga gtcatttgac agagataaaa 660

```
ccatcgcgct gattatgaat tcctcgggta gcaccggttt gccaaagggg gtggcgttgc    720

cccaccgcac tgcttgtgtg cggttctcgc acgctaggga tcctatcttt ggtaatcaga    780

tcattcccga cacagcaatc ctgtccgtgg taccttttca tcacggtttt ggcatgttca    840

cgactctcgg ctatttgatt tgcggtttca gggtcgtact tatgtatcgg ttcgaggaag    900

aactgttttt gagatccttg caagattaca agatccagtc ggccctcctt gtgccaacgc    960

ttttctcatt ctttgcgaaa tcgacactta ttgataagta tgacctttcc aatctgcatg   1020

agattgcctc agggggagcg ccgcttagca aggaagtcgg ggaggcagtg gccaagcgct   1080

tccaccttcc cggaattcgg cagggatacg ggctcacgga gacaacatcc gcgatcctta   1140

tcacgcccga gggtgacgat aagccgggag ccgtcggaaa agtggtcccc ttctttgaag   1200

ccaaggtcgt agacctcgac acgggaaaaa ccctcggagt gaaccagagg ggcgagctct   1260

gcgtgagagg gccgatgatc atgtcaggtt acgtgaataa ccctgaagcg acgaatgcgc   1320

tgatcgacaa ggatgggtgg ttgcattcgg gagacattgc ctattgggat gaggatgagc   1380

acttctttat cgtagatcga cttaagagct tgatcaaata caaaggctat caggtagcgc   1440

ctgccgagct cgagtcaatc ctgctccagc accccaacat tttcgacgcc ggagtggccg   1500

ggttgcccga tgacgacgcg ggtgagctgc cagcggccgt ggtagtcctc gaacatggga   1560

aaacaatgac cgaaaaggag atcgtggact acgtagcatc acaagtgacg actgcgaaga   1620

aactgagggg aggggtagtc tttgtggacg aggtcccgaa aggcttgact gggaagcttg   1680

acgctcgcaa aatccgggaa atcctgatta aggcaaagaa aggcgggaaa atcgctgtct   1740

gataagctgc cttctgcggg gcttgccttc tggccatgcc cttcttctct cccttgcacc   1800

tgtacctctt ggtctttgaa taaagcctga gtaggaaggc ggccgctcga gcatgcatct   1860

agagggccc                                                           1869
```

<210> SEQ ID NO 11
<211> LENGTH: 930
<212> TYPE: DNA
<213> ORGANISM: Homo sapiens

<400> SEQUENCE: 11

```
tcaagctttt ggaccctcgt acagaagcta atacgactca ctatagggaa ataagagaga     60

aaagaagagt aagaagaaat ataagagcca ccatggtgag caagggcgag gagctgttca    120

ccggggtggt gcccatcctg gtcgagctgg acggcgacgt aaacggccac aagttcagcg    180

tgtccggcga gggcgagggc gatgccacct acggcaagct gaccctgaag ttcatctgca    240

ccaccggcaa gctgcccgtg ccctggccca ccctcgtgac caccctgacc tacggcgtgc    300

agtgcttcag ccgctacccc gaccacatga agcagcacga cttcttcaag tccgccatgc    360

ccgaaggcta cgtccaggag cgcaccatct tcttcaagga cgacggcaac tacaagaccc    420

gcgccgaggt gaagttcgag ggcgacaccc tggtgaaccg catcgagctg aagggcatcg    480

acttcaagga ggacggcaac atcctggggc acaagctgga gtacaactac aacagccaca    540

acgtctatat catggccgac aagcagaaga acggcatcaa ggtgaacttc aagatccgcc    600

acaacatcga ggacggcagc gtgcagctcg ccgaccacta ccagcagaac acccccatcg    660

gcgacggccc cgtgctgctg cccgacaacc actacctgag cacccagtcc gccctgagca    720

aagaccccaa cgagaagcgc gatcacatgg tcctgctgga gttcgtgacc gccgccggga    780

tcactctcgg catggacgag ctgtacaagt aagctgcctt ctgcggggct tgccttctgg    840

ccatgccctt cttctctccc ttgcacctgt acctcttggt ctttgaataa agcctgagta    900
```

```
ggaaggcggc cgctcgagca tgcatctaga                                    930


<210> SEQ ID NO 12
<211> LENGTH: 716
<212> TYPE: RNA
<213> ORGANISM: Homo sapiens

<400> SEQUENCE: 12

gggaaauaag agagaaaaga agaguaagaa gaaauauaag agccaccaug aacuuucucu     60

ugucaugggu gcacuggagc cuugcgcugc ugcuguaucu ucaucacgcu aaguggagcc    120

aggccgcacc cauggcggag gguggcggac agaaucacca cgaaguaguc aaauucaugg    180

acguguacca gaggucguau ugccauccga uugaaacucu uguggauauc uuucaagaau    240

accccgauga aaucgaguac auuuucaaac cgucgugugu cccucucaug aggugcgggg    300

gaugcugcaa ugaugaaggg uuggagugug uccccacgga ggagucgaau aucacaaugc    360

aaaucaugcg caucaaacca caucagggu agcauauugg agagaugucc uuucuccagc    420

acaacaaaug ugaguguaga ccgaagaagg accgagcccg acaggaaaac ccaugcggac    480

cgugcuccga gcggcgcaaa cacuuguucg uacaagaccc ccagacaugc aagugcucau    540

guaagaauac cgauucgcgg uguaaggcga gacagcugga auugaacgag cgcacgugua    600

ggugcgacaa gccuagacgg ugagcugccu ucugcggggc uugccuucug gccaugcccu    660

ucuucucucc cuugcaccug uaccucuugg ucuuugaaua aagccugagu aggaag        716


<210> SEQ ID NO 13
<211> LENGTH: 30
<212> TYPE: PRT
<213> ORGANISM: Homo sapiens

<400> SEQUENCE: 13

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala
            20                  25                  30


<210> SEQ ID NO 14
<211> LENGTH: 25
<212> TYPE: PRT
<213> ORGANISM: Homo sapiens

<400> SEQUENCE: 14

Met Met Pro Ser Ser Val Ser Trp Gly Ile Leu Leu Leu Ala Gly Leu
1               5                   10                  15

Cys Cys Leu Val Pro Val Ser Leu Ala
            20                  25


<210> SEQ ID NO 15
<211> LENGTH: 46
<212> TYPE: PRT
<213> ORGANISM: Homo sapiens

<400> SEQUENCE: 15

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg
        35                  40                  45
```

```
<210> SEQ ID NO 16
<211> LENGTH: 21
<212> TYPE: PRT
<213> ORGANISM: Homo sapiens

<400> SEQUENCE: 16

Met Lys Gly Ser Leu Leu Leu Leu Leu Val Ser Asn Leu Leu Leu Cys
1               5                   10                  15

Gln Ser Val Ala Pro
            20


<210> SEQ ID NO 17
<211> LENGTH: 24
<212> TYPE: PRT
<213> ORGANISM: Homo sapiens

<400> SEQUENCE: 17

Met Lys Trp Val Thr Phe Ile Ser Leu Leu Phe Leu Phe Ser Ser Ala
1               5                   10                  15

Tyr Ser Arg Gly Val Phe Arg Arg
            20


<210> SEQ ID NO 18
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa                          160


<210> SEQ ID NO 19
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(250)
<223> OTHER INFORMATION: This sequence may encompass 100-250 bases in
      length

<400> SEQUENCE: 19

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa                                                           250


<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<223> OTHER INFORMATION: See specification as filed for detailed
      description of substitutions and preferred embodiments

<400> SEQUENCE: 20

aaaaaaaaaa aaaaaaaaaa aaaaaaaaaa                                    30


<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

tttttttttt tttttttttt tttttttttt tttttttttt tttttttttt tttttttttt      60

tttttttttt tttttttttt tttttttttt tttttttttt tttttttttt tttttttttt     120


<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120


<210> SEQ ID NO 23
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(165)
<223> OTHER INFORMATION: This sequence may encompass 150-165 bases in
      length; See specification as filed for detailed description of
      substitutions and preferred embodiments

<400> SEQUENCE: 23

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120

aaaaaaaaaa aaaaaaaaaa aaaaaaaaaa aaaaaaaaaa aaaaa                    165
```

DELIVERY AND FORMULATION OF ENGINEERED NUCLEIC ACIDS

CROSS REFERENCE TO RELATED APPLICATIONS

This application is a divisional of U.S. patent application Ser. No. 14/337,513, filed Jul. 22, 2014, now U.S. Pat. No. 9,533,047, which is a continuation of U.S. patent application Ser. No. 13/897,362, filed May 18, 2013, now abandoned, which is a continuation of U.S. patent application Ser. No. 13/437,034, filed Apr. 2, 2012, now U.S. Pat. No. 8,710,200, which claims the benefit of U.S. Provisional Patent Application No. 61/470,451, filed Mar. 31, 2011, each of which is incorporated by reference in its entirety.

REFERENCE TO SEQUENCE LISTING

The content of the electronically submitted sequence listing in ASCII text file (Name: 3529_1130004_SeqListing.txt; Size: 20,616 bytes; Date of Creation: Jan. 24, 2017) filed electronically is incorporated herein by reference in its entirety.

FIELD OF THE INVENTION

The invention relates to delivery methods. These methods are specifically useful in therapeutic delivery of modified nucleic acids such as modified mRNA (mmRNA).

BACKGROUND OF THE INVENTION

There are multiple problems with prior methodologies of delivering pharmaceutical compositions in order to achieve effective protein expression both for therapeutics and bioprocessing applications. For example, introduced DNA can integrate into host cell genomic DNA at some frequency, resulting in alterations and/or damage to the host cell genomic DNA. Alternatively, the heterologous deoxyribonucleic acid (DNA) introduced into a cell can be inherited by daughter cells (whether or not the heterologous DNA has integrated into the chromosome) or by offspring.

In addition, there are multiple steps which must occur after delivery but before the encoded protein is made which can effect protein expression. Once inside the cell, DNA must be transported into the nucleus where it is transcribed into RNA. The RNA transcribed from DNA must then enter the cytoplasm where it is translated into protein. Not only do the multiple processing steps from administered DNA to protein create lag times before the generation of the functional protein, each step represents an opportunity for error and damage to the cell. Further, it is known to be difficult to obtain DNA expression in cells as frequently DNA enters a cell but is not expressed or not expressed at reasonable rates or concentrations. This can be a particular problem when DNA is introduced into primary cells or modified cell lines.

Assuming the proper management of the foregoing, effective delivery and achievement of therapeutically relevant levels of proteins for a time sufficient to product clinical outcomes remains a significant hurdle.

Consequently, there is a need in the art for the delivery of biological modalities to address pitfalls surrounding the modulation of intracellular translation and processing of nucleic acids encoding polypeptides and therefore optimizing protein expression from the delivered modalities.

The present invention addresses this need by delivering pharmaceutical compositions which can contain modified nucleic acids such as modified mRNA (mmRNA) and may further include formulations to avoid the problems in the art.

SUMMARY OF THE INVENTION

Described herein are compositions and methods for delivery of biological moieties, such as modified nucleic acids, engineered messenger RNA and isolated polynucleotides into cells in order to modulate protein expression.

An isolated polynucleotide may comprise a sequence such as, but not limited to, SEQ ID NO: 4, 7, 8 and 12. The polynucleotide may further comprise a 5'Cap1 structure and a polyA tail of approximately 160 nucleotides in length. Further, the isolated polynucleotide may be formulated in a pharmaceutical composition. A polypeptide of interest may be produced in a cell, tissue or bodily fluid in a subject in need thereof by administering to the subject a pharmaceutical composition comprising a polynucleotide. The polynucleotide may comprise a sequence selected from the group consisting of SEQ ID NO: 4, 7, 8 and 12. The polynucleotide may further comprise a 5'Cap1 structure and a poly-A tail of approximately 160 nucleotides in length.

The pharmaceutical composition may be formulated where the formulation may be selected from, but is not limited to, saline or a lipid formulation. The pharmaceutical composition may be administered by any route of administration such as, but not limited to, intravenous, intramuscular, subcutaneous, and local administration. The lipid formulation may be selected from, but is not limited to, such as, but not limited to, liposomes, lipoplexes, copolymers such as PLGA and lipid nanoparticles.

The pharmaceutical composition may be administered at a total dose of about 0.1 mg/kg to about 40 mg/kg. The total dose may be administered by multiple administrations. The administration and/or the multiple administration may occur on a schedule such as, but not limited to, three time a day, twice a day, once a day, every other day, every third day, weekly, biweekly, every three weeks, every four weekly, and monthly.

The modified polypeptide may include a polynucleotide modification such as, but not limited to, a nucleoside modification. The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

An increase in the level of a polypeptide of interest can be observed in tissue such as, but not limited to, the liver, spleen, kidney, lung, heart, pen-renal adipose tissue, thymus and muscle and/or in a bodily fluid such as, but not limited to, peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. The increased level can be observed in the tissue and/or bodily fluid of the subject within 2, 8 and/or 24 hours after administration. Further, the increased level can be determined from the level of a modified polypeptide in an exosome.

The details of various embodiments of the invention are set forth in the description below. Other features, objects, and advantages of the invention will be apparent from the description and the drawings, and from the claims.

BRIEF DESCRIPTION OF THE FIGURES

FIG. 3A shows the screening results in HEK293 cells and FIG. 3B shows the screening results in HepG2 cells.

FIG. 4A shows the screening results in HEK293 cells and FIG. 4B shows the screening results in HepG2 cells.

FIG. 5A shows the screening results of 98N15-2 in HEK293 cells, and FIGS. 5B and 5C show[[s]] the screening results of DLin-KC2-DMA in HEK293 cells.

FIG. 6A shows the mean fluorescence intensity of mCherry in HEK293 cells containing 60 ng of modified mCherry mRNA per well. FIGS. 6B and 6C show the mean fluorescence intensity of mCherry in HEK293 cells which contained nanoparticles formulations having a concentration of 62.5 ng/well of modified mCherry mRNA. FIGS. 6D and 6E show the mean fluorescence intensity of mCherry in HepG2 cells which contained nanoparticle formulations having a concentration of 62.5 ng/well of modified mCherry mRNA.

FIG. 7A shows the concentration in pg/ml of human erythropoietin after intramuscular administration. FIG. 7B shows the concentration in pg/ml of human erythropoietin after subcutaneous administration.

FIG. 8A is a histogram of bioluminescence (photon/sec) from the intramuscular injection of 5 ug in the left hind leg. FIG. 8B is a histogram of bioluminescence from the intramuscular injection of 50 ug in the right hind leg. FIG. 8C is a histogram showing in vivo screening results from biophotoic imaging after a subcutaneous injection of 50 ug. FIG. 8D is a histogram showing in vivo screening results from biophotoic imaging after an administration of 50 ug intravenously.

FIG. 11A shows the concentration in pg/ml of human G-CSF in serum after the administration of modified G-CSF intramuscularly. FIG. 11B shows the concentration in pg/ml of human G-CSF in serum after the administration of modified G-CSF subcutaneously.

Figure 1:
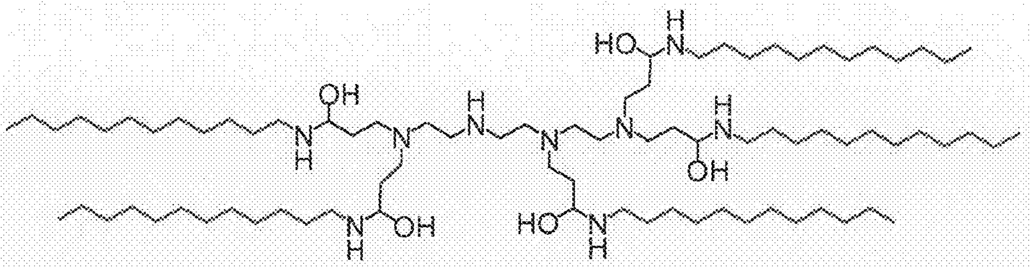
FIG. 1 illustrates lipid structures in the prior art useful in the present invention. Shown are the structures for 98N12-5 (TETA5-LAP), DLin-DMA, DLin-K-DMA (2,2-Dilinoleyl-4-dimethylaminomethyl-[1,3]-dioxolane), DLin-KC2-DMA, DLin-MC3-DMA and C12-200.
Figure 1:
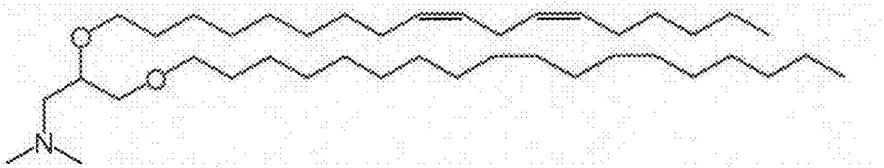
Figure 1:
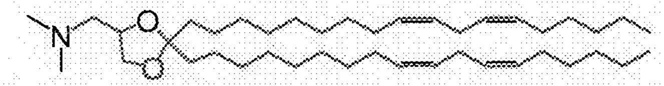
Figure 1:
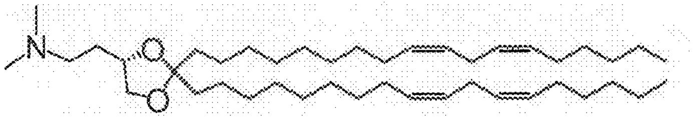
Figure 1:
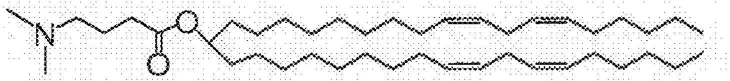
Figure 1:
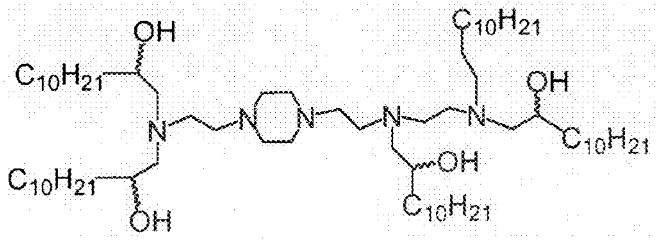

Unless defined otherwise, all technical and scientific terms used herein have the same meaning as those commonly understood to one of ordinary skill in the art to which this invention pertains.

DETAILED DESCRIPTION

Described herein are compositions and methods for the delivery of modified mRNA molecules in order to modulate protein expression.

As described herein and as in copending, co-owned applications International Application PCT/US2011/046861 filed Aug. 5, 2011 and PCT/US2011/054636 filed Oct. 3, 2011, the contents of which are incorporated by reference herein in their entirety, these modified nucleic acid molecules are capable of reducing the innate immune activity of a population of cells into which they are introduced, thus increasing the efficiency of protein production in that cell population.

Modified mRNAs (mmRNAs)

This invention provides nucleic acids, including RNAs, specifically mRNAs, that encode at least one polypeptide and contain one or more modified nucleosides (termed "modified nucleic acids" or "modified nucleic acid molecules" or "engineered nucleic acids"), which have useful properties including the lack of a substantial induction of the innate immune response of a cell into which the mRNA is introduced. Because these mmRNAs enhance the efficiency of protein production, intracellular retention of nucleic acids, and viability of contacted cells, as well as possess reduced immunogenicity, these nucleic acids having these properties are termed "enhanced" nucleic acids or modified RNAs herein.

The term "nucleic acid," in its broadest sense, includes any compound and/or substance that comprise a polymer of nucleotides linked via a phospohdiester bond. These polymers are often referred to as oligonucleotides.

Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc.

In preferred embodiments, the nucleic acid is one or more modified messenger RNAs (mmRNAs). As described herein, in some embodiments the mmRNAs of the invention do not substantially induce an innate immune response of a cell into which the mRNA is introduced.

The mmRNA of the present invention may encode one or more polypeptides. Generally the polypeptides of interest are those which are naturally occurring in the mammalian genome.

According to the present invention, the shortest length of a modified mRNA, herein "mmRNA," of the present disclosure can be the length of an mRNA sequence that may be sufficient to encode for a dipeptide. In another embodiment, the length of the mRNA sequence may be sufficient to encode for a tripeptide. In another embodiment, the length of an mRNA sequence may be sufficient to encode for a tetrapeptide. In another embodiment, the length of an mRNA sequence may be sufficient to encode for a pentapeptide. In another embodiment, the length of an mRNA sequence may be sufficient to encode for a hexapeptide. In another embodiment, the length of an mRNA sequence may be sufficient to encode for a heptapeptide. In another embodiment, the length of an mRNA sequence may be sufficient to encode for an octapeptide. In another embodiment, the length of an mRNA sequence may be sufficient to encode for a nonapeptide. In another embodiment, the length of an mRNA sequence may be sufficient to encode for a decapeptide.

Generally, the length of a modified mRNA of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the modified mRNA of the present invention includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

Polypeptide Variants

The mmRNA of the present invention may encode variant polypeptides, which have a certain identity with a reference polypeptide sequence, for example a wild type mRNA. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this invention.

For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a protein sequence to be utilized in accordance with the invention includes 2, 3, 4, 5, 6, 7, 8, 9, 10, or more mutations as shown in any of the sequences provided or referenced herein.

Targeting Moieties

In embodiments of the invention, mmRNAs are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides.

Cell Penetrating Peptides

The mmRNAs disclosed herein may encode a cell-penetrating polypeptide. As used herein, "cell-penetrating polypeptide" refers to a polypeptide which may facilitate the cellular uptake of molecules. It is known in the art that "CPP" refers to cell-penetration polypeptides and cell-penetrating peptides. When used herein, it will be clarified as to which of either cell-penetrating polypeptides or cell-penetrating peptides the abbreviation CPP refers to.

A cell-penetrating polypeptide of the present invention may contain one or more detectable labels. The polypeptides may be partially labeled or completely labeled throughout. The mmRNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

Fusion Proteins

The modified nucleic acids and mmRNA may encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

Synthesis of Modified mRNAs

Nucleic acids for use in accordance with the invention may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The modified nucleosides and nucleotides used in the synthesis of modified RNAs disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The manufacturing process herein can be monitored according to any suitable method known in the art. For example, product formation can be monitored by spectroscopic means, such as nuclear magnetic resonance spectroscopy (e.g., $_1H$ or $_{13}C$) infrared spectroscopy, spectrophotometry (e.g., UV-visible), or mass spectrometry, or by chromatography such as high performance liquid chromatography (HPLC) or thin layer chromatography.

Modification of mRNAs

Provided are mmRNAs containing a translatable region and one, two, or more than two different modifications.

In some embodiments, the chemical modifications can be located on the nucleobase of the nucleotide.

In some embodiments, the chemical modifications can be located on the sugar moiety of the nucleotide.

In some embodiments, the chemical modifications can be located on the phosphate backbone of the nucleotide.

Preparation of modified nucleosides and nucleotides used in the manufacture or synthesis of modified RNAs of the present invention can involve the protection and deprotection of various chemical groups. The need for protection and deprotection, and the selection of appropriate protecting groups can be readily determined by one skilled in the art.

The chemistry of protecting groups can be found, for example, in Greene, et al., *Protective Groups in Organic Synthesis,* 2d. Ed., Wiley & Sons, 1991, which is incorporated herein by reference in its entirety.

Modified nucleosides and nucleotides can be prepared according to the synthetic methods described in Ogata et al. *Journal of Organic Chemistry* 74:2585-2588, 2009; Purmal et al. *Nucleic Acids Research* 22(1): 72-78, 1994; Fukuhara et al. *Biochemistry* 1(4): 563-568, 1962; and Xu et al. *Tetrahedron* 48(9): 1729-1740, 1992, each of which are incorporated by reference in their entirety.

Modified mRNAs need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides.

For example, the mmRNAs may contain a modified pyrimidine such as uracil or cytosine. In some embodiments, at least 5%, at least 10%, at least 25%, at least 50%, at least 80%, at least 90% or 100% of the uracil in the nucleic acid may be replaced with a modified uracil. The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid may be replaced with a modified cytosine. The modified cytosine can be replaced by a compound having a single unique structure, or can be replaced by a plurality of compounds having different structures (e.g., 2, 3, 4 or more unique structures).

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-0-(1-Thiophosphate)-Adenosine, 5'-0-(1-Thiophosphate)-Cytidine, 5'-0-(1-Thiophosphate)-Guanosine, 5'-0-(1-Thiophosphate)-Uridine or 5'-0-(1-Thiophosphate)-Pseudouridine.

Further examples of modified nucleotides and modified nucleotide combinations are provided below in Table 1.

TABLE 1

| Modified Nucleotides | Modified Nucleotide Combinations |
|---|---|
| 6-aza-cytidine | α-thio-cytidine/5-iodo-uridine |
| 2-thio-cytidine | α-thio-cytidine/N1-methyl-pseudo-uridine |
| α-thio-cytidine | α-thio-cytidine/α-thio-uridine |
| Pseudo-iso-cytidine | α-thio-cytidine/5-methyl-uridine |
| 5-aminoallyl-uridine | α-thio-cytidine/pseudo-uridine |
| 5-iodo-uridine | Pseudo-iso-cytidine/5-iodo-uridine |
| N1-methyl-pseudouridine | Pseudo-iso-cytidine/N1-methyl-pseudo-uridine |
| 5,6-dihydrouridine | Pseudo-iso-cytidine/α-thio-uridine |
| α-thio-uridine | Pseudo-iso-cytidine/5-methyl-uridine |
| 4-thio-uridine | Pseudo-iso-cytidine/Pseudo-uridine |
| 6-aza-uridine | Pyrrolo-cytidine |
| 5-hydroxy-uridine | Pyrrolo-cytidine/5-iodo-uridine |
| Deoxy-thymidine | Pyrrolo-cytidine/N1-methyl-pseudo-uridine |
| Pseudo-uridine | Pyrrolo-cytidine/α-thio-uridine |
| Inosine | Pyrrolo-cytidine/5-methyl-uridine |
| α-thio-guanosine | Pyrrolo-cytidine/Pseudo-uridine |
| 8-oxo-guanosine | 5-methyl-cytidine/5-iodo-uridine |
| O6-methyl-guanosine | 5-methyl-cytidine/N1-methyl-pseudo-uridine |
| 7-deaza-guanosine | 5-methyl-cytidine/α-thio-uridine |
| No modification | 5-methyl-cytidine/5-methyl-uridine |
| N1-methyl-adenosine | 5-methyl-cytidine/Pseudo-uridine |
| 2-amino-6-Chloro-purine | 5-methyl-cytidine |
| N6-methyl-2-amino-purine | 25% Pseudo-iso-cytidine |
| 6-Chloro-purine | 25% N1-methyl-pseudo-uridine |
| N6-methyl-adenosine | 25% N1-Methyl-pseudo-uridine/75%-pseudo-uridine |
| α-thio-adenosine | 5-methyl-uridine |
| 8-azido-adenosine | 5-iodo-cytidine |
| 7-deaza-adenosine | |

In some embodiments, at least 25% of the cytosines are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines and 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Linkers and Payloads

The nucleobase of the nucleotide, which may be incorporated into a mmRNA, can be covalently linked at any chemically appropriate position to a payload, e.g. detectable agent or therapeutic agent. For example, the nucleobase can be deaza-adenosine or deaza-guanosine and the linker can be attached at the C-7 or C-8 positions of the deaza-adenosine or deaza-guanosine. In other embodiments, the nucleobase can be cytosine or uracil and the linker can be attached to the N-3 or C-5 positions of cytosine or uracil.

Linker

The term "linker" as used herein refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., detectable or therapeutic agent, at a second end. The linker may be of sufficient length as to not interfere with incorporation into a nucleic acid sequence.

Examples of chemical groups that can be incorporated into the linker include, but are not limited to, an alkyl, an alkene, an alkyne, an amido, an ether, a thioether or an ester group. The linker chain can also comprise part of a saturated, unsaturated or aromatic ring, including polycyclic and heteroaromatic rings wherein the heteroaromatic ring may be an aryl group containing one to four heteroatoms, N, 0 or S. Specific examples of linkers include, but are not limited to, unsaturated alkanes, polyethylene glycols, and dextran polymers.

For example, the linker can include, but is not limited to, ethylene or propylene glycol monomeric units, e.g., diethylene glycol, dipropylene glycol, triethylene glycol, tripropylene glycol, tetraethylene glycol, or tetraethylene glycol. In some embodiments, the linker can include, but is not limited to, a divalent alkyl, alkenyl, and/or alkynyl moiety. The linker can include an ester, amide, or ether moiety.

Other examples include, but are not limited to, cleavable moieties within the linker, such as, for example, a disulfide bond (—S—S—) or an azo bond (—N═N—), which can be cleaved using a reducing agent or photolysis. When a cleavable bond which has been incorporated into the linker and attached to a modified nucleotide, is cleaved, a short "scar" or chemical modification on the nucleotide may result. For example, after cleaving, the resulting scar on a nucleotide base, which formed part of the modified nucleotide, and is incorporated into a polynucleotide strand, is unreactive and does not need to be chemically neutralized. This increases the ease with which a subsequent nucleotide can be incorporated during sequencing of a nucleic acid polymer template. For example, conditions include the use of tris(2-carboxyethyl)phosphine (TCEP), dithiothreitol (DTT) and/or other reducing agents for cleavage of a disulfide bond. A selectively severable bond that includes an amido bond can be cleaved for example by the use of TCEP or other reducing agents, and/or photolysis. A selectively severable bond that includes an ester bond can be cleaved for example by acidic or basic hydrolysis.

Detectable Agents

The mmRNAs of the present invention may also be linked or conjugated to one or more detectable agents. Examples of detectable substances include, but are not limited to, various organic small molecules, inorganic compounds, nanoparticles, enzymes or enzyme substrates, fluorescent materials, luminescent materials, bioluminescent materials, chemiluminescent materials, radioactive materials, and contrast agents.

Labels, other than those described herein, are contemplated by the present disclosure, including, but not limited to, other optically-detectable labels. Labels can be attached to the modified nucleotide of the present disclosure at any position using standard chemistries such that the label can be removed from the incorporated base upon cleavage of the cleavable linker.

Terminal Architecture Modifications: 5'-Capping

Endogenous eukaryotic cellular messenger RNA (mRNA) molecules contain a 5'-cap structure on the 5'-end of a mature mRNA molecule. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group. The 5'-cap structure is responsible for binding the mRNA Cap Binding Protein (CBP), which is responsibility for mRNA stability in the cell and translation competency.

Multiple distinct 5'-cap structures can be used to generate the 5'-cap of a synthetic mRNA molecule. Many chemical cap analogs are used to co-transcriptionally cap a synthetic mRNA molecule. For example, the Anti-Reverse Cap Analog (ARCA) cap contains a 5'-5'-triphosphate guanine-guanine linkage where one guanine contains an N7 methyl group as well as a 3'-0-methyl group. While chemical cap analogs allow for the concomitant capping of an RNA molecule, up 20% of transcripts remain uncapped and the synthetic cap analog is not identical to an endogenous 5'-cap structure of an authentic cellular mRNA. This may lead to reduced translationally-competency and reduced cellular stability.

Synthetic mRNA molecules may also be capped post-transcriptionally using enzymes responsible for generating a more authentic 5'-cap structure. As used herein the phrase "more authentic" refers to a feature that closely mirrors or mimics, either structurally or functionally an endogenous or wild type feature. More authentic 5'cap structures of the present invention are those which, among other things, have enhanced binding of cap binding proteins, increased half life, reduced susceptibility to 5' endonucleases and/or reduced 5'decapping. For example, recombinant Vaccinia Virus Capping Enzyme and recombinant 2'-0-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-0-methyl generating the Cap1 structure. This results in a cap with higher translational-competency and cellular stability and reduced activation of cellular pro-inflammatory cytokines. Because the synthetic mRNA is caped post-transcriptionally, nearly 100% of the mRNA molecules are capped in contrast to 80% of synthetic mRNAs containing a chemical cap analog.

Terminal Architecture Modifications: Poly-A Tails

During RNA processing, a long chain of adenine nucleotides (poly-A tail) is normally added to a messenger RNA (mRNA) molecules to increase the stability of the molecule. Immediately after transcription, the 3' end of the transcript is cleaved to free a 3' hydroxyl. Then poly-A polymerase adds a chain of adenine nucleotides to the RNA. The process, called polyadenylation, adds a poly-A tail that is between 100 and 250 residues long.

It has been discovered that unique poly-A tail lengths provide certain advantages to the modified RNAs of the present invention.

Generally, the length of a poly-A tail of the present invention is greater than 30 nucleotides in length. In another embodiment, the poly-A tail is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides.

In one embodiment, the poly-A tail is designed relative to the length of the overall modified RNA molecule. This design may be based on the length of the coding region of the modified RNA, the length of a particular feature or region of the modified RNA (such as the mRNA), or based on the length of the ultimate product expressed from the modified RNA. In this context the poly-A tail may be 10, 20, 30, 40, 50, 60, 70, 80, 90 or 100% greater in length than the modified RNA or feature thereof. The poly-A tail may also be designed as a fraction of the modified RNA to which it belongs. In this context, the poly-A tail may be 10, 20, 30, 40, 50, 60, 70, 80, or 90% or more of the total length of the construct or the total length of the construct minus the poly-A tail.

Use of Modified mRNAs

The mmRNAs of the present invention may find uses in many areas of research, discovery, therapeutics, diagnostics and in kits and devices.

Therapeutics

The mmRNAs (modified RNAs) and the proteins translated from the mmRNAs described herein can be used as therapeutic agents. For example, an mmRNA described herein can be administered to a subject, wherein the mmRNA is translated in vivo to produce a therapeutic polypeptide in the subject. Provided are compositions, methods, kits, and reagents for treatment or prevention of disease or conditions in humans and other mammals. The active therapeutic agents of the invention include mmRNAs, cells containing mmRNAs or polypeptides translated from the mmRNAs, polypeptides translated from mmRNAs.

Provided herein are methods of inducing translation of a recombinant polypeptide in a cell population using the mmRNAs described herein. Such translation can be in vivo, ex vivo, in culture, or in vitro. The cell population is contacted with an effective amount of a composition containing a mmRNA that has at least one nucleoside modification, and a translatable region encoding the recombinant polypeptide. The population is contacted under conditions such that the mmRNA is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a mmRNA), or reduced innate immune response of the host cell.

Aspects of the invention are directed to methods of inducing in vivo translation of a recombinant polypeptide in a mammalian subject in need thereof. Therein, an effective amount of a composition containing a mmRNA that has at least one nucleoside modification and a translatable region encoding the recombinant polypeptide is administered to the subject using the delivery methods and split dosing regimens described herein. The mmRNA is provided in an amount and under other conditions such that the nucleic acid is localized into a cell of the subject and the recombinant polypeptide is translated in the cell from the mmRNA. The cell in which the mmRNA is localized, or the tissue in which the cell is present, may be targeted with one or more than one rounds of mmRNA administration.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered mmRNA directs production of one or more recombinant polypeptides that provide a functional activity which is substantially absent in the cell in which the recombinant polypeptide is translated. For example, the missing functional activity may be enzymatic, structural, or gene regulatory in nature. In related embodiments, the administered mmRNA directs production of one or more recombinant polypeptides that increases (e.g., synergistically) a functional activity which is present but substantially deficient in the cell in which the recombinant polypeptide is translated.

In other embodiments, the administered mmRNA directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject; for example, do to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity.

The polypeptides encoded by the mmRNA described herein are engineered for localization within the cell, potentially within a specific compartment such as the nucleus, or are engineered for secretion from the cell or translocation to the plasma membrane of the cell.

In one embodiment of the invention are bifunctional mmRNA. As the name implies, bifunctional mmRNA are those having or capable of at least two functions.

The multiple functionalities of bifunctional_mmRNAs may be encoded by the mRNA (the function may not manifest until the encoded product is translated) or may be a property of the RNA itself. It may be structural or chemical. Bifunctional modified RNAs may comprise a function that is covalently associated with the RNA or electrostatically associated.

In some embodiments, modified mRNAs and their encoded polypeptides in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Avoidance of the Innate Immune Response

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell, the invention provides modified mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unmodified nucleic acid. Such a reduction can be measured by expression or activity level of Type 1 interferons or the expression of interferon-regulated genes such as the toll-like receptors (e.g., TLR7 and TLR8). Reduction of innate immune response can also be measured by decreased cell death following one or more administrations of modified RNAs to a cell population; e.g., cell death is 10%, 25%, 50%, 75%, 85%, 90%, 95%, or over 95% less than the cell death frequency observed with a corresponding unmodified nucleic acid. Moreover, cell death may affect fewer than 50%, 40%, 30%, 20%, 10%, 5%, 1%, 0.1%, 0.01% or fewer than 0.01% of cells contacted with the mmRNAs.

The invention provides therapeutic methods for the repeated introduction (e.g., transfection) of mmRNAs into a target cell population, e.g., in vitro, ex vivo, or in vivo. The step of contacting the cell population may be repeated one or more times (such as two, three, four, five or more than five times). In some embodiments, the step of contacting the cell population with the mmRNAs is repeated a number of times sufficient such that a predetermined efficiency of protein translation in the cell population is achieved. Given the reduced cytotoxicity of the target cell population provided by the nucleic acid modifications, such repeated transfections are achievable in a diverse array of cell types.

Protein Production

The methods provided herein are useful for enhancing protein product yield in a cell culture process. In a cell culture containing a plurality of host cells, introduction of the modified mRNAs described herein results in increased protein production efficiency relative to a corresponding unmodified nucleic acid. Such increased protein production efficiency can be demonstrated, e.g., by showing increased cell transfection, increased protein translation from the nucleic acid, decreased nucleic acid degradation, and/or reduced innate immune response of the host cell. Protein production can be measured by ELISA, and protein activity can be measured by various functional assays known in the art. The protein production may be generated in a continuous or a fed-batch mammalian process.

Additionally, it is useful to optimize the expression of a specific polypeptide in a cell line or collection of cell lines of potential interest, particularly an engineered protein such as a protein variant of a reference protein having a known activity. In one embodiment, provided is a method of optimizing expression of an engineered protein in a target cell, by providing a plurality of target cell types, and independently contacting with each of the plurality of target cell types a modified mRNA encoding an engineered polypeptide. Additionally, culture conditions may be altered to increase protein production efficiency. Subsequently, the presence and/or level of the engineered polypeptide in the plurality of target cell types is detected and/or quantitated, allowing for the optimization of an engineered polypeptide's expression by selection of an efficient target cell and cell culture conditions relating thereto. Such methods are particularly useful when the engineered polypeptide contains one or more post-translational modifications or has substantial tertiary structure, situations which often complicate efficient protein production.

Gene Silencing

The modified mRNAs described herein are useful to silence (i.e., prevent or substantially reduce) expression of one or more target genes in a cell population. A modified mRNA encoding a polypeptide capable of directing sequence-specific histone H3 methylation is introduced into the cells in the population under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Co-administration of modified mRNAs and siRNAs are also provided herein. As demonstrated in yeast, sequence-specific trans silencing is an effective mechanism for altering cell function. Fission yeast require two RNAi complexes for siRNA-mediated heterochromatin assembly: the RNA-induced transcriptional silencing (RITS) complex and the RNA-directed RNA polymerase complex (RDRC) (Motamedi et al. Cell 2004, 119, 789-802). In fission yeast, the RITS complex contains the siRNA binding Argonaute family protein Ago1, a chromodomain protein Chp1, and Tas3. The fission yeast RDRC complex is composed of an RNA-dependent RNA Polymerase Rdp1, a putative RNA helicase Hrr1, and a polyA polymerase family protein Cid12. These two complexes require the Dicer ribonuclease and Clr4 histone H3 methyltransferase for activity. Together, Ago1 binds siRNA molecules generated through Dicer-mediated cleavage of Rdp1 co-transcriptionally generated dsRNA transcripts and allows for the sequence-specific direct association of Chp1, Tas3, Hrr1, and Clr4 to regions of DNA destined for methylation and histone modification and subsequent compaction into transcriptionally silenced heterochromatic. While this mechanism functions in cis- with centromeric regions of DNA, sequence-specific trans silencing is possible through co-transfection with double-stranded siRNAs for specific regions of DNA and concomitant RNAi-directed silencing of the siRNA ribonuclease Eril (Buhler et al. Cell 2006, 125, 873-886).

Modulation of Biological Pathways

The rapid translation of modified mRNAs introduced into cells provides a desirable mechanism of modulating target biological pathways. Such modulation includes antagonism or agonism of a given pathway. In one embodiment, a method is provided for antagonizing a biological pathway in a cell by contacting the cell with an effective amount of a composition comprising a modified nucleic acid encoding a recombinant polypeptide, under conditions such that the nucleic acid is localized into the cell and the recombinant polypeptide is capable of being translated in the cell from the nucleic acid, wherein the recombinant polypeptide inhibits the activity of a polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5).

Further, provided are modified nucleic acids encoding an antagonist for chemokine receptors; chemokine receptors CXCR-4 and CCR-5 are required for, e.g., HIV entry into host cells (et al, (1996) October 3; 383(6599):400).

Alternatively, provided are methods of agonizing a biological pathway in a cell by contacting the cell with an effective amount of a modified nucleic acid encoding a recombinant polypeptide under conditions such that the nucleic acid is localized into the cell and the recombinant polypeptide is capable of being translated in the cell from the nucleic acid, and the recombinant polypeptide induces the activity of a polypeptide functional in the biological pathway. Exemplary agonized biological pathways include pathways that modulate cell fate determination. Such agonization is reversible or, alternatively, irreversible.

Cellular Nucleic Acid Delivery

Methods of the present invention enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. The retention of the enhanced nucleic acid is greater than the retention of the unmodified nucleic acid. In some embodiments, it is at least about 50%, 75%, 90%, 95%, 100%, 150%, 200% or more than 200% greater than the retention of the unmodified nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be modified nucleic acids or unmodified nucleic acids. It is understood that the initial presence of the enhanced nucleic acids does not substantially induce an innate immune response of the cell population and, moreover, that the innate immune response will not be activated by the later presence of the unmodified nucleic acids. In this regard, the enhanced nucleic acid may not itself contain a translatable region, if the protein desired to be present in the target cell population is translated from the unmodified nucleic acids.

Expression of Ligand or Receptor on Cell Surface

In some aspects and embodiments of the aspects described herein, the modified RNAs can be used to express a ligand or ligand receptor on the surface of a cell (e.g., a homing moiety). A ligand or ligand receptor moiety attached to a cell surface can permit the cell to have a desired biological interaction with a tissue or an agent in vivo. A ligand can be an antibody, an antibody fragment, an aptamer, a peptide, a vitamin, a carbohydrate, a protein or polypeptide, a receptor, e.g., cell-surface receptor, an adhesion molecule, a glycoprotein, a sugar residue, a therapeutic agent, a drug, a glycosaminoglycan, or any combination thereof. For example, a ligand can be an antibody that recognizes a cancer-cell specific antigen, rendering the cell capable of preferentially interacting with tumor cells to permit tumor-specific localization of a modified cell. A ligand can confer the ability of a cell composition to accumulate in a tissue to be treated, since a preferred ligand may be capable of interacting with a target molecule on the external face of a tissue to be treated. Ligands having limited cross-reactivity to other tissues are generally preferred.

In some cases, a ligand can act as a homing moiety which permits the cell to target to a specific tissue or interact with a specific ligand. Such homing moieties can include, but are not limited to, any member of a specific binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((SCFV)2 fragments), diabodies, tribodies or tetrabodies, which typically are covalently linked or otherwise stabilized (i.e., leucine zipper or helix stabilized) scFv fragments; and other homing moieties include for example, aptamers, receptors, and fusion proteins.

In some embodiments, the homing moiety may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of homing interactions.

A skilled artisan can select any homing moiety based on the desired localization or function of the cell, for example an estrogen receptor ligand, such as tamoxifen, can target cells to estrogen-dependent breast cancer cells that have an increased number of estrogen receptors on the cell surface. Other non-limiting examples of ligand/receptor interactions include CCRI (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), VLA-4NCAM-1 (e.g., targeting to endothelium). In general, any receptor involved in targeting (e.g., cancer metastasis) can be harnessed for use in the methods and compositions described herein.

Mediators of Cell Death

In one embodiment, a modified nucleic acid molecule composition can be used to induce apoptosis in a cell (e.g., a cancer cell) by increasing the expression of a death receptor, a death receptor ligand or a combination thereof. This method can be used to induce cell death in any desired cell and has particular usefulness in the treatment of cancer where cells escape natural apoptotic signals.

Apoptosis can be induced by multiple independent signaling pathways that converge upon a final effector mechanism consisting of multiple interactions between several "death receptors" and their ligands, which belong to the tumor necrosis factor (TNF) receptor/ligand superfamily. The best-characterized death receptors are CD95 ("Fas"), TNFRI (p55), death receptor 3 (DR3 or Apo3/TRAMO), DR4 and DRS (apo2-TRAIL-R2). The final effector mechanism of apoptosis may be the activation of a series of proteinases designated as caspases. The activation of these caspases results in the cleavage of a series of vital cellular proteins and cell death. The molecular mechanism of death receptors/ligands-induced apoptosis is well known in the art. For example, Fas/FasL-mediated apoptosis is induced by binding of three FasL molecules which induces trimerization of Fas receptor via C-terminus death domains (DDs), which in turn recruits an adapter protein FADD (Pas-associated protein with death domain) and Caspase-8. The oligomerization of this trimolecular complex, Fas/FAIDD/caspase-8, results in proteolytic cleavage of proenzyme caspase-8 into active caspase-8 that, in turn, initiates the apoptosis process by activating other downstream caspases through proteolysis, including caspase-3. Death ligands in general are apoptotic when formed into trimers or higher order of structures. As monomers, they may serve as antiapoptotic agents by competing with the trimers for binding to the death receptors.

In one embodiment, the modified nucleic acid molecule composition encodes for a death receptor (e.g., Fas, TRAIL, TRAMO, TNFR, TLR, etc.). Cells made to express a death receptor by transfection of modified RNA become susceptible to death induced by the ligand that activates that receptor. Similarly, cells made to express a death ligand, e.g., on their surface, will induce death of cells with the receptor when the transfected cell contacts the target cell. In another embodiment, the modified RNA composition encodes for a death receptor ligand (e.g., FasL, TNF, etc.). In another embodiment, the modified RNA composition encodes a caspase (e.g., caspase 3, caspase 8, caspase 9 etc.). Where cancer cells often exhibit a failure to properly differentiate to a non-proliferative or controlled proliferative form, in another embodiment, the synthetic, modified RNA composition encodes for both a death receptor and its appropriate activating ligand. In another embodiment, the synthetic, modified RNA composition encodes for a differentiation factor that when expressed in the cancer cell, such as a cancer stem cell, will induce the cell to differentiate to a non-pathogenic or nonself-renewing phenotype (e.g., reduced cell growth rate, reduced cell division etc.) or to induce the cell to enter a dormant cell phase (e.g., $G_0$ resting phase).

One of skill in the art will appreciate that the use of apoptosis-inducing techniques may require that the modified nucleic acid molecules are appropriately targeted to e.g., tumor cells to prevent unwanted wide-spread cell death. Thus, one can use a delivery mechanism (e.g., attached ligand or antibody, targeted liposome, etc.) that recognizes a cancer antigen such that the modified nucleic acid molecules are expressed only in cancer cells.

Formulations of Modified mRNAs

Provided herein are formulations containing an effective amount of an mmRNA.

In certain embodiments, the formulations include one or more cell penetration agents, e.g., transfection agents. In one specific embodiment, an mmRNA is mixed or admixed with a transfection agent (or mixture thereof) and the resulting mixture is employed to transfect cells. Preferred transfection agents are cationic lipid compositions, particularly monovalent and polyvalent cationic lipid compositions, more particularly LIPOFECTIN®, LIPOFECTACE®, LIPOFECTAMINE™, CELLFECTIN®, DMRIE-C, DMRIE, DOTAP, DOSPA, and DOSPER, and dendrimer compositions, particularly G5-G10 dendrimers, including dense star dendrimers, PAMAM dendrimers, grafted dendrimers, and dendrimers known as dendrigrafts and SUPERFECT®.

In a second specific transfection method, a ribonucleic acid is conjugated to a nucleic acid-binding group, for example a polyamine and more particularly a spermine, which is then introduced into the cell or admixed with a transfection agent (or mixture thereof) and the resulting mixture is employed to transfect cells. In a third specific embodiment, a mixture of one or more transfection-enhancing peptides, proteins, or protein fragments, including fusagenic peptides or proteins, transport or trafficking peptides or proteins, receptor-ligand peptides or proteins, or nuclear localization peptides or proteins and/or their modified analogs (e.g., spermine modified peptides or proteins) or combinations thereof are mixed with and complexed with a ribonucleic acid to be introduced into a cell, optionally being admixed with transfection agent and the resulting mixture is employed to transfect cells. Further, a component of a transfection agent (e.g., lipids, cationic lipids or dendrimers) is covalently conjugated to selected peptides, proteins, or protein fragments directly or via a linking or spacer group. Of particular interest in this embodiment are peptides or proteins that are fusagenic, membrane-permeabilizing, transport or trafficking, or which function for cell-targeting. The peptide- or protein-transfection agent complex is combined with a ribonucleic acid and employed for transfection.

In certain embodiments, the formulations include a pharmaceutically acceptable carrier that causes the effective amount of mmRNA to be substantially retained in a target tissue containing the cell.

In certain embodiments, the formulation may include at least an mmRNA and a delivery agent. In some embodiments, the delivery agent may comprise lipidoid-based formulations allowed for localized and systemic delivery of mmRNA.

Also provided are compositions for generation of an in vivo depot containing an engineered ribonucleotide. For example, the composition contains a bioerodible, biocompatible polymer, a solvent present in an amount effective to plasticize the polymer and form a gel therewith, and an engineered ribonucleic acid. In certain embodiments the composition also includes a cell penetration agent as described herein. In other embodiments, the composition also contains a thixotropic amount of a thixotropic agent mixable with the polymer so as to be effective to form a thixotropic composition. Further compositions include a stabilizing agent, a bulking agent, a chelating agent, or a buffering agent.

In other embodiments, provided are sustained-release delivery depots, such as for administration of a mmRNA to an environment (meaning an organ or tissue site) in a patient. Such depots generally contain a mmRNA and a flexible chain polymer where both the mmRNA and the flexible chain polymer are entrapped within a porous matrix of a crosslinked matrix protein. Usually, the pore size is less than 1 mm, such as 900 nm, 800 nm, 700 nm, 600 nm, 500 nm, 400 nm, 300 nm, 200 nm, 100 nm, or less than 100 nm. Usually the flexible chain polymer is hydrophilic. Usually the flexible chain polymer has a molecular weight of at least 50 kDa, such as 75 kDa, 100 kDa, 150 kDa, 200 kDa, 250 kDa, 300 kDa, 400 kDa, 500 kDa, or greater than 500 kDa. Usually the flexible chain polymer has a persistence length of less than 10%, such as 9, 8, 7, 6, 5, 4, 3, 2, 1 or less than 1% of the persistence length of the matrix protein. Usually the flexible chain polymer has a charge similar to that of the matrix protein. In some embodiments, the flexible chain polymer alters the effective pore size of a matrix of cross-linked matrix protein to a size capable of sustaining the diffusion of the mmRNA from the matrix into a surrounding tissue comprising a cell into which the mmRNA is capable of entering.

Formulation Using Lipidoids

The pharmaceutical compositions described herein include lipidoid-based formulations allowing for localized and systemic delivery of mmRNA. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein by reference in their entireties).

According to the present invention, complexes, micelles, liposomes or particles can be prepared containing these lipidoids and therefore, result in an effective delivery of mmRNA, as judged by the production of an encoded protein, following the injection of an mmRNA-formulated lipidoids via localized and systemic routes of administration. Modified mRNA-lipidoid complexes can be administered by various means disclosed herein.

The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879 herein incorporated by reference), use of lipidoid oligonucleotides to deliver the formulation to other cells types including, but not limited to, endothelial cells, myeloid cells, and muscle cells may not be similarly size-limited.

In one aspect, effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the mmRNA molecule for delivery to different cell types including, but not limited to, hepatocytes, myeloid cells, muscle cells, etc. For example, the component molar ratio may include, but is not limited to, 50% lipid, 10% disteroylphosphatidyl choline, 38.5% cholesterol, and %1.5 PEG. The lipid may be selected from, but is not limited to, DLin-DMA, DLin-K-DMA, DLin-KC2-DMA, 98N12-5, C12-200 (including variants and derivatives), DLin-MC3-DMA and analogs thereof. The use of lipidoid formulations for the localized delivery of nucleic acids to cells (such as, but not limited to, adipose cells and muscle cells) via either subcutaneous or intramuscular delivery, may also not require all of the formulation components which may be required for systemic delivery, and as such may comprise the lipidoid and the mmRNA.

In a further embodiment, combinations of different lipidoids may be used to improve the efficacy of mmRNA-directed protein.

According to the present invention, modified mRNA may be formulated by mixing the mmRNA with the lipidoid at a set ratio prior to addition to cells. In vivo formulations may require the addition of extra ingredients to facilitate circulation throughout the body. To test the ability of these lipidoids to form particles suitable for in vivo work, a standard formulation process used for siRNA-lipidoid formulations may be used as a starting point. Initial mmRNA-lipidoid formulations consist of particles composed of 42% lipidoid, 48% cholesterol and 10% PEG, with further optimization of ratios possible. After formation of the particle, mmRNA is added and allowed to integrate with the complex. The encapsulation efficiency is determined using a standard dye exclusion assays.

In vivo delivery of nucleic acids may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-SLAP; aka 98N12-5, see Murugaiah et al., Analytical Biochemistry, 401:61 (2010)), C12-200 (including derivatives and variants), MD1, DLin-DMA, DLin-K-DMA, DLin-KC2-DMA and DLin-MC3-DMA (see FIG. 1), can be tested for in vivo activity.

The lipidoid referred to herein as "98N12-5" is disclosed by Akinc et al., Mol Ther. 2009 17:872-879 and is incorporated by reference in its entirety. (See FIG. 1)

The lipidoid referred to herein as "C12-200" is disclosed by Love et al., Proc Natl Acad Sci USA. 2010 107:1864-1869 (see FIG. 1) and Liu and Huang, Molecular Therapy. 2010 669-670 (see FIG. 1); both of which are herein incorporated by reference in their entirety. The lipidoid formulations can include particles comprising either 3 or 4 or more components in addition to polynucleotide, primary construct, or mmRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

The ratio of mmRNA to lipidoid used to test for in vitro transfection is tested empirically at different lipidoid:mmRNA ratios. Previous work using siRNA and lipidoids have utilized 2.5:1, 5:1, 10:1, and 15:1 lipidoid:siRNA wt:wt ratios. Given the longer length of mmRNA relative to siRNA, a lower wt:wt ratio of lipidoid to mmRNA is likely to be effective. In addition, for comparison mmRNA are also formulated using RNAiMax (Invitrogen, Carlsbad, Calif.) or TRANSIT-mRNA (Mirus Bio, Madison Wis.) cationic lipid delivery vehicles.

The ability of lipidoid-formulated mmRNA to express the desired protein product can be confirmed by luminescence for luciferase expression, flow cytometry for expression, and by ELISA for secretion.

The expression of mmRNA-encoded proteins can be assessed both within the muscle or subcutaneous tissue and systemically in blood and other organs and fluids such as the liver and spleen, urine, saliva, etc.

For example, single dose studies allow an assessment of the magnitude, dose responsiveness, and longevity of expression of the desired product. After formulation of mmRNA with the lipidoid formulations, as described previously, animals are divided into groups receiving either a saline formulation, or a lipidoid-formulation containing one of several different mmRNA. Prior to injection, mmRNA-containing lipidoid formulations are diluted in PBS and animals administered a single intramuscular dose of formulated mmRNA ranging from 50 mg/kg to doses as low as 1 ng/kg with a preferred range to be 10 mg/kg to 100 ng/kg. If the animal tested is a mouse the maximum dose can be roughly 1 mg mmRNA or as low as 0.02 ng mmRNA if administered once into the hind limb. Likewise for subcutaneous administration, mmRNA-containing lipidoid formulations are diluted in PBS before the animals are administered a single subcutaneous dose of formulated mmRNA ranging from 400 mg/kg-to doses as low as 1 ng/kg. A preferred dosage range comprises 80 mg/kg to 100 ng/kg. If the animal tested is a mouse, the maximum dose administered can be roughly 8 mg mmRNA or as low as 0.02 ng mmRNA if the dose is administered once subcutaneously.

It is preferred that the volume of a single intramuscular injection is maximally 0.025 ml and of a single subcutaneous injection is maximally 0.2 ml for a 20 gram mouse. The dose of the mmRNA administered to the animal is calculated depending on the body weight of the animal. At various points in time points following the administration of the mmRNA-lipidoid, serum, tissues, and tissue lysates can be obtained and the level of the mmRNA-encoded product determined. The ability of lipidoid-formulated mmRNA to express the desired protein product can be confirmed by luminescence for luciferase expression, flow cytometry, and by ELISA.

Additional studies for a multi-dose regimen can also be performed to determine the maximal expression using mmRNA, to evaluate the saturability of the mmRNA-driven expression (achieved by giving a control and active mmRNA formulation in parallel or in sequence), and to determine the feasibility of repeat drug administration (by giving mmRNA in doses separated by weeks or months and then determining whether expression level is affected by factors such as immunogenicity).

Administration

The present invention provides methods comprising administering modified mRNAs and or complexes in accordance with the invention to a subject in need thereof. mmRNA or complexes, or pharmaceutical, imaging, diagnostic, or prophylactic compositions thereof, may be administered to a subject using any amount and any route of administration which may be effective for preventing, treating, diagnosing, or imaging a disease, disorder, and/or condition (e.g., a disease, disorder, and/or condition relating to working memory deficits). The exact amount required will vary from subject to subject, depending on factors such as, but not limited to, the species, age, and general condition of the subject, the severity of the disease, the particular composition, its mode of administration, its mode of activity, and the like.

mmRNA to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, pharmaceutical, prophylactic, diagnostic, or imaging compositions thereof are administered to humans.

mmRNA may be administered by any route. In some embodiments, mmRNA are administered by one or more of a variety of routes, including, but not limited to, local, oral, intravenous, intramuscular, intra-arterial, intramedullary, intrathecal, subcutaneous, intraventricular, transdermal, interdermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter.

In some embodiments, mmRNA are administered by systemic intravenous injection. In specific embodiments, mmRNA may be administered intravenously and/or orally. In specific embodiments, mmRNA may be administered in a way which allows the mmRNA to cross the blood-brain barrier, vascular barrier, or other epithelial barrier.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Dosage forms for local, topical and/or transdermal administration of a composition may include ointments, pastes, creams, lotions, gels, powders, solutions, sprays, inhalants and/or patches. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

In general the most appropriate route of administration will depend upon a variety of factors including the nature of the mmRNA to be delivered (e.g., its stability in the environment of the gastrointestinal tract, bloodstream, etc.), the condition of the patient (e.g., whether the patient is able to tolerate particular routes of administration), etc. The invention encompasses the delivery of the mmRNA by any appropriate route taking into consideration likely advances in the sciences of drug delivery.

In certain embodiments, compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administration is employed, split dosing regimens such as those described herein may be used.

According to the present invention, it has been discovered that administration of mmRNA in split-dose regimens produce higher levels of proteins in mammalian subjects. As used herein, a "split dose" is the division of single unit dose or total daily dose into two or more doses. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the mmRNA of the present invention are administered to a subject in split doses. The mmRNA may be formulated in buffer only or in a formulation described herein.

Modified nucleic acid molecules or complexes may be used or administered in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens described herein.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the invention may be administered concurrently with a chemotherapeutic agent), or they may achieve different effects (e.g., control of any adverse effects).

Compositions containing mmRNAs are formulated for administration intramuscularly, transarterially, intraocularly, vaginally, rectally, intraperitoneally, intravenously, intranasally, subcutaneously, endoscopically, transdermally, intramuscularly, intraventricularly, intradermally, intrathecally, topically (e.g. by powders, ointments, creams, gels, lotions, and/or drops), mucosally, nasal, enterally, intratumorally, by intratracheal instillation, bronchial instillation, and/or inhalation; nasal spray and/or aerosol, and/or through a portal vein catheter.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like. In some embodiments, the composition is formulated for extended release. In specific embodiments, mmRNA molecules or complexes, and/or pharmaceutical, prophylactic, diagnostic, or imaging compositions thereof, may be administered in a way which allows the mmRNA molecules or complex to cross the blood-brain barrier, vascular barrier, or other epithelial barrier.

In some aspects of the invention, the nucleic acids (particularly ribonucleic acids encoding polypeptides) are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a ribonucleic acid engineered to avoid an innate immune response of a cell into which the ribonucleic acid enters, where the ribonucleic acid contains a nucleotide sequence encoding a polypeptide of interest, under conditions such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains a ribonucleic acid that is engineered to avoid an innate immune response of a cell into which the ribonucleic acid enters and encodes the polypeptide of interest and the composition is characterized in that a unit quantity of composition has been determined to produce the polypeptide of interest in a substantial percentage of cells contained within a predetermined volume of the target tissue. In some embodiments, the composition includes a plurality of different ribonucleic acids, where one or more than one of the ribonucleic acids is engineered to avoid an innate immune response of a cell into which the ribonucleic acid enters, and where one or more than one of the ribonucleic acids encodes a polypeptide of interest. Optionally, the composition also contains a cell penetration agent to assist in the intracellular delivery of the ribonucleic acid. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

Formulations which may be administered intramuscularly and/or subcutaneously may include, but are not limited to, polymers, copolymers, and gels. The polymers, copolymers and/or gels may further be adjusted to modify release kinetics by adjusting factors such as, but not limited to, molecular weight, particle size, payload and/or ratio of the monomers. As a non-limiting example, formulations administered intramuscularly and/or subcutaneously may include a copolymer such as poly(lactic-co-glycolic acid).

Localized delivery of the compositions described herein may be administered by methods such as, but not limited to, topical delivery, ocular delivery, transdermal delivery, and the like. The composition may also be administered locally to a part of the body not normally available for localized delivery such as, but not limited to, when a subject's body is open to the environment during treatment. The composition may further be delivered by bathing, soaking and/or surrounding the body part with the composition.

However, the present disclosure encompasses the delivery of mmRNA molecules or complexes, and/or pharmaceutical, prophylactic, diagnostic, or imaging compositions thereof, by any appropriate route taking into consideration likely advances in the sciences of drug delivery.

The level or concentration of a mmRNA may be characterized using exosomes. A level or concentration of the mmRNA in exosomes can represent an expression level, presence, absence, truncation or alteration of the mmRNA. The level or concentration may be determined by a method such as, but not limited to, an assay using construct specific probes, cytometry, qRT-PCR, realtime PCR, PCR, flow cytometry, electrophoresis, mass spectrometry, or combinations thereof. Further, the level or concentration may be associated with a clinical phenotype. For analysis, the exosome may be isolated by a method such as, but not limited to, immunohistochemcial methods such as enzyme linked immunosorbent assay (ELISA) methods, size exclusion chromatography, density gradient centrifugation, differential centrifugation, nanomembrane ultrafiltration, immunoabsorbent capture, affinity purification, microfluidic separation, or combinations thereof.

Pharmaceutical Compositions

When administered to a subject the pharmaceutical compositions described herein may provide proteins which have been generated from modified mRNAs. Pharmaceutical compositions may optionally comprise one or more additional therapeutically active substances. In accordance with some embodiments, a method of administering pharmaceutical compositions comprising one or more proteins to be delivered to a subject in need thereof is provided. In some embodiments, compositions are administered to human subjects. In a further embodiment, the compositions are administered to a subject who is a patient.

Pharmaceutical compositions may optionally comprise one or more additional therapeutically active substances.

In some embodiments, compositions are administered to humans. For the purposes of the present disclosure, the phrase "active ingredient" generally refers to a mmRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21st Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use.

In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate

[MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyllaurate, sodium lauryl sulfate, PLURONIC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUMe), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

General considerations in the formulation and/or manufacture of pharmaceutical agents may be found, for example, in *Remington: The Science and Practice of Pharmacy* 21st ed., Lippincott Williams & Wilkins, 2005 (incorporated herein by reference).

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient. Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65 op at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein.

A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Properties of the Pharmaceutical Compositions

The pharmaceutical compositions described herein can be characterized by one or more of the following properties:

Bioavailability

The mmRNA molecules, when formulated into a composition with a delivery agent as described herein, can exhibit an increase in bioavailability as compared to a composition lacking a delivery agent as described herein. As used herein, the term "bioavailability" refers to the systemic availability of a given amount of a mmRNA molecule administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modem Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first mmRNA molecule, measured as AUC, $C_{max}$, or $C_{min}$ in a mammal is greater, when co-administered with a delivery agent as described herein, than when such co-administration does not take place. In some embodiments, the bioavailability of the mmRNA molecule can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

The mmRNA molecules, when formulated into a composition as described herein, can exhibit an increase in the therapeutic window of the administered mmRNA molecule composition as compared to the therapeutic window of the administered mmRNA molecule composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the mmRNA molecule when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

The mmRNA molecules, when formulated into a composition as described herein, can exhibit an improved volume of distribution ($V_{dist}$). The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: ($V_{dist}$) equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, ($V_{dist}$) can be used to determine a loading dose to achieve a steady state concentration. In some embodiments, the volume of distribution of the mmRNA molecule when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Devices and Methods for Multi-Administration

Methods and devices for multi-administration may be employed to deliver the mmRNA of the present invention according to the split dosing regimens taught herein. Such methods and devices are described below.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices may be utilized to deliver the split doses contemplated herein.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

A method for delivering therapeutic agents to a solid tissue has been described by Bahrami et al and is taught for example in US Patent Publication 20110230839, the contents of which are incorporated herein by reference in their entirety. According to Bahrami, an array of needles is incorporated into a device which delivers a substantially equal amount of fluid at any location in said solid tissue along each needle's length.

A device for delivery of biological material across the biological tissue has been described by Kodgule et al and is taught for example in US Patent Publication 20110172610, the contents of which are incorporated herein by reference in their entirety. According to Kodgule, multiple hollow micro-needles made of one or more metals and having outer diameters from about 200 microns to about 350 microns and lengths of at least 100 microns are incorporated into the device which delivers peptides, proteins, carbohydrates, nucleic acid molecules, lipids and other pharmaceutically active ingredients or combinations thereof.

A delivery probe for delivering a therapeutic agent to a tissue has been described by Gunday et al and is taught for example in US Patent Publication 20110270184, the contents of which are incorporated herein by reference in their entirety. According to Gunday, multiple needles are incorporated into the device which moves the attached capsules between an activated position and an inactivated position to force the agent out of the capsules through the needles.

A multiple-injection medical apparatus has been described by Assaf and is taught for example in US Patent Publication 20110218497, the contents of which are incorporated herein by reference in their entirety. According to Assaf, multiple needles are incorporated into the device which has a chamber connected to one or more of said needles and a means for continuously refilling the chamber with the medical fluid after each injection.

An at least partially implantable system for injecting a substance into a patient's body, in particular a penis erection stimulation system has been described by Forsell and is taught for example in US Patent Publication 20110196198, the contents of which are incorporated herein by reference in their entirety. According to Forsell, multiple needles are incorporated into the device which is implanted along with one or more housings adjacent the patient's left and right corpora cavernosa. A reservoir and a pump are also implanted to supply drugs through the needles.

A method for the transdermal delivery of a therapeutic effective amount of iron has been described by Berenson and is taught for example in US Patent Publication 20100130910, the contents of which are incorporated herein by reference in their entirety. According to Berenson, multiple needles may be used to create multiple micro channels in stratum corneum to enhance transdermal delivery of the ionic iron on an iontophoretic patch.

A method for delivery of biological material across the biological tissue has been described by Kodgule et al and is taught for example in US Patent Publication 20110196308, the contents of which are incorporated herein by reference in their entirety. According to Kodgule, multiple biodegradable microneedles containing a therapeutic active ingredient are incorporated in a device which delivers proteins, carbohydrates, nucleic acid molecules, lipids and other pharmaceutically active ingredients or combinations thereof.

A transdermal patch comprising a botulinum toxin composition has been described by Donovan and is taught for example in US Patent Publication 20080220020, the contents of which are incorporated herein by reference in their entirety. According to Donovan, multiple needles are incorporated into the patch which delivers botulinum toxin under stratum corneum through said needles which project through the stratum corneum of the skin without rupturing a blood vessel.

A cryoprobe for administration of an active agent to a location of cryogenic treatment has been described by Toubia and is taught for example in US Patent Publication 20080140061, the contents of which are incorporated herein by reference in their entirety. According to Toubia, multiple needles are incorporated into the probe which receives the active agent into a chamber and administers the agent to the tissue.

A method for treating or preventing inflammation or promoting healthy joints has been described by Stock et al and is taught for example in US Patent Publication 20090155186, the contents of which are incorporated herein by reference in their entirety. According to Stock, multiple needles are incorporated in a device which administers compositions containing signal transduction modulator compounds.

A multi-site injection system has been described by Kimmell et al and is taught for example in US Patent Publication 20100256594, the contents of which are incorporated herein by reference in their entirety. According to Kimmell, multiple needles are incorporated into a device which delivers a medication into a stratum corneum through the needles.

A method for delivering interferons to the intradermal compartment has been described by Dekker et al and is taught for example in US Patent Publication 20050181033, the contents of which are incorporated herein by reference in their entirety. According to Dekker, multiple needles having an outlet with an exposed height between 0 and 1 mm are incorporated into a device which improves pharmacokinetics and bioavailability by delivering the substance at a depth between 0.3 mm and 2 mm.

A method for delivering genes, enzymes and biological agents to tissue cells has described by Desai and is taught for example in US Patent Publication 20030073908, the contents of which are incorporated herein by reference in their entirety. According to Desai, multiple needles are incorporated into a device which is inserted into a body and delivers a medication fluid through said needles.

A method for treating cardiac arrhythmias with fibroblast cells has been described by Lee et al and is taught for example in US Patent Publication 20040005295, the contents of which are incorporated herein by reference in their entirety. According to Lee, multiple needles are incorporated into the device which delivers fibroblast cells into the local region of the tissue.

A method using a magnetically controlled pump for treating a brain tumor has been described by Shachar et al and is taught for example in U.S. Pat. No. 7,799,012 (method) and U.S. Pat. No. 7,799,016 (device), the contents of which are incorporated herein by reference in their entirety. According Shachar, multiple needles were incorporated into the pump which pushes a medicating agent through the needles at a controlled rate.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A micro-needle transdermal transport device has been described by Angel et al and is taught for example in U.S. Pat. No. 7,364,568, the contents of which are incorporated herein by reference in their entirety. According to Angel, multiple needles are incorporated into the device which transports a substance into a body surface through the needles which are inserted into the surface from different directions.

A device for subcutaneous infusion has been described by Dalton et al and is taught for example in U.S. Pat. No. 7,150,726, the contents of which are incorporated herein by reference in their entirety. According to Dalton, multiple needles are incorporated into the device which delivers fluid through the needles into a subcutaneous tissue.

A device and a method for intradermal delivery of vaccines and gene therapeutic agents through microcannula have been described by Mikszta et al and are taught for example in U.S. Pat. No. 7,473,247, the contents of which are incorporated herein by reference in their entirety. According to Mitszta, at least one hollow micro-needle is incorporated into the device which delivers the vaccines to the subject's skin to a depth of between 0.025 mm and 2 mm.

A method of delivering insulin has been described by Pettis et al and is taught for example in U.S. Pat. No. 7,722,595, the contents of which are incorporated herein by reference in their entirety. According to Pettis, two needles are incorporated into a device wherein both needles insert essentially simultaneously into the skin with the first at a depth of less than 2.5 mm to deliver insulin to intradermal compartment and the second at a depth of greater than 2.5 mm and less than 5.0 mm to deliver insulin to subcutaneous compartment.

Cutaneous injection delivery under suction has been described by Kochamba et al and is taught for example in U.S. Pat. No. 6,896,666, the contents of which are incorporated herein by reference in their entirety. According to Kochamba, multiple needles in relative adjacency with each other are incorporated into a device which injects a fluid below the cutaneous layer.

A device for withdrawing or delivering a substance through the skin has been described by Down et al and is taught for example in U.S. Pat. No. 6,607,513, the contents of which are incorporated herein by reference in their entirety. According to Down, multiple skin penetrating members which are incorporated into the device have lengths of about 100 microns to about 2000 microns and are about 30 to 50 gauge.

A device for delivering a substance to the skin has been described by Palmer et al and is taught for example in U.S. Pat. No. 6,537,242, the contents of which are incorporated herein by reference in their entirety. According to Palmer, an array of micro-needles is incorporated into the device which uses a stretching assembly to enhance the contact of the needles with the skin and provides a more uniform delivery of the substance.

A perfusion device for localized drug delivery has been described by Zamoyski and is taught for example in U.S. Pat. No. 6,468,247, the contents of which are incorporated herein by reference in their entirety. According to Zamoyski, multiple hypodermic needles are incorporated into the device which injects the contents of the hypodermics into a tissue as said hypodermics are being retracted.

A method for enhanced transport of drugs and biological molecules across tissue by improving the interaction between micro-needles and human skin has been described by Prausnitz et al and is taught for example in U.S. Pat. No. 6,743,211, the contents of which are incorporated herein by reference in their entirety. According to Prausnitz, multiple micro-needles are incorporated into a device which is able to present a more rigid and less deformable surface to which the micro-needles are applied.

A device for intraorgan administration of medicinal agents has been described by Ting et al and is taught for example in U.S. Pat. No. 6,077,251, the contents of which are incorporated herein by reference in their entirety. According to Ting, multiple needles having side openings for enhanced administration are incorporated into a device which by extending and retracting said needles from and into the needle chamber forces a medicinal agent from a reservoir into said needles and injects said medicinal agent into a target organ.

A multiple needle holder and a subcutaneous multiple channel infusion port has been described by Brown and is taught for example in U.S. Pat. No. 4,695,273, the contents of which are incorporated herein by reference in their entirety. According to Brown, multiple needles on the needle holder are inserted through the septum of the infusion port and communicate with isolated chambers in said infusion port.

A dual hypodermic syringe has been described by Horn and is taught for example in U.S. Pat. No. 3,552,394, the contents of which are incorporated herein by reference in their entirety. According to Horn, two needles incorporated into the device are spaced apart less than 68 mm and may be of different styles and lengths, thus enabling injections to be made to different depths.

A syringe with multiple needles and multiple fluid compartments has been described by Hershberg and is taught for example in U.S. Pat. No. 3,572,336, the contents of which are incorporated herein by reference in their entirety. According to Hershberg, multiple needles are incorporated into the syringe which has multiple fluid compartments and is capable of simultaneously administering incompatible drugs which are not able to be mixed for one injection.

A surgical instrument for intradermal injection of fluids has been described by Eliscu et al and is taught for example in U.S. Pat. No. 2,588,623, the contents of which are incorporated herein by reference in their entirety. According to Eliscu, multiple needles are incorporated into the instrument which injects fluids intradermally with a wider disperse.

An apparatus for simultaneous delivery of a substance to multiple breast milk ducts has been described by Hung and is taught for example in EP 1818017, the contents of which are incorporated herein by reference in their entirety. According to Hung, multiple lumens are incorporated into the device which inserts though the orifices of the ductal networks and delivers a fluid to the ductal networks.

A catheter for introduction of medications to the tissue of a heart or other organs has been described by Tkebuchava and is taught for example in WO2006138109, the contents of which are incorporated herein by reference in their entirety. According to Tkebuchava, two curved needles are incorporated which enter the organ wall in a flattened trajectory.

Devices for delivering medical agents have been described by Mckay et al and are taught for example in WO2006118804, the content of which are incorporated herein by reference in their entirety. According to Mckay, multiple needles with multiple orifices on each needle are incorporated into the devices to facilitate regional delivery to a tissue, such as the interior disc space of a spinal disc.

A method for directly delivering an immunomodulatory substance into an intradermal space within a mammalian skin has been described by Pettis and is taught for example in WO2004020014, the contents of which are incorporated herein by reference in their entirety. According to Pettis, multiple needles are incorporated into a device which delivers the substance through the needles to a depth between 0.3 mm and 2 mm.

Methods and devices for administration of substances into at least two compartments in skin for systemic absorption and improved pharmacokinetics have been described by Pettis et al and are taught for example in WO2003094995, the contents of which are incorporated herein by reference in their entirety. According to Pettis, multiple needles having lengths between about 300 um and about 5 mm are incorporated into a device which delivers to intradermal and subcutaneous tissue compartments simultaneously.

A drug delivery device with needles and a roller has been described by Zimmerman et al and is taught for example in WO2012006259, the contents of which are incorporated herein by reference in their entirety. According to Zimmerman, multiple hollow needles positioned in a roller are incorporated into the device which delivers the content in a reservoir through the needles as the roller rotates.

Methods and Devices Utilizing Catheters and/or Lumens

Methods and devices using catheters and lumens may be employed to administer the mmRNA of the present invention on a split dosing schedule. Such methods and devices are described below.

A catheter-based delivery of skeletal myoblasts to the myocardium of damaged hearts has been described by Jacoby et al and is taught for example in US Patent Publication 20060263338, the contents of which are incorporated herein by reference in their entirety. According to Jacoby, multiple needles are incorporated into the device at least part of which is inserted into a blood vessel and delivers the cell composition through the needles into the localized region of the subject's heart.

An apparatus for treating asthma using neurotoxin has been described by Deem et al and is taught for example in US Patent Publication 20060225742, the contents of which are incorporated herein by reference in their entirety. According to Deem, multiple needles are incorporated into the device which delivers neurotoxin through the needles into the bronchial tissue.

A method for administering multiple-component therapies has been described by Nayak and is taught for example in U.S. Pat. No. 7,699,803, the contents of which are incorporated herein by reference in their entirety. According to Nayak, multiple injection cannulas may be incorporated into a device wherein depth slots may be included for controlling the depth at which the therapeutic substance is delivered within the tissue.

A surgical device for ablating a channel and delivering at least one therapeutic agent into a desired region of the tissue has been described by Mcintyre et al and is taught for example in U.S. Pat. No. 8,012,096, the contents of which are incorporated herein by reference in their entirety. According to Mcintyre, multiple needles are incorporated into the device which dispenses a therapeutic agent into a region of tissue surrounding the channel and is particularly well suited for transmyocardial revascularization operations.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A device and a method for delivering fluid into a flexible biological barrier have been described by Yeshurun et al and are taught for example in U.S. Pat. No. 7,998,119 (device) and U.S. Pat. No. 8,007,466 (method), the contents of which are incorporated herein by reference in their entirety. According to Yeshurun, the micro-needles on the device penetrate and extend into the flexible biological barrier and fluid is injected through the bore of the hollow micro-needles.

A method for epicardially injecting a substance into an area of tissue of a heart having an epicardial surface and disposed within a torso has been described by Bonner et al and is taught for example in U.S. Pat. No. 7,628,780, the contents of which are incorporated herein by reference in their entirety. According to Bonner, the devices have elongate shafts and distal injection heads for driving needles into tissue and injecting medical agents into the tissue through the needles.

A device for sealing a puncture has been described by Nielsen et al and is taught for example in U.S. Pat. No. 7,972,358, the contents of which are incorporated herein by reference in their entirety. According to Nielsen, multiple needles are incorporated into the device which delivers a closure agent into the tissue surrounding the puncture tract.

A method for myogenesis and angiogenesis has been described by Chiu et al and is taught for example in U.S. Pat. No. 6,551,338, the contents of which are incorporated herein by reference in their entirety. According to Chiu, 5 to 15 needles having a maximum diameter of at least 1.25 mm and a length effective to provide a puncture depth of 6 to 20 mm are incorporated into a device which inserts into proximity with a myocardium and supplies an exogeneous angiogenic or myogenic factor to said myocardium through the conduits which are in at least some of said needles.

A method for the treatment of prostate tissue has been described by Bolmsj et al and is taught for example in U.S. Pat. No. 6,524,270, the contents of which are incorporated herein by reference in their entirety. According to Bolmsj, a device comprising a catheter which is inserted through the urethra has at least one hollow tip extendible into the surrounding prostate tissue. An astringent and analgesic medicine is administered through said tip into said prostate tissue.

A method for infusing fluids to an intraosseous site has been described by Findlay et al and is taught for example in U.S. Pat. No. 6,761,726, the contents of which are incorporated herein by reference in their entirety. According to Findlay, multiple needles are incorporated into a device which is capable of penetrating a hard shell of material covered by a layer of soft material and delivers a fluid at a predetermined distance below said hard shell of material.

A device for injecting medications into a vessel wall has been described by Vigil et al and is taught for example in U.S. Pat. No. 5,713,863, the contents of which are incorporated herein by reference in their entirety. According to Vigil, multiple injectors are mounted on each of the flexible tubes in the device which introduces a medication fluid through a multi-lumen catheter, into said flexible tubes and out of said injectors for infusion into the vessel wall.

A catheter for delivering therapeutic and/or diagnostic agents to the tissue surrounding a bodily passageway has been described by Faxon et al and is taught for example in U.S. Pat. No. 5,464,395, the contents of which are incorporated herein by reference in their entirety. According to Faxon, at least one needle cannula is incorporated into the catheter which delivers the desired agents to the tissue through said needles which project outboard of the catheter.

Balloon catheters for delivering therapeutic agents have been described by Orr and are taught for example in WO2010024871, the contents of which are incorporated herein by reference in their entirety. According to Orr, multiple needles are incorporated into the devices which deliver the therapeutic agents to different depths within the tissue.

Methods and Devices Utilizing Electrical Current

Methods and devices utilizing electric current may be employed to deliver the mmRNA of the present invention according to the split dosing regimens taught herein. Such methods and devices are described below.

An electro collagen induction therapy device has been described by Marquez and is taught for example in US Patent Publication 20090137945, the contents of which are incorporated herein by reference in their entirety. According to Marquez, multiple needles are incorporated into the device which repeatedly pierce the skin and draw in the skin a portion of the substance which is applied to the skin first.

An electrokinetic system has been described by Etheredge et al and is taught for example in US Patent Publication 20070185432, the contents of which are incorporated herein by reference in their entirety. According to Etheredge, micro-needles are incorporated into a device which drives by an electrical current the medication through the needles into the targeted treatment site.

An iontophoresis device has been described by Matsumura et al and is taught for example in U.S. Pat. No. 7,437,189, the contents of which are incorporated herein by reference in their entirety. According to Matsumura, multiple needles are incorporated into the device which is capable of delivering ionizable drug into a living body at higher speed or with higher efficiency.

Intradermal delivery of biologically active agents by needle-free injection and electroporation has been described by Hoffmann et al and is taught for example in U.S. Pat. No. 7,171,264, the contents of which are incorporated herein by reference in their entirety. According to Hoffmann, one or more needle-free injectors are incorporated into an electroporation device and the combination of needle-free injection and electroporation is sufficient to introduce the agent into cells in skin, muscle or mucosa.

A method for electropermeabilization-mediated intracellular delivery has been described by Lundkvist et al and is taught for example in U.S. Pat. No. 6,625,486, the contents of which are incorporated herein by reference in their entirety. According to Lundkvist, a pair of needle electrodes is incorporated into a catheter. Said catheter is positioned into a body lumen followed by extending said needle electrodes to penetrate into the tissue surrounding said lumen. Then the device introduces an agent through at least one of said needle electrodes and applies electric field by said pair of needle electrodes to allow said agent pass through the cell membranes into the cells at the treatment site.

A delivery system for transdermal immunization has been described by Levin et al and is taught for example in WO2006003659, the contents of which are incorporated herein by reference in their entirety. According to Levin, multiple electrodes are incorporated into the device which applies electrical energy between the electrodes to generate micro channels in the skin to facilitate transdermal delivery.

A method for delivering RF energy into skin has been described by Schomacker and is taught for example in WO2011163264, the contents of which are incorporated herein by reference in their entirety. According to Schomacker, multiple needles are incorporated into a device which applies vacuum to draw skin into contact with a plate so that needles insert into skin through the holes on the plate and deliver RF energy.

Devices and Kits

Devices may also be used in conjunction with the present invention. In one embodiment, a device is used to assess levels of a protein which has been administered in the form of a modified mRNA. The device may comprise a blood, urine or other biofluidic test. It may be as large as to include an automated central lab platform or a small decentralized bench top device. It may be point of care or a handheld device. The device may be useful in drug discovery efforts as a companion diagnostic.

In some embodiments the device is self-contained, and is optionally capable of wireless remote access to obtain instructions for synthesis and/or analysis of the generated nucleic acid. The device is capable of mobile synthesis of at least one nucleic acid, and preferably an unlimited number of different nucleic acid sequences. In certain embodiments, the device is capable of being transported by one or a small number of individuals. In other embodiments, the device is scaled to fit on a benchtop or desk. In other embodiments, the device is scaled to fit into a suitcase, backpack or similarly sized object. In further embodiments, the device is scaled to fit into a vehicle, such as a car, truck or ambulance, or a military vehicle such as a tank or personnel carrier. The information necessary to generate a modified mRNA encoding protein of interest is present within a computer readable medium present in the device.

In some embodiments, the device is capable of communication (e.g., wireless communication) with a database of nucleic acid and polypeptide sequences. The device contains at least one least one sample block for insertion of one or more sample vessels. Such sample vessels are capable of accepting in liquid or other form any number of materials such as template DNA, nucleotides, enzymes, buffers, and other reagents. The sample vessels are also capable of being heated and cooled by contact with the sample block. The sample block is generally in communication with a device base with one or more electronic control units for the at least one sample block. The sample block preferably contains a heating module, such heating molecule capable of heating and/or cooling the sample vessels and contents thereof to temperatures between about −20 C and above +100 C. The device base is in communication with a voltage supply such as a battery or external voltage supply. The device also contains means for storing and distributing the materials for RNA synthesis.

Optionally, the sample block contains a module for separating the synthesized nucleic acids. Alternatively, the device contains a separation module operably linked to the sample block. Preferably the device contains a means for analysis of the synthesized nucleic acid. Such analysis includes sequence identity (demonstrated such as by hybridization), absence of non-desired sequences, measurement of integrity of synthesized mRNA (such has by microfluidic viscometry combined with spectrophotometry), and concentration and/or potency of modified RNA (such as by spectrophotometry).

In certain embodiments, the device is combined with a means for detection of pathogens present in a biological material obtained from a subject, e.g., the IBIS PLEX-ID system (Abbott) for microbial identification.

The present invention provides for devices which incorporate mmRNA that encode proteins of interest. These devices may be implantable in an animal subject or may supply mmRNA formulations via a catheter or lumen. The device may be connected to or incorporate a pump. Such devices include those which can deliver therapeutics to areas of the body not readily accessible such as the CNS or across the blood brain barrier. In this embodiment the split dosing regimen can be implemented using a regulated pump.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits for protein production, comprising a first isolated nucleic acid comprising a translatable region and a nucleic acid modification, wherein the nucleic acid may be capable of evading an innate immune response of a cell into which the first isolated nucleic acid may be introduced, and packaging and instructions. The kit may further comprise a delivery agent to form a formulation composition. The delivery composition may comprise a lipidoid. The lipoid may be selected from, but is not limited to, C12-200, 98N12-5, MD1, DLin-DMA, DLin-K-DMA, DLin-KC2-DMA, DLin-MC3-DMA and analogs thereof.

In one aspect, the present invention provides kits for protein production, comprising a first isolated nucleic acid comprising a translatable region and a nucleoside modification, wherein the nucleic acid exhibits reduced degradation by a cellular nuclease, and packaging and instructions.

In one aspect, the present invention provides kits for protein production, comprising a first isolated nucleic acid comprising a translatable region and at least two different nucleoside modifications, wherein the nucleic acid exhibits reduced degradation by a cellular nuclease, and packaging and instructions.

In some embodiments, kits would provide split doses or instructions for the administration of split dosages of the mmRNA of the kit.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may effect the same outcome or a different outcome. The structure that produces the function may be the same or different. For example, bifunctional modified RNAs of the present invention may encode a cytotoxic peptide (a first function) while those nucleosides which comprise the encoding RNA are, in and of themselves, cytotoxic (second function). In this example, delivery of the bifunctional modified RNA to a cancer cell would produce not only a peptide or protein molecule which may ameliorate or treat the cancer but would also deliver a cytotoxic payload of nucleosides to the cell should degradation, instead of translation of the modified RNA, occur.

Biologically active: As used herein, the phrase "biologically active" refers to a characteristic of any substance that has activity in a biological system and/or organism. For instance, a substance that, when administered to an organism, has a biological affect on that organism, is considered to be biologically active. In particular embodiments, a nucleic acid molecule of the present invention may be considered biologically active if even a portion of the nucleic acid molecule is biologically active or mimics an activity considered biologically relevant.

Chemical terms: As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkoxy" refers to an —O-alkyl group. Example alkoxy groups include methoxy, ethoxy, propoxy (e.g., n-propoxy and isopropoxy), t-butoxy, and the like.

As used herein, "alkenyl" refers to an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, "alkynyl" refers to an alkyl group having one or more triple carbon-carbon bonds. Example alkynyl groups include ethynyl, propynyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "halo" or "halogen" includes fluoro, chloro, bromo, and iodo.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a nucleic acid molecule to targeted cells.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, strepavidin and haptens, quantum dots, and the like. Detectable labels may be located at any position in the peptides or proteins disclosed herein. They may be within the amino acids, the peptides, or proteins, or located at the N- or C-termini.

Distal: As used herein "distal" means farther from center mass or line of symmetry of subject or reference point. For limbs, it is farther from body.

Dosing regimen: As used herein, a "dosing regimen" is a schedule of administration or physician determined regimen of treatment, prophylaxis, or palliative care.

Dose splitting factor (DSF)-ratio of PUD of dose split treatment divided by PUD of total daily dose or single unit dose. The value is derived from comparison of dosing regimens groups.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Formulation: As used herein, a "formulation" includes at least a modified nucleic acid molecule and a delivery agent.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (polynucleotide or polypeptide sequences).

In accordance with the invention, two polynucleotide sequences are considered to be homologous if the polypeptides they encode are at least about 50% identical, at least about 60% identical, at least about 70% identical, at least about 80% identical, or at least about 90% identical for at least one stretch of at least about 20 amino acids.

In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and PASTA Atschul, S. F. et al., *J Malec. Biol.,* 215,403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides. Modified, as it pertains to a modified mRNA may also mean any alteration which is different from the wild type.

Naturally occurring: As used herein, "naturally occurring" means existing in nature without artificial aid.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Polypeptide: As used herein, "polypeptide" means a polymer of amino acid residues linked together by peptide bonds. The term, as used herein, refers to proteins, polypeptides, and peptides of any size, structure, or function. Typically, however, a polypeptide will be at least 50 amino acids long. In some instances the polypeptide encoded is smaller than about 50 amino acids and the polypeptide is termed a peptide. If the polypeptide is a peptide, it will be at least about 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. The term polypeptide may also apply to amino acid polymers in which one or more amino acid residues are an artificial chemical analogue of a corresponding naturally occurring amino acid.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc divided by the measure in the body fluid.

Proximal: As used herein, "proximal" means closer to center mass or line of symmetry of subject or reference point. For limbs, it is closer to body.

Sample: As used herein, the term "sample" refers to a subset of its tissues, cells or component parts (e.g. body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Stable: As used herein "stable" refers to a compound that is sufficiently robust to survive isolation to a useful degree of purity from a reaction mixture, and preferably capable of formulation into an efficacious therapeutic agent.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Simultaneously: As used herein, "simultaneously" means within scientific reproducibility, at same time.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Single unit dose: As used herein, a "single unit dose" is a dose of any therapeutic administration in one dose/at one time/single route/single point of contact, i.e., single administration event.

Total daily dose: As used herein, a "total daily dose" is an amount given or prescribed in 24 hr period. It may be administered as a single unit dose.

Split dose: As used herein, a "split dose" is the division of single unit dose or total daily dose into two or more doses.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents, oligonucleotide sequences identified by gene identification numbers, and other publications identified herein are expressly incorporated by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1. Modified mRNA Production

Modified mRNAs (mmRNA) according to the invention may be made using standard laboratory methods and materials. The open reading frame (ORF) of the gene of interest may be flanked by a 5' untranslated region (UTR) which may contain a strong Kozak translational initiation signal and/or an alpha-globin 3' UTR which may include an oligo(dT) sequence for templated addition of a poly-A tail. The modified mRNAs may be modified to reduce the cellular innate immune response. The modifications to reduce the cellular response may include pseudouridine (ψ) and 5-methyl-cytidine (5meC or $m_5C$). (see, Kariko Ketal. Immunity 23:165-75 (2005), Kariko Ketal. Mol Ther 16:1833-40 (2008), Anderson B R et al. NAR (2010); herein incorporated by reference).

The ORF may also include various upstream or downstream additions (such as, but not limited to β-globin, tags, etc.) may be ordered from an optimization service such as, but limited to, DNA2.0 (Menlo Park, Calif.) and may contain multiple cloning sites which may have XbaI recognition. Upon receipt of the construct, it may be reconstituted and transformed into chemically competent *E. coli*.

For the present invention, NEB DH5-alpha Competent *E. coli* are used. Transformations are performed according to NEB instructions using 100 ng of plasmid. The protocol is as follows:

1. Thaw a tube of NEB 5-alpha Competent *E. coli* cells on ice for 10 minutes.
2. Add 1-5 μl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 μl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.
10. Spread 50-100 μl of each dilution onto a selection plate and incubate overnight at 37° C.
    Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 μg), a maxi prep is performed using the Invitrogen PURELINK™ HiPure Maxiprep Kit (Carlsbad, Calif.), following the manufacturer's instructions.

Figure 2:
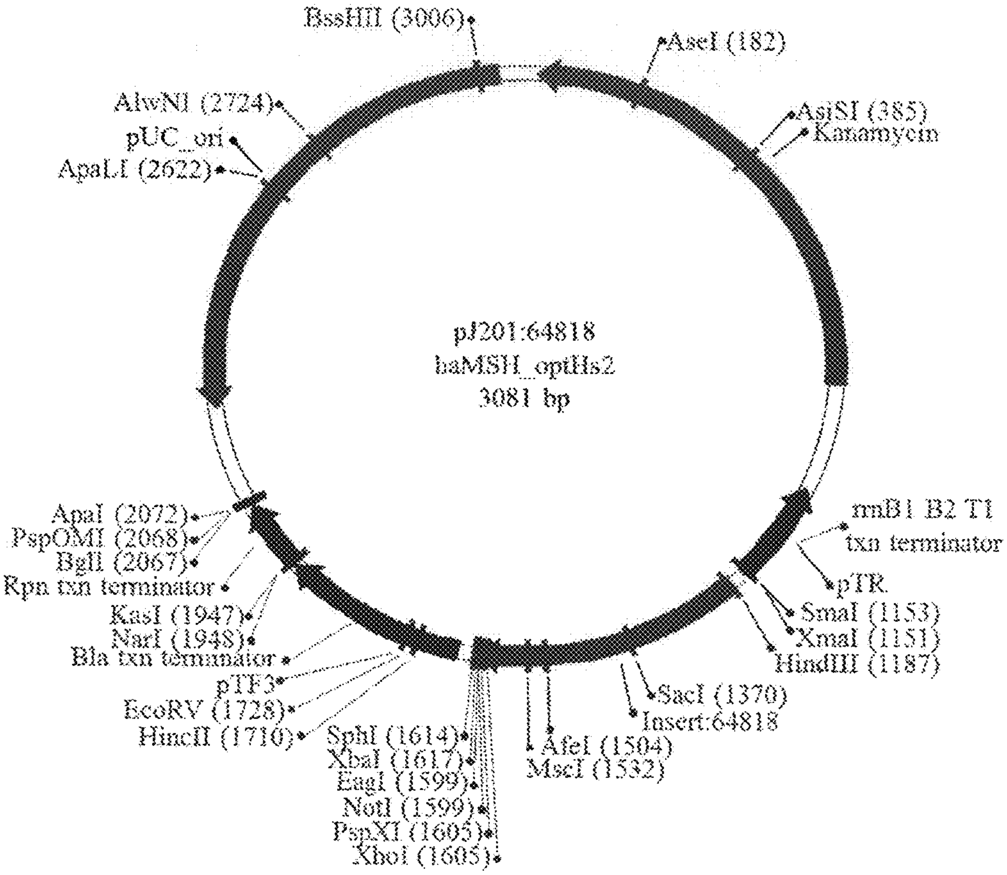
FIG. 2 is a representative plasmid useful in the IVT reactions taught herein. The plasmid contains Insert 64818, designed by the instant inventors.

In order to generate cDNA for In Vitro Transcription (IVT), the plasmid (an Example of which is shown in FIG. 2) is first linearized using a restriction enzyme such as XbaI. A typical restriction digest with XbaI will comprise the following: Plasmid 1.0 μg; 10× Buffer 1.0 μl; XbaI 1.5 μl; $dH_2O$ up to 10 μl; incubated at 37° C. for 1 hr. If performing at lab scale (<5 μg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

As a non-limiting example, G-CSF may represent the polypeptide of interest. Sequences used in the steps outlined in Examples 1-5 are shown in Table 2. It should be noted that the start codon (ATG) has been underlined in each sequence of Table 2.

TABLE 2

G-CSF Sequences

| SEQ ID NO | Description |
|---|---|
| 1 | cDNAsequence:<br>ATGGCTGGACCTGCCACCCAGAGCCCCATGAAGCTGATGGCCCTGCAGCTGCTGCTGTGGCACAGTGCACTCTG<br>GACAGTGCAGGAAGCCACCCCCCTGGGCCCTGCCAGCTCCCTGCCCCAGAGCTTCCTGCTCAAGTGCTTAGAGC<br>AAGTGAGGAAGATCCAGGGCGATGGCGCAGCGCTCCAGGAGAAGCTGGTGAGTGAGTGTGCCACCTACAAGCTG<br>TGCCACCCCGAGGAGCTGGTGCTGCTCGGACACTCTCTGGGCATCCCCTGGGCTCCCCTGAGCAGCTGCCCCAG<br>CCAGGCCCTGCAGCTGGCAGGCTGCTTGAGCCAACTCCATAGCGGCCTTTTCCTCTACCAGGGGCTCCTGCAGG<br>CCCTGGAAGGGATCTCCCCCGAGTTGGGTCCCACCTTGGACACACTGCAGCTGGACGTCGCCGACTTTGCCACC<br>ACCATCTGGCAGCAGATGGAAGAACTGGGAATGGCCCCTGCCCTGCAGCCCACCCAGGGTGCCATGCCGGCCTT<br>CGCCTCTGCTTTCCAGCGCCGGGCAGGAGGGGTCCTGGTTGCCTCCCATCTGCAGAGCTTCCTGGAGGTGTCGT<br>ACCGCGTTCTACGCCACCTTGCCCAGCCCTGA |
| 2 | cDNA having T7 polyermase site and Xba restriction site:<br>TTGGACCCTCGTACAGAAGCTAATACGACTCACTATAGGGAAATAAGAGAGAAAAGAAGAGTAAGAAGAAATAT<br>AAGAGCCACCATGGCTGGACCTGCCACCCAGAGCCCCATGAAGCTGATGGCCCTGCAGCTGCTGCTGTGGCACA<br>GTGCACTCTGGACAGTGCAGGAAGCCACCCCCCTGGGCCCTGCCAGCTCCCTGCCCCAGAGCTTCCTGCTCAAG<br>TGCTTAGAGCAAGTGAGGAAGATCCAGGGCGATGGCGCAGCGCTCCAGGAGAAGCTGGTGAGTGAGTGTGCCAC<br>CTACAAGCTGTGCCACCCCGAGGAGCTGGTGCTGCTCGGACACTCTCTGGGCATCCCCTGGGCTCCCCTGAGCA<br>GCTGCCCCAGCCAGGCCCTGCAGCTGGCAGGCTGCTTGAGCCAACTCCATAGCGGCCTTTTCCTCTACCAGGGG<br>CTCCTGCAGGCCCTGGAAGGGATCTCCCCCGAGTTGGGTCCCACCTTGGACACACTGCAGCTGGACGTCGCCGA<br>CTTTGCCACCACCATCTGGCAGCAGATGGAAGAACTGGGAATGGCCCCTGCCCTGCAGCCCACCCAGGGTGCCA<br>TGCCGGCCTTCGCCTCTGCTTTCCAGCGCCGGGCAGGAGGGGTCCTGGTTGCCTCCCATCTGCAGAGCTTCCTG<br>GAGGTGTCGTACCGCGTTCTACGCCACCTTGCCCAGCCCTGAAGCGCTGCCTTCTGCGGGGCTTGCCTTCTGGC<br>CATGCCCTTCTTCTCTCCCTTGCACCTGTACCTCTTGGTCTTTGAATAAAGCCTGAGTAGGAAGGCGGCCGCTC<br>GAGCATGCATCTAGA |
| 3 | Optimized sequence; containing T7 polymerase site and Xba restriction site<br>TTGGACCCTCGTACAGAAGCTAATACGACTCACTATAGGGAAATAAGAGAGAAAAGAAGAGTAAGAAGAAATAT<br>AAGAGCCACCATGGCCCTGCAGTTGCTGCTTTGGCACTCGGCCCTCTGGACAGTCCAAGAAGCGACTCCTCTCG<br>GACCTGCCTCATCGTTGCCGCAGTCATTCCTTTTGAAGTGTCTGGAGCAGGTGCGAAAGATTCAGGGCGATGGA<br>GCCGCACTCCAAGAGAAGCTCTGCGCGACATACAAACTTTGCCATCCCGAGGAGCTCGTACTGCTCGGGCACAG<br>CTTGGGGATTCCCTGGGCTCCTCTCTCGTCCTGTCCGTCGCAGGCTTTGCAGTTGGCAGGGTGCCTTTCCCAGC<br>TCCACTCCGGTTTGTTCTTGTATCAGGGACTGCTGCAAGCCCTTGAGGGAATCTCGCCAGAATTGGGCCCGACG<br>CTGGACACGTTGCAGCTCGACGTGGCGGATTTCGCAACAACCATCTGGCAGCAGATGGAGGAACTGGGGATGGC<br>ACCCGCGCTGCAGCCCACGCAGGGGGCAATGCCGGCCTTTGCGTCCGCGTTTCAGCGCAGGGCGGGTGGAGTCC<br>TCGTAGCGAGCCACCTTCAATCATTTTTGGAAGTCTCGTACCGGGTGCTGAGACATCTTGCGCAGCCGTGAGCC<br>TTCTGCGGGGCTTGCCTTCTGGCCATGCCCTTCTTCTCTCCCTTGCACCTGTACCTCTTGGTCTTTGAATAAAG<br>CCTGAGTAGGAAGGCGGCCGCTCGAGCATGCA |
| 4 | mRNA sequence (transcribed)<br>CUCACUAUAGGGAAAUAAGAGAGAAAAGAAGAGUAAGAAGAAAUAUAAGAGCCACCAAUGGCCCUGCAGUUGCU<br>GCUUUGGCACUCGGCCCUCUGGACAGUCCAAGAAGCGACUCCUCUCGGACCUGCCUCAUCGUUGCCGCAGUCAU<br>UCCUUUUGAAGUGUCUGGAGCAGGUGCGAAAGAUUCAGGGCGAUGGAGCCGCACUCCAAGAGAAGCUCUGCGCG<br>ACAUACAAACUUUGCCAUCCCGAGGAGCUCGUACUGCUCGGGCACAGCUUGGGGAUUCCCUGGGCUCCUCUCUC<br>GUCCUGUCCGUCGCAGGCUUUGCAGUUGGCAGGGUGCCUUUCCCAGCUCCACUCCGGUUUGUUCUUGUAUCAGG<br>GACUGCUGCAAGCCCUUGAGGGAAUCUCGCCAGAAUUGGGCCCGACGCUGGACACGUUGCAGCUCGACGUGGCG<br>GAUUUCGCAACAACCAUCUGGCAGCAGAUGGAGGAACUGGGGAUGGCACCCGCGCUGCAGCCCACGCAGGGGGC<br>AAUGCCGGCCUUUGCGUCCGCGUUUCAGCGCAGGGCGGGUGGAGUCCUCGUAGCGAGCCACCUUCAAUCAUUUU<br>UGGAAGUCUCGUACCGGGUGCUGAGACAUCUUGCGCAGCCGUGAGCCUUCUGCGGGGCUUGCCUUCUGGCCAUG<br>CCCUUCUUCUCUCCCUUGCACCUGUACCUCUUGGUCUUUGAAUAAAGCCUGAGUAGGAAGGCGGCCGCUCGAGC<br>AUGCAU |

Example 2: PCR for eDNA Production

PCR procedures for the preparation of eDNA are performed using 2×KAPA HIFI™ HotStart ReadyMix by Kapa Biosystems (Woburn, Mass.). This system includes 2×KAPA ReadyMix 12.5 μl; Forward Primer (10 uM) 0.75 μl; Reverse Primer (10 uM) 0.75 μl; Template cDNA 100 ng; and $dH_2O$ diluted to 25.0 The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-$T_{120}$ for a poly-$A_{120}$ in the mRNA. Other reverse primers with longer or shorter poly(T) tracts can be used to adjust the length of the poly(A) tail in the mRNA.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 3. In Vitro Transcription (IVT)

The in vitro transcription reaction generates mRNA containing modified nucleotides or modified RNA. The input nucleotide triphosphate (NTP) mix is made in-house using natural and un-natural NTPs.

A typical in vitro transcription reaction includes the following:

| | | |
|---|---|---|
| 1. | Template cDNA | 1.0 µg |
| 2. | 10X transcription buffer (400 mM Tris-HCl pH 8.0, 190 mM $MgCl_2$, 50 mM DTT, 10 mM Spermidine) | 2.0 µl |
| 3. | Custom NTPs (25 mM each) | 7.2 µl |
| 4. | RNase Inhibitor | 20 U |
| 5. | T7 RNA polymerase | 3000 U |
| 6. | $dH_2O$ | Up to 20.0 µl, and |
| 7. | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

Example 4. Enzymatic Capping of mRNA

Capping of the mRNA is performed as follows where the mixture includes: IVT RNA 60 µg-180 µg and $dH_2O$ up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 µl); 20 mM GTP (5.0 µl); 20 mM S-Adenosyl Methionine (2.5 µl); RNase Inhibitor (100 U); 2'-0-Methyltransferase (400 U); Vaccinia capping enzyme (Guanylyl transferase) (40 U); $dH_2O$ (Up to 28 µl); and incubation at 37° C. for 30 minutes for 60 µg RNA or up to 2 hours for 180 µg of RNA.

The mRNA is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 5. PolyA Tailing Reaction

Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM $MgCl_2$) (12.0 µl); 20 mM ATP (6.0 µl); Poly-A Polymerase (20 U); $dH_2O$ up to 123.5 µl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 µg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the Poly-A tailing reaction may not always result in exactly 160 nucleotides. Hence Poly-A tails of approximately 160 nucleotides, e.g., about 150-165, 155, 156, 157, 158, 159, 160, 161, 162, 163, 164 or 165 are within the scope of the invention.

Example 6. Formulation of Modified mRNA Using Lipidoids

5'-capping of modified RNA may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-0 methyl-transferase to generate: m7G(5')ppp(5')G-2'-0-methyl. Cap 2 structure may be generated from the Cap 1 structure followed by the 2'-0-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 7. Capping

A. Protein Expression Assay

Synthetic mRNAs encoding human G-CSF (cDNA shown in SEQ ID NO: 1) containing the ARCA (3' O-Me-m7G(5')ppp(5')G) cap analog or the Cap1 structure can be transfected into human primary keratinocytes at equal concentrations. 6, 12, 24 and 36 hours post-transfection the amount of G-CSF secreted into the culture medium can be assayed by ELISA. Synthetic mRNAs that secrete higher levels of G-CSF into the medium would correspond to a synthetic mRNA with a higher translationally-competent Cap structure.

B. Purity Analysis Synthesis mRNAs encoding human G-CSF (cDNA shown in SEQ ID NO: 1) containing the ARCA cap analog or the Cap1 structure crude synthesis products can be compared for purity using denaturing Agarose-Urea gel electrophoresis or HPLC analysis. Synthetic mRNAs with a single, consolidated band by electrophoresis correspond to the higher purity product compared to a synthetic mRNA with multiple bands or streaking bands. Synthetic mRNAs with a single HPLC peak would also correspond to a higher purity product. The capping reaction with a higher efficiency would provide a more pure mRNA population.

C. Cytokine Analysis

Synthetic mRNAs encoding human G-CSF (cDNA shown in SEQ ID NO: 1) containing the ARCA cap analog or the Cap1 structure can be transfected into human primary keratinocytes at multiple concentrations. 6, 12, 24 and 36 hours post-transfection the amount of pro-inflammatory cytokines such as TNF-alpha and IFN-beta secreted into the culture medium can be assayed by ELISA. Synthetic mRNAs that secrete higher levels of pro-inflammatory cytokines into the medium would correspond to a synthetic mRNA containing an immune-activating cap structure.

D. Capping Reaction Efficiency

Synthetic mRNAs encoding human G-CSF (cDNA shown in SEQ ID NO: 1) containing the ARCA cap analog or the Cap1 structure can be analyzed for capping reaction efficiency by LC-MS after capped mRNA nuclease treatment. Nuclease treatment of capped mRNAs would yield a mixture of free nucleotides and the capped 5'-5-triphosphate cap structure detectable by LC-MS. The amount of capped product on the LC-MS spectra can be expressed as a percent of total mRNA from the reaction and would correspond to capping reaction efficiency. The cap structure with a higher capping reaction efficiency would have a higher amount of capped product by LC-MS.

Example 8. Formulation of Modified mRNA Using Lipidoids

Modified mRNAs (mmRNA) are formulated for in vitro experiments by mixing the mmRNA with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations was used as a starting point. Initial mmRNA-lipidoid formulations may consist of particles composed of 42% lipidoid, 48% cholesterol and 10% PEG, with further optimization of ratios possible. After formation of the particle, mmRNA is added and allowed to integrate with the complex. The encapsulation efficiency is determined using a standard dye exclusion assays.

Materials and Methods for Examples 9-13

A. Lipid Synthesis

Six lipids, DLin-DMA, DLin-K-DMA, DLin-KC2-DMA, 98N12-5, C12-200 and DLin-MC3-DMA, were synthesized by methods outlined in the art in order to be formulated with modified RNA. DLin-DMA and precursors_were synthesized as described in Reyes et. al, J. Control Release, 2005, 107, 276-287. DLin-K-DMA and DLin-KC2-DMA and precursors were synthesized as described in Semple et. al, Nature Biotechnology, 2010, 28, 172-176. 98N12-5 and precursor were synthesized as described in Akinc et. al, *Nature Biotechnology,* 2008, 26, 561-569.

C12-200 and precursors were synthesized according to the method outlined in Love et. al, PNAS, 2010, 107, 1864-1869. 2-epoxydodecane (5.10 g, 27.7 mmol, 8.2 eq) was added to a vial containing Amine 200 (0.723 g, 3.36 mmol, 1 eq) and a stirring bar. The vial was sealed and warmed to 80° C. The reaction was stirred for 4 days at 80° C. Then the mixture was purified by silica gel chromatography using a gradient from pure dichloromethane (DCM) to DCM:MeOH 98:2. The target compound was further purified by RP-HPLC to afford the desired compound.

DLin-MC3-DMA and precursors were synthesized according to procedures described in WO 2010054401 herein incorporated by reference in its entirety. A mixture of dilinoleyl methanol (1.5 g, 2.8 mmol, 1 eq), N,N-dimethylaminobutyric acid (1.5 g, 2.8 mmol, 1 eq), DIPEA (0.73 mL, 4.2 mmol, 1.5 eq) and TBTU (1.35 g, 4.2 mmol, 1.5 eq) in 10 mL of DMF was stirred for 10 h at room temperature. Then the reaction mixture was diluted in ether and washed with water. The organic layer was dried over anhydrous sodium sulfate, filtrated and concentrated under reduced pressure. The crude product was purified by silica gel chromatography using a gradient DCM to DCM:MeOH 98:2. Subsequently the target compound was subjected to an additional RP-HPLC purification which was done using a YMC-Pack C4 column to afford the target compound.

B. Formulation of Modified RNA Nanoparticles

Solutions of synthesized lipid, 1,2-distearoyl-3-phosphatidylcholine (DSPC) (Avanti Polar Lipids, Alabaster, Ala.), cholesterol (Sigma-Aldrich, Taufkirchen, Germany), and α-[3'-(1,2-dimyristoyl-3-propanoxy)-carboxamide-propyl]-ω-methoxy-polyoxyethylene (PEG-c-DOMG) (NOF, Bouwelven, Belgium) were prepared at concentrations of 50 mM in ethanol and stored at −20° C. The lipids were combined to yield molar ratio of 50:10:38.5:1.5 (Lipid: DSPC: Cholesterol: PEG-c-DOMG) and diluted with ethanol to a final lipid concentration of 25 mM. Solutions of modified mRNA at a concentration of 1-2 mg/mL in water were diluted in 50 mM sodium citrate buffer at a pH of 3 to form a stock modified mRNA solution. Formulations of the lipid and modified mRNA were prepared by combining the synthesized lipid solution with the modified mRNA solution at total lipid to modified mRNA weight ratio of 10:1, 15:1, 20:1 and 30:1. The lipid ethanolic solution was rapidly injected into aqueous modified mRNA solution to afford a suspension containing 33% ethanol. The solutions were injected either manually (MI) or by the aid of a syringe pump (SP) (Harvard Pump 33 Dual Syringe Pump Harvard Apparatus Holliston, Mass.).

To remove the ethanol and to achieve the buffer-exchange, the formulations were dialyzed twice against phosphate buffered saline (PBS), pH 7.4 at volumes 200-times of the primary product using a Slide-A-Lyzer cassettes (Thermo Fisher Scientific Inc. Rockford, Ill.) with a molecular weight cutoff (MWCO) of 10 kD. The first dialysis was carried at room temperature for 3 hours and then the formulations were dialyzed overnight at 4° C. The resulting nanoparticle suspension was filtered through 0.2 μm sterile filter (Sarstedt, Numbrecht, Germany) into glass vials and sealed with a crimp closure.

C. Characterization of Formulations

A Zetasizer Nano ZS (Malvern Instruments Ltd, Malvern, Worcestershire, UK) was used to determine the particle size, the polydispersity index (PDI) and the zeta potential of the modified mRNA nanoparticles in IX PBS in determining particle size and 15 mM PBS in determining zeta potential.

Ultraviolet-visible spectroscopy was used to determine the concentration of modified mRNA nanoparticle formulation. 100 μL of the diluted formulation in IX PBS was added to 900 μL of a 4:1 (v/v) mixture of methanol and chloroform. After mixing, the absorbance spectrum of the solution was recorded between 230 nm and 330 nm on a DU 800 spectrophotometer (Beckman Coulter, Beckman Coulter, Inc., Brea, Calif.). The modified RNA concentration in the nanoparticle formulation was calculated based on the extinction coefficient of the modified RNA used in the formulation and on the difference between the absorbance at a wavelength of 260 nm and the baseline value at a wavelength of 330 nm.

QUANT-IT™ RIBOGREEN® RNA assay (Invitrogen Corporation Carlsbad, Calif.) was used to evaluate the encapsulation of modified RNA by the nanoparticle. The samples were diluted to a concentration of approximately 5 μg/mL in TE buffer (10 mM Tris-HCl, 1 mM EDTA, pH 7.5). 50 μL of the diluted samples were transferred to a polystyrene 96 well plate, then either 50 μL of TE buffer or 50 μL of a 2% Triton X-100 solution was added. The plate was incubated at a temperature of 37° C. for 15 minutes. The RIBOGREEN® reagent was diluted 1:100 in TE buffer, 100 μL of this solution was added to each well. The fluorescence intensity was measured using a fluorescence plate reader (Wallac Victor 1420 Multilabel Counter; Perkin Elmer, Waltham, Mass.) at an excitation wavelength of ~480 nm and an emission wavelength of ~520 nm. The fluorescence values of the reagent blank were subtracted from that of each of the samples and the percentage of free modified RNA was determined by dividing the fluorescence intensity of the intact sample (without addition of Triton X-100) by the fluorescence value of the disrupted sample (caused by the addition of Triton X-100).

D. In Vitro Incubation

Human embryonic kidney epithelial (HEK293) and hepatocellular carcinoma epithelial (HepG2) cells (LGC standards GmbH, Wesel, Germany) were seeded on 96-well plates (Greiner Bio-one GmbH, Frickenhausen, Germany) and plates for HEK293 cells were precoated with collagen typel. HEK293 were seeded at a density of 30,000 and HepG2 were seeded at a density of 35,000 cells per well in 100 μl cell culture medium. For HEK293 the cell culture medium was DMEM, 10% FCS, adding 2 mM L-Glutamine, 1 mM Sodium pyruvate and 1× non-essential amino acids (Biochrom AG, Berlin, Germany) and 1.2 μg/ml Sodium bicarbonate (Sigma-Aldrich, Munich, Germany) and for HepG2 the culture medium was MEM (Gibco Life Technologies, Darmstadt, Germany), 10% FCS adding 2 mM L-Glutamine, 1 mM Sodium pyruvate and 1× non-essential amino acids (Biochrom AG, Berlin, Germany. Formulations containing mCherry mRNA (mRNA sequence shown in SEQ ID NO: 5; poly-A tail of approximately 160 nucleotides not shown in sequence; 5' cap, Cap1) were added in quadruplicates directly after seeding the cells and incubated. The mCherry cDNA with the T7 promoter, 5'untranslated region (UTR) and 3' UTR used in in vitro transcription (IVT) is given in SEQ ID NO: 6.

Cells were harvested by transferring the culture media supernatants to a 96-well Pro-Bind U-bottom plate (Becton Dickinson GmbH, Heidelberg, Germany). Cells were trypsinized with 1 h volume Trypsin/EDTA (Biochrom AG, Berlin, Germany), pooled with respective supernatants and fixed by adding one volume PBS/2% FCS (both Biochrom AG, Berlin, Germany)/0.5% formaldehyde (Merck, Darmstadt, Germany). Samples then were submitted to a flow cytometer measurement with a 532 nm excitation laser and the 610/20 filter for PE-Texas Red in a LSRII cytometer (Becton Dickinson GmbH, Heidelberg, Germany). The mean fluorescence intensity (MFI) of all events and the standard deviation of four independent wells are presented in for samples analyzed.

Example 9. Purification on Nanoparticle Formulations

Figure 3A:
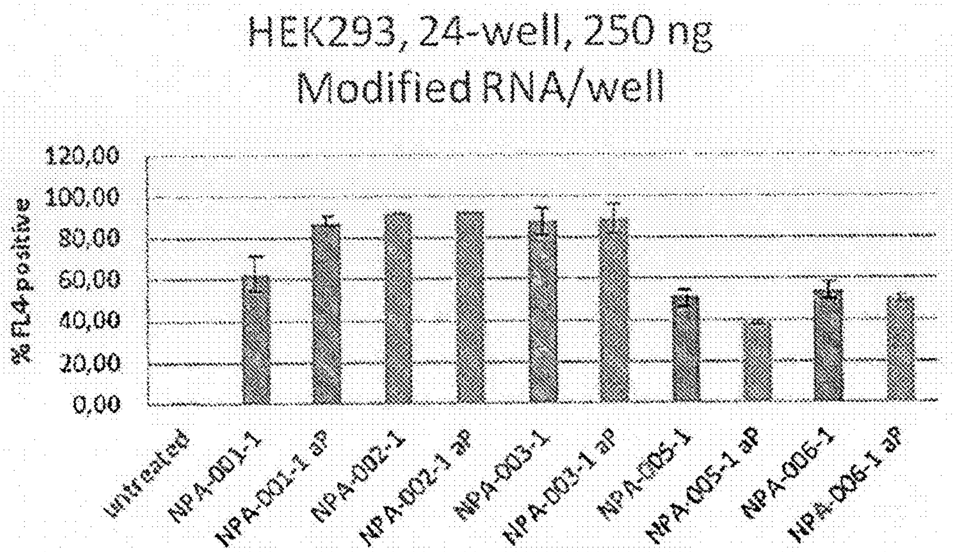
FIGS. 3A and 3B are histograms showing in vitro screening results for nanoparticle formulations of DLin-KC2-DMA and 98N12-15 (before and after purification) that contain mCherry mmRNA.
Figure 3B:
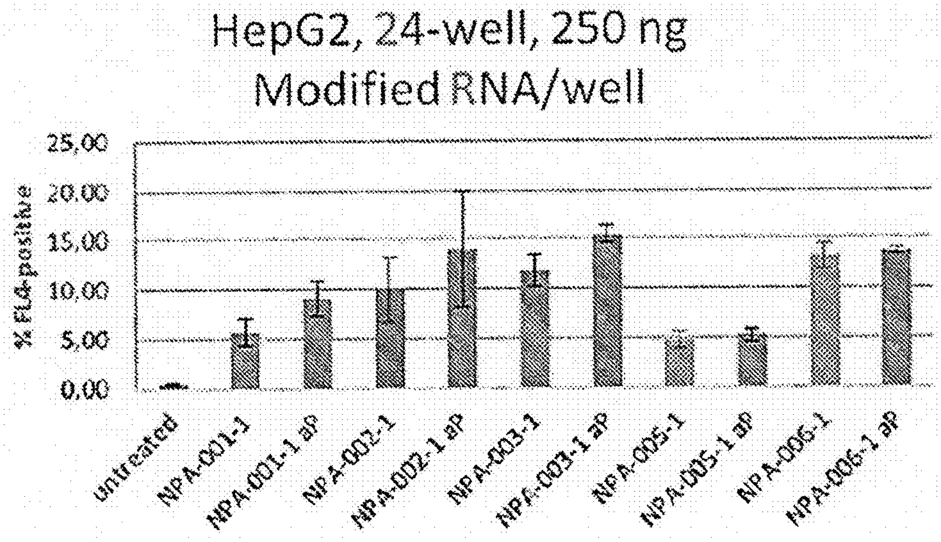
Figure 4A:
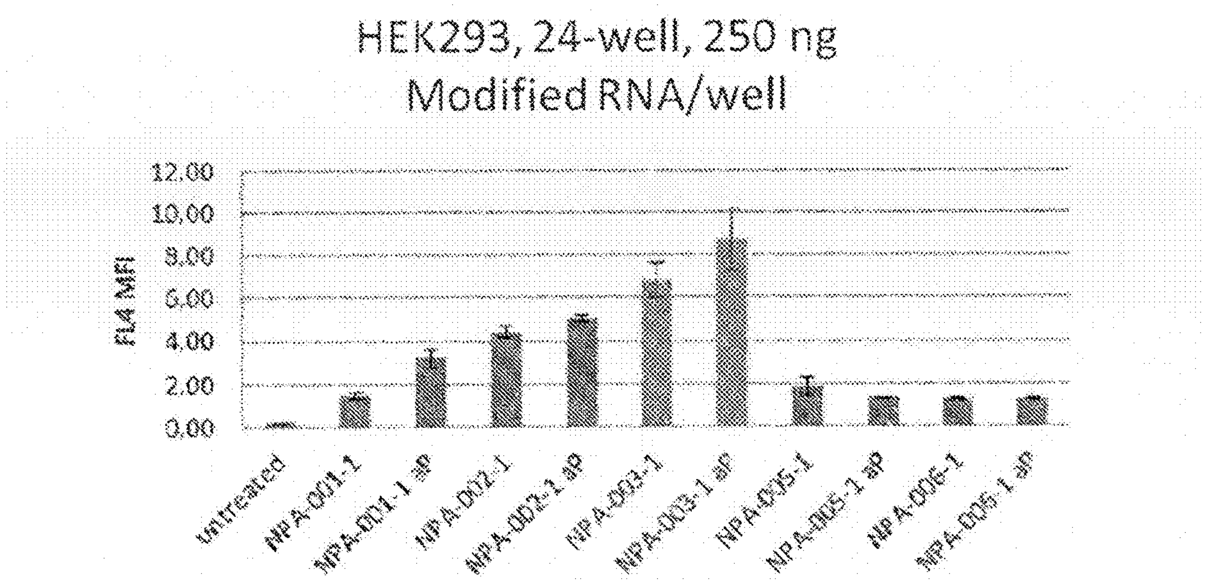
FIGS. 4A and 4B are histograms showing in vitro screening results for mean fluorescence intensity for nanoparticle formulations of DLin-KC2-DMA and 98N12-15 (before and after purification) that contain mCherry mmRNA.
Figure 4B:
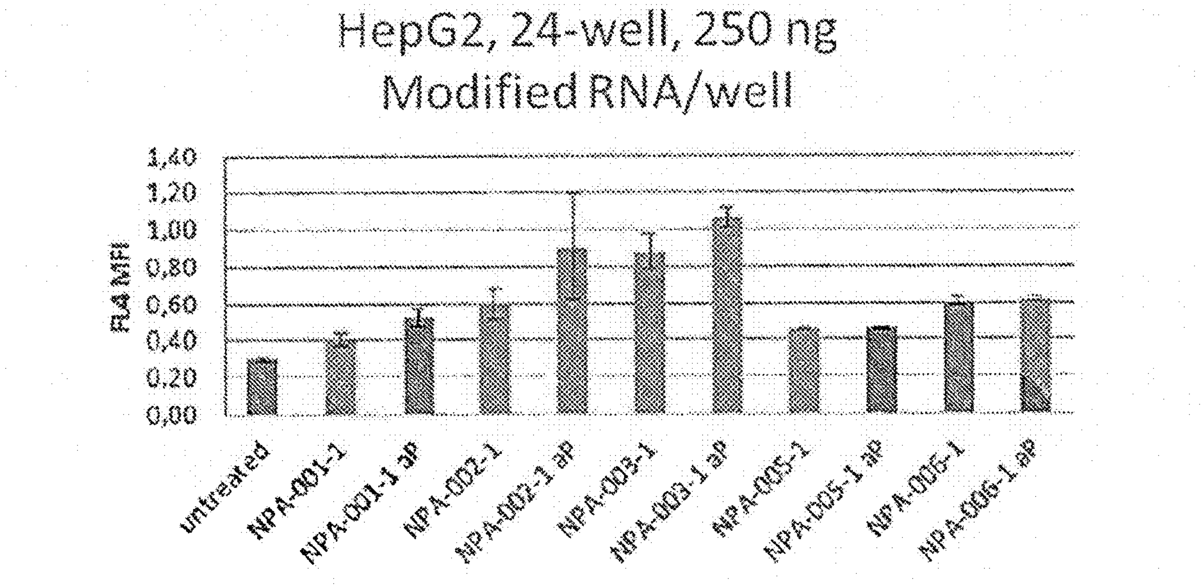

Nanoparticle formulations of DLin-KC2-DMA and 98N12-5 in HEK293 and HepG2 were tested to determine if the mean fluorescent intensity (MFI) was dependent on the lipid to modified RNA ratio and/or purification. Three formulations of DLin-KC2-DMA and two formulations of 98N12-5 were produced using a syringe pump to the specifications described in Table 3. Purified samples were purified by SEPHADEX™ G-25 DNA grade (GE Healthcare, Sweden). Each formulation before and after purification (aP) were tested at concentration of 250 ng modified RNA per well in a 24 well plate. The percentage of cells that are positive for the marker for FL4 channel (% FL4-positive) when analyzed by the flow cytometer for each formulation and the background sample are shown in FIGS. 3A and 3B, and the MFI of the marker for the FL4 channel for each formulation and the background sample are shown in FIGS. 4A and 4B. The formulations which had been purified had a slightly higher MFI than those formulations tested before purification.

TABLE 3

| Formulations | | | |
|---|---|---|---|
| Formulation # | Lipid | Lipid/RNA wt/wt | Mean size (nm) |
| NPA-001-1 | DLin-KC2-DMA | 10 | 155 nm<br>PDI: 0.08 |
| NPA-001-1 aP | DLin-KC2-DMA | 10 | 141 nm<br>PDI: 0.14 |
| NPA-002-1 | DLin-KC2-DMA | 15 | 140 nm<br>PDI: 0.11 |
| NPA-002-1 aP | DLin-KC2-DMA | 15 | 125 nm<br>PDI: 0.12 |
| NPA-003-1 | DLin-KC2-DMA | 20 | 114 nm<br>PDI: 0.08 |
| NPA-003-1 aP | DLin-KC2-DMA | 20 | 104 nm<br>PDI: 0.06 |
| NPA-005-1 | 98N12-5 | 15 | 127 nm<br>PDI: 0.12 |
| NPA-005-1 aP | 98N12-5 | 15 | 134 nm<br>PDI: 0.17 |
| NPA-006-1 | 98N12 | 20 | 126 nm<br>PDI: 0.08 |
| NPA-006-1 aP | 98N12 | 20 | 118 nm<br>PDI: 0.13 |

Example 10. Concentration Response Curve

Figure 5A:
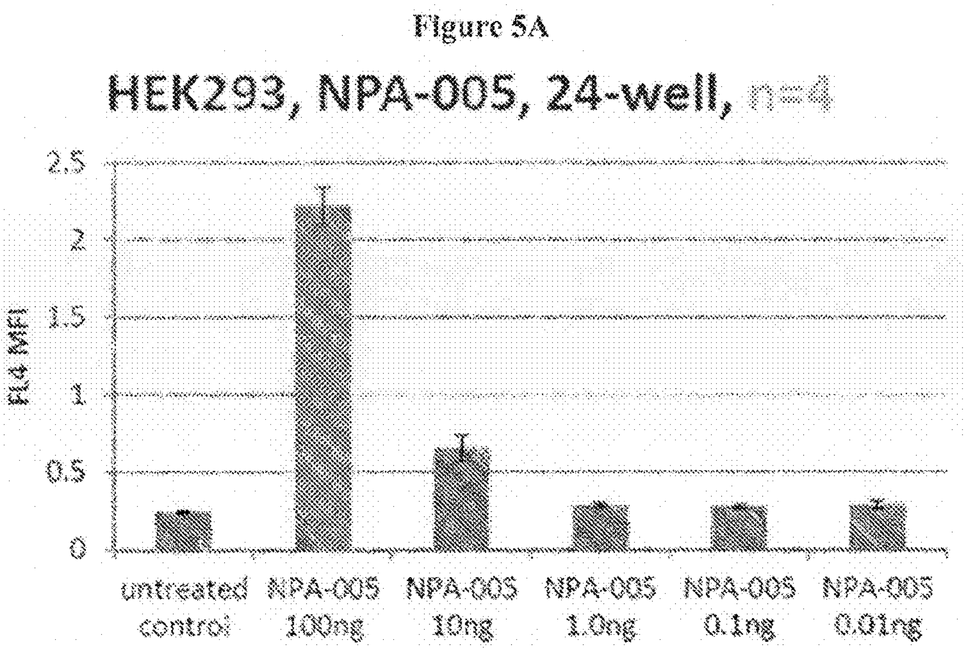
FIGS. 5A, 5B, and 5C are histograms showing in vitro screening results for nanoparticle formulations of DLin-KC2-DMA and 98N12-15 before and after purification.
Figure 5B:
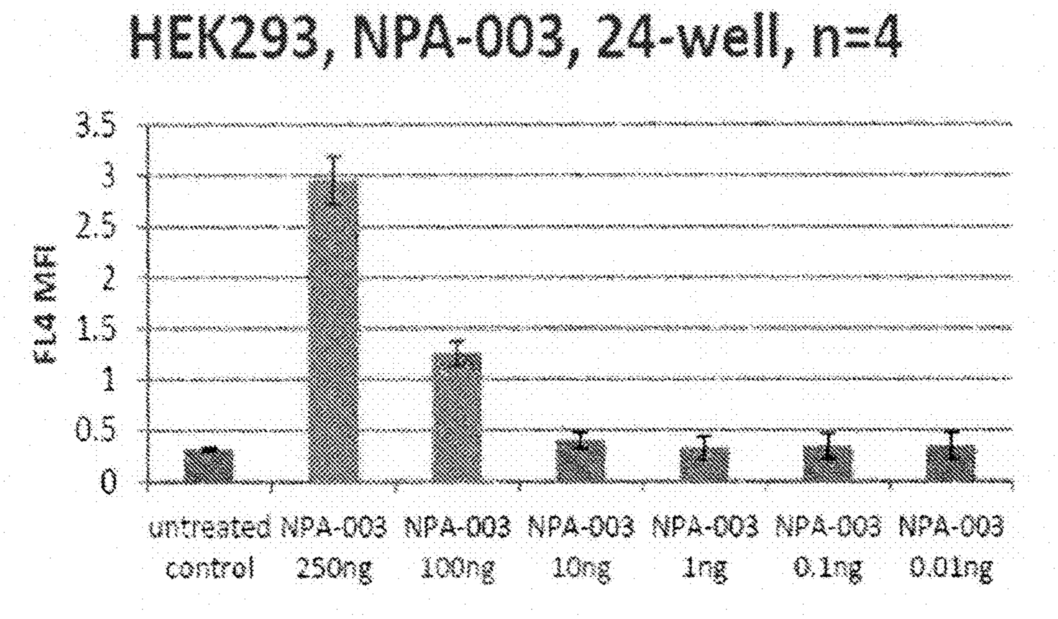
Figure 5C:
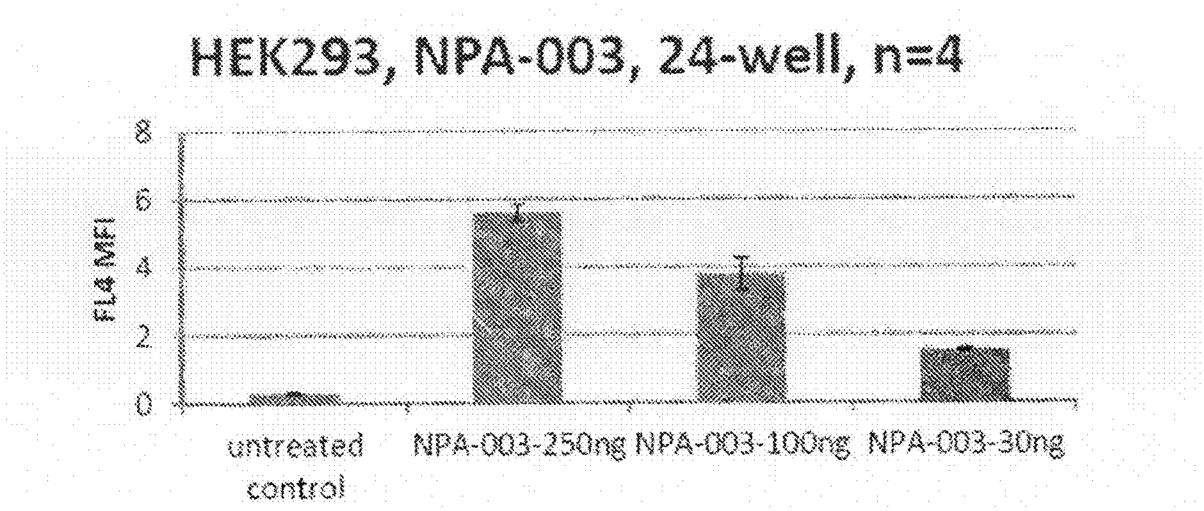

Nanoparticle formulations of 98N12-5 (NPA-005) and DLin-KC2-DMA (NPA-003) were tested at varying concentrations to determine the MFI of FL4 or mCherry (mRNA sequence shown in SEQ ID NO: 5; poly-A tail of approximately 160 nucleotides not shown in sequence; 5' cap, Cap1) over a range of doses. The formulations tested are outlined in Table 4. To determine the optimal concentration of nanoparticle formulations of 98N12-5, varying concentrations of formulated modified RNA (100 ng, 10 ng, 1.0 ng, 0.1 ng and 0.01 ng per well) were tested in a 24-well plate of HEK293, and the results of the FL4 MFI of each dose are shown in FIG. 5A. Likewise, to determine the optimal concentration of nanoparticle formulations of DLin-KC2-DMA, varying concentrations of formulated modified RNA (250 ng 100 ng, 10 ng, 1.0 ng, 0.1 ng and 0.01 ng per well) were tested in a 24-well plate of HEK293, and the results of the FL4 MFI of each dose are shown in FIG. 5B. Nanoparticle formulations of DLin-KC2-DMA were also tested at varying concentrations of formulated modified RNA (250 ng, 100 ng and 30 ng per well) in a 24 well plate of HEK293, and the results of the FL4 MFI of each dose are shown in FIG. 5C. A dose of 1 ng/well for 98N12-5 and a dose of 10 ng/well for DLin-K2-DMA were found to resemble the FL4 MFI of the background.

To determine how close the concentrations resembled the background, we utilized a flow cytometer with optimized filter sets for detection of mCherry expression, and were able to obtain results with increased sensitivity relative to background levels. Doses of 25 ng/well, 0.25 ng/well, 0.025 ng/well and 0.0025 ng/well were analyzed for 98N12-5

(NPA-005) and DLin-K2-DMA (NPA-003) to determine the MFI of mCherry. As shown in Table 5, the concentration of 0.025 ng/well and lesser concentrations are similar to the background MFI level of mCherry which is about 386.125.

TABLE 4

| Formulations | | |
|---|---|---|
| Formulation # | NPA-003 | NPA-005 |
| Lipid | DLin-KC2-DMA | 98N12-5 |
| Lipid/RNA wt/wt | 20 | 15 |
| Mean size | 114 nm PDI: 0.08 | 106 nm PDI: 0.12 |

TABLE 5

| Concentration and MFI | | |
|---|---|---|
| | MFI mCherry | |
| Formulation | NPA-003 | NPA-005 |
| 25 ng/well | 11963.25 | 12256.75 |
| 0.25 ng/well | 1349.75 | 2572.75 |
| 0.025 ng/well | 459.50 | 534.75 |
| 0.0025 ng/well | 310.75 | 471.75 |

Example 11. Manual Injection and Syringe Pump Formulations

Two formulations of DLin-KC2-DMA and 98N12-5 were prepared by manual injection (MI) and syringe pump injection (SP) and analyzed along with a background sample to compare the MFI of mCherry (mRNA shown in SEQ ID NO: 5; poly-A tail of approximately 160 nucleotides not shown in sequence; 5' cap, Cap1) of the different formulations. Table 5 shows that the syringe pump formulations had a higher MFI as compared to the manual injection formulations of the same lipid and lipid/RNA ratio.

TABLE 5

| Formulations and MFI | | | | | |
|---|---|---|---|---|---|
| Formulation # | Lipid | Lipid/ RNA wt/wt | Mean size (nm) | Method of formulation | MFI |
| Untreated Control | N/A | N/A | N/A | N/A | 674.67 |
| NPA-002 | DLin-KC2-DMA | 15 | 140 nm PDI: 0.11 | MI | 10318.25 |
| NPA-002-2 | DLin-KC2-DMA | 15 | 105 nm PDI: 0.04 | SP | 37054.75 |
| NPA-003 | DLin-KC2-DMA | 20 | 114 nm PDI: 0.08 | MI | 22037.5 |
| NPA-003-2 | DLin-KC2-DMA | 20 | 95 nm PDI: 0.02 | SP | 37868.75 |
| NPA-005 | 98N12-5 | 15 | 127 nm PDI: 0.12 | MI | 11504.75 |
| NPA-005-2 | 98N12-5 | 15 | 106 nm PDI: 0.07 | SP | 9343.75 |
| NPA-006 | 98N12-5 | 20 | 126 nm PDI: 0.08 | MI | 11182.25 |
| NPA-006-2 | 98N12-5 | 20 | 93 nm PDI: 0.08 | SP | 5167 |

Example 12. mCherry Fluorescence of Formulations

Figure 6A:
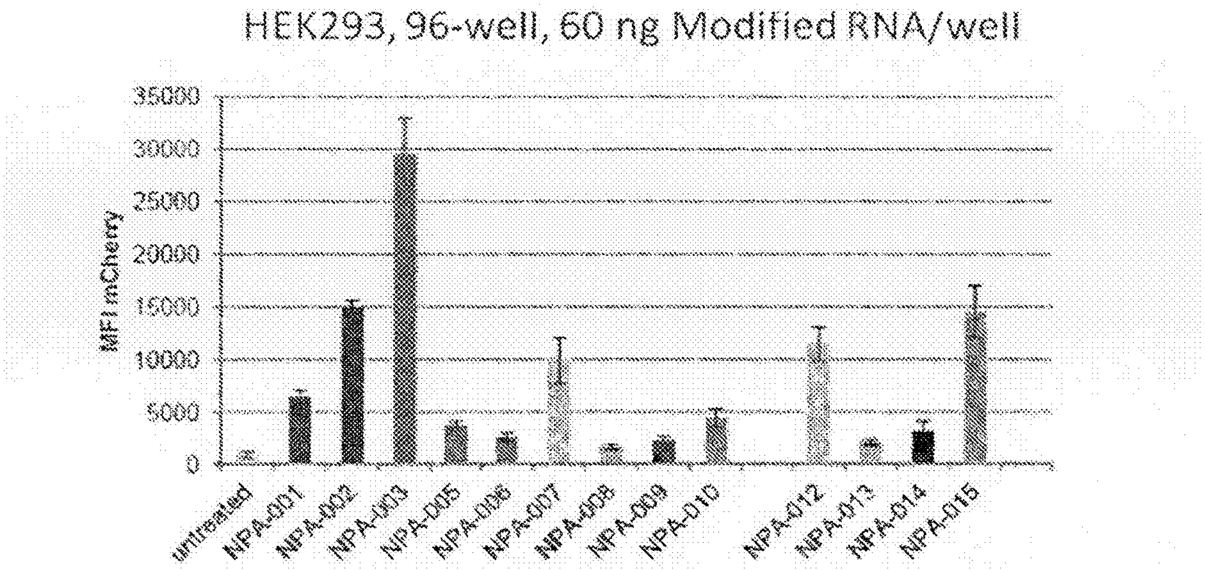
FIGS. 6A, 6B, 6C, and 6D are histograms showing in vitro screening results for nanoparticle formulations of DLin-DMA, DLin-K-DMA, DLin-KC2-DMA, 98N12-5, C12-200 and DLin-MC3-DMA that contain mCherry mmRNA.
Figure 6B:
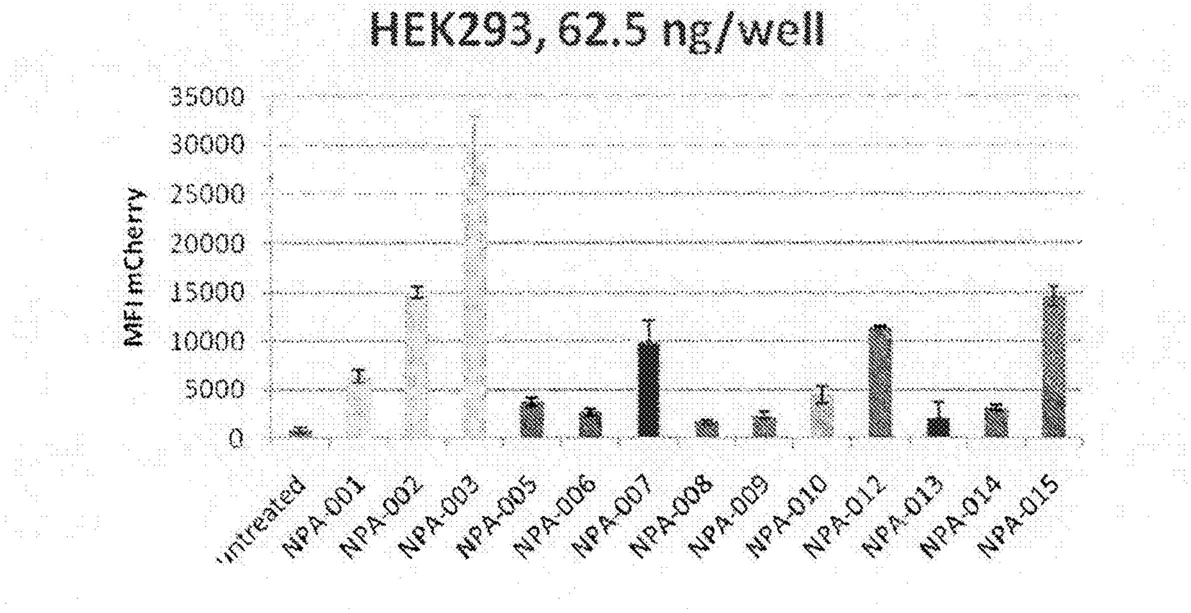
Figure 6C:
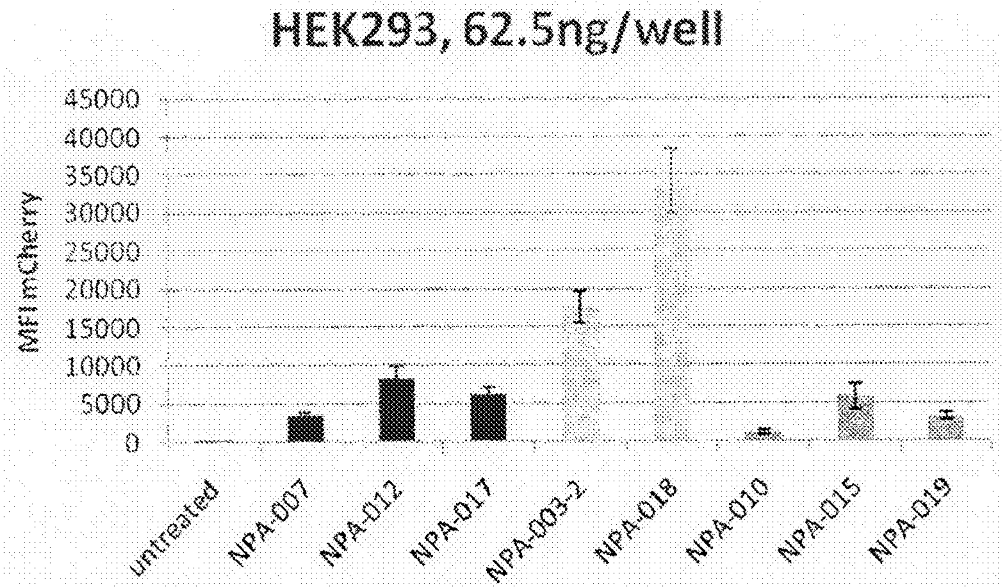
Figure 6D:
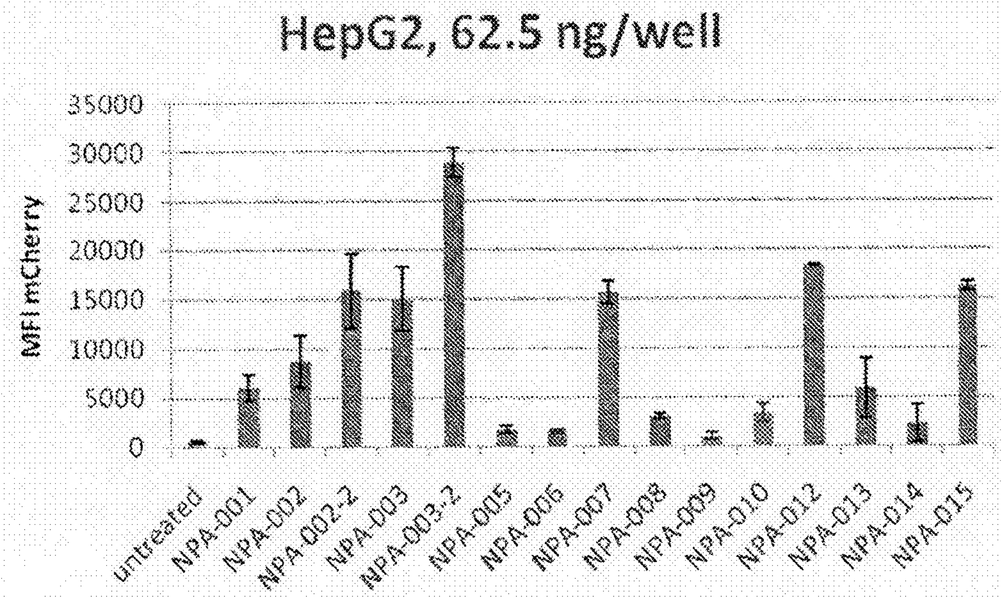
Figure 6E:
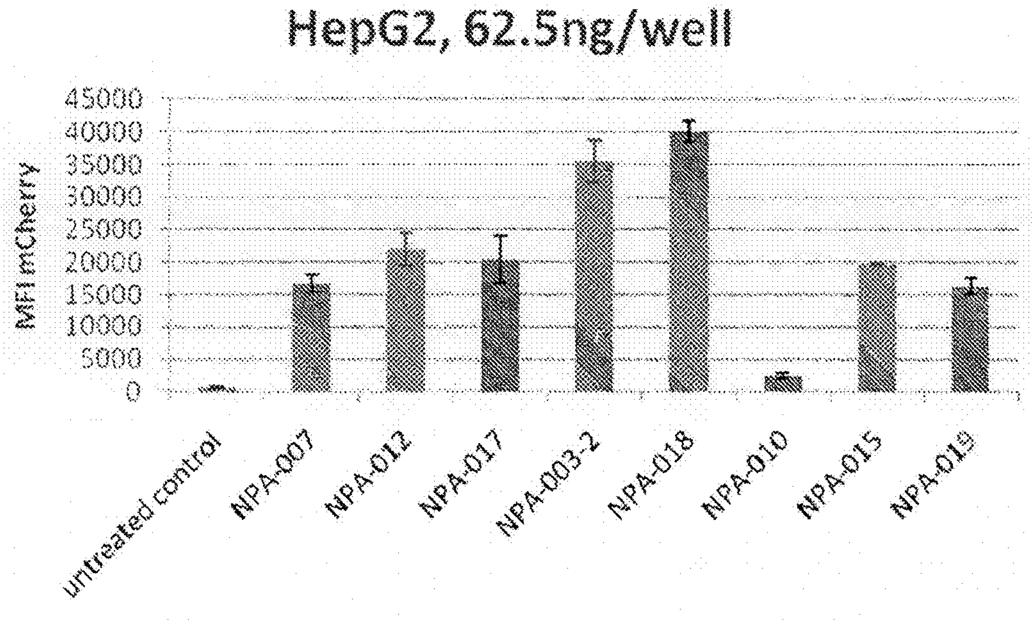

Formulations of DLin-DMA, DLin-K-DMA, DLin-KC2-DMA, 98N12-5, C12-200 and DLin-MC3-DMA were incubated at a concentration of 60 ng/well or 62.5 ng/well in a plate of HEK293 and 62.5 ng/well in a plate of HepG2 cells for 24 hours to determine the MFI of mCherry (mRNA shown in SEQ ID NO: 5; poly-A tail of approximately 160 nucleotides not shown in sequence; 5' cap, Cap1) for each formulation. The formulations tested are outlined in Table 6 below. As shown in FIG. 6A for the 60 ng/well and FIGS. 6B, 6C, 6D, and 6E for the 62.5 ng/well, the formulation of NPA-003 and NPA-018 have the highest mCherry MFI and the formulations of NPA-008, NPA-010 and NPA-013 are most the similar to the background sample mCherry MFI value.

TABLE 6

| Formulations | | | |
|---|---|---|---|
| Formulation # | Lipid | Lipid/RNA wt/wt | Mean size (nm) |
| NPA-001 | DLin-KC2-DMA | 10 | 155 nm PDI: 0.08 |
| NPA-002 | DLin-KC2-DMA | 15 | 140 nm PDI: 0.11 |
| NPA-002-2 | DLin-KC2-DMA | 15 | 105 nm PDI: 0.04 |
| NPA-003 | DLin-KC2-DMA | 20 | 114 nm PDI: 0.08 |
| NPA-003-2 | DLin-KC2-DMA | 20 | 95 nm PDI: 0.02 |
| NPA-005 | 98N12-5 | 15 | 127 nm PDI: 0.12 |
| NPA-006 | 98N12-5 | 20 | 126 nm PDI: 0.08 |
| NPA-007 | DLin-DMA | 15 | 148 nm PDI: 0.09 |
| NPA-008 | DLin-K-DMA | 15 | 121 nm PDI: 0.08 |
| NPA-009 | C12-200 | 15 | 138 nm PDI: 0.15 |
| NPA-010 | DLin-MC3-DMA | 15 | 126 nm PDI: 0.09 |
| NPA-012 | DLin-DMA | 20 | 86 nm PDI: 0.08 |
| NPA-013 | DLin-K-DMA | 20 | 104 nm PDI: 0.03 |
| NPA-014 | C12-200 | 20 | 101 nm PDI: 0.06 |
| NPA-015 | DLin-MC3 -DMA | 20 | 109 nm PDI: 0.07 |

Example 13. In Vivo Formulation Studies

Mice (n=5) are administered intravenously a single dose of a formulation containing a modified mRNA and a lipid. The modified mRNA administered to the mice is selected from G-CSF (mRNA shown in SEQ ID NO: 4; poly-A tail of approximately 160 nucleotides not shown in sequence; 5' cap, Cap1), erythropoietin (EPO) (mRNA shown in SEQ ID NO: 7; poly-A tail of approximately 160 nucleotides not shown in sequence; 5' cap, Cap1), Factor IX (mRNA shown in SEQ ID NO: 8; poly-A tail of approximately 160 nucleotides not shown in sequence; 5' cap, Cap1) or mCherry (mRNA sequence shown in SEQ ID NO: 5; poly-A tail of approximately 160 nucleotides not shown in sequence; 5' cap, Cap1). The erythropoietin cDNA with the T7 promoter, 5'untranslated region (UTR) and 3' UTR used in in vitro transcription (IVT) is given in SEQ ID NO: 9.

Each formulation also contains a lipid which is selected from one of DLin-DMA, DLin-K-DMA, DLin-KC2-DMA, 98N12-5, C12-200 or DLin-MC3-DMA. The mice are injected with 100 ug, 10 ug or 1 ug of the formulated modified mRNA and are sacrificed 8 hours after they are administered the formulation. Serum from the mice administered formulations containing human G-CSF modified mRNA are measured by specific G-CSF ELISA and serum from mice administered human Factor IX modified RNA is analyzed by specific Factor IX ELISA or chromogenic assay. The liver and spleen from the mice administered with mCherry modified mRNA are analyzed by immunohistochemistry (IHC) or fluorescence-activated cell sorting (FACS). As a control, a group of mice are not injected with any formulation and their serum and tissue are collected analyzed by ELISA, FACS and/or IHC.

Example 14. In Vitro and In Vivo Expression

A. In Vitro Expression in Human Cells Using Lipidoid Formulations

The ratio of mmRNA to lipidoid used to test for in vitro transfection is tested empirically at different lipidoid:mmRNA ratios. Previous work using siRNA and lipidoids have utilized 2.5:1, 5:1, 10:1, and 15:1 lipidoid:siRNA wt:wt ratios. Given the longer length of mmRNA relative to siRNA, a lower wt:wt ratio of lipidoid to mmRNA may be effective. In addition, for comparison mmRNA were also formulated using RNAIMAX™ (Invitrogen, Carlsbad, Calif.) or TRANSIT-mRNA (Mirus Bio, Madison, Wis.) cationic lipid delivery vehicles. The ability of lipidoid-formulated Luciferase (IVT cDNA sequence as shown in SEQ ID NO: 10), green fluorescent protein (GFP) (IVT cDNA sequence as shown in SEQ ID NO: 11), G-CSF (mRNA sequence shown in SEQ ID NO: 4; poly-A tail of approximately 160 nucleotides not shown in sequence; 5' cap, Cap1), and EPO mmRNA (mRNA sequence shown in SEQ ID NO: 7; poly-A tail of approximately 160 nucleotides not shown in sequence; 5' cap, Cap1) to express the desired protein product can be confirmed by luminescence for luciferase expression, flow cytometry for GFP expression, and by ELISA for G-CSF and Erythropoietin (EPO) secretion.

B. In Vivo Expression Following Intravenous Injection

Systemic intravenous administration of the formulations are created using various different lipidoids including, but not limited to, 98N12-5, C12-200, and MD1

Lipidoid formulations containing mmRNA are injected intravenously into animals. The expression of the modified mRNA (mmRNA)-encoded proteins are assessed in blood and/or other organs samples such as, but not limited to, the liver and spleen collected from the animal. Conducting single dose intravenous studies will also allow an assessment of the magnitude, dose responsiveness, and longevity of expression of the desired product.

In one embodiment, lipidoid based formulations of 98N12-5, C12-200, MD1 and other lipidoids, are used to deliver luciferase, green fluorescent protein (GFP), mCherry fluorescent protein, secreted alkaline phosphatase (sAP), human G-CSF, human Factor IX, or human Erythropoietin (EPO) mmRNA into the animal. After formulating mmRNA with a lipid, as described previously, animals are divided into groups to receive either a saline formulation, or a lipidoid-formulation which contains one of a different mmRNA selected from luciferase, GFP, mCherry, sAP, human G-CSF, human Factor IX, and human EPO. Prior to injection into the animal, mmRNA-containing lipidoid formulations are diluted in PBS. Animals are then administered a single dose of formulated mmRNA ranging from a dose of 10 mg/kg to doses as low as 1 ng/kg, with a preferred range to be 10 mg/kg to 100 ng/kg, where the dose of mmRNA depends on the animal body weight such as a 20 gram mouse receiving a maximum formulation of 0.2 ml (dosing is based no mmRNA per kg body weight). After the administration of the mmRNA-lipidoid formulation, serum, tissues, and/or tissue lysates are obtained and the level of the mmRNA-encoded product is determined at a single and/or a range of time intervals. The ability of lipidoid-formulated Luciferase, GFP, mCherry, sAP, G-CSF, Factor IX, and EPO mmRNA to express the desired protein product is confirmed by luminescence for the expression of Luciferase, flow cytometry for the expression of GFP and mCherry expression, by enzymatic activity for sAP, or by ELISA for the section of G-CSF, Factor IX and/or EPO.

Further studies for a multi-dose regimen are also performed to determine the maximal expression of mmRNA, to evaluate the saturability of the mmRNA-driven expression (by giving a control and active mmRNA formulation in parallel or in sequence), and to determine the feasibility of repeat drug administration (by giving mmRNA in doses separated by weeks or months and then determining whether expression level is affected by factors such as immunogenicity). An assessment of the physiological function of proteins such as G-CSF and EPO are also determined through analyzing samples from the animal tested and detecting increases in granulocyte and red blood cell counts, respectively. Activity of an expressed protein product such as Factor IX, in animals can also be assessed through analysis of Factor IX enzymatic activity (such as an activated partial thromboplastin time assay) and effect of clotting times.

C. In Vitro Expression Following Intramuscular and/or Subcutaneous Injection

The use of lipidoid formulations to deliver oligonucleotides, including mRNA, via an intramuscular route or a subcutaneous route of injection needs to be evaluated as it has not been previously reported. Intramuscular and/or subcutaneous injection of mmRNA are evaluated to determine if mmRNA-containing lipidoid formulations are capable to produce both localized and systemic expression of a desired-protein.

Lipidoid formulations of 98N12-5, C12-200, and MD1 containing mmRNA selected from luciferase, green fluorescent protein (GFP), mCherry fluorescent protein, secreted alkaline phosphatase (sAP), human G-CSF, human factor IX, or human Erythropoietin (EPO) mmRNA are injected intramuscularly and/or subcutaneously into animals. The expression of mmRNA-encoded proteins are assessed both within the muscle or subcutaneous tissue and systemically in blood and other organs such as the liver and spleen. Single dose studies allow an assessment of the magnitude, dose responsiveness, and longevity of expression of the desired product.

Animals are divided into groups to receive either a saline formulation or a formulation containing modified mRNA. Prior to injection mmRNA-containing lipidoid formulations are diluted in PBS. Animals are administered a single intramuscular dose of formulated mmRNA ranging from 50 mg/kg to doses as low as 1 ng/kg with a preferred range to be 10 mg/kg to 100 ng/kg. A maximum dose for intramuscular administration, for a mouse, is roughly 1 μg mmRNA or as low as 0.02 ng mmRNA for an intramuscular injection into the hind limb of the mouse. For subcutaneous administration, the animals are administered a single subcutaneous dose of formulated mmRNA ranging from 400 mg/kg to doses as low as 1 ng/kg with a preferred range to be 80 mg/kg to 100 ng/kg. A maximum dose for subcutaneous administration, for a mouse, is roughly 8 μg mmRNA or as low as 0.02 ng mmRNA.

For a 20 gram mouse the volume of a single intramuscular injection is maximally 0.025 ml and a single subcutaneous injection is maximally 0.2 ml. The optimal dose of mmRNA administered is calculated from the body weight of the animal. At various points in time points following the administration of the mmRNA-lipidoid, serum, tissues, and tissue lysates is obtained and the level of the mmRNA-encoded product is determined. The ability of lipidoid-formulated luciferase, green fluorescent protein (GFP), mCherry fluorescent protein, secreted alkaline phosphatase (sAP), human G-CSF, human factor IX, or human Erythropoietin (EPO) mmRNA to express the desired protein product is confirmed by luminescence for luciferase expression, flow cytometry for GFP and mCherry expression, by enzymatic activity for sAP, and by ELISA for G-CSF, Factor IX and Erythropoietin (EPO) secretion.

Additional studies for a multi-dose regimen are also performed to determine the maximal expression using mmRNA, to evaluate the saturability of the mmRNA-driven expression (achieved by giving a control and active mmRNA formulation in parallel or in sequence), and to determine the feasibility of repeat drug administration (by giving mmRNA in doses separated by weeks or months and then determining whether expression level is affected by factors such as immunogenicity). Studies utilizing multiple subcutaneous or intramuscular injection sites at one time point, are also utilized to further increase mmRNA drug exposure and improve protein production. An assessment of the physiological function of proteins, such as GFP, mCherry, sAP, human G-CSF, human factor IX, and human EPO, are determined through analyzing samples from the tested animals and detecting a change in granulocyte and/or red blood cell counts. Activity of an expressed protein product such as Factor IX, in animals can also be assessed through analysis of Factor IX enzymatic activity (such as an activated partial thromboplastin time assay) and effect of clotting times.

Example 15. Split Dose Studies

Studies utilizing multiple subcutaneous or intramuscular injection sites at one time point were designed and performed to investigate ways to increase mmRNA drug exposure and improve protein production. In addition to detection of the expressed protein product, an assessment of the physiological function of proteins was also determined through analyzing samples from the animal tested.

Surprisingly, it has been determined that split dosing of mmRNA produces greater protein production and phenotypic responses than those produced by single unit dosing or multi-dosing schemes.

The design of a single unit dose, multi-dose and split dose experiment involved using human erythropoietin (EPO) mmRNA (mRNA sequence shown in SEQ ID NO: 7; poly-A tail of approximately 160 nucleotides not shown in sequence; 5' cap, Cap1) administered in buffer alone. The dosing vehicle (F. buffer) consisted of 150 mM NaCl, 2 mM $CaCl_2$, 2 mM Na+-phosphate (1.4 mM monobasic sodium phosphate; 0.6 mM dibasic sodium phosphate), and 0.5 mM EDTA, pH 6.5. The pH was adjusted using sodium hydroxide and the final solution was filter sterilized. The mmRNA was modified with 5meC at each cytosine and pseudouridine replacement at each uridine site.

Animals (n=5) were injected IM (intramuscular) for the single unit dose of 100 ug. For multi-dosing, two schedules were used, 3 doses of 100 ug and 6 doses of 100 ug. For the split dosing scheme, two schedules were used, 3 doses at 33.3 ug and 6 doses of 16.5 ug mmRNA. Control dosing involved use of buffer only at 6 doses. Control mmRNA involved the use of luciferase mmRNA (IVT cDNA sequence shown in SEQ ID NO: 10) dosed 6 times at 100 ug. Blood and muscle tissue were evaluated 13 hrs post injection.

Human EPO protein was measured in mouse serum 13 h post I.M. single, multi- or split dosing of the EPO mmRNA in buffer. Seven groups of mice (n=5 mice per group) were treated and evaluated. The results are shown in Table 7.

TABLE 7

Split dose study

| Group | Treatment | Dose of mmRNA | Total Dose | Avg. pmol/mL human EPO | Polypeptide per unit drug (pmol/ug) | Dose Splitting Factor |
|---|---|---|---|---|---|---|
| 1 | Human EPO mmRNA | 1 × 100 ug | 100 ug | 14.3 | .14 | 1 |
| 2 | Human EPO mmRNA | 3 × 100 ug | 300 ug | 82.5 | .28 | 2 |
| 3 | Human EPO mmRNA | 6 × 100 ug | 600 ug | 273.0 | .46 | 3.3 |
| 4 | Human EPO mmRNA | 3 × 33.3 ug | 100 ug | 104.7 | 1.1 | 7.9 |
| 5 | Human EPO mmRNA | 6 × 16.5 ug | 100 ug | 127.9 | 1.3 | 9.3 |
| 6 | Luciferase mmRNA | 6 × 100 ug | 600 ug | 0 | — | — |
| 7 | Buffer Alone | — | — | 0 | — | — |

The splitting factor is defined as the product per unit drug divided by the single dose product per unit drug (PUD). For example for treatment group 2 the value 0.28 or product (EPO) per unit drug (mmRNA) is divided by the single dose product per unit drug of 0.14. The result is 2. Likewise, for treatment group 4, the value 1.1 or product (EPO) per unit drug (mmRNA) is divided by the single dose product per unit drug of 0.14. The result is 7.9. Consequently, the dose splitting factor (DSF) may be used as an indicator of the efficacy of a split dose regimen. For any single administration of a total daily dose, the DSF should be equal to 1. Therefore any DSF greater than this value in a split dose regimen is an indication of increased efficacy.

To determine the dose response trends, impact of injection site and impact of injection timing, studies are performed. In these studies, varied doses of 1 ug, 5 ug, 10 ug, 25 ug, 50 ug, and values in between are used to determine dose response outcomes. Split dosing for a 100 ug total dose includes three or six doses of 1.6 ug, 4.2 ug, 8.3 ug, 16.6 ug, or values and total doses equal to administration of the total dose selected.

Injection sites are chosen from the limbs or any body surface presenting enough area suitable for injection. This may also include a selection of injection depth to target the dermis (Intradermal), epidermis (Epidermal), subcutaneous tissue (SC) or muscle (IM). Injection angle will vary based on targeted delivery site with injections targeting the intradermal site to be 10-15 degree angles from the plane of the surface of the skin, between 20-45 degrees from the plane of the surface of the skin for subcutaneous injections and angles of between 60-90 degrees for injections substantially into the muscle.

Example 16: Dose Response and Infection Site Selection and Timing

To determine the dose response trends, impact of injection site and impact of injection timing, studies are performed following the protocol outlined in Example 15. In these studies, varied doses of 1 ug, 5 ug, 10 ug, 25 ug, 50 ug, and values in between are used to determine dose response outcomes. Split dosing for a 100 ug total dose includes three or six doses of 1.6 ug, 4.2 ug, 8.3 ug, 16.6 ug, or values and total doses equal to administration of the total dose selected.

Injection sites are chosen from the limbs or any body surface presenting enough area suitable for injection. This may also include a selection of injection depth to target the dermis (Intradermal), epidermis (Epidermal), subcutaneous tissue (SC) or muscle (IM). Injection angle will vary based on targeted delivery site with injections targeting the intradermal site to be 10-15 degree angles from the plane of the surface of the skin, between 20-45 degrees from the plane of the surface of the skin for subcutaneous injections and angles of between 60-90 degrees for injections substantially into the muscle. RNAIMAX™

Example 17. Routes of Administration

Figure 7A:
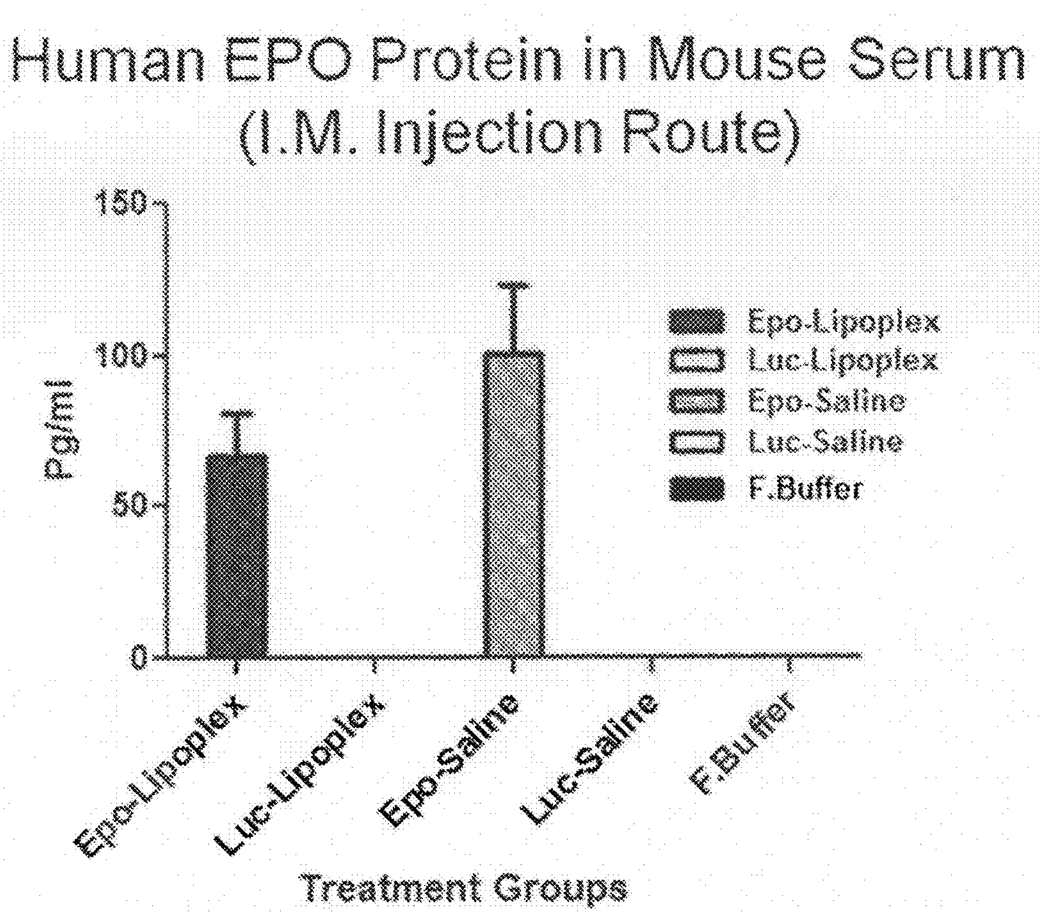
FIGS. 7A and 7B are histograms showing in vivo screening results of human erythropoietin in serum after the administration of modified human erythropoietin mmRNA or luciferase mmRNA in mice.
Figure 7B:
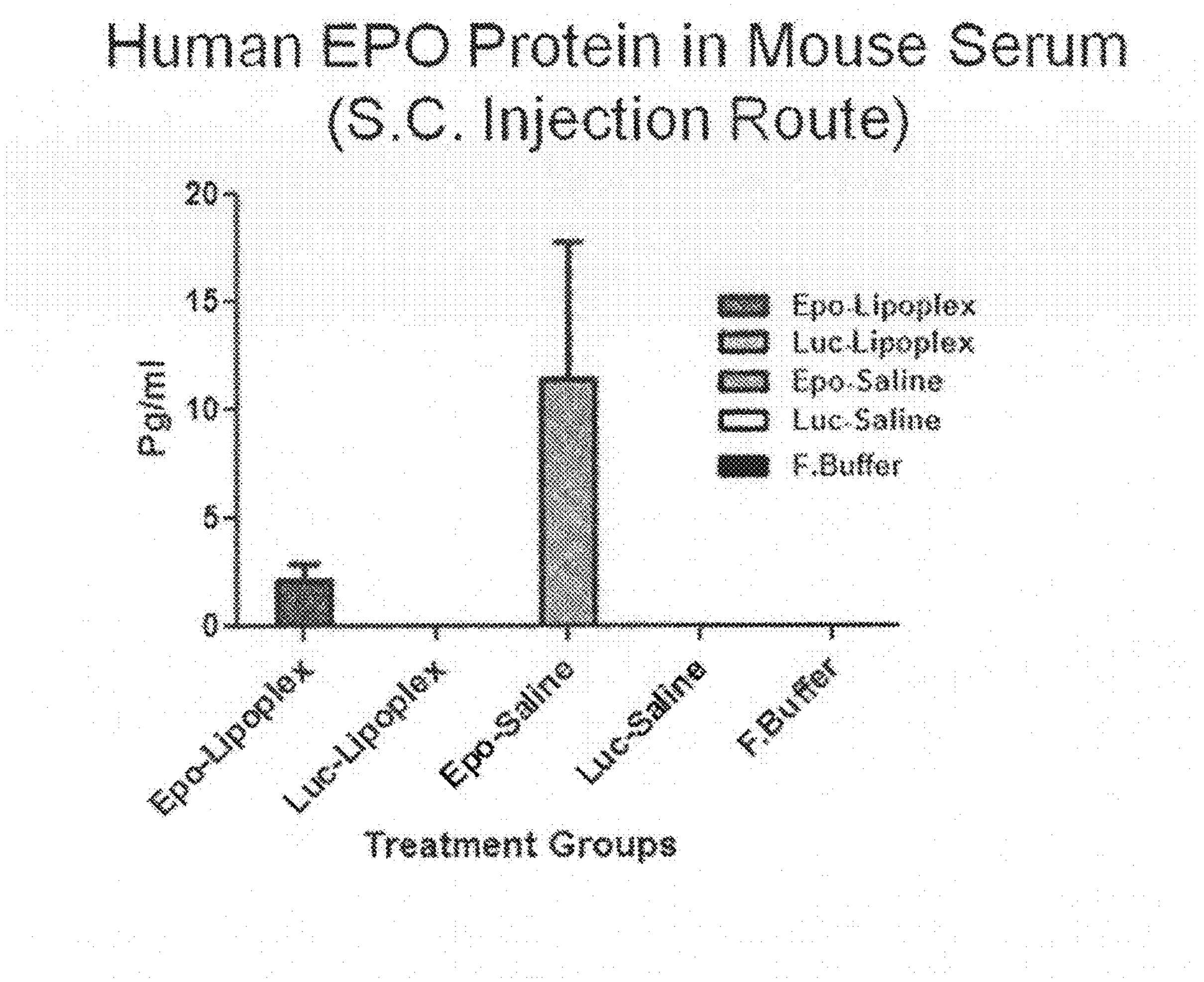

Further studies were performed to investigate dosing using different routes of administration. Following the protocol outlined in Example 15, 4 mice per group were dosed intramuscularly (I.M.), intravenously (IV) or subcutaneously (S.C.) by the dosing chart outlined in Table 8. Serum was collected 13 hours post injection from all mice, tissue was collected from the site of injection from the intramuscular and subcutaneous group and the spleen, liver and kidneys were collected from the intravenous group. The results from the intramuscular group are show in FIG. 7A and the subcutaneous group results are shown in FIG. 7B.

TABLE 8

| Dosing Chart | | | | | |
|---|---|---|---|---|---|
| Group | Treatment | Route | Dose of mmRNA | Total Dose | Dosing Vehicle |
| 1 | Lipoplex-human EPO mmRNA | I.M. | 4 × 100 ug + 30% Lipoplex | 4 × 70 ul | Lipoplex |
| 2 | Lipoplex-human EPO mmRNA | I.M. | 4 × 100 ug | 4 × 70 ul | Buffer |
| 3 | Lipoplex-human EPO mmRNA | S.C. | 4 × 100 ug + 30% Lipoplex | 4 × 70 ul | Lipoplex |
| 4 | Lipoplex-human EPO mmRNA | S.C. | 4 × 100 ug | 4 × 70 ul | Buffer |
| 5 | Lipoplex-human EPO mmRNA | I.V. | 200 ug + 30% Lipoplex | 140 ul | Lipoplex |
| 6 | Lipoplexed-Luciferase mmRNA | I.M. | 100 ug + 30% Lipoplex | 4 × 70 ul | Lipoplex |
| 7 | Lipoplexed-Luciferase mmRNA | I.M. | 100 ug | 4 × 70 ul | Buffer |
| 8 | Lipoplexed-Luciferase mmRNA | S.C. | 100 ug + 30% Lipoplex | 4 × 70 ul | Lipoplex |
| 9 | Lipoplexed-Luciferase mmRNA | S.C. | 100 ug | 4 × 70 ul | Buffer |
| 10 | Lipoplexed-human EPO mmRNA | I.V. | 200 ug + 30% Lipoplex | 140 ul | Lipoplex |
| 11 | Formulation Buffer | I.M. | 4x multi dosing | 4 × 70 ul | Buffer |

Example 18: In Vivo Delivery of Modified mRNA

Modified RNA was delivered to C57/BL6 mice intramuscularly, subcutaneously, or intravenously to evaluate the bio-distribution of modified RNA using luciferase. A formulation buffer used with all delivery methods contained 150 mM sodium chloride, 2 mM calcium chloride, 2 mM Na+-phosphate which included 1.4 mM monobasic sodium phosphate and 0.6 mM of dibasic sodium phosphate, and 0.5 mM ethylenediaminetetraacetic acid (EDTA) was adjusted using sodium hydroxide to reach a final pH of 6.5 before being filtered and sterilized. A 1× concentration was used as the delivery buffer. To create the lipoplexed solution delivered to the mice, in one vial 50 μg of RNA was equilibrated for 10 minutes at room temperature in the delivery buffer and in a second vial 10 μl RNAiMAX™ was equilibrated for 10 minutes at room temperature in the delivery buffer. After equilibrium, the vials were combined and delivery buffer was added to reach a final volume of 100 μl which was then incubated for 20 minutes at room temperature. Luciferin was administered by intraperitoneal injection (IP) at 150 mg/kg to each mouse prior to imaging during the plateau phase of the luciferin exposure curve which was between 15 and 30 minutes. To create luciferin, 1 g of D-luciferin potassium or sodium salt was dissolved in 66.6 ml of distilled phosphate buffer solution (DPBS), not containing Mg2+ or Ca2+, to make a 15 μg/ml solution. The solution was gently mixed and passed through a 0.2 μm syringe filter, before being purged with nitrogen, aliquoted and frozen at −80° C. while being protected from light as much as possible. The solution was thawed using a waterbath if luciferin was not dissolved, gently mixed and kept on ice on the day of dosing.

Whole body images were taken of each mouse 2, 8 and 24 hours after dosing. Tissue images and serum was collected from each mouse 24 hours after dosing. Mice administered doses intravenously had their liver, spleen, kidneys, lungs, heart, pen-renal adipose tissue and thymus imaged. Mice administered doses intramuscularly or subcutaneously had their liver, spleen, kidneys, lungs, pen-renal adipose tissue, and muscle at the injection site. From the whole body images the bioluminescence was measured in photon per second for each route of administration and dosing regimen.

A. Intramuscular Administration

Figure 8A:
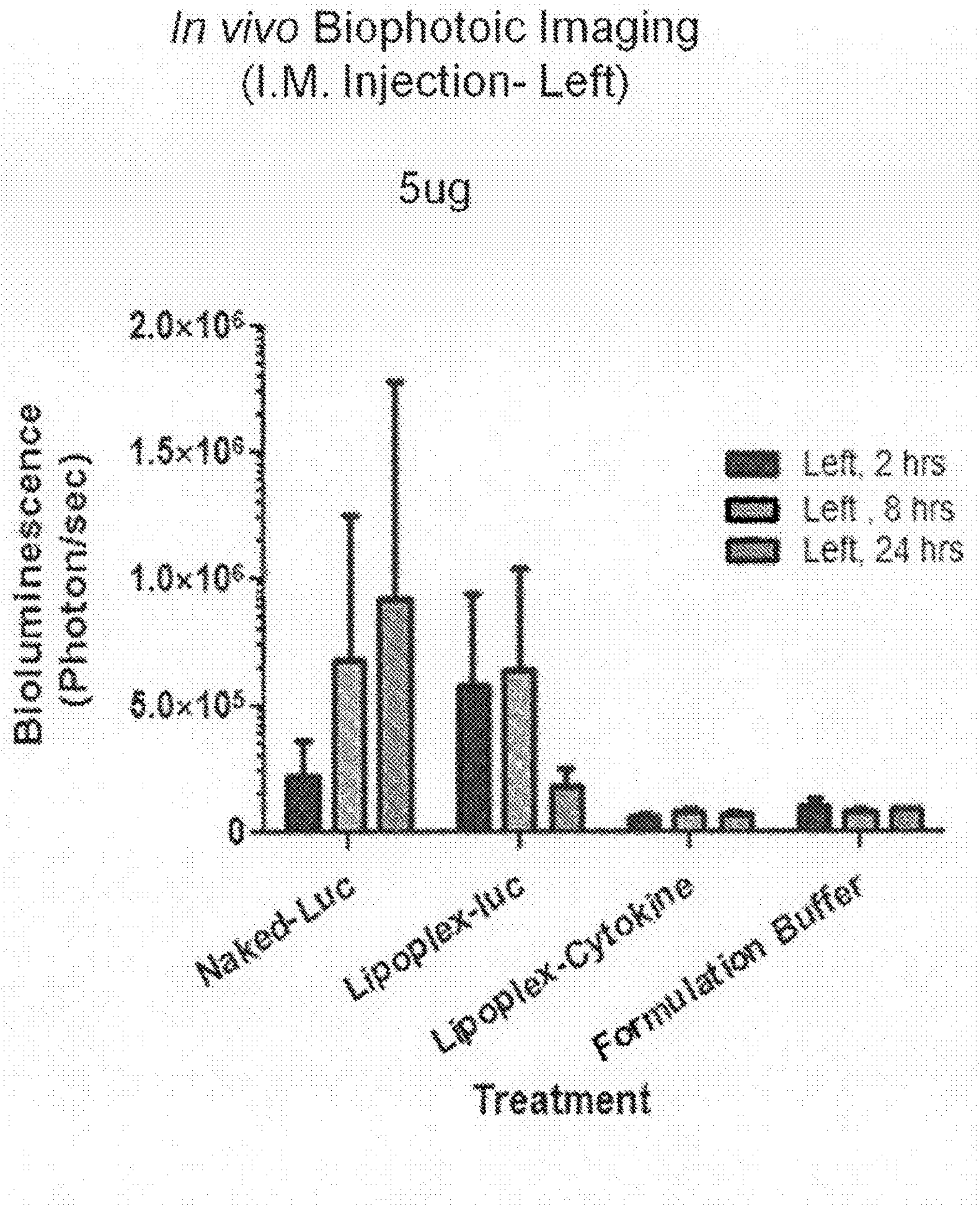
FIGS. 8A, 8B, 8C, and 8D are histograms of in vivo screening results from biophotoic imaging.
Figure 8B:
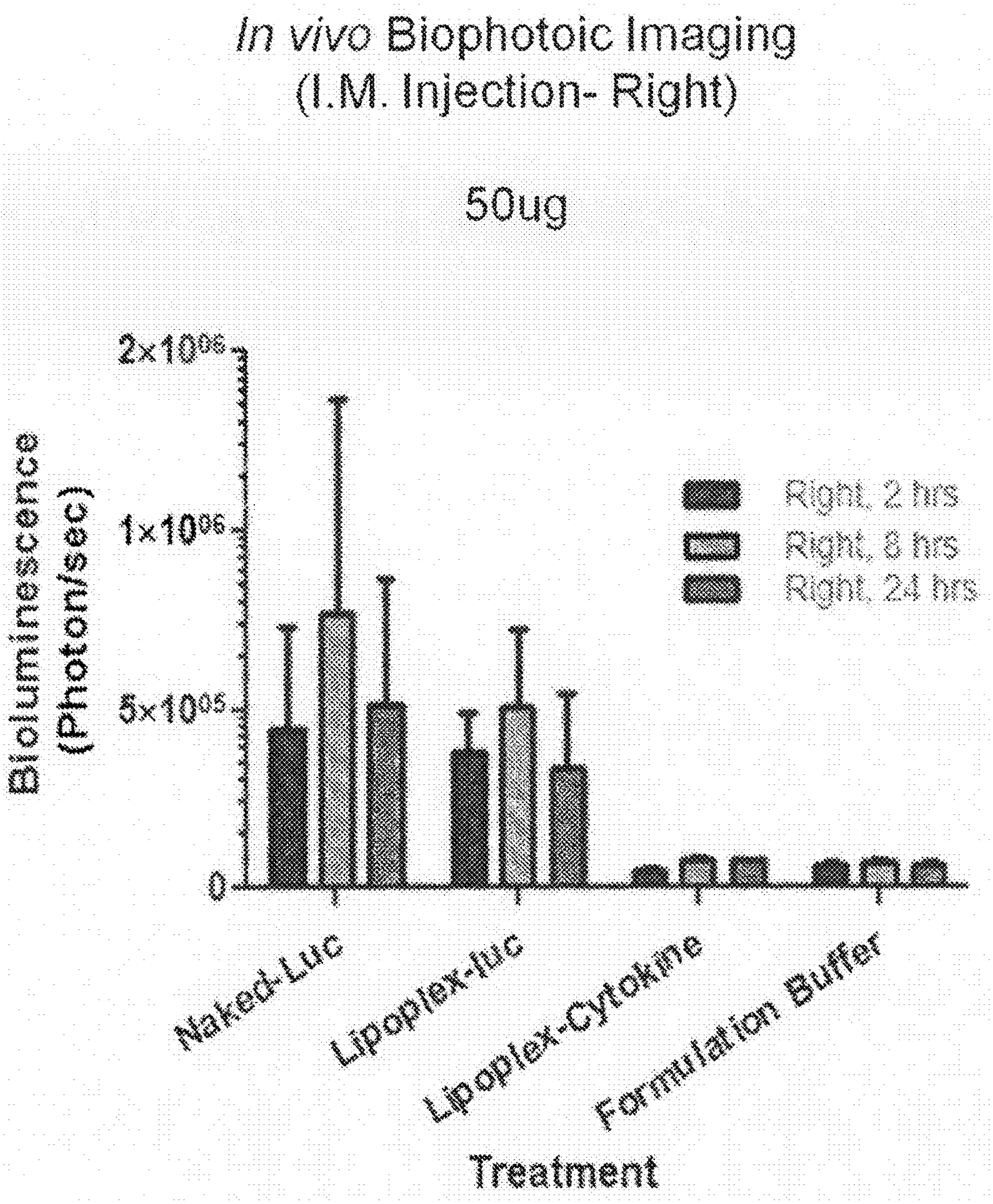

Mice were intramuscularly (I.M.) administered either modified luciferase mRNA (IVT cDNA sequence shown in SEQ ID NO: 10) (Naked-Luc), lipoplexed modified luciferase mRNA (Lipoplex-luc), lipoplexed modified granulocyte colony-stimulating factor (G-CSF) mRNA (mRNA sequence shown in SEQ ID NO: 4; poly-A tail of approximately 160 nucleotides not shown in sequence; 5' cap, Cap1) (Lipoplex-Cytokine) or the formation buffer at a single dose of 50 μg of modified RNA in an injection volume of 50 μl for each formulation in the right hind limb and a single dose of 5 μg of modified RNA in an injection volume of 50 μl in the left hind limb. The bioluminescence average for the luciferase expression signals for each group at 2, 8 and 24 hours after dosing are shown in FIG. 8A for the left hind limb and FIG. 8B for the right hind limb. The bioluminescence showed a positive signal at the injection site of the 5 μg and 50 μg modified RNA formulations containing and not containing lipoplex.

B. Subcutaneous Administration

Figure 8C:
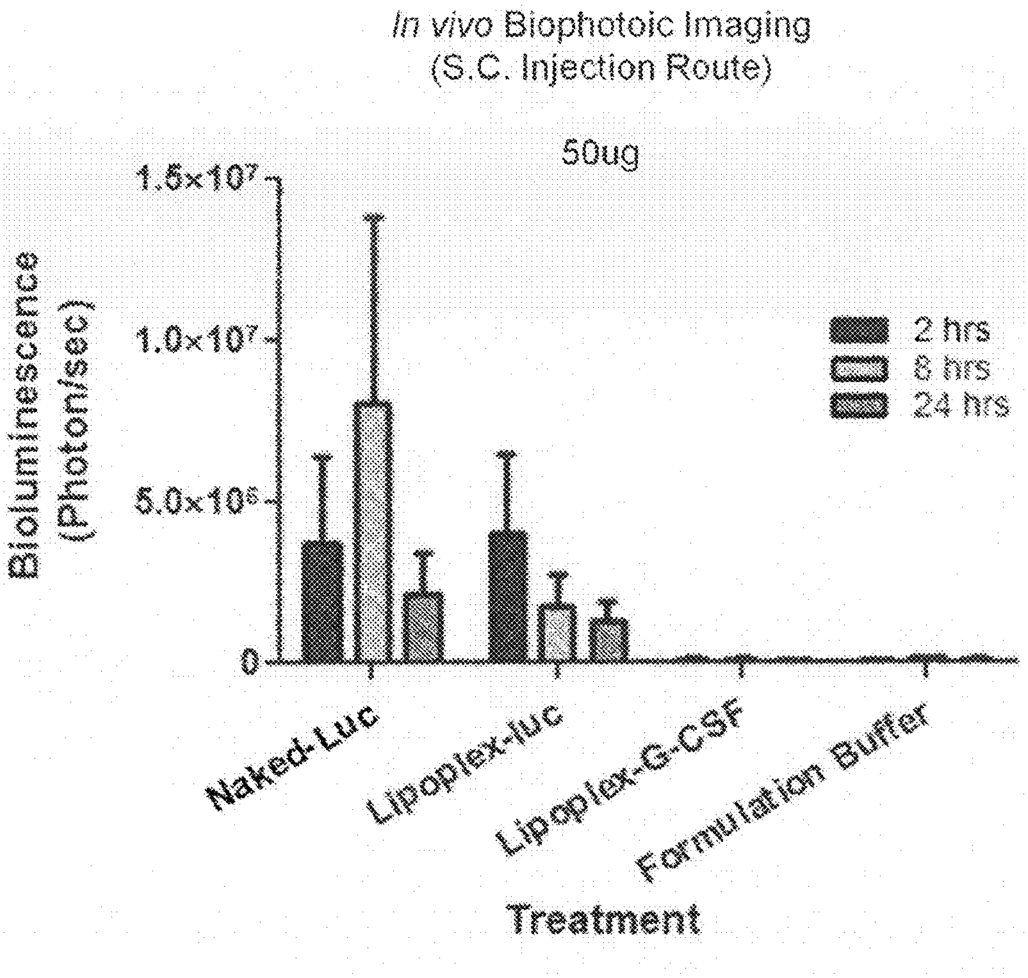

Mice were subcutaneously (S.C.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50)lg of modified mRNA in an injection volume of 100)ll for each formulation. The bioluminescence average for the luciferase expression signals for each group at 2, 8 and 24 hours after dosing are shown in FIG. 8C. The bioluminescence showed a positive signal at the injection site of the 50 μg modified mRNA formulations containing and not containing lipoplex.

C. Intravenous Administration

Figure 8D:
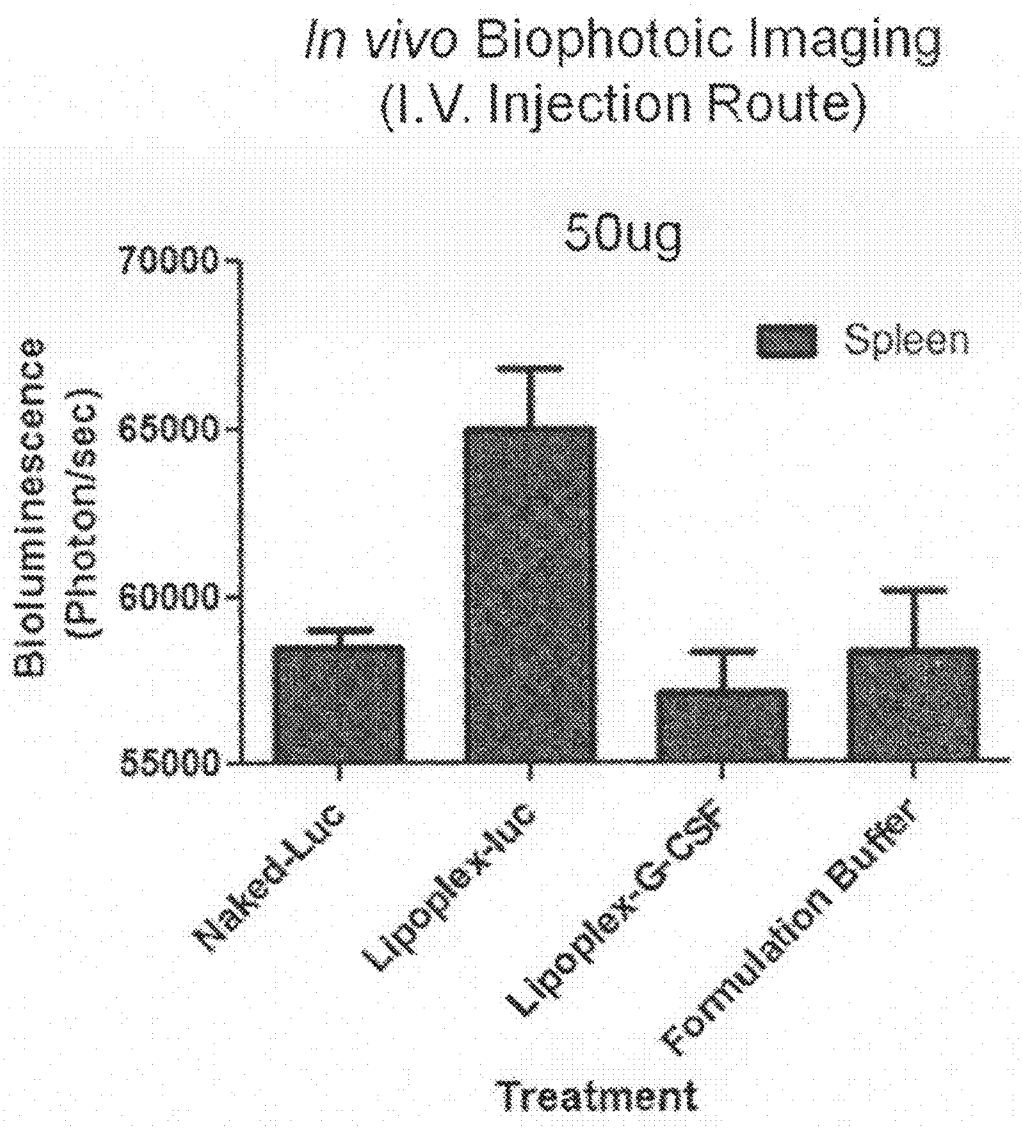

Mice were intravenously (I.V.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50 μg of modified mRNA in an injection volume of 100 μl for each formulation. The bioluminescence average for the luciferase expression signal in the spleen from each group at 2 hours after dosing is shown in FIG. 8D. The bioluminescence showed a positive signal in the spleen of the 50 μg modified mRNA formulations containing lipoplex.

Example 19: In Vivo Delivery Using Lipoplexes

A. Human EPO Modified RNA Lipoplex

Figure 9:
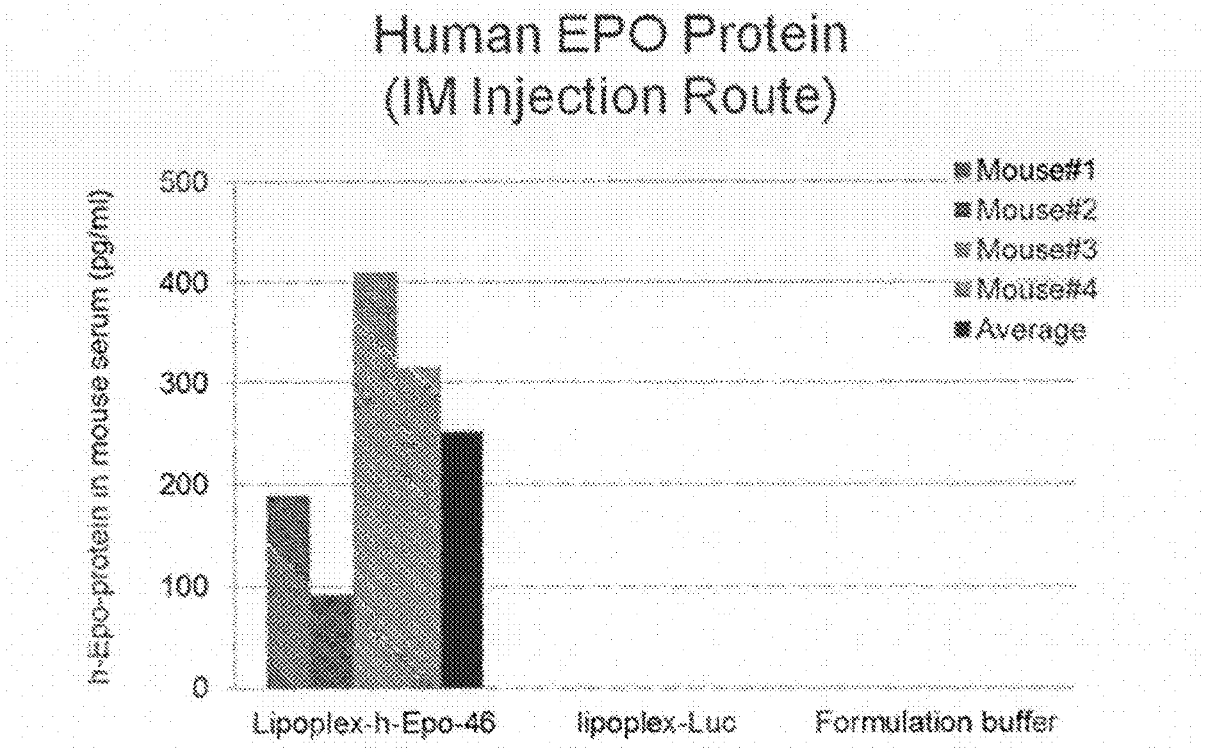
FIG. 9 is a histogram showing in vivo screening results for modified human G-CSF mmRNA administered intramuscularly, subcutaneously or intravenously in mice.

A formulation containing 100 μg of modified human erythropoietin mRNA (mRNA sequence shown in SEQ ID NO: 7; poly-A tail of approximately 160 nucleotides not shown in sequence; 5' cap, Cap1) (EPO; fully modified 5-methylcytosine; N1-methylpseudouridine) was lipoplexed with 30% by volume of RNAIMAX™ (Lipoplex-h-Epo-46; Generation 2 or Gen2) in 50-70 uL delivered intramuscularly to four C57/BL6 mice. Other groups consisted of mice receiving an injection of the lipoplexed modified luciferase mRNA (Lipoplex-luc) (IVT eDNA sequence shown in SEQ ID NO: 10) which served as a control containing 100 μg of modified luciferase mRNA was lipoplexed with 30% by volume of RNAIMAX™ or mice receiving an injection of the formulation buffer as negative control at a dose volume of 65 ul. 13 hours after the intramuscular injection, serum was collected from each mouse to measure the amount of human EPO protein in the mouse serum by human EPO ELISA and the results are shown in FIG. 9.

B. Human G-CSF Modified RNA Lipoplex

Figure 10:
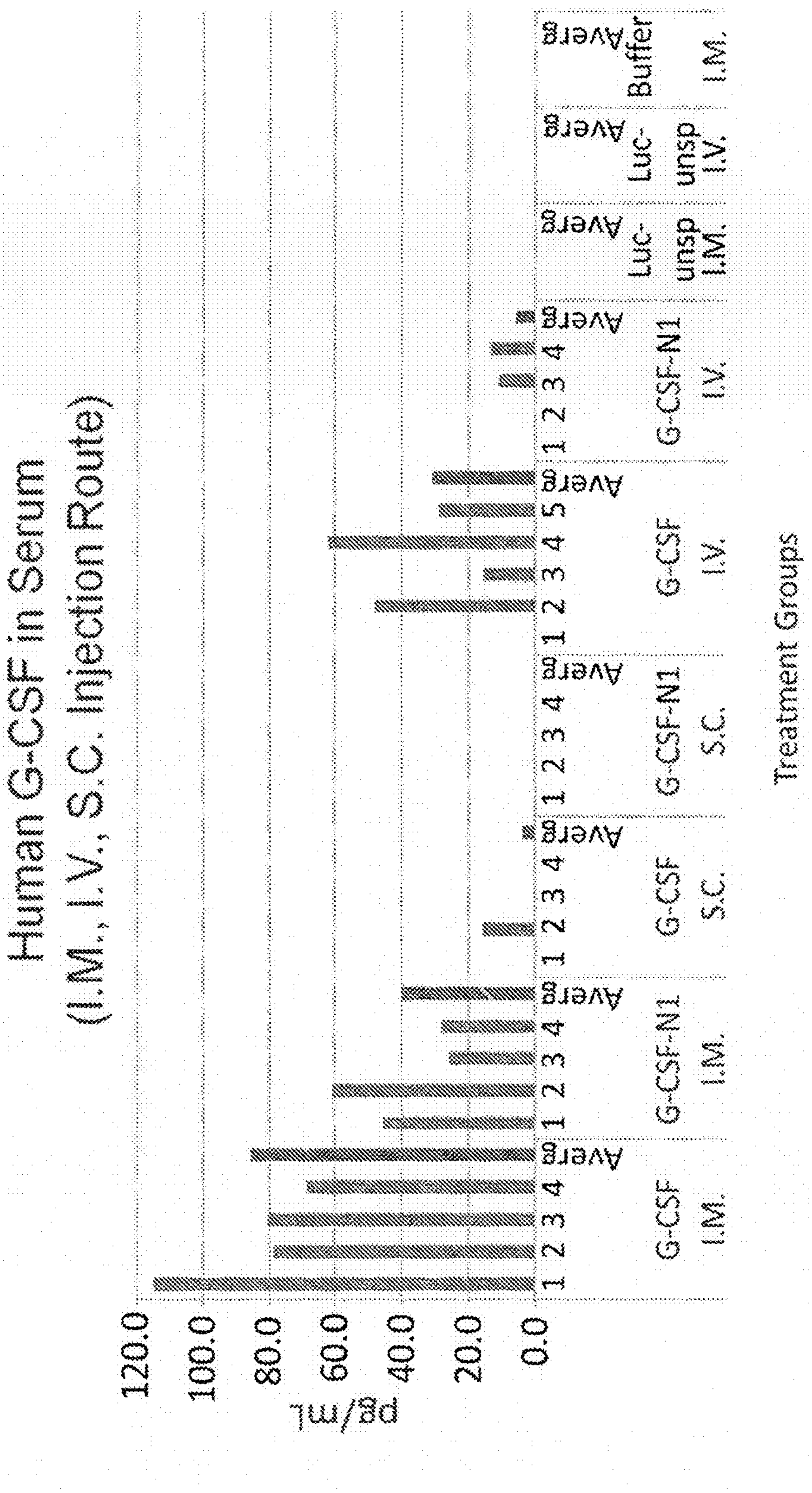
FIG. 10 is a histogram showing in vivo screening results for modified G-CSF administered intramuscularly, subcutaneously or intravenously.

A formulation containing 100 μg of one of the two types of modified human G-CSF mRNA (mRNA sequence shown in SEQ ID NO: 4; poly-A tail of approximately 160 nucleotides not shown in sequence; 5' cap, Cap1) (G-CSF fully modified with 5-methylcytosine and pseudouridine (G-CSF) or G-CSF fully modified with 5-methylcytosine and N1-methyl-pseudouridine (G-CSF-N1) lipoplexed with 30% by volume of RNAIMAX™ and delivered in 150 uL intramuscularly (I.M.), in 150 uL subcutaneously (S.C.) and in 225 uL intravenously (I.V.) to C57/BL6 mice. Three control groups were administered either 100 μg of modified luciferase mRNA (IVT cDNA sequence shown in SEQ ID NO: 10) intramuscularly (Luc-unsp I.M.) or 150 μg of modified luciferase mRNA intravenously (Luc-unsp I.V.) or 150 uL of the formulation buffer intramuscularly (Buffer I.M.). 6 hours after administration of a formulation, serum was collected from each mouse to measure the amount of human G-CSF protein in the mouse serum by human G-CSF ELISA and the results are shown in FIG. 10.

C. Human G-CSF Modified RNA Lipoplex Comparison

Figure 11A:
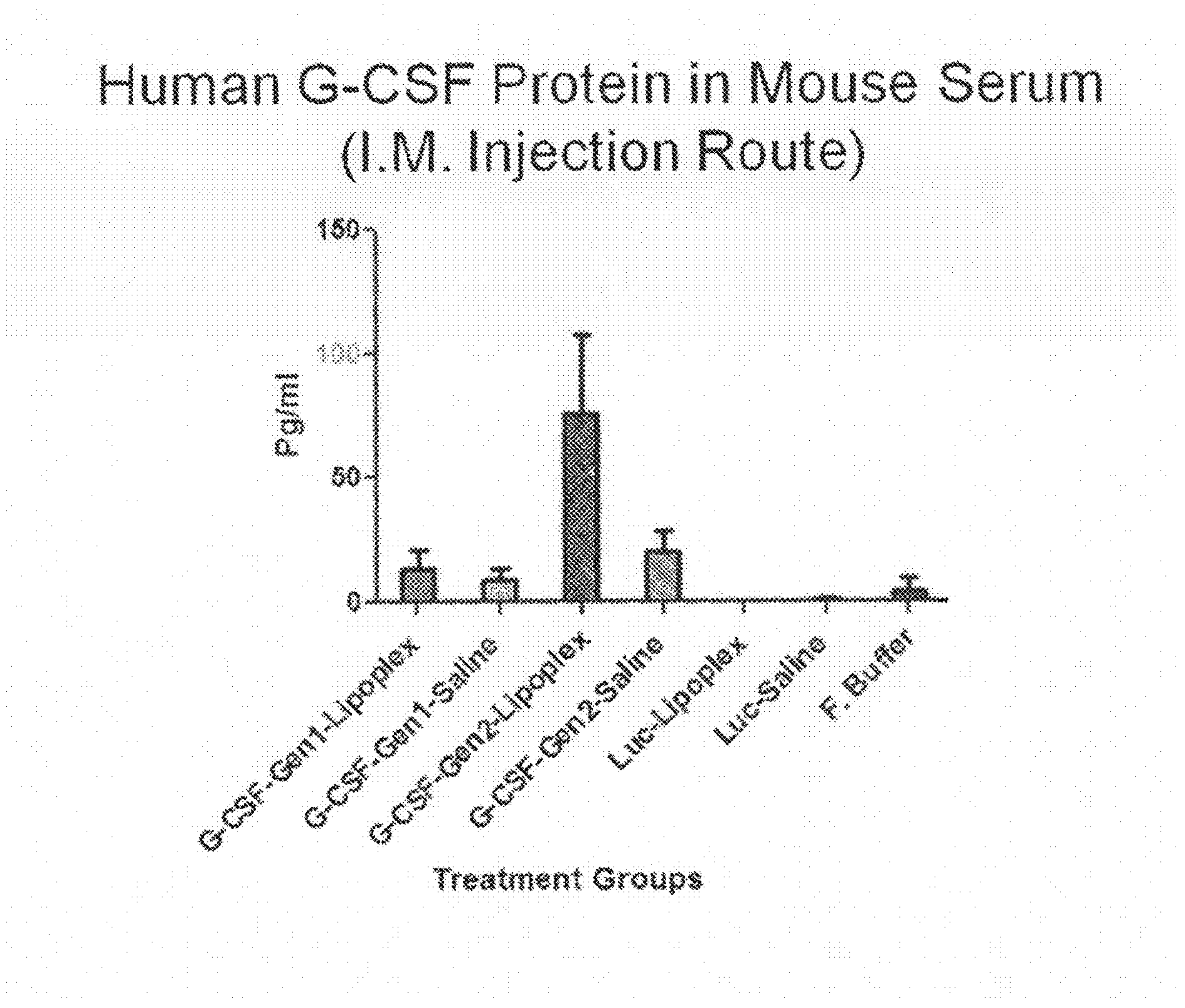
FIGS. 11A and 11B are histograms showing in vivo screening results of modified human G-CSF mmRNA administered intramuscularly or subcutaneously in mice.
Figure 11B:
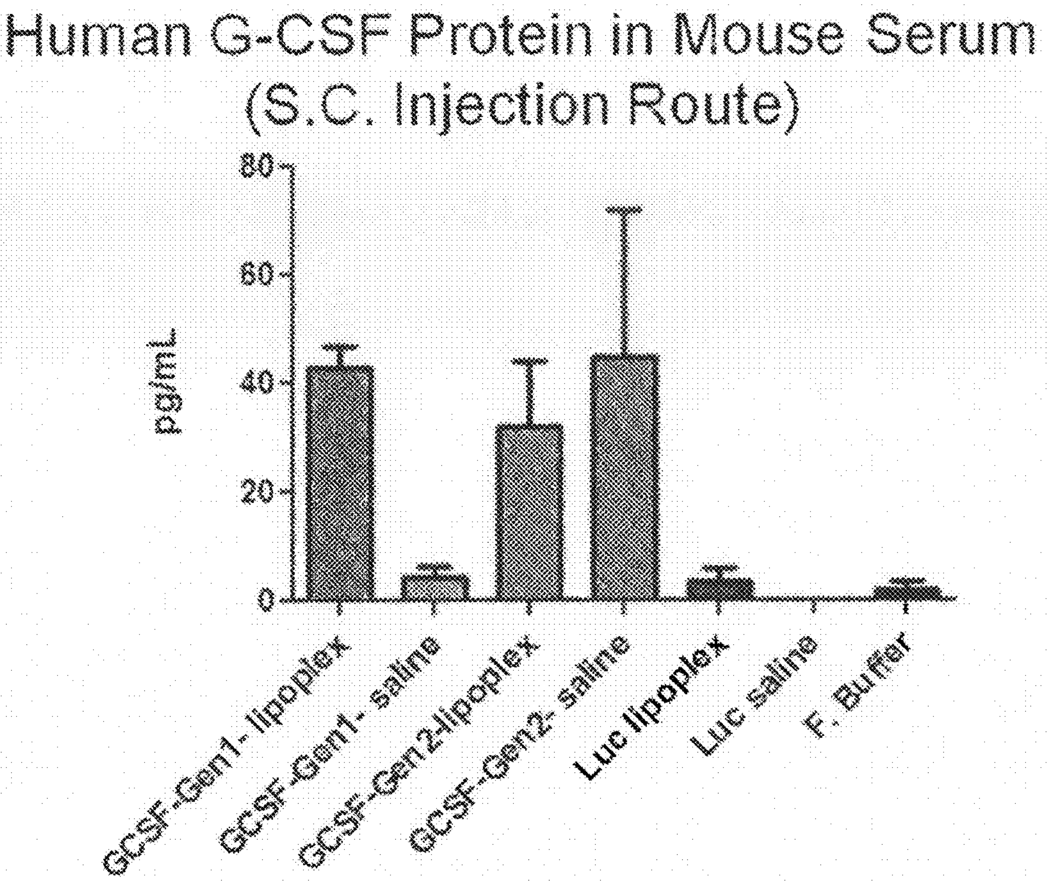

A formulation containing 100 μg of either modified human G-CSF mRNA lipoplexed with 30% by volume of RNAIMAX™ with a 5-methylcytosine (5mc) and a pseudouridine (ψ) modification (G-CSF-Gen1-Lipoplex), modified human G-CSF mRNA with a 5mc and ψ modification in saline (G-CSF-Gen1-Saline), modified human G-CSF mRNA with a N1-5-methylcytosine (N1-5mc) and a ψ modification lipoplexed with 30% by volume of RNAIMAX™ (G-CSF-Gen2-Lipoplex), modified human G-CSF mRNA with a N1-5mc and ψ modification in saline (G-CSF-Gen2-Saline), modified luciferase with a 5mc and ψ modification lipoplexed with 30% by volume of RNAIMAX™ (Luc-Lipoplex), or modified luciferase mRNA with a 5mc and ψ modification in saline (Luc-Saline) was delivered intramuscularly (I.M.) or subcutaneously (S.C.) and a control group for each method of administration was giving a dose of 80 uL of the formulation buffer (F. Buffer) to C57/BL6 mice. 13 hours post injection serum and tissue from the site of injection were collected from each mouse and analyzed by G-CSF ELISA to compare human G-CSF protein levels. The results of the human G-CSF protein in mouse serum from the intramuscular administration are shown in FIG. 11A, and the subcutaneous administration results are shown in FIG. 11B.

D. mCherry Modified RNA Lipoplex Comparison

Intramuscular and Subcutaneous Administration

A formulation containing 100 μg of either modified mCherry mRNA (mRNA sequence shown in SEQ ID NO: 5; poly-A tail of approximately 160 nucleotides not shown in sequence; 5' cap, Cap1) lipoplexed with 30% by volume of RNAIMAX™ or modified mCherry mRNA in saline is delivered intramuscularly and subcutaneously to mice. A formulation buffer is also administered to a control group of mice either intramuscularly or subcutaneously. The site of injection on the mice may be collected 17 hours post injection for sectioning to determine the cell type(s) responsible for producing protein.

Intravitreal Administration

A formulation containing 10 μg of either modified mCherry mRNA lipoplexed with RNAIMAX™, modified mCherry mRNA in a formulation buffer, modified luciferase mRNA lipoplexed with RNAMAX™, modified luciferase mRNA in a formulation buffer can be administered by intravitreal injection (IVT) in rats in a dose volume of 5

μl/eye. A formulation buffer is also administered by IVT to a control group of rats in a dose volume of 5 μl/eye. Eyes from treated rats can be collected after 18 hours post injection for sectioning and lysating to determine whether mmRNA can be effectively delivered in vivo to the eye and result in protein production, and to also determine the cell type(s) responsible for producing protein in vivo.

Intranasal Administration

A formulation containing 100 μg of either modified mCherry mRNA lipoplexed with 30% by volume of RNAIMAX™, modified mCherry mRNA in saline, modified luciferase mRNA lipoplexed with 30% by volume of RNAIMAX™ or modified luciferase mRNA in saline is delivered intranasally. A formulation buffer is also administered to a control group intranasally. Lungs may be collected about 13 hours post instillation for sectioning (for those receiving mCherry mRNA) or homogenization (for those receiving luciferase mRNA). These samples will be used to determine whether mmRNA can be effectively delivered in vivo to the lungs and result in protein production, and to also determine the cell type(s) responsible for producing protein in vivo.

Example 20: In Vivo Delivery Using Varying Lipid Ratios

Figure 12:
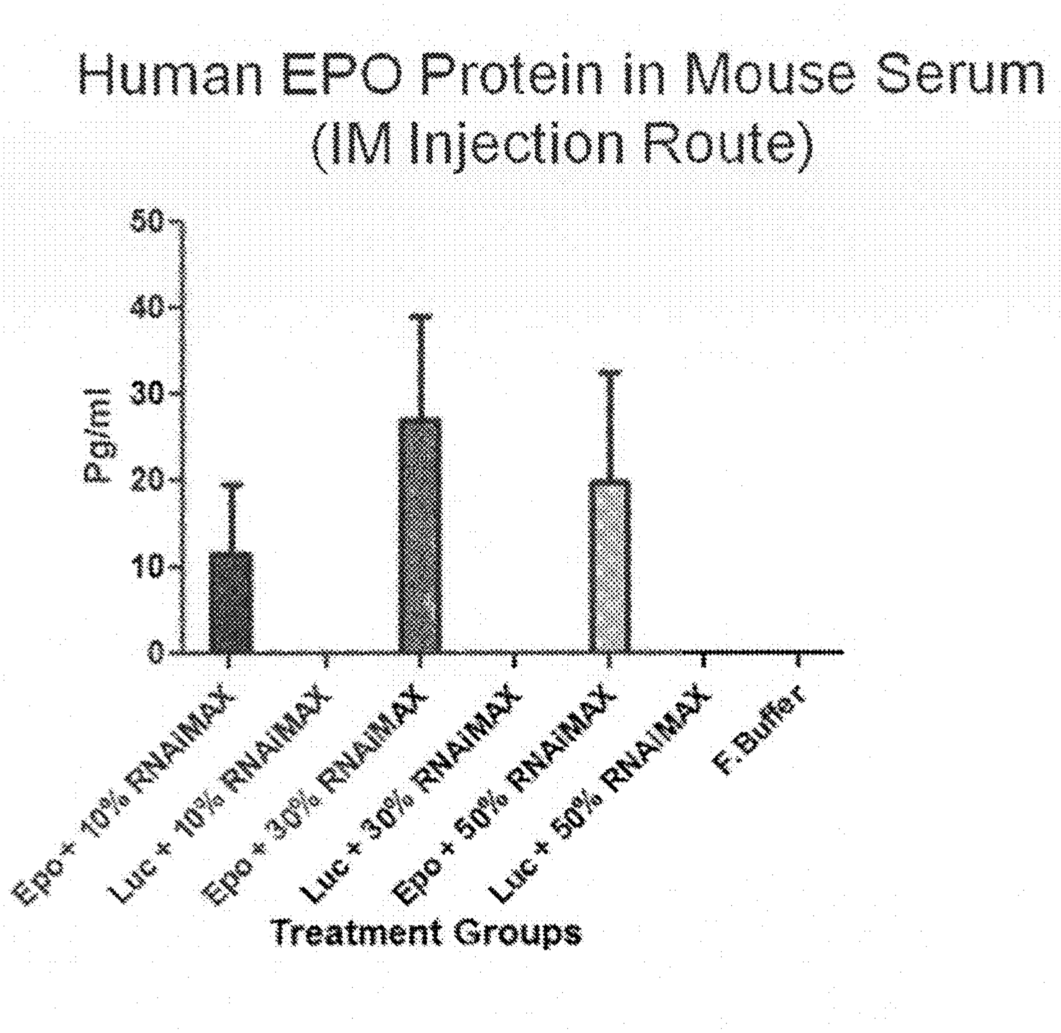
FIG. 12 is a histogram showing in vivo screening results of human erythropoietin in serum after the administration of modified human erythropoietin mmRNA or luciferase mmRNA administered intramuscularly in mice.

Modified mRNA was delivered to C57/BL6 mice to evaluate varying lipid ratios and the resulting protein expression. Formulations of 100 μg modified human EPO mRNA (mRNA sequence shown in SEQ ID NO: 7; poly-A tail of approximately 160 nucleotides not shown in sequence; 5' cap, Cap1) lipoplexed with 10%, 30% or 50% RNAIMAX™, 100 μg modified luciferase mRNA (IVT cDNA sequence shown in SEQ ID NO: 10) lipoplexed with 10%, 30% or 50% RNAIMAX™ or a formulation buffer were administered intramuscularly to mice in a single 70 μl dose. Serum was collected 13 hours post injection to undergo a human EPO ELISA to determine the human EPO protein level in each mouse. The results of the human EPO ELISA, shown in FIG. 12, show that modified human EPO expressed in the muscle is secreted into the serum for each of the different percentage of RNAIMAX™.

Example 21: Intramuscular and Subcutaneous In Vivo Delivery in Mammals

Modified human EPO mRNA (mRNA sequence shown in SEQ ID NO: 7; poly-A tail of approximately 160 nucleotides not shown in sequence; 5' cap, Cap1) formulated in saline was delivered to either C57/BL6 mice or Sprague-Dawley rats to evaluate the dose dependency on human EPO production. Rats were intramuscularly injected with 50 μl of the modified human EPO mRNA (h-EPO), modified luciferase mRNA (Luc) (IVT cDNA sequence shown in SEQ ID NO: 10) or the formulation buffer (F.Buffer) as described in the dosing chart Table 9.

Mice were intramuscularly or subcutaneously injected with 50 μl of the modified human EPO mRNA (h-EPO), modified luciferase mRNA (Luc) or the formulation buffer (F.Buffer) as described in the dosing chart Table 10. 13 hours post injection blood was collected and serum was analyzed to determine the amount human EPO for each mouse or rat. The average and geometric mean in pg/ml for the rat study are also shown in Table 9.

TABLE 9

| Rat Study | | | | | | | | | | |
|---|---|---|---|---|---|---|---|---|---|---|
| | Group | Dose | R#1 | R#2 | R#3 | R#4 | R#S | R#6 | Avg. pg/ml | Geometric-mean pg/ml |
| h-EPO | G#1 | 150 μg | 61.8 | 86.3 | 69.9 | 55.2 | 59 | 74.2 | 67.7 | 67.1 |
| h-EPO | G#2 | 100 μg | 69.4 | 77.8 | 48.2 | 17.6 | 101.9 | 161.5 | 79.4 | 66.9 |
| h-EPO | G#3 | 50 μg | 143.6 | 60.9 | 173.4 | 145.9 | 61.5 | 23.9 | 101.5 | 85.4 |
| h-EPO | G#4 | 10 μg | 7.8 | 11.8 | 30.9 | 36.2 | 40.6 | 150.3 | 46.3 | 31.2 |
| h-EPO | G#5 | 1 μg | 9.1 | 35.8 | — | 46.2 | 18.1 | 34.1 | 28.7 | 25.4 |
| Luc | G#6 | 100 μg | 34.1 | 36.5 | 13.5 | 13.7 | — | — | 24.5 | 22.4 |
| F. Buffer | G#7 | — | 14.7 | 18.5 | 21.2 | 20.3 | — | — | 18.7 | 18.5 |

TABLE 10

| Mouse Study | | | | |
|---|---|---|---|---|
| Route | Treatment | Group | Dose | Average Level in serum pg/ml |
| IM | h-EPO | 1 | 100 μg | 96.2 |
| IM | h-EPO | 2 | 50 μg | 63.5 |
| IM | h-EPO | 3 | 25 μg | 18.7 |
| IM | h-EPO | 4 | 10 μg | 25.9 |
| IM | h-EPO | 5 | 1 μg | 2.6 |
| IM | Luc | 6 | 100 μg | 0 |
| IM | F. Buffer | 7 | — | 1.0 |
| SC | h-EPO | 1 | 100 μg | 72.0 |
| SC | Luc | 2 | 100 μg | 26.7 |
| SC | F. Buffer | 3 | — | 17.4 |

Example 22: Duration of Activity after Intramuscular In Vivo Delivery in Rats Modified human EPO mRNA (mRNA sequence shown in SEQ ID NO: 7; poly-A tail of approximately 160 nucleotides not shown in sequence; 5' cap, Cap1) formulated in saline was delivered to Sprague-Dawley rats to determine the duration of the dose response. Rats were intramuscularly injected with 50 μl of the modified human EPO mRNA (h-EPO), modified luciferase mRNA (IVT cDNA sequence shown in SEQ ID NO: 10) (Luc) or the formulation buffer (F.Buffer) as described in the dosing chart Table 11. The rats were bled 2, 6, 12, 24, 48 and 72 hours after the intramuscular injection to determine the concentration of human EPO in serum at a given time. The average and geometric mean in pg/ml for this study are also shown in Table 11.

TABLE 11

| Dosing Chart | | | | | | | | | | | | |
|---|---|---|---|---|---|---|---|---|---|---|---|---|
| | Group | Dose | R#1 | R#2 | R#3 | R#4 | R#S | R#6 | R#7 | Avg. pg/ml | Geometric-mean pg/ml |
| h-EPO | 2 hour | 100 μg | 60.0 | 62.4 | 53.6 | 33.2 | 68.6 | 66.4 | 72.8 | 59.6 | 58.2 |
| h-EPO | 6 hour | 100 μg | 66.4 | 102.5 | 45.6 | 78.1 | 56.8 | 122.5 | 8.1 | 68.6 | 55.8 |
| h-EPO | 12 hour | 100 μg | 132.9 | 55.1 | 89.0 | 80.1 | 85.6 | 105.6 | 63.3 | 87.4 | 84.5 |
| h-EPO | 24 hour | 100 μg | 51.1 | 76.3 | 264.3 | 142.4 | 77.6 | 73.5 | 75.0 | 108.6 | 95.3 |
| h-EPO | 48 hour | 100 μg | 96.3 | 59.0 | 85.7 | 82.6 | 63.5 | 80.3 | — | 77.9 | 77.0 |
| h-EPO | 72 hour | 100 μg | 46.3 | 66.9 | 73.5 | 57.3 | 136.7 | 110 | 69.7 | 80.1 | 75.8 |
| Luc | 24, 48 and 72 hour | 100 μg | 60.2 | 38.5 | 48.8 | 46.1 | 3.6 | 26.1 | — | 37.2 | 29.2 |
| F. Buffer | 24, 48 and 72 hour | — | 50.0 | 10.0 | 80.9 | 54.7 | — | — | — | 48.9 | 10.4 |

Example 23. In Vitro Transfection of VEGF-A

Human vascular endothelial growth factor-isoform A (VEGF-A) modified mRNA (mRNA sequence shown in SEQ ID NO: 12; poly-A tail of approximately 160 nucleotides not shown in sequence; 5' cap, Cap1) was transfected via reverse transfection in Human Keratinocyte cells in 24 multi-well plates. Human Keratinocytes cells were grown in EPILIFE® medium with Supplement S7 from Invitrogen (Carlsbad, Calif.) until they reached a confluence of 50-70%. The cells were transfected with 0, 46.875, 93.75, 187.5, 375, 750, and 1500 ng of modified mRNA (mmRNA) encoding VEGF-A which had been complexed with RNAIMAX™ from Invitrogen (Carlsbad, Calif.). The RNA: RNAIMAX™ complex was formed by first incubating the RNA with Supplement-free EPILIFE® media in a 5× volumetric dilution for 10 minutes at room temperature. In a second vial, RNAIMAX™ reagent was incubated with Supplement-free EPILIFE® Media in a 10× volumetric dilution for 10 minutes at room temperature. The RNA vial was then mixed with the RNAIMAX™ vial and incubated for 20-30 minutes at room temperature before being added to the cells in a drop-wise fashion.

The fully optimized mRNA encoding VEGF-A transfected with the Human Keratinocyte cells included modifications during translation such as natural nucleoside triphosphates (NTP), pseudouridine at each uridine site and 5-methylcytosine at each cytosine site (pseudo-U/5mC), and N1-methyl-pseudouridine at each uridine site and 5-methylcytosine at each cytosine site (N1-methyl-Pseudo-U/5mC). Cells were transfected with the mmRNA encoding VEGF-A and secreted VEGF-A concentration (pg/ml) in the culture medium was measured at 6, 12, 24, and 48 hours post-transfection for each of the concentrations using an ELISA kit from Invitrogen (Carlsbad, Calif.) following the manufacturers recommended instructions. These data, shown in Table 12, show that modified mRNA encoding VEGF-A is capable of being translated in Human Keratinocyte cells and that VEGF-A is transported out of the cells and released into the extracellular environment.

TABLE 12

| VEGF-A Dosing and Protein Secretion | | | | |
|---|---|---|---|---|
| Dose (ng) | 6 hours (pg/ml) | 12 hours (pg/ml) | 24 hours (pg/ml) | 48 hours (pg/ml) |
| VEGF-A Dose Containing Natural NTPs | | | | |
| 46.875 | 10.37 | 18.07 | 33.90 | 67.02 |
| 93.75 | 9.79 | 20.54 | 41.95 | 65.75 |
| 187.5 | 14.07 | 24.56 | 45.25 | 64.39 |
| 375 | 19.16 | 37.53 | 53.61 | 88.28 |

TABLE 12-continued

| VEGF-A Dosing and Protein Secretion | | | | |
|---|---|---|---|---|
| Dose (ng) | 6 hours (pg/ml) | 12 hours (pg/ml) | 24 hours (pg/ml) | 48 hours (pg/ml) |
| 750 | 21.51 | 38.90 | 51.44 | 61.79 |
| 1500 | 36.11 | 61.90 | 76.70 | 86.54 |
| VEGF-A Dose Containing Pseudo-U/5 mC | | | | |
| 46.875 | 10.13 | 16.67 | 33.99 | 72.88 |
| 93.75 | 11.00 | 20.00 | 46.47 | 145.61 |
| 187.5 | 16.04 | 34.07 | 83.00 | 120.77 |
| 375 | 69.15 | 188.10 | 448.50 | 392.44 |
| 750 | 133.95 | 304.30 | 524.02 | 526.58 |
| 1500 | 198.96 | 345.65 | 426.97 | 505.41 |
| VEGF-A Dose Containing N1-methyl-Pseudo-U/5 mC | | | | |
| 46.875 | 0.03 | 6.02 | 27.65 | 100.42 |
| 93.75 | 12.37 | 46.38 | 121.23 | 167.56 |
| 187.5 | 104.55 | 365.71 | 1025.41 | 1056.91 |
| 375 | 605.89 | 1201.23 | 1653.63 | 1889.23 |
| 750 | 445.41 | 1036.45 | 1522.86 | 1954.81 |
| 1500 | 261.61 | 714.68 | 1053.12 | 1513.39 |

Example 24. In Vivo Studies of Factor IX

Human Factor IX mmRNA (mRNA shown in SEQ ID NO: 8; poly-A tail of approximately 160 nucleotides not shown in sequence; 5' cap, Cap1) (Gent; fully modified 5-methycytosine and pseudouridine) formulated in saline was delivered to mice via intramuscular injection. The results demonstrate that Factor IX protein was elevated in serum as measured 13 hours after administration.

In this study, mice (N=5 for Factor IX, N=3 for Luciferase or Buffer controls) were intramuscularly injected with 50 μl of the Factor IX mmRNA (mRNA sequence shown in SEQ ID NO: 8; poly-A tail of approximately 160 nucleotides not shown in sequence; 5' cap, Cap1), Luciferase (cDNA sequence for IVT shown in SEQ ID NO: 10) or the formulation buffer (F.Buffer) at 2×100 ug/mouse. The mice were bled at 13 hours after the intramuscular injection to determine the concentration of human the polypeptide in serum in pg/mL. The results revealed that administration of Factor IX mmRNA resulted in levels of 1600 pg/mL at 13 hours as compared to less than 100 pg/mL of Factor IX for either Luciferase or buffer control administration.

Example 24. Multi-Site Administration: Intramuscular and Subcutaneous

Human G-CSF mmRNA (mRNA sequence shown in SEQ ID NO: 4; poly-A tail of approximately 160 nucleotides not shown in sequence; 5' cap, Cap1) modified as either Gent or Gen2 (5-methylcytosine (5mc) and a pseudouridine (ψ) modification, G-CSF-Gen1; or N1-5-methylcytosine (N1-5mc) and a ψ modification, G-CSF-Gen2) and formulated in saline were delivered to mice via intramuscular (IM) or subcutaneous (SC) injection. Injection of four doses or 2×50 ug (two sites) daily for three days (24 hrs interval) was performed. The fourth dose was administered 6 hrs before blood collection and CBC analysis. Controls included Luciferase (cDNA sequence for IVT shown in SEQ ID NO: 10) or the formulation buffer (F.Buffer). The mice were bled at 72 hours after the first mmRNA injection (6 hours after the last mmRNA dose) to determine the effect of mmRNA-encoded human G-CSF on the neutrophil count. The dosing regimen is shown in Table 13 as are the resulting neutrophil counts (thousands/uL). Asterisks indicate statistical significance at p<0.05.

For intramuscular administration, the data reveal a four fold increase in neutrophil count above control at day 3 for the Gent G-CSF mmRNA and a two fold increase for the Gen2 G-CSF mmRNA. For subcutaneous administration, the data reveal a two fold increase in neutrophil count above control at day 3 for the Gen2 G-CSF mmRNA.

TABLE 13

| Dosing Regimen | | | | | | | |
|---|---|---|---|---|---|---|---|
| Gr. | Treatment | Route | N= | Dose (μg/mouse) | Dose Vol. (μl/mouse) | Dosing Vehicle | Neutrophil Thous/uL |
| 1 | G-CSF (Gen1) | I.M | 5 | 2 × 50 ug (four doses) | 50 | F. buffer | 840* |
| 2 | G-CSF (Gen1) | S.C | 5 | 2 × 50 ug (four doses) | 50 | F. buffer | 430 |
| 3 | G-CSF (Gen2) | I.M | 5 | 2 × 50 ug (four doses) | 50 | F. buffer | 746* |
| 4 | G-CSF (Gen2) | S.C | 5 | 2 × 50 ug (four doses) | 50 | F. buffer | 683 |
| 5 | Luc (Gen1) | I.M. | 5 | 2 × 50 ug (four doses) | 50 | F. buffer | 201 |
| 6 | Luc (Gen1) | S.C. | 5 | 2 × 50 ug (four doses) | 50 | F. buffer | 307 |
| 7 | Luc (Gen2) | I.M | 5 | 2 × 50 ug (four doses) | 50 | F. buffer | 336 |
| 8 | Luc (Gen2) | S.C | 5 | 2 × 50 ug (four doses) | 50 | F. buffer | 357 |
| 9 | F. Buffer | I.M | 4 | 0 (four doses) | 50 | F. buffer | 245 |
| 10 | F. Buffer | S.C. | 4 | 0 (four doses) | 50 | F. buffer | 509 |
| 11 | Untreated | — | 4 | | | — | 312 |

Example 26. Intravenous Administration

Human G-CSF mmRNA (mRNA sequence shown in SEQ ID NO: 4; poly-A tail of approximately 160 nucleotides not shown in sequence; 5' cap, Cap1) modified with 5-methylcytosine (5mc) and a pseudouridine (ψ) modification; or having no modifications and formulated in 10% lipoplex (RNAIMAX™) were delivered to mice at a dose of 50 ug RNA and in a volume of 100 ul via intravenous (IV) injection at days 0, 2 and 4. Neutrophils were measured at days 1, 5 and 8. Controls included non-specific mammalian RNA or the formulation buffer alone (F.Buffer). The mice were bled at days 1, 5 and 8 to determine the effect of mmRNA-encoded human G-CSF to increase neutrophil count. The dosing regimen is shown in Table 14 as are the resulting neutrophil counts (thousands/uL; K/uL).

For intravenous administration, the data reveal a four to five fold increase in neutrophil count above control at day 5 with G-CSF mmRNA but not with unmodified G-CSF mRNA or non-specific controls. Blood count returned to baseline four days after the final injection. No other changes in leukocyte populations were observed.

An asterisk indicates statistical significance at p<0.001 compared to buffer.

TABLE 14

| Dosing Regimen | | | | | |
|---|---|---|---|---|---|
| Gr. | Treatment | N = | Dose Vol. (μl/mouse) | Dosing Vehicle | Neutrophil K/uL |
| 1 | G-CSF (Gen1) Day 1 | 5 | 100 | 10% lipoplex | 2.91 |
| 2 | G-CSF (Gen1) Day 5 | 5 | 100 | 10% lipoplex | 5.32* |
| 3 | G-CSF (Gen1) Day 8 | 5 | 100 | 10% lipoplex | 2.06 |
| 4 | G-CSF (no modification) Day 1 | 5 | 100 | 10% lipoplex | 1.88 |
| 5 | G-CSF (no modification) Day 5 | 5 | 100 | 10% lipoplex | 1.95 |
| 6 | G-CSF (no modification) Day 8 | 5 | 100 | 10% lipoplex | 2.09 |
| 7 | RNA Control Day 1 | 5 | 100 | 10% lipoplex | 2.90 |
| 8 | RNA Control Day 5 | 5 | 100 | 10% lipoplex | 1.68 |
| 9 | RNA Control Day 8 | 4 | 100 | 10% lipoplex | 1.72 |
| 10 | F. Buffer Day 1 | 4 | 100 | 10% lipoplex | 2.51 |
| 11 | F. Buffer Day 5 | 4 | 100 | 10% lipoplex | 1.31 |
| 12 | F. Buffer Day 8 | 4 | 100 | 10% lipoplex | 1.92 |

Example 27. Saline Formulation: Intramuscular Administration

Human G-CSF mmRNA (mRNA sequence shown in SEQ ID NO: 4; poly-A tail of approximately 160 nucleotides not shown in sequence; 5' cap, Cap1) and human EPO mmRNA (mRNA sequence shown in SEQ ID NO: 7; poly-A tail of approximately 160 nucleotides not shown in sequence; 5' cap, Cap1); G-CSF mmRNA (modified with 5-methylcytosine (5mc) and pseudouridine (ψ)) and EPO mmRNA (modified with N1-5-methylcytosine (N1-5mc) and ψ modification), were formulated in saline and delivered to mice via intramuscular (IM) injection at a dose of 100 ug.

Controls included Luciferase (IVT cDNA sequence shown in SEQ ID NO: 10) or the formulation buffer (F.Buffer). The mice were bled at 13 hours after the injection to determine the concentration of the human polypeptide in serum in pg/mL (G-CSF groups measured human G-CSF in mouse serum and EPO groups measured human EPO in mouse serum). The data are shown in Table 15.

TABLE 15

| Dosing Regimen | | | | | |
|---|---|---|---|---|---|
| Group | Treatment | N = | Dose Vol. (μl/mouse) | Dosing Vehicle | Average Protein Product pg/mL, serum |
| G-CSF | G-CSF | 5 | 50 | Saline | 19.8 |
| G-CSF | Luciferase | 5 | 50 | Saline | 0.5 |
| G-CSF | F. buffer | 5 | 50 | F. buffer | 0.5 |
| EPO | EPO | 5 | 50 | Saline | 191.5 |
| EPO | Luciferase | 5 | 50 | Saline | 15.0 |
| EPO | F. buffer | | | F. buffer | 4.8 |

Example 28. EPO Multi-Dose/Multi-Administration

Studies utilizing multiple intramuscular injection sites at one time point were designed and performed.

The design of a single multi-dose experiment involved using human erythropoietin (EPO) mmRNA (mRNA sequence shown in SEQ ID NO: 7; poly-A tail of approximately 160 nucleotides not shown in sequence; 5' cap, Cap1) or G-CSF (mRNA sequence shown in SEQ ID NO: 4; poly-A tail of approximately 160 nucleotides not shown in sequence; 5' cap, Cap1) administered in saline. The dosing vehicle (F. buffer) was used as a control. The EPO and G-CSF mmRNA were modified with 5-methylcytosine at each cytosine and pseudouridine replacement at each uridine site.

Animals (n=5), Sprague-Dawley rats, were injected IM (intramuscular) for the single unit dose of 100 ug (delivered to one thigh). For multi-dosing 6 doses of 100 ug (delivered to two thighs) were used for both EPO and G-CSF mmRNA. Control dosing involved use of buffer at a single dose. Human EPO blood levels were evaluated 13 hours post injection.

Human EPO protein was measured in rat serum 13 hours post I.M. Five groups of rats were treated and evaluated. The results are shown in Table 16.

TABLE 16

| Multi-dose study | | | | |
|---|---|---|---|---|
| Group | Treatment | Dose of mmRNA | Total Dose | Avg. Pg/mL human EPO, serum |
| 1 | Human EPO mmRNA | 1 × 100 ug | 100 ug | 143 |
| 2 | Human EPO mmRNA | 6 × 100 ug | 600 ug | 256 |
| 3 | G-CSFmmRNA | 1 × 100 ug | 100 ug | 43 |
| 4 | G-CSFmmRNA | 6 × 100 ug | 600 ug | 58 |
| 5 | Buffer Alone | — | — | 20 |

Example 29. Signal Sequence Exchange Study

Several variants of mmRNAs encoding human Granulocyte colony stimulating factor (G-CSF) (mRNA sequence shown in SEQ ID NO: 4; poly-A tail of approximately 160 nucleotides not shown in sequence; 5' cap, Cap1) were synthesized using modified nucleotides pseudouridine and 5-methylcytosine (pseudo-U/5mC). These variants included the G-CSF constructs encoding either the wild-type N terminal secretory signal peptide sequence (MAGPATQSP-MKLMALQLLLWHSALWTVQEA; SEQ ID NO: 13), no secretory signal peptide sequence, or secretory signal peptide sequences taken from other mRNAs. These included sequences where the wild type GCSF signal peptide sequence was replaced with the signal peptide sequence of either: human a-1-anti trypsin (MMPSSVSWGILLLAGL-CCLVPVSLA; SEQ ID NO: 14), human Factor IX (MQRVNMIMAESPSLITICLLGYLLSAECTVFLD-HENANKILNRPKR; SEQ ID NO: 15), human Prolactin (MKGSLLLLLVSNLLLCQSVAP; SEQ ID NO: 16), or human Albumin (MKWVTFISLLFLFSSAYSRGVFRR; SEQ ID NO: 17).

250 ng of modified mRNA encoding each G-CSF variant was transfected into HEK293A (293A in the table), mouse myoblast (MM in the table) (C2C12, CRL-1772, ATCC) and rat myoblast (RM in the table) (L6line, CRL-1458, ATCC) cell lines in a 24 well plate using 1 ul of Lipofectamine 2000 (Life Technologies), each well containing 300,000 cells. The supernatants were harvested after 24 hrs and the secreted G-CSF protein was analyzed by ELISA using the Human G-CSF ELISA kit (Life Technologies). The data shown in Table 17 reveal that cells transfected with G-CSF mmRNA encoding the Albumin signal peptide secrete at least 12 fold more G-CSF protein than its wild type counterpart.

TABLE 17

| Signal Peptide Exchange | | | |
|---|---|---|---|
| | 293A (pg/ml) | MM (pg/ml) | RM (pg/ml) |
| G-CSF Natural | 9650 | 3450 | 6050 |
| α-1-anti trypsin | 9950 | 5000 | 8475 |
| Factor IX | 11675 | 6175 | 11675 |
| Prolactin | 7875 | 1525 | 9800 |
| Albumin | 122050 | 81050 | 173300 |
| No signal peptide | 0 | 0 | 0 |

Example 30. Cytokine Study: PBMC

PBMC Isolation and Culture:

50 mL of human blood from two donors was received from Research Blood Components (lots KP30928 and KP30931) in sodium heparin tubes. For each donor, the blood was pooled and diluted to 70 mL with DPBS (SAFC Bioscience 59331C, lot 071M8408) and split evenly between two 50 mL conical tubes. 10 mL of Ficoll Paque (GE Healthcare 17-5442-03, lot 10074400) was gently dispensed below the blood layer. The tubes were centrifuged at 2000 rpm for 30 minutes with low acceleration and braking. The tubes were removed and the buffy coat PMBC layers were gently transferred to a fresh 50 mL conical and washed with DPBS. The tubes were centrifuged at 1450 rpm for 10 minutes.

The supernatant was aspirated and the PBMC pellets were resuspended and washed in 50 mL of DPBS. The tubes were centrifuged at 1250 rpm for 10 minutes. This wash step was repeated, and the PBMC pellets were resuspended in 19 mL of Optimem I (Gibco 11058, lot 1072088) and counted. The cell suspensions were adjusted to a concentration of 3.0× 10^6 cells I mL live cells.

These cells were then plated on five 96 well tissue culture treated round bottom plates (Costar 3799) per donor at 50 uL per well. Within 30 minutes, transfection mixtures were added to each well at a volume of 50 uL per well. After 4 hours post transfection, the media was supplemented with 10 uL of Fetal Bovine Serum (Gibco 10082, lot 1012368)

Transfection Preparation:

mmRNA encoding human G-CSF (mRNA sequence shown in SEQ ID NO: 4; poly-A tail of approximately 160 nucleotides not shown in sequence; 5' cap, Cap1) (containing either (1) natural NTPs, (2) 100% substitution with 5-methyl cytidine and pseudouridine, or (3) 100% substitution with 5-methyl cytidine and N1-methyl pseudouridine; mmRNA encoding luciferase (WT cDNA sequence shown in SEQ ID NO: 10) (containing either (1) natural NTPs or (2) 100% substitution with 5-methyl cytidine and pseudouridine) and TLR agonist R848 (Invivogen tlrl-r848) were diluted to 38.4 ng/uL in a final volume of 2500 uL Optimem I.

Separately, 432 uL of Lipofectamine 2000 (Invitrogen 11668-027, lot 1070962) was diluted with 13.1 mL Optimem I. In a 96 well plate nine aliquots of 135 uL of each mmRNA, positive control (R-848) or negative control (Optimem I) was added to 135 uL of the diluted Lipofectamine 2000. The plate containing the material to be transfected was incubated for 20 minutes. The transfection mixtures were then transferred to each of the human PBMC plates at 50 uL per well. The plates were then incubated at 37 C. At 2, 4, 8, 20, and 44 hours each plate was removed from the incubator, and the supernatants were frozen.

After the last plate was removed, the supernatants were assayed using a human G-CSF ELISA kit (Invitrogen KHC2032) and human IFN-alpha ELISA kit (Thermo Scientific 41105-2). Each condition was done in duplicate.

Results:

The ability of unmodified and modified mRNA (mmRNAs) to produce the encoded protein was assessed (G-CSF production) over time as was the ability of the mRNA to trigger innate immune recognition as measured by interferon-alpha production. Use of in vitro PBMC cultures is an accepted way to measure the immunostimulatory potential of oligonucleotides (Robbins et al., Oligonucleotides 2009 19:89-102).

Results were interpolated against the standard curve of each ELISA plate using a four parameter logistic curve fit. Shown in Tables 18 and 19 are the average from 2 separate PBMC donors of the G-CSF and IFN-alpha production over time as measured by specific ELISA.

In the G-CSF ELISA, background signal from the Lipofectamine 2000 untreated condition was subtracted at each timepoint. The data demonstrated specific production of human G-CSF protein by human peripheral blood mononuclear is seen with G-CSF mRNA containing natural NTPs, 100% substitution with 5-methyl cytidine and pseudouridine, or 100% substitution with 5-methyl cytidine and N1-methyl pseudouridine. Production of G-CSF was significantly increased through the use of modified mRNA relative to unmodified mRNA, with the 5-methyl cytidine and N1-methyl pseudouridine containing G-CSF mmRNA showing the highest level of G-CSF production. With regards to innate immune recognition, unmodified mRNA resulted in substantial IFN-alpha production, while the modified mRNA largely prevented interferon-alpha production.

TABLE 18

| G-CSF Signal<br>G-CSF signal-2 Donor Average | | | | | |
|---|---|---|---|---|---|
| pg/mL | 2 Hr | 4 Hr | 8 Hr | 20 Hr | 44 Hr |
| G-CSF (5 mC/pseudouridine) | 120.3 | 136.8 | 421.0 | 346.1 | 431.8 |
| G-CSF (5 mC/N1-methyl pseudouridine) | 256.3 | 273.7 | 919.3 | 1603.3 | 1843.3 |
| GCSF(Natural-no modification) | 63.5 | 92.6 | 129.6 | 258.3 | 242.4 |
| Luciferase (5 mC/pseudouridine) | 4.5 | 153.7 | 33.0 | 186.5 | 58.0 |

TABLE 19

| IFN-alpha signal<br>IFN-alpha signal-2 donor average | | | | | |
|---|---|---|---|---|---|
| pg/mL | 2 Hr | 4 Hr | 8 Hr | 20 Hr | 44 Hr |
| G-CSF (5 mC/pseudouridine) | 21.1 | 2.9 | 3.7 | 22.7 | 4.3 |
| G-CSF (5 mC/N1-methyl pseudouridine) | 0.5 | 0.4 | 3.0 | 2.3 | 2.1 |
| G-CSF(Natural) | 0.0 | 2.1 | 23.3 | 74.9 | 119.7 |
| Luciferase (5 mC/pseudouridine) | 0.4 | 0.4 | 4.7 | 1.0 | 2.4 |
| R-848 | 39.1 | 151.3 | 278.4 | 362.2 | 208.1 |
| Lipofectamine 2000 control | 0.8 | 17.2 | 16.5 | 0.7 | 3.1 |

Example 31. Quantification in Exosomes

The quantity and localization of the mmRNA of the present invention can be determined by measuring the amounts (initial, timecourse, or residual basis) in isolated exosomes. In this study, since the mmRNA are typically codon-optimized and distinct in sequence from endogenous mRNA, the levels of mmRNA are quantitated as compared to endogenous levels of native or wild type mRNA by using the methods of Gibbings, PCT/IB2009/005878, the contents of which are incorporated herein by reference in their entirety.

In these studies, the method is performed by first isolating exosomes or vesicles preferably from a bodily fluid of a patient previously treated with a polynucleotide, primary construct or mmRNA of the invention, then measuring, in said exosomes, the polynucleotide, primary construct or mmRNA levels by one of mRNA microarray, qRT-PCR, or other means for measuring RNA in the art including by suitable antibody or immunohistochemical methods.

Example 32: Bifunctional mmRNA

Using the teachings and synthesis methods described herein, modified RNAs are designed and synthesized to be bifunctional, thereby encoding one or more cytotoxic protein molecules as well as be synthesized using cytotoxic nucleosides.

Administration of the bifunctional modified mRNAs is effected using either saline or a lipid carrier. Once administered, the bifunctional modified mRNA is translated to produce the encoded cytotoxic peptide. Upon degradation of the delivered modified mRNA, the cytotoxic nucleosides are released which also effect therapeutic benefit to the subject.

Example 33. Synthesis of Modified mRNA

Modified mRNA is generated from a cDNA template containing a T7 RNA-polymerase promoter sequence using a commercially available T7 RNA polymerase transcription kit (MEGASCRIPT® High Yield Transcription KIT, AMBION®, Austin, Tex.; MSCRIPT™ mRNA Production Kit, EPICENTRE® Biotechnologies, Madison, Wis.). An in vitro transcription reaction contains between 1-2 μg of template DNA in the form of a linearized plasmid, PCR product, or single-stranded oligonucleotide with a double-stranded polymerase promoter region. The template DNA encodes a strong translation initiation sequence such as a strong consensus Kozak sequence or an optimized, high-expression IRES including the EMCV IRES. Reaction volumes are between 20-40 μl and contain 3'-O-Me-m7-G(5') ppp(5')G ARCA cap analog (NEW ENGLAND BIOLABS®) in addition to an optimized ribonucleotide mixture of determined modified adenine, guanine, cytidine and uridine ribonucleotide analogs. Final reaction concentrations for nucleotide are 6 mM for the cap analog and 1.5-7.5 mM for each of the other nucleotides. The temperature and duration of the in vitro transcription reaction are optimized for efficiency, fidelity and yield. Reactions may be incubated from 3-6 hours and up to 16 hours at 37° C. Following the in vitro transcription reaction, the capped mRNA undergoes polyadenylation using a commercially available poly-A tailing kit (EPICENTRE® Biotechnologies, Madison, Wis.). The resulting capped and polyadenylated synthetic mRNA is then purified by denaturing agarose gel electrophoresis to confirm production of full-length product and to remove any degradation products followed by spin column filtration (RNeasy Kit, Qiagen, Valencia, Calif.; MEGACLEAR™ AMBION®, Austin, Tex.). Purified synthetic mRNAs are resuspended in RNase-free water containing an RNase inhibitor (RNASIN® Plus RNase Inhibitor, Promega, Madison, Wis.), quantified by NANODROP™ (Thermo Scientific, Logan, Utah) and stored at −20° C.

Example 34: Bulk Transfection of Modified mRNA into Cell Culture

A. Cationic Lipid Delivery Vehicles

RNA transfections are carried out using RNAIMax (Invitrogen, Carlsbad, Calif.) or TRANSIT-mRNA (Mirus Bio, Madison, Wis.) cationic lipid delivery vehicles. RNA and reagent are first diluted in Opti-MEM basal media (Invitrogen, Carlsbad, Calif.). 100 ng/uL RNA is diluted 5× and 5 μL of RNAIMax per μg of RNA is diluted 10×. The diluted components are pooled and incubated 15 minutes at room temperature before they are dispensed to culture media. For TRANSIT-mRNA transfections, 100 ng/uL RNA is diluted 10× in Opti-MEM and BOOST reagent is added (at a concentration of 2 μL per μg of RNA), TRANSIT-mRNA is added (at a concentration of 2 μL per μg of RNA), and then the RNA-lipid complexes are delivered to the culture media after a 2-minute incubation at room temperature. RNA transfections are performed in Nutristem xenofree hES media (STEMGENT®, Cambridge, Mass.) for RiPS derivations, Dermal Cell Basal Medium plus Keratinocyte Growth Kit (ATCC) for keratinocyte experiments, and Opti-MEM plus 2% FBS for all other experiments. Successful introduction of a modified mRNA (mmRNA) into host cells can be monitored using various known methods, such as a fluorescent marker, such as Green Fluorescent Protein (GFP). Successful transfection of a modified mRNA can also be determined by measuring the protein expression level of the target polypeptide by e.g., Western Blotting or immunocytochemistry. Similar methods may be followed for large volume scale-up to multi-liter (5-10,000 L) culture format following similar RNA-lipid complex ratios.

B. Electroporation Delivery of Exogenous Synthetic mRNA Transcripts

Electroporation parameters are optimized by transfecting MRC-5 fibroblasts with in vitro synthetic modified mRNA (mmRNA) transcripts and measuring transfection efficiency by quantitative RT-PCR with primers designed to specifically detect the exogenous transcripts. Discharging a 150 uF capacitor charged to F into $10\times10^6$ cells suspended in 50 μl of Opti-MEM (Invitrogen, Carlsbad, Calif.) in a standard electroporation cuvette with a 2 mm gap is sufficient for repeated delivery in excess of 10,000 copies of modified mRNA transcripts per cell, as determined using the standard curve method, while maintaining high viability (>70%). Further experiments may reveal that the voltage required to efficiently transfect cells with mmRNA transcripts can depend on the cell density during electroporation. Cell density may vary from $1\times10^6$ cell/50 μl to a density of $2.5\times10^6$ cell/50 μl and require from 110V to 145V to transfect cells with similar efficiencies measured in transcript copies per cell. Large multi-liter (5-10,000 L) electroporation may be performed similar to large volume flow electroporation strategies similar to methods described with the above described constraints (Li et al., 2002; Geng et al., 2010).

Example 35. Overexpression of Ceramide Transfer Protein to Increase Therapeutic Antibody Protein Production in Established CHO Cell Lines A. Batch Culture An antibody producing CHO cell line (CHO DG44) secreting a humanized therapeutic IgG antibody is transfected a single time with lipid cationic delivery agent alone (control) or a synthetic mRNA transcript encoding wild type ceramide transfer protein (CERT) or a non-phosphorylation competent Ser132A CERT mutant. The sequences are taught in for example, U.S. Ser. No. 13/252,049, the contents of which are incorporated herein by reference in their entirety. CERT is an essential cytosolic protein in mammalian cells that transfers the sphingolipid ceramide from the endoplasmic reticulum to the Golgi complex where it is converted to sphingomyelin (Hanada et al., 2003). Overexpression of CERT significantly enhances the transport of secreted proteins to the plasma membrane and improves the production of proteins that are transported via the secretory pathway from eukaryotic cells thereby enhancing secretion of proteins in the culture medium. Synthetic mRNA transcripts are pre-mixed with a lipid cationic delivery agent at a 2-5:1 carrier:RNA ratio. The initial seeding density is about $2\times10^5$ viable cells/mL. The synthetic mRNA transcript is delivered after initial culture seeding during the exponential culture growth phase to achieve a final synthetic mRNA copy number between $10\times10^2$ and $10\times10_3$ per cell. The basal cell culture medium used for all phases of cell inoculum generation and for growth of cultures in bioreactors was modified CD-CHO medium containing glutamine, sodium bicarbonate, insulin and methotrexate. The pH of the medium was adjusted to 7.0 with 1 N HCl or IN NaOH after addition of all components. Culture run times ended on days 7, 14, 21 or 28+. Production-level 50 L scale reactors (stainless steel reactor with two marine impellers) were used and are scalable to >10,000 L stainless steel reactors (described in commonly-assigned patent application U.S. Ser. No. 60/436,050, filed Dec. 23, 2002, and U.S. Ser. No. 10/740,645). A data acquisition system (Intellution Fix 32, OSlsoft, LLC, San Leandro, Calif.) recorded temperature, pH, and dissolved oxygen (DO) throughout runs. Gas flows were controlled via rotameters. Air was sparged into the reactor via a submerged frit (5 !lm pore size) and through the reactor head space for $CO_2$ removal. Molecular oxygen was sparged through the same frit for DO control. $CO_2$ was sparged through same frit as used for pH control. Samples of cells were removed from the reactor on a daily basis. A sample used for cell counting was stained with trypan blue (Sigma, St. Louis, Mo.). Cell count and cell viability determination were performed via hemocytometry using a microscope. For analysis of metabolites, additional samples were centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C. To measure secreted humanized IgG antibody titers, supernatant is taken from seed-stock cultures of all stable cell pools, the IgG titer is determined by ELISA and divided by the mean number of cells to calculate the specific productivity. The highest values are the cell pools with the Ser132A CERT mutant, followed by wild type CERT. In both, IgG expression is markedly enhanced compared to carrier-alone or untransfected cells.

Continuous or Batch-Fed Culture

An antibody producing CHO cell line (CHO DG44) secreting humanized IgG antibody is transfected with lipid cationic delivery agent alone (control) or a synthetic mRNA transcript encoding wild type ceramide transfer protein or a non-phosphorylation competent Ser132A CERT mutant. Synthetic mRNA transcripts are pre-mixed with a lipid cationic delivery agent at a 2-5:1 carrier:RNA ratio. The initial seeding density was about $2\times10^5$ viable cells/mL. Synthetic mRNA transcript is delivered after initial culture seeding during the exponential culture growth phase to achieve a final synthetic mRNA copy number between $10\times10^2$ and $10\times10^3$ per cell. The basal cell culture medium used for all phases of cell inoculum generation and for growth of cultures in bioreactors was modified CD-CHO medium containing glutamine, sodium bicarbonate, insulin and methotrexate. The pH of the medium was adjusted to 7.0 with 1 N HCl or IN NaOH after addition of all components. Bioreactors of 5 L scale (glass reactor with one marine impeller) were used to obtain maximum CERT protein production and secreted humanized IgG antibody curves. For continuous or fed-batch cultures, the culturing run time is increased by supplementing the culture medium one or more times daily (or continuously) with fresh medium during the run. In the a continuous and fed-batch feeding regimens, the cultures receive feeding medium as a continuously-supplied infusion, or other automated addition to the culture, in a timed, regulated, and/or programmed fashion so as to achieve and maintain the appropriate amount of synthetic mRNA: carrier in the culture. The preferred method is a feeding regimen of a once per day bolus feed with feeding medium containing synthetic mRNA: carrier on each day of the culture run, from the beginning of the culture run to the day of harvesting the cells. The daily feed amount was recorded on batch sheets. Production-level 50 L scale reactors (stainless steel reactor with two marine impellers) were used and are scalable to >10,000 L stainless steel reactors. A data acquisition system (Intellution Fix 32) recorded temperature, pH, and dissolved oxygen (DO) throughout runs. Gas flows were controlled via rotameters. Air was sparged into the reactor via a submerged frit (5 μm pore size) and through the reactor head space for $CO_2$ removal. Molecular oxygen was sparged through the same frit for DO control. $CO_2$ was sparged through same frit as used for pH control. Samples of cells were removed from the reactor on a daily basis. A sample used for cell counting was stained with trypan blue (Sigma, St. Louis, Mo.). Cell count and cell viability determination were performed via hemocytometry using a microscope. For analysis of metabolites, additional samples were centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C. To measure secreted humanized IgG antibody titers, supernatant is taken from seed-stock cultures of all stable cell pools, the IgG titer is determined by ELISA and divided by the mean number of cells to calculate the specific productivity. The highest values are the cell pools with the Ser132A CERT mutant, followed by wild type CERT. In both, IgG expression is markedly enhanced compared to carrier-alone or untransfected cells.

Example 36. De Novo Generation of a Mammalian Cell Line Expressing Human Erythropoietin as a Therapeutic Agent A. Batch Culture This Example describes the production of human erythropoietin protein (EPO) from cultured primary CHO cells. Erythropoietin is a glycoprotein hormone that is required for red blood cell synthesis. EPO protein may be used as a therapeutic agent for anemia from cancer, heart failure, chronic kidney disease and myelodysplasia. Primary CHO cells are isolated and cultured as described (Tjio and Puck, 1958). Primary CHO cells were then expanded in modified CD-CHO medium containing glutamine, sodium bicarbonate, insulin, and methotrexate (see Example 35) using T-75 flasks (Coming, N.Y.) and 250 and 500 mL spinners (Bellco, Vineland, N.J.). T-flasks and spinners were incubated at 37° C. in 6% $CO_2$. After sufficient inoculum was generated, the culture was transferred into a either a 5 L or a 50 L bioreactor as described above (see Example 35). Synthetic mRNA transcript encoding the human erythropoietin protein are pre-mixed with a lipid cationic delivery agent at a 2-5:1 carrier:RNA ratio in a minimum of 1% total culture volume. The initial seeding density is about $2\times10^5$ viable cells/mL. The synthetic mRNA transcript is delivered after initial culture seeding during the exponential culture growth phase to achieve a final synthetic mRNA copy number between $10\times10^2$ and $10\times10^3$ per cell. Culture growth and analysis were performed as described above (see Example 34).

B. Continuous or Batch-Fed Culture

A primary CHO cell line derived and expanded as described above (see Example 36a) is transfected with lipid cationic delivery agent alone (control) or a synthetic mRNA transcript encoding human erythropoietin protein. Synthetic mRNA transcripts are pre-mixed with a lipid cationic delivery agent at a 2-5:1 carrier:RNA ratio. The initial seeding density was about $2\times10^5$ viable cells/mL. Synthetic mRNA transcript is delivered after initial culture seeding during the exponential culture growth phase to achieve a final synthetic mRNA copy number between $10\times10^2$ and $10\times10^3$ per cell. Culture conditions were as described above (Example 35a). For continuous or fed-batch cultures, the culturing run time is increased by supplementing the culture medium one or more times daily (or continuously) with fresh medium during the run. In the a continuous and fed-batch feeding regimens, the cultures receive feeding medium as a continuously-supplied infusion, or other automated addition to the culture, in a timed, regulated, and/or programmed fashion so as to achieve and maintain the appropriate amount of synthetic mRNA:carrier in the culture. The preferred method is a feeding regimen of a once per day bolus feed with feeding medium containing synthetic mRNA: carrier on each day of the culture run, from the beginning of the culture run to the day of harvesting the cells. The daily feed amount was recorded on batch sheets. Production-level 50 L scale reactors (stainless steel reactor with two marine impellers) were used and are scalable to >10,000 L stainless steel reactors. Culture growth and analysis were performed as described herein (see Example 35).

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:

1. A pharmaceutical composition, comprising:

a modified messenger RNA (mRNA) encoding a polypeptide of interest, wherein the modified mRNA comprises one or more uridines and one or more cytidines and wherein substantially all uridines are modified, and the modified mRNA is in a lipid nanoparticle formulation comprising a lipid selected from the group consisting of DLin-DMA, DLin-K-DMA, DLin-KC2-DMA, DLin-MC3-DMA, 98N12-5, and C12-200; a cholesterol; and a PEG-lipid.

2. The pharmaceutical composition of claim 1, wherein the modified uridine is a pyridin-4-one ribonucleoside, 5-aza-uridine, 2-thio-5-aza-uridine, 2-thiouridine, 4-thio-pseudouridine, 2-thio-pseudouridine, 5-hydroxy uridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, or pseudouridine.

3. The pharmaceutical composition of claim 1, wherein the one or more uridines are modified on the major groove face of the uridine.

4. The pharmaceutical composition of claim 1, wherein the modified uridine is pseudouridine or 1-methyl-pseudouridine.

5. The pharmaceutical composition of claim 4, wherein the modified uridine is 1-methyl-pseudouridine.

6. The pharmaceutical composition of claim 2, wherein the modified mRNA further comprises one or more modified cytidines.

7. The pharmaceutical composition of claim 6, wherein the modified cytidine is 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 5-methyl-cytidine, or 4-methoxy-1-methyl-pseudoisocytidine.

8. The pharmaceutical composition of claim 7, wherein the modified cytidine is 5-methyl-cytidine.

9. The pharmaceutical composition of claim 7, wherein at least about 95% of the uridines are modified and at least about 95% of the cytidines are modified.

10. The pharmaceutical composition of claim 7, wherein about 100% of the uridines are modified and about 100% of the cytidines are modified.

11. The pharmaceutical composition of claim 1, wherein the modified mRNA comprises a 5' Cap1 structure and a polyA tail of 160 nucleotides in length.

12. The pharmaceutical composition of claim 1, wherein the modified mRNA and lipid nanoparticle are formulated at a total lipid to mRNA weight ratio of 10:1, 15:1, 20:1, or 30:1.

13. The pharmaceutical composition of claim 1, wherein the lipid is DLin-KC2-DMA or 98N12-5.

14. The pharmaceutical composition of claim 1, wherein the lipid nanoparticle formulation comprises about 42% lipid, about 48% cholesterol, and about 10% PEG-lipid.

15. The pharmaceutical composition of claim 1, wherein the lipid nanoparticle formulation comprises about 50% lipid, about 38.5% cholesterol, and about 1.5% PEG-lipid.

16. The pharmaceutical composition of claim 1, wherein the modified mRNA further comprises an operably-linked signal sequence, wherein the signal sequence is that of either (i) the polypeptide of interest or (ii) a heterologous protein.

17. The pharmaceutical composition of claim 1, wherein the lipid nanoparticle has a mean particle size between 86 nm and 155 nm.

18. The pharmaceutical composition of claim 1, wherein the lipid nanoparticle has a polydisperity index between 0.02 and 0.17.

19. The pharmaceutical composition of claim 1 further comprising a formulation buffer for in vivo delivery, wherein the formulation buffer has a pH of 6.5 and comprises sodium chloride, calcium chloride, and Na+-phosphate.

20. The pharmaceutical composition of claim 19, wherein the formulation buffer comprises 150 mM sodium chloride, 2 mM calcium chloride, and 2 mM Na+-phosphate.

* * * * *

UNITED STATES PATENT AND TRADEMARK OFFICE
CERTIFICATE OF CORRECTION

PATENT NO. : 9,950,068 B2  
APPLICATION NO. : 15/379284  
DATED : April 24, 2018  
INVENTOR(S) : Antonin De Fougerolles et al.

Page 1 of 1

It is certified that error appears in the above-identified patent and that said Letters Patent is hereby corrected as shown below:

In the Claims

Column 108, Line 23, in Claim 18, replace "polydisperity index" with --polydispersity index--.

Signed and Sealed this
Tenth Day of July, 2018

Andrei Iancu
*Director of the United States Patent and Trademark Office*